(12) United States Patent
Donofrio et al.

(10) Patent No.: US 9,597,505 B2
(45) Date of Patent: *Mar. 21, 2017

(54) IMPLANTABLE MEDICAL DEVICE CROSSTALK EVALUATION AND MITIGATION

(75) Inventors: William T. Donofrio, Andover, MN (US); John E. Burnes, Coon Rapids, MN (US); Paul G. Krause, Shoreview, MN (US); Xiaohong Zhou, Woodbury, MN (US); Gerald P. Arne, Long Lake, MN (US); David J. Peichel, Minneapolis, MN (US); James D. Reinke, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 1812 days.

This patent is subject to a terminal disclaimer.

(21) Appl. No.: 12/362,781

(22) Filed: Jan. 30, 2009

(65) Prior Publication Data

US 2010/0114198 A1    May 6, 2010

Related U.S. Application Data

(60) Provisional application No. 61/110,312, filed on Oct. 31, 2008.

(51) Int. Cl.
*A61N 1/36*    (2006.01)
*A61N 1/37*    (2006.01)
(Continued)

(52) U.S. Cl.
CPC ........ *A61N 1/36114* (2013.01); *A61B 5/7217* (2013.01); *A61N 1/3702* (2013.01);
(Continued)

(58) Field of Classification Search
CPC .............. A61N 1/36114; A61N 1/3702; A61N 1/37247; A61N 1/37282; A61N 1/3962;
(Continued)

(56) References Cited

U.S. PATENT DOCUMENTS 3,421,511 A    1/1969    Schwartz et al.
3,522,811 A    8/1970    Seymour et al.
(Continued)

FOREIGN PATENT DOCUMENTS

DE    10103288 A1    8/2002
EP    0688577 A1    12/1995
(Continued)

OTHER PUBLICATIONS

Siu et a., "Inappropriate Implantable Cardioverter Defibrillator Shock from a Transcutaneous Muscle Stimulation Device Therapy" Journal of Interventional Cardiac Electrophysiology 13:73-75, 2005.
(Continued)

*Primary Examiner* — Catherine Voorhees
(74) *Attorney, Agent, or Firm* — Carol F. Barry

(57) ABSTRACT

Electrical crosstalk between two implantable medical devices or two different therapy modules of a common implantable medical device may be evaluated, and, in some examples, mitigated. In some examples, one of the implantable medical devices or therapy modules delivers electrical stimulation to a nonmyocardial tissue site or a nonvascular cardiac tissue site, and the other implantable medical device or therapy module delivers cardiac rhythm management therapy to a heart of the patient.

52 Claims, 40 Drawing Sheets

(51) Int. Cl.
  *A61N 1/372* (2006.01)
  *A61N 1/39* (2006.01)
  *A61N 1/365* (2006.01)
  *A61N 1/08* (2006.01)
  *A61B 5/00* (2006.01)
  *A61B 5/0428* (2006.01)
  *A61N 1/362* (2006.01)
  *A61N 1/368* (2006.01)

(52) U.S. Cl.
  CPC ..... *A61N 1/37247* (2013.01); *A61N 1/37282* (2013.01); *A61N 1/3962* (2013.01); *A61B 5/04288* (2013.01); *A61N 1/3621* (2013.01); *A61N 1/3688* (2013.01); *A61N 1/36521* (2013.01); *A61N 2001/083* (2013.01)

(58) Field of Classification Search
  CPC .............. A61N 1/3621; A61N 1/36521; A61N 1/3688; A61N 2001/083; A61B 5/7217; A61B 5/04288
  USPC ........... 607/2–9, 17–18, 27–30, 60; 600/301, 600/508–512
  See application file for complete search history.

(56) References Cited

U.S. PATENT DOCUMENTS

| | | |
|---|---|---|
| 3,593,718 A | 7/1971 | Krasner et al. |
| 3,645,267 A | 2/1972 | Hagfors |
| 3,650,277 A | 3/1972 | Sjostrand et al. |
| 3,796,221 A | 3/1974 | Hagfors |
| 3,878,564 A | 4/1975 | Yao et al. |
| 4,044,774 A | 8/1977 | Corbin et al. |
| 4,146,029 A | 3/1979 | Ellinwood, Jr. |
| 4,202,340 A * | 5/1980 | Langer et al. ............... 607/5 |
| 4,340,063 A | 7/1982 | Maurer |
| 4,374,382 A | 2/1983 | Markowitz |
| 4,428,378 A | 1/1984 | Anderson et al. |
| 4,458,696 A | 7/1984 | Larimore |
| 4,485,813 A | 12/1984 | Anderson et al. |
| 4,535,774 A | 8/1985 | Olson |
| 4,549,556 A | 10/1985 | Tarjan et al. |
| 4,686,988 A | 8/1987 | Sholder |
| 4,694,835 A | 9/1987 | Strand |
| 4,750,495 A | 6/1988 | Moore et al. |
| 4,880,005 A | 11/1989 | Pless et al. |
| 4,903,701 A | 2/1990 | Moore et al. |
| 4,987,897 A | 1/1991 | Funke |
| 4,998,974 A | 3/1991 | Aker |
| 5,031,618 A | 7/1991 | Mullett |
| 5,058,584 A | 10/1991 | Bourgeois |
| 5,117,824 A | 6/1992 | Keimel et al. |
| 5,135,004 A | 8/1992 | Adams et al. |
| 5,149,713 A | 9/1992 | Bousquet |
| 5,189,609 A | 2/1993 | Tivig et al. |
| 5,199,428 A | 4/1993 | Obel et al. |
| 5,203,326 A | 4/1993 | Collins |
| 5,213,098 A | 5/1993 | Bennett et al. |
| 5,220,917 A | 6/1993 | Cammilli et al. |
| 5,243,980 A | 9/1993 | Mehra |
| 5,251,621 A | 10/1993 | Collins |
| 5,255,691 A | 10/1993 | Otten |
| 5,261,400 A | 11/1993 | Bardy |
| 5,292,336 A | 3/1994 | Spence, Jr. et al. |
| 5,292,338 A | 3/1994 | Bardy |
| 5,330,505 A | 7/1994 | Cohen |
| 5,330,507 A | 7/1994 | Schwartz |
| 5,330,515 A | 7/1994 | Rutecki et al. |
| 5,331,966 A | 7/1994 | Bennett et al. |
| 5,334,221 A | 8/1994 | Bardy |
| 5,342,409 A | 8/1994 | Mullett |
| 5,360,441 A | 11/1994 | Otten |
| 5,388,586 A | 2/1995 | Lee et al. |
| 5,464,434 A | 11/1995 | Alt |
| 5,496,363 A | 3/1996 | Burgio et al. |
| 5,522,860 A | 6/1996 | Molin et al. |
| 5,545,186 A | 8/1996 | Olson et al. |
| 5,564,434 A | 10/1996 | Halperin et al. |
| 5,607,418 A | 3/1997 | Arzbaecher |
| 5,651,378 A | 7/1997 | Matheny et al. |
| 5,690,681 A | 11/1997 | Geddes et al. |
| 5,700,282 A | 12/1997 | Zabara |
| 5,702,429 A | 12/1997 | King |
| 5,755,736 A | 5/1998 | Gillberg et al. |
| 5,776,170 A | 7/1998 | MacDonald et al. |
| 5,792,187 A | 8/1998 | Adams |
| 5,817,131 A | 10/1998 | Elsberry et al. |
| 5,824,021 A | 10/1998 | Rise |
| 5,913,876 A | 6/1999 | Taylor et al. |
| 5,978,710 A | 11/1999 | Prutchi et al. |
| 6,006,134 A | 12/1999 | Hill et al. |
| 6,058,331 A | 5/2000 | King |
| 6,073,048 A | 6/2000 | Kieval et al. |
| 6,134,470 A | 10/2000 | Hartlaub |
| 6,141,586 A | 10/2000 | Mower |
| 6,178,349 B1 | 1/2001 | Kieval |
| 6,272,377 B1 | 8/2001 | Sweeney et al. |
| 6,473,644 B1 | 10/2002 | Terry, Jr. et al. |
| 6,587,726 B2 | 7/2003 | Lurie et al. |
| 6,885,888 B2 | 4/2005 | Rezai |
| 6,993,385 B1 | 1/2006 | Routh et al. |
| 7,010,345 B2 | 3/2006 | Hill et al. |
| 7,076,283 B2 | 7/2006 | Cho et al. |
| 7,218,964 B2 | 5/2007 | Hill et al. |
| 7,945,325 B2 * | 5/2011 | Stahmann et al. ................ 607/9 |
| 8,774,918 B2 * | 7/2014 | Donofrio ............... A61N 1/025 600/515 |
| 2001/0001126 A1 | 5/2001 | Cammilli et al. |
| 2002/0107553 A1 | 8/2002 | Hill et al. |
| 2004/0176782 A1 | 9/2004 | Hanse et al. |
| 2005/0115561 A1 | 6/2005 | Stahmann et al. |
| 2005/0149133 A1 | 7/2005 | Libbus et al. |
| 2005/0197675 A1 | 9/2005 | David et al. |
| 2005/0197680 A1 | 9/2005 | DelMain et al. |
| 2005/0267542 A1 | 12/2005 | David et al. |
| 2006/0095080 A1 | 5/2006 | Libbus et al. |
| 2006/0116737 A1 | 6/2006 | Libbus |
| 2006/0190051 A1 | 8/2006 | Gerber et al. |
| 2006/0241699 A1 | 10/2006 | Libbus et al. |
| 2006/0241737 A1 | 10/2006 | Tockman et al. |
| 2006/0253157 A1 | 11/2006 | Libbus et al. |
| 2006/0271118 A1 | 11/2006 | Libbus et al. |
| 2007/0043393 A1 | 2/2007 | Brockway et al. |
| 2007/0049983 A1 | 3/2007 | Freeberg |
| 2007/0050005 A1 | 3/2007 | Lauro |
| 2007/0135861 A1 | 6/2007 | Wallace et al. |
| 2007/0150011 A1 | 6/2007 | Meyer et al. |
| 2007/0150014 A1 | 6/2007 | Kramer et al. |
| 2007/0208381 A1 | 9/2007 | Hill et al. |
| 2007/0239215 A1 | 10/2007 | Bhunia et al. |
| 2007/0239229 A1 | 10/2007 | Masoud et al. |
| 2007/0250121 A1 | 10/2007 | Miesel |
| 2007/0260283 A1 | 11/2007 | Li |
| 2007/0260285 A1 | 11/2007 | Libbus et al. |
| 2007/0282412 A1 | 12/2007 | Soltis et al. |
| 2008/0015659 A1 | 1/2008 | Zhang et al. |
| 2008/0021507 A1 | 1/2008 | Libbus et al. |
| 2008/0051839 A1 | 2/2008 | Libbus et al. |
| 2008/0147140 A1 | 6/2008 | Ternes et al. |
| 2008/0167696 A1 | 7/2008 | Cates et al. |
| 2008/0200959 A1 | 8/2008 | Libbus et al. |
| 2008/0215118 A1 | 9/2008 | Goetz et al. |
| 2008/0249583 A1 * | 10/2008 | Salo et al. ............ 607/11 |
| 2008/0275522 A1 * | 11/2008 | Dong et al. ............ 607/28 |
| 2009/0026201 A1 | 1/2009 | Hall et al. |
| 2009/0054828 A1 | 2/2009 | Stolen et al. |
| 2009/0198294 A1 * | 8/2009 | Rossing et al. ............... 607/4 |
| 2010/0114201 A1 | 5/2010 | Donofrio et al. |
| 2011/0112419 A1 | 5/2011 | Bjorling et al. |
| 2011/0144511 A1 * | 6/2011 | Zhang et al. ............... 600/510 |

(56) References Cited

U.S. PATENT DOCUMENTS

FOREIGN PATENT DOCUMENTS

| EP | 1857141 A1 | 11/2007 |
| --- | --- | --- |
| EP | 1870129 A1 | 12/2007 |
| WO | 03/061760 A1 | 7/2003 |
| WO | 2005063332 A1 | 7/2005 |
| WO | 2006119131 A1 | 11/2006 |
| WO | 2008073235 A1 | 6/2008 |

OTHER PUBLICATIONS

International Search Report and Written Opinion of international application No. PCT/US2009/062805, mailed Jan. 12, 2010, 12 pp.
U.S. Appl. No. 61/110,300, filed Oct. 31, 2008 entitled "Implantable Medical Device Crosstalk Evaluation and Mitigation", by Burnes et al.
U.S. Appl. No. 12/362,768, filed Jan. 30, 2009 entitled "Implantable Medical Device Crosstalk Evaluation and Mitigation", by Burnes et al.
U.S. Appl. No. 61/110,312, filed Oct. 31, 2008 entitled "Implantable Medical Device Crosstalk Evaluation and Mitigation", by Donofrio et al.
U.S. Appl. No. 61/110,239, filed Oct. 31, 2008 entitled "Implantable Medical Device Crosstalk Evaluation and Mitigation", by Donofrio et al.
U.S. Appl. No. 12/362,792, filed Jan. 30, 2009 entitled "Implantable Medical Device Crosstalk Evaluation and Mitigation", by Donofrio et al.
U.S. Appl. No. 61/110,328, filed Oct. 31, 2008 entitled "Implantable Medical Device Crosstalk Evaluation and Mitigation", by Krause et al.
U.S. Appl. No. 12/362,809, filed Jan. 30, 2009 entitled "Implantable Medical Device Crosstalk Evaluation and Mitigation", by Krause et al.
U.S. Appl. No. 12/362,814, filed Jan. 30, 2009 entitled "Implantable Medical Device Crosstalk Evaluation and Mitigation", by Krause et al.
U.S. Appl. No. 12/362,822, filed Jan. 30, 2009 entitled "Implantable Medical Device Crosstalk Evaluation and Mitigation", by Krause et al.
U.S. Appl. No. 12/362,838, filed Jan. 30, 2009 entitled "Implantable Medical Device Crosstalk Evaluation and Mitigation", by Donofrio et al.
U.S. Appl. No. 12/362,842, filed Jan. 30, 2009 entitled "Implantable Medical Device Crosstalk Evaluation and Mitigation", by Donofrio et al.
U.S. Appl. No. 12/362,773, filed Jan. 30, 2009 entitled "Implantable Medical Device Crosstalk Evaluation and Mitigation", by Burnes et al.
U.S. Appl. No. 12/362,859, filed Jan. 30, 2009 entitled "Implantable Medical Device Crosstalk Evaluation and Mitigation", by Burnes et al.
Bilgutay et al, "Vagal Tuning—A New Concept in the Treatment of Supraventricular Arrhythmias, Angina Pectoris, and Heart Failure," *Journal of Thoracic Cardiovascular Surgery* 56(1): 71-82, Jul. 1968.
Braunwald et al., "Carotid Sinus Nerve Stimulation in the Treatment of Angina Pectoris and Supraventricular Tachycardia," *California Medicine* 112(3): 41-50, Mar. 1970.
Armour, "Instant to Instant Reflex Cardiac Regulation," *Cardiology* 61: 309-328, 1976.
Schwartz et al., "Effect of dorsal root section on the arrhythmias associated with coronary occlusion," *American Journal of Physiology* 231(3): 923-928, Sep. 1976.
Blair et al., "Responses of Thoracic Spinothalamic Neurons to Intracardiac Injection of Bradykinin in the Monkey," *Circulation Research* 51(1): 83-94, Jul. 1982.
Ammons et al., "Vagal Afferent Inhibition of Spinothalamic Cell Responses to Sympathetic Afferents and Bradykinin in the Monkey," *Circulation Research* 53(5): 603-612, Nov. 1983.
Blair et al., "Responses of Thoracic Spinothalamic and Spinoreticular Cells to Coronary Artery Occlusion," *Journal of Neurophysiology* 51(4): 636-648, Apr. 1984.
Ammons et al., "Effects of intracardiac bradykinin on $T_2$—$T_5$ medial spinothalamic cells," *American Journal of Physiology* 249: R147-R152, 1985.
Blair et al., "Activation of Feline Spinal Neurones by Potentiated Ventricular Contractions and Other Mechanical Cardiac Stimuli," *Journal of Physiology* 404: 649-667, 1988.
Schwartz et al., "Autonomic Mechanisms and Sudden Death—New Insights From Analysis of Baroreceptor Reflexes in Conscious Dogs With and Without a Myocardial Infarction," *Circulation* 78(4): 969-979, Oct. 1988.
Hobbs et al., "Cardiac and Abdominal Vagal Afferent Inhibition of Primate $T_9$—$S_1$ Spinothalamic Cells," *The American Physiological Society* 257: R889-R895, 1989.
Butler et al., "Cardiac Responses to Electrical Stimulation of Discrete Loci in Canine Atrial and Ventricular Ganglionated Plexi," *The American Physiological Society* 259: H1365-H1373, 1990.
Hull et al., "Heart Rate Variability Before and After Myocardial Infarction in Conscious Dogs At High and Low Risk of Sudden Death," *The American College of Cardiology* 16(4): 978-985, Oct. 1990.
Armour, "Intrinsic Cardiac Neurons," *Journal of Cardiovascular Electrophysiology* 2(4): 331-341, Aug. 1991.
Chandler et al., "Effects of Vagal Afferent Stimulation on Cervical Spinothalamic Tract Neurons in Monkeys," *Pain* 44: 81-87, 1991.
Linderoth et al., "Effects of Sympathectomy on Skin and Muscle Microcirculation During Dorsal Column Stimulation: Animal Studies," *Neurosurgery* 29(6): 874-879, 1991.
Vanoli et al., "Vagal Stimulation and Prevention of Sudden Death in Conscious Dogs With a Healed Myocardial Infarction," *Circulation Research* 68(5): 1471-1481, May 1991.
Cardinal et al., "Distinct Activation Patterns of Idioventricular Rhythms and Sympathetically-Induced Ventricular Tachycardias in Dogs With Atrioventricular Block," *PACE* 15: 1300-1316, Sep. 1992.
Fu et al., "Vagal Afferent Fibers Excite Upper Cervical Neurons and Inhibit Activity of Lumbar Spinal Cord Neurons in the Rat," *Pain* 51: 91-100, 1992.
Hobbs et al., "Evidence That $C_1$ and $C_2$ Propriospinal Neurons Meditate the Inhibitory Effects of Viscerosomatic Spinal Afferent Input on Primate Spinothalamic Tract Neurons," *Journal of Neurophysiology* 67(4): 852-860, Apr. 1992.
Hobbs et al., "Segmental Organization of Visceral and Somatic Input Onto $C_3$—$T_6$ Spinothalamic Tract Cells of the Monkey," *Journal of Neurophysiology* 68(5): 1575-1588, Nov. 1992.
Chandler et al., "A Mechanism of Cardiac Pain Suppression by Spinal Cord Stimulation: Implications for Patients With Angina Pectoris," *European Heart Journal* 14: 96-105, 1993.
Huang et al., "Effects of Transient Coronary Artery Occlusion on Canine Intrinsic Cardiac Neuronal Activity," *Integrative Physiological and Behavioral Science* 28(1): 5-21, Jan.-Mar. 1993.
Adamson et al., "Unexpected Interaction Between β-Adrenergic Blockade and Heart Rate Variability Before and After Myocardial Infarction—A Longitudinal Study in Dogs At High and Low Risk for Sudden Death," *Circulation* 90(2): 976-982, Aug. 1994.
Ardell, "Structure and Function of Mammalian Intrinsic Cardiac Neurons," *Neurocardiology*: 95-114, 1994.
Armour, "Peripheral Autonomic Neuronal Interactions in Cardiac Regulation," *Neurocardiology*: 219-244, 1994.
Foreman, "Spinal Cord Neuronal Regulation of the Cardiovascular System," *Neurocardiology*: 245-276, 1994.
Hull et al., "Exercise Training Confers Anticipatory Protection From Sudden Death During Acute Myocardial Ischemia," *Circulation* 89(2): 548-552, Feb. 1994.
Linderoth et al., "Sympathetic Mediation of Peripheral Vasodilation Induced by Spinal Cord Stimulation: Animal Studies of the Role of Cholinergic and Adrenergic Receptor Subtypes," *Neurosurgery* 35(4): 711-719, Oct. 1994.

(56) References Cited

OTHER PUBLICATIONS

Yuan et al., "Gross and Microscopic Anatomy of the Canine Intrinsic Cardiac Nervous System," *The Anatomical Record* 239: 75-87, 1994.
Armour, "Intrinsic Cardiac Neurons Involved in Cardiac Regulation Possess alpha$_1$, alpha$_2$, beta$_1$ and beta$_2$—Adrenoreceptors," *Can. J. Cardiol.* 13(3): 277-284, Mar. 1997.
Cardinal et al., "Reduced Capacity of Cardiac Efferent Sympathetic Neurons to Release Noradrenaline and Modify Cardiac Function in Tachycardia-Induced Canine Heart Failure," *Can. J. Physiol. Pharmacol.* 74: 1070-1078, 1996.
Chandler et al., "Vagal, Sympathetic and Somatic Sensory Inputs to Upper Cervical ($C_1$-$C_3$) Spinothalamic Tract Neurons in Monkeys," *Journal of Neurophysiology* 76(4): 2555-2567, 1996.
Zhang et al., "Thoracic Visceral Inputs Use Upper Cervical Segments to Inhibit Lumbar Spinal Neurons in Rats" *Brain Research* 709: 337-342, 1996.
Armour et al., "Gross and Microscopic Anatomy of the Human Intrinsic Cardiac Nervous System," *The Anatomical Record* 247: 289-298, 1997.
Croom et al., "Cutaneous Vasodilation During Dorsal Column Stimulation Is Mediated By Dorsal Roots and CGRP," *Am. J. Physiol.* 272 (*Heart Circ. Physiol.* 41): H950-H957, 1997.
Hautvast et al., "Spinal Cord Stimulation in Chronic Intractable Angina Pectoris: A Randomized, Controlled Efficacy Study," *American Heart Journal*, 136(6): 1114-1120, 1998.
Barron et al., "Spinal Integration of Antidromic Mediated Cutaneous Vasodilation During Dorsal Spinal Cord Stimulation in the Rat," *Neuroscience Letters* 260: 173-176, 1999.
Foreman, "Mechanisms of Cardiac Pain," *Annu. Rev. Physiol.* 61: 143-167, 1999.
Linderoth et al., "Physiology of Spinal Cord Stimulation: Review and Update," *Neuromodulation* 2(3):150-164, 1999.
Qin et al., "Chemical Activation of Cervical Cell Bodies: Effects on Responses to Colorectal Distension in Lumbosacral Spinal Cord of Rats," *J Neurophysiol* 82: 3423-3433, 1999.
Chandler et al., "Intrapericardiac Injections of Algogenic Chemicals Excite Primate $C_1$—$C_2$ Spinothalamic Tract Neurons," *Am J. Physiol. Regulatory Integrative Comp. Physiol.* 279: R560-568, 2000.
Foreman et al., "Modulation of Intrinsic Cardiac Neurons by Spinal Cord Stimulation: Implications for Its Therapeutic Use in Angina Pectoris," *Cardiovascular Research* 47: 367-375, 2000.
Hopkins et al., "Pathology of Intrinsic Cardiac Neurons From Ischemic Human Hearts," *The Anatomical Record* 259: 424-436, 2000.
Kember et al., "Aperiodic Stochastic Resonance in a Hysteretic Population of Cardiac Neurons," *The American Physical Society* Physical Review E 61(2): 1816-1824, Feb. 2000.
Meyerson et al., "Spinal Cord Stimulation," *Bonica's Management of Pain*: 1857-1876, 2001.
Ardell, "Neurohumoral Control of Cardiac Function," *Heart Physiology and Pathophysiology, Fourth Edition*: 45-49, 2001.
Farrell et al., "Angiotensin II Modulates Catecholamine Release Into Interstitial Fluid of Canine Myocardium In Vivo," *Am. J. Physiol. Heart Cir. Physiol.* 281: H813-H822, 2001.

Kingma, Jr. et al., "Neuromodulation Therapy Does Not Influence Blood Flow Distribution or Left-Ventricular Dynamics During Acute Myocardial Ischemia," *Autonomic Neuroscience: Basic & Clinical* 91: 47-54, 2001.
Tanaka et al., "Low Intensity Spinal Cord Stimulation May Induce Cutaneous Vasodilation Via CGRP Release," *Brain Research* 896: 183-187, 2001.
Qin et al., "Responses and Afferent Pathways of Superficial and Deeper $C_1$—$C_2$ Spinal Cells to Intrapericardial Algogenic Chemicals in Rats," *J. Neurophysiol* 85:1522-1532, 2001.
Armour et al., "Long-Term Modulation of the Intrinsic Cardiac Nervous System by Spinal Cord Neurons in Normal and Ischaemic Hearts," *Autonomic Neuroscience: Basic & Clinical* 95: 71-79, 2002.
Chandler et al., "Spinal Inhibitory Effects of Cardiopulmonary Afferent Inputs in Monkeys: Neuronal Processing in High Cervical Segments," *J. Neurophysiol* 87: 1290-1302, 2002.
Cardinal et al., "Spinal Cord Activation Differentially Modulates Ischaemic Electrical Responses to Different Stressors in Canine Ventricles," *Autonomic Neuroscience: Basic & Clinical* 111: 37-47, 2004.
Ardell, "Intrathoracic Neuronal Regulation of Cardiac Function," *Basic and Clinical Neurocardiology* 118-152, 2004.
Siddons et al., "Special Considerations: Pacing in Acute Myocardial Infarction," *Cardiac Pacemakers* Chapter 11: 200-217, 1967.
Bluemel et al., "Parasympathetic Postganglionic Pathways to the Sinoatrial Node," *American Journal of Physiology* 259 (*Heart Circ. Physiol.* 28): H1504-H1510, 1990.
Cooper et al, "Neural Effects on Sinus Rate and Atrioventricular Conduction Produced by Electrical Stimulation from a Transvenous Electrode Catheter in the Canine Right Pulmonary Artery," *Circulation Research* 46(1): 48-57, Jan. 1980.
Randall et al, "Functional Anatomy of the Cardiac Efferent Innervation," *Neurocardiology* Chapter 1: 3-24, 1988.
International Preliminary Report on Patentability from corresponding international application No. PCT/US2009/062805, mailed May 12, 2011, 7 pp.
Final Office Action from U.S. Appl. No. 12/362,838, dated Aug. 1, 2013, 20 pp.
Response to Office Action dated Aug. 1, 2013, from U.S. Appl. No. 12/362,838, filed Oct. 1, 2013, 8 pp.
Notice of Allowance from U.S. Appl. No. 12/362,838 dated Feb. 28, 2014, 11 pp.
Response to Office Action dated Apr. 16, 2012, from U.S. Appl. No. 12/362,838, filed Aug. 15, 2012, 19 pp.
Notice of Appeal and Pre-Appeal Brief Request for Review for U.S. Appl. No. 12/362,838, filed Dec. 5, 2013, 7 pages.
Office Action from U.S. Appl. No. 12/362,838, dated Apr. 16, 2012, 20 pp.
Office Action from U.S. Appl. No. 12/362,842, dated Mar. 5, 2012, 15 pp.
Response to Office Action mailed Mar. 5, 2012, from U.S. Appl. No. 13/362,842, filed Jun. 5, 2012, 23 pp.
Office Action from U.S. Appl. No. 12/362,838, dated Dec. 21, 2011, 8 pp.
Response to Office Action mailed Dec. 21, 2011, from U.S. Appl. No. 12/362,838, filed Jan. 23, 2012, 2 pp.
Final Office Action from U.S. Appl. No. 12/362,842, dated May 8, 2013, 12 pp.
Amendment in Response to Office Action mailed May 8, 2013, from U.S. Appl. No. 12/362,842, filed Jul. 8, 2013, 20 pp.

* cited by examiner

IMPLANTABLE MEDICAL DEVICE CROSSTALK EVALUATION AND MITIGATION

This application claims the benefit of U.S. Provisional Application No. 61/110,312, entitled, "IMPLANTABLE MEDICAL DEVICE CROSSTALK EVALUATION AND MITIGATION," and filed on Oct. 31, 2008, the entire content of which is incorporated herein by reference.

TECHNICAL FIELD

The disclosure relates to therapy systems, and, more particularly, therapy systems including at least two therapy delivery modules.

BACKGROUND

A wide variety of implantable medical devices that deliver a therapy or monitor a physiologic condition of a patient have been clinically implanted or proposed for clinical implantation in patients. Some implantable medical devices may employ one or more elongated electrical leads and/or sensors. Such implantable medical devices may deliver therapy or monitor the heart, muscle, nerve, brain, stomach or other organs. In some cases, implantable medical devices deliver electrical stimulation therapy and/or monitor physiological signals via one or more electrodes or sensor elements, at least some of which may be included as part of one or more elongated implantable medical leads. Implantable medical leads may be configured to allow electrodes or sensors to be positioned at desired locations for delivery of stimulation or sensing electrical depolarizations. For example, electrodes or sensors may be located at a distal portion of the lead. A proximal portion of the lead may be coupled to an implantable medical device housing, which may contain electronic circuitry such as stimulation generation and/or sensing circuitry. In some cases, electrodes or sensors may be positioned on an IMD housing as an alternative or in addition to electrodes or sensors deployed on one or more leads.

For example, implantable cardiac devices, such as cardiac pacemakers or implantable cardioverter defibrillators, provide therapeutic electrical stimulation to the heart by delivering electrical therapy signals such as pulses or shocks for pacing, cardioversion or defibrillation pulses via electrodes of one or more implantable leads. In some cases, an implantable cardiac device may sense intrinsic depolarizations of the heart, and control the delivery of therapeutic stimulation to the heart based on the sensing. When an abnormal rhythm of the heart is detected, such as bradycardia, tachycardia or fibrillation, an appropriate electrical therapy (e.g., in the form of pulses) may be delivered to restore the normal rhythm. For example, in some cases, an implantable medical device may deliver pacing, cardioversion or defibrillation signals to the heart of the patient upon detecting ventricular tachycardia, and deliver cardioversion or defibrillation therapy to a patient's heart upon detecting ventricular fibrillation. Some medical device systems that include a neurostimulator in addition to implantable cardiac device have also been proposed.

SUMMARY

In general, the disclosure is directed toward therapy systems that deliver electrical stimulation therapy to a tissue site within a patient and cardiac rhythm management therapy to a heart of a patient. The tissue site for the electrical stimulation therapy may be, for example, a nonmyocardial tissue site or nonvascular cardiac tissue site (e.g., a cardiac fat pad). In some examples, the therapy system may include a first implantable medical device (IMD) that delivers electrical stimulation to a tissue site within a patient, such as proximate a nerve (e.g., a vagus nerve or a spinal cord) or another nonmyocardial tissue site, and a second implantable medical device (IMD) that delivers cardiac rhythm management therapy, such as at least one of pacing, cardioversion or defibrillation therapy to a heart of the patient. The first IMD may be referred to as an implantable neurostimulator (INS) or an electrical stimulator, and the second IMD may be referred to as an implantable cardiac device (ICD). The INS may deliver electrical stimulation to nonmyocardial tissue sites other than sites adjacent nerves, and the ICD may deliver any combination of pacing, cardioversion, and defibrillation pulses. In other examples, the therapy system may include an implantable medical device that includes a first therapy module that delivers stimulation therapy to a nonmyocardial tissue site within a patient and a second therapy module that delivers at least one of pacing, cardioversion or defibrillation therapy to the heart of the patient, where the first and second therapy modules are disposed in a common housing.

Techniques for minimizing interference between the INS and the ICD or between the different therapy modules of a common medical device are described herein. In some examples, the therapy parameter values that define the electrical stimulation delivered by the INS may be modified in order to reduce the possibility that the ICD senses the electrical stimulation signals delivered by the INS and mischaracterizes the sensed signals as cardiac signals. In other examples, the INS may switch therapy programs that define the electrical stimulation signals generated and delivered by the INS upon the detection of an arrhythmia by the ICD, the INS or another device. In addition to or instead of modifying the operation of the INS, some examples described herein modify one or more sensing parameter values of an ICD order to reduce the possibility that the ICD senses the electrical stimulation signals delivered by the INS and mischaracterizes the sensed signals as cardiac signals.

In addition, the disclosure describes techniques for evaluating the amount of interference (or "crosstalk") between an INS and ICD implanted within a patient. The measured interference may be used to modify operation of the INS or ICD, and, in some cases, may be recorded for later analysis by a clinician.

In one aspect, the disclosure is directed to a method comprising determining whether a therapy module is delivering electrical stimulation to a tissue site within a patient, sensing electrical cardiac signals according to a first sense mode if the therapy module is delivering electrical stimulation to the tissue site, and sensing electrical cardiac signals according to a second sense mode if the therapy module is not delivering electrical stimulation to the tissue site, wherein the first and second sense modes define different sense vectors for sensing the electrical cardiac signals.

In another aspect, the disclosure is directed to a system comprising a therapy module that delivers electrical stimulation to a tissue site within a patient, a sensing module that senses electrical cardiac signals of the patient, and a processor that determines whether the therapy module is delivering electrical stimulation to the tissue site, controls the sensing module to sense electrical cardiac signals according to a first sense mode if the therapy module is delivering electrical stimulation to the tissue site, and controls the sensing module to sense electrical cardiac signals according to a second sense mode site if the therapy module is not delivering electrical stimulation to the tissue site, wherein the first and second sense modes define different sense vectors for sensing the electrical cardiac signals In another aspect, the disclosure is directed to a system comprising means for determining whether a therapy module is delivering electrical stimulation to a tissue site within a patient, means for sensing electrical cardiac signals according to a first sense mode if the therapy module is delivering electrical stimulation to the tissue site, and means for sensing electrical cardiac signals according to a second sense mode if the therapy module is not delivering electrical stimulation to the tissue site. The first and second sense modes define different sense vectors for sensing the electrical cardiac signals In another aspect, the disclosure is directed to a computer-readable medium comprising instructions. The instructions cause a programmable processor to determine whether a therapy module is delivering electrical stimulation to a tissue site within a patient, control a sensing module to sense electrical cardiac signals according to a first sense mode if the therapy module is delivering electrical stimulation to the tissue site, and control the sensing module to sense electrical cardiac signals according to a second sense mode if the therapy module is not delivering electrical stimulation to the tissue site, wherein the first and second sense modes define different sense vectors for sensing the electrical cardiac signals.

In another aspect, the disclosure is directed to a method comprising determining whether a therapy module is delivering electrical stimulation to a tissue site within a patient, monitoring cardiac function of a heart of the patient according to a first sense mode if the therapy module is delivering electrical stimulation to the tissue site, and monitoring cardiac function of the heart of the patient according to a second sense mode if the therapy module is not delivering electrical stimulation to the tissue site. The first and second sense modes monitor at least one different non-electrophysiological parameter of the patient.

In another aspect, the disclosure is directed to a system comprising a therapy module that delivers electrical stimulation to a tissue site within a patient, a sensing module that monitors cardiac function of a heart of the patient, and a processor that determines whether the therapy module is delivering electrical stimulation to the tissue site, controls the sensing module to sense electrical cardiac signals according to a first sense mode if the therapy module is delivering electrical stimulation to the tissue site, and controls the sensing module to sense electrical cardiac signals according to a second sense mode site if the therapy module is not delivering electrical stimulation to the tissue site. The first and second sense modes monitor at least one different non-electrophysiological parameter of the patient In another aspect, the disclosure is directed to a system comprising means for determining whether a therapy module is delivering electrical stimulation to a tissue site within a patient, means for monitoring cardiac function of a heart of the patient according to a first sense mode if the therapy module is delivering electrical stimulation to the tissue site, and means for monitoring cardiac function of the heart of the patient according to a second sense mode if the therapy module is not delivering electrical stimulation to the tissue site. The first and second sense modes monitor at least one different non-electrophysiological parameter of the patient.

In another aspect, the disclosure is directed to a computer-readable medium comprising instructions. The instructions cause a programmable processor to determine whether a therapy module is delivering electrical stimulation to a tissue site within a patient, control a sensing module to monitor cardiac function of a heart of the patient according to a first sense mode if the therapy module is delivering electrical stimulation to the tissue site, and control a sensing module to monitor cardiac function of the heart of the patient according to a second sense mode if the therapy module is not delivering electrical stimulation to the tissue site. The first and second sense modes monitor at least one different non-electrophysiological parameter of the patient.

In another aspect, the disclosure is directed to a method comprising determining whether a therapy module is delivering electrical stimulation to a tissue site within a patient, monitoring cardiac function of a heart of a patient according to a first sense mode if the therapy module is delivering electrical stimulation to the tissue site, detecting a potential arrhythmia of the heart of the patient based on the cardiac function monitored according to the first sense mode, upon detecting the potential arrhythmia, stopping the monitoring of cardiac function according to the first sense mode and monitoring cardiac function of the heart of the patient according to a second sense mode, wherein the first and second sense modes comprise at least one different sensing parameter, and determining whether the potential arrhythmia is detected based on the cardiac function monitored according to the second sense mode.

In another aspect, the disclosure is directed to a system comprising a first therapy module that delivers electrical stimulation to a tissue site within a patient, a second therapy module that delivers at least one of a pacing, cardioversion or defibrillation electrical signal to the heart of the patient, a sensing module that monitors cardiac function of the heart of the patient, and a processor. The processor determines whether the first therapy module is delivering electrical stimulation to the tissue site, controls the sensing module to monitor cardiac function of the heart of the patient according to a first sense mode if the first therapy module is delivering electrical stimulation to the tissue site, detects a potential arrhythmia of the heart of the patient based on the cardiac function monitored according to the first sense mode, upon detecting the potential arrhythmia, controls the sensing module to stop monitoring cardiac function according to the first sense mode and monitor cardiac function of the heart of the patient according to a second sense mode, wherein the first and second sense modes comprise at least one different sensing parameter value, and determines whether the potential arrhythmia is detected based on the cardiac function monitored according to the second sense mode.

In another aspect, the disclosure is directed to a system comprising means for determining whether a first therapy module is delivering electrical stimulation to a tissue site within a patient, means for monitoring cardiac function of a heart of a patient according to a first sense mode if the therapy module is delivering electrical stimulation to the tissue site, means for detecting a potential arrhythmia of the heart of the patient based on the cardiac function monitored according to the first sense mode, means for stopping the monitoring of cardiac according to a first sense mode and monitoring cardiac function of the heart of the patient according to a second sense mode upon detecting the potential arrhythmia, wherein the first and second sense modes comprise at least one different sensing parameter value, means for determining whether the potential arrhythmia is detected based on the cardiac function monitored according to the second sense mode, and means for delivering at least one of a pacing, cardioversion or defibrillation electrical signal to the heart of the patient with a second therapy module if the potential arrhythmia is detected based on the cardiac function monitored according to the second sense mode.

In another aspect, the disclosure is directed to a computer-readable medium comprising instructions. The instructions cause a programmable processor to determine whether a first therapy module is delivering electrical stimulation to a tissue site within a patient, control a sensing module to monitor cardiac function of a heart of a patient according to a first sense mode if the therapy module is delivering electrical stimulation to the tissue site, detect a potential arrhythmia of the heart of the patient based on the cardiac function monitored according to the first sense mode, upon detecting the potential arrhythmia, control the sensing module to stop the monitoring of cardiac according to a first sense mode and monitor cardiac function of the heart of the patient according to a second sense mode, wherein the first and second sense modes comprise at least one different sensing parameter value, determine whether the potential arrhythmia is detected based on the cardiac function monitored according to the second sense mode, and control a second therapy module to deliver at least one of a pacing, cardioversion or defibrillation electrical signal to the heart of the patient if the potential arrhythmia is detected based on the cardiac function monitored according to the second sense mode.

In another aspect, the disclosure is directed to a computer-readable medium comprising instructions. The instructions cause a programmable processor to perform any part of the techniques described herein.

The details of one or more examples of the disclosure are set forth in the accompanying drawings and the description below. Other features, objects, and advantages of the disclosure will be apparent from the description and drawings, and from the example statements provided below.

DETAILED DESCRIPTION

Figure 1:
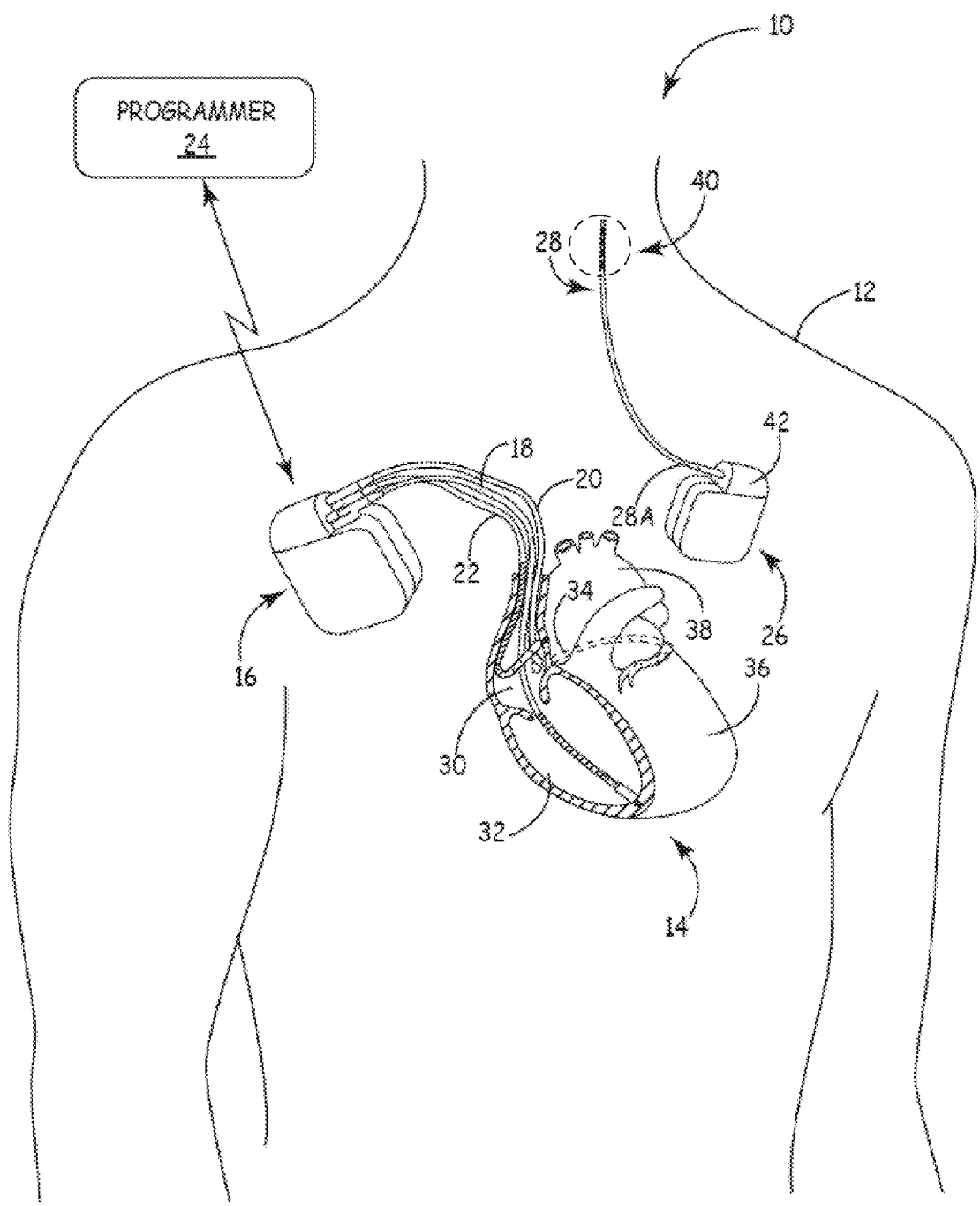
FIG. 1 is a conceptual diagram illustrating an example therapy system including an implantable cardiac device (ICD) and an implantable neurostimulator (INS).

FIG. 1 is a conceptual diagram illustrating an example therapy system 10 that provides therapy to patient 12. Therapy system 10 includes implantable cardiac device (ICD) 16, which is connected to leads 18, 20, and 22, and programmer 24. ICD 16 may be, for example, a device that provides cardiac rhythm management therapy to heart 14, and may include, for example, an implantable pacemaker, cardioverter, and/or defibrillator that provide therapy to heart 14 of patient 12 via electrodes coupled to one or more of leads 18, 20, and 22. In some examples, ICD 16 may deliver pacing pulses, but not cardioversion or defibrillation pulses, while in other examples, ICD 16 may deliver cardioversion or defibrillation pulses, but not pacing pulses. In addition, in further examples, ICD 16 may deliver pacing, cardioversion, and defibrillation pulses.

In some examples, ICD 16 may not deliver cardiac rhythm management therapy to heart 14, but may instead only sense electrical cardiac signals of heart 14 and/or other physiological parameters of patient 12 (e.g., blood oxygen saturation, blood pressure, temperature, heart rate, respiratory rate, and the like), and store the electrical cardiac signals and/or other physiological parameters of patient 12 for later analysis by a clinician. In such examples, ICD 16 may be referred to as a patient monitoring device. Examples of patient monitoring devices include, but are not limited to, the Reveal Plus Insertable Loop Recorder, which is available from Medtronic, Inc. of Minneapolis, Minn. For ease of description, ICD 16 will be referred to herein as a cardiac rhythm management therapy delivery device.

Therapy system 10 further comprises implantable electrical stimulator 26, which is coupled to lead 28. Electrical stimulator 26 may also be referred to as an implantable neurostimulator (INS) 26. INS 26 may be any suitable implantable medical device (IMD) that includes a signal generator that generates electrical stimulation signals that may be delivered to a tissue site of patient 12, e.g., tissue proximate a vagus nerve, a spinal cord or heart 14 of patient 12.

In some examples, the tissue site may include at least one of a nonmyocardial tissue site or a nonvascular cardiac tissue site. A nonmyocardial tissue site may include a tissue site that does not include cardiac muscle (e.g., the myocardium). For example, a nonmyocardial tissue site may be proximate a muscle other than cardiac muscle, an organ other than the heart, or neural tissue. A tissue site proximate a nerve may be a neural tissue site to which delivery of electrical stimulation may activate the nerve. In some examples, a tissue site proximate a nerve may be in a range of about zero centimeters to about ten centimeters from the nerve, although other distance ranges are contemplated and may depend upon the nerve. The nonmyocardial tissue site may include extravascular tissue sites or intravascular tissue sites. A nonvascular cardiac tissue site may include, for example, a cardiac fat pad.

In some examples, delivery of electrical stimulation to a tissue site proximate a nerve or a nonmyocardial tissue site that may not be proximate a nerve may help modulate an autonomic nervous system of patient 12. In some examples, INS 26 may deliver electrical stimulation therapy to a nerve of patient 12 via a lead implanted within vasculature (e.g., a blood vessel) of patient 12. In some examples, INS 26 may deliver electrical stimulation that is delivered to peripheral nerves that innervate heart 14, or fat pads on heart 14 that may contain nerve bundles. The fat pads may be referred to as a nonvascular cardiac tissue site.

In the example shown in FIG. 1, electrodes of lead 28 are positioned outside the vasculature of patient 12 and positioned to deliver electrical stimulation to a vagus nerve (not shown) of patient 12. Stimulation may be delivered to extravascular tissue sites, for example, when lead 28 is not implanted within vasculature, such as within a vein, artery or heart 14. In other examples, stimulation may be delivered to a nonmyocardial tissue site via electrodes of an intravascular lead that is implanted within vasculature.

In the example shown in FIG. 1, the components of ICD 16 and INS 26 are enclosed in separate housings, such that ICD 16 and INS 26 are physically separate devices. In other examples, as described with respect to FIG. 31, the functionality of ICD 16 and INS 26 may be performed by an IMD that includes both a cardiac therapy module that generates and delivers at least one of pacing, cardioversion or defibrillation therapy to patient 12 and an electrical stimulation therapy module that generates and delivers electrical stimulation to a target tissue site within patient 12, which may be proximate a nerve or may be an extravascular tissue site that is not proximate a nerve.

Leads 18, 20, 22 extend into the heart 14 of patient 12 to sense electrical activity of heart 14 and/or deliver electrical stimulation to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. As described in further detail with reference to FIG. 5, in other examples, an ICD may deliver stimulation therapy to heart 14 by delivering stimulation to a nonmyocardial tissue site in addition to or instead of delivering stimulation via electrodes of intravascular leads 18, 20, 22.

ICD 16 may sense electrical signals attendant to the depolarization and repolarization of heart 14 via electrodes (not shown in FIG. 1) coupled to at least one of the leads 18, 20, 22. In some examples, ICD 16 provides pacing pulses to heart 14 based on the electrical signals sensed within heart 14. These electrical signals sensed within heart 14 may also be referred to as cardiac signals or electrical cardiac signals. The configurations of electrodes used by ICD 16 for sensing and pacing may be unipolar or bipolar. ICD 16 may also provide defibrillation therapy and/or cardioversion therapy via electrodes located on at least one of the leads 18, 20, 22. ICD 16 may detect arrhythmia of heart 14, such as fibrillation of ventricles 32 and 36, and deliver defibrillation therapy to heart 14 in the form of electrical pulses. In some examples, ICD 16 may be programmed to deliver a progression of therapies, e.g., pulses with increasing energy levels, until a fibrillation of heart 14 is stopped. ICD 16 may detect fibrillation employing one or more fibrillation detection techniques known in the art.

In the example of FIG. 1, INS 26 has been implanted in patient 12 proximate to an nonmyocardial target stimulation site 40, such as a tissue site proximate a vagus nerve. For example, INS 26 may be subcutaneously or submuscularly implanted in the body of a patient 12 (e.g., in a chest cavity, lower back, lower abdomen, or buttocks of patient 12). INS 26 provides a programmable stimulation signal (e.g., in the form of electrical pulses or a continuous signal) that is delivered to target stimulation site 40 by implantable medical lead 28, and more particularly, via one or more stimulation electrodes carried by lead 28. Proximal end 28A of lead 28 may be both electrically and mechanically coupled to connector 42 of INS 26 either directly or indirectly (e.g., via a lead extension). In particular, conductors disposed in the lead body may electrically connect stimulation electrodes (and sense electrodes, if present) of lead 28 to INS 26.

INS 26 may also be referred to as a signal generator. In some examples, lead 28 may also carry one or more sense electrodes to permit INS 26 to sense electrical signals from target stimulation site 40. Furthermore, in some examples, INS 26 may be coupled to two or more leads, e.g., for bilateral or multi-lateral stimulation.

Delivery of electrical stimulation by INS 26 to one or more target tissues sites proximate to a nerve, nerve site, cardiac fat pad, or an extravascular target tissue site that is not proximate a nerve may provide cardioprotective benefits to patient 12. An extravascular tissue site may be outside of heart 14 and outside of arteries, veins, or other vasculature of patient 12. For example, delivery of electrical stimulation to a tissue site proximate a nerve of patient 12 may help treat heart failure. In addition, delivery of electrical stimulation to a tissue site proximate a nerve of patient 12 to modulate an autonomic nervous system of patient 12 may help reduce or eliminate cardiovascular conditions such as bradycardia, tachycardia, unhealthy cardiac contractions, ischemia, inefficient heart pumping, inefficient collateral circulation of heart 14 or cardiac muscle trauma. Delivery of electrical stimulation by INS 26 may compliment antitachycardia therapy (e.g., antitachycardia pacing, cardioversion or defibrillation) by ICD 16 or provide back-up therapy to the cardiac rhythm therapy provided by ICD 16. For example, if ICD 16 is unavailable to provide therapy to patient 12, e.g., due to a low power level, INS 26 may deliver therapy to patient 12 to help terminate or prevent a cardiac event (e.g., tachycardia).

In some examples, INS 26 delivers electrical stimulation to peripheral nerves that innervate heart 14, or fat pads on heart 14 that may contain nerve bundles. In the example shown in FIG. 1, electrodes of lead 28 are positioned to deliver electrical stimulation to a vagus nerve (not shown) of patient 12. Although INS 26 is referred to throughout the remainder of the disclosure as a "neurostimulator" and as delivering neurostimulation pulses, in other examples, INS 26 may deliver electrical stimulation to any suitable nonmyocardial tissue site within patient 12, which may or may not be proximate a nerve.

In the example shown in FIG. 1, INS 26 provides electrical stimulation therapy of a parasympathetic nerve, such as a vagus nerve, of patient 12. Stimulation of a parasympathetic nerve of patient 12 may help slow intrinsic rhythms of heart 14, which may facilitate antiarrhythmia therapy (e.g., antitachycardia pacing, cardioversion or defibrillation) delivered by ICD 16. In this way, neurostimulation by INS 26 may help control a heart rate of patient 12 or otherwise control cardiac function.

In other examples, electrodes of lead 28 may be positioned to deliver electrical stimulation to any other suitable nerve, organ, muscle or muscle group in patient 12, which may be selected based on, for example, a therapy regimen selected for a particular patient. In some examples, INS 26 may deliver electrical stimulation to other parasympathetic nerves, baroreceptors, the carotid sinus or a cardiac branch of the vagal trunk of patient 12 in order to compliment the delivery of therapy by ICD 16.

The electrical stimulation signals generated and delivered by INS 26 may be referred to as neurostimulation signals. However, in some examples, INS 26 may deliver electrical stimulation to a target tissue site 40 that is not proximate to a nerve. For example, in some examples, INS 26 may deliver electrical stimulation to a peripheral nerve field site, whereby electrodes 124 (FIG. 7) are implanted in a region where patient 12 experiences pain. The pain may be related to stimulation delivered by ICD 16 or a patient condition, such as angina or chronic back pain. As other examples, INS 26 may deliver electrical stimulation to a muscle, muscle group, organ, or other sites that may not be proximate a nerve. Thus, while "neurostimulation" signals are primarily referred to herein, the disclosure is also applicable to examples in which INS 26 delivers electrical stimulation to other tissue sites.

Figure 2:
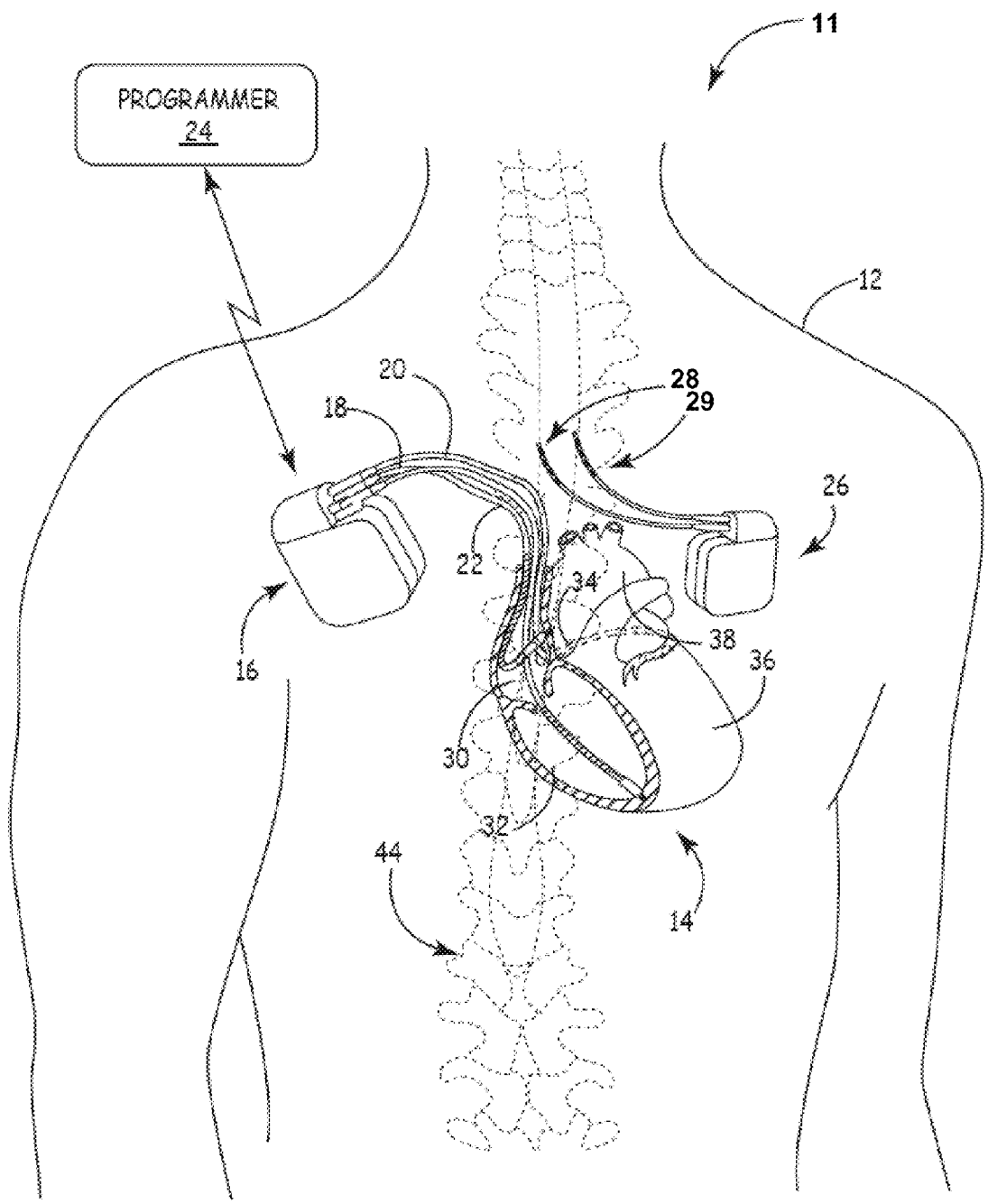
FIG. 2 is a conceptual diagram illustrating another example therapy system that includes the ICD and the INS.

As another example, as shown in FIG. 2, INS 26 may be positioned to deliver electrical stimulation to spinal cord 44 of patient 12. Stimulation of spinal cord 44 or nerves branching therefrom by INS 26 may help prevent or mitigate occurrences of tachyarrhythmias and may facilitate reduction of the level of aggressiveness of the cardiac therapy, such as pacing, cardioversion or defibrillation therapy, delivered by ICD 16. In this way, ICD 16 and INS 26 may operate in conjunction with each other to help prevent arrhythmias of heart 14 of patient 12, as well as to terminate detected arrhythmias.

In some examples, depending upon the neurostimulation target, the delivery of electrical stimulation by INS 26 may also mitigate perceptible discomfort generated from the delivery of pacing pulses or cardioversion/defibrillation shocks by ICD 16. For example, if INS 26 delivers electrical stimulation to spinal cord 44 of patient 12, the neurostimulation may produce paresthesia, which may help reduce the discomfort felt by patient 12 from the delivery of stimulation by ICD 16.

In the example shown in FIG. 2, in therapy system 11, INS 26 is coupled to two leads 28, 29 to provide bilateral stimulation of spinal cord 44. Leads 28, 29 may be introduced into spinal cord 44 in the thoracic region, as shown in FIG. 2. In other examples, leads 28, 29 may be introduced into spinal cord 44 in the cervical or lumbar regions. Electrodes of leads 28, 29 may be positioned within an intrathecal space or epidural space of spinal cord 44, or, in some examples, adjacent nerves that branch off of spinal cord 44. In some examples, leads 28, 29 are implanted within patient 12 and positioned such that electrodes of leads 28, 29 deliver electrical stimulation to locations proximate to the T1 to T6 thoracic vertebrae of the patient's vertebral column. For example, electrodes of at least one of the leads 28, 29 may span the T3 to T6 thoracic vertebrae or deliver electrical stimulation to a tissue site proximate at least one of the T3 to T6 thoracic vertebrae. In other examples, leads 28, 29 may be implanted to deliver electrical stimulation to other regions proximate or within spinal cord 44, such as over or near other vertebrae.

In some examples, INS 26 delivers therapy to patient 12 with a voltage amplitude of about 0.2 volts to about 12 volts, a pulse duration of about 40 microseconds (µs) to about 600 µs, such as about 50 µs to about 500 µs), and a pulse rate of about 1 Hz to about 1 kilohertz (e.g., about 10 Hz to about 100 Hz). However, other stimulation parameter values for INS 26 are contemplated. INS 26 may deliver electrical stimulation to patient 12 substantially continuously or periodically. In some examples, INS 26 may deliver electrical stimulation to patient 12 based on the timing of electrical stimulation by ICD 16, such as prior to the delivery of electrical stimulation (e.g., antitachycardia pacing or a defibrillation or cardioversion pulse) by ICD 16, during the delivery of electrical stimulation by ICD 16, subsequent to the delivery of electrical stimulation by ICD 16 or any combination of the aforementioned times. In addition, in some examples, INS 26 may deliver electrical stimulation to patient 12 based on a sensed event or, such as atrial or ventricular depolarization, or based on a sensed physiological condition. The event or physiological condition may be sensed by ICD 16, INS 26 or another sensing device.

ICD 16 and INS 26 may communicate with each other in order for INS 26 to time the delivery of electrical stimulation based on the delivery of stimulation pulses by ICD 16, where the stimulation pulses may be pacing pulses or cardioversion/defibrillation pulses. ICD 16 and INS 26 may communicate directly or indirectly (e.g., via an intermediate device, such as programmer 24) using any suitable communication technique. Examples communication techniques that may be implemented to facilitate communication between ICD 16 and INS 26 may include, for example, radiofrequency (RF) communication techniques, optical communication techniques, ultrasonic communication techniques, and the like. Communication between ICD 16 and INS 26 may be periodic, e.g., according to a regular schedule, or on an as-needed basis, e.g., when INS 26 delivers electrical stimulation to patient 12 or when excessive crosstalk is detected by ICD 16, programmer 24, INS 26 or another device. Example techniques for evaluating the crosstalk between ICD 16 and INS 26 are described below with reference to FIGS. 20, 21, and 23-30.

In other examples, INS 26 may deliver electrical stimulation to patient 12 independently of the cardiac rhythm therapy delivered by ICD 16. For example, INS 26 may be programmed to deliver electrical stimulation to patient 12 according to a schedule that is determined independently of the actual delivery of stimulation pulses by ICD 16. The schedule may be determined, for example, by a clinician based on a trial stimulation period in which multiple therapy schedules for INS 26 are tested on patient 12. The schedule may dictate when INS 26 actively delivers electrical stimulation to patient 12 and when INS 26 does not actively deliver electrical stimulation to patient 12. For example, the schedule may include a mandatory sleep period for INS 26 during which INS 26 reverts to a relatively low-power sleep mode. During the sleep mode, INS 26 may not deliver therapy to patient 12 or may deliver a relatively minimal amount of electrical stimulation therapy to patient 12. The sleep period may be, for example, when patient 12 is sleeping or otherwise has a relatively low activity level. The sleep period may be useful for conserving the power source of INS 26.

In some examples, a stimulation schedule for INS 26 may comprise a first period of time in which stimulation is delivered to patient 12 substantially continuously or for brief durations (e.g., 0.1 seconds to about five seconds) and a second period of time during which no stimulation is delivered to patient 12. The first and second periods of time may be on the order of seconds, minutes, hours or days.

Delivering stimulation to patient 12 via INS 26 periodically rather than substantially continuously may help elongate the useful life of therapy delivery by INS 26 or therapy delivery by INS 26 according to a particular set of stimulation parameter values. Patient 12 may adapt to stimulation provided by INS 26 over time. That is, a certain level of electrical stimulation provided to a target tissue site by INS 26 may be less effective over time. This phenomenon may be referred to as "adaptation." As a result, any beneficial effects to patient 12 from the stimulation delivery by INS 26 may decrease over time. While the electrical stimulation levels (e.g., amplitude or frequency of the electrical stimulation signal) may be increased to overcome the adaptation, the increase in stimulation levels may consume more power, and may eventually reach undesirable or harmful levels of stimulation. Adaptation to therapy delivery by INS 26 may be reduced by decreasing the total amount of stimulation delivered to patient 12 by INS 26, such as by delivering stimulation to patient 12 when needed (e.g., upon the detection of an arrhythmia) or according to a schedule in which therapy is turned off or minimized for a period of time. Moreover, noncontinuous therapy delivery to patient 12 by INS 26 may be more energy efficient.

In addition, delivering stimulation to patient 12 via INS 26 periodically rather than substantially continuously may help elongate the useful life of therapy delivery by INS 26 by extending the life of the power source of INS 26. Increasing the amount of time between INS 26 recharge or power source replacement may be useful because the inconvenience to patient 12 from the recharge or battery placement may be minimized.

The values for the therapy parameters that define the electrical stimulation delivered by INS 26 may be organized into a group of parameter values referred to as a "therapy program" or "therapy parameter set." "Therapy program" and "therapy parameter set" are used interchangeably herein. In the case of electrical stimulation, the therapy parameters may include an electrode combination, an amplitude, which may be a current or voltage amplitude, a slew rate, and a frequency, and, if INS 26 delivers electrical pulses, a pulse width, and a pulse rate for stimulation signals to be delivered to the patient. An electrode combination may include a selected subset of one or more electrodes of lead 28, as well as lead 29 if INS 26 is connected to two leads 28, 29. The electrode combination may also refer to the polarities of the electrodes in the selected subset. By selecting particular electrode combinations, a clinician may target particular anatomic structures within patient 12. In some cases, INS 26 may deliver stimulation to patient 12 according to a program group that includes more than one therapy program. The stimulation signals according to the different therapy programs in a therapy group may be delivered on a time-interleaved basis or substantially simultaneously.

The electrical stimulation parameters may also include a duty cycle of stimulation signals, a timing of the delivery of the electrical stimulation relative to a cardiac cycle of heart 14 of patient 12, and a waveform shape or a signal envelope of the electrical stimulation signal. A signal envelope may generally trace the outline of the amplitude of a stimulation signal for a given period of time. The signal envelope may characterize the amplitude ramp-up and ramp-down times, which may be gradual or abrupt.

If INS 26 delivers therapy to patient 12 according to two or more electrode combinations, e.g., according to a therapy program group including two or more therapy programs defining at least two different electrode combinations, time-interleaving the stimulation signals defined each of the therapy programs may result in stimulation that is sequentially applied to different electrodes. Varying the tissue site at which INS 26 delivers stimulation by delivering therapy according to different electrode combinations may also help reduce the patient's adaptation to therapy delivery by INS 26. For example, sequentially delivering stimulation via different electrode combinations may help reduce the amount of time that a particular tissue site is stimulated.

In some examples, the therapy parameter values with which INS 26 generates electrical stimulation therapy for patient 12 may be selected based on an effect the stimulation has on heart 14. For example, INS 26 may deliver stimulation to a nonmyocardial tissue site within patient 12 according to a first therapy program defining values for a set of therapy parameters, and ICD 16 may assess the response of heart 14 or other portions of the cardiovascular system to the delivery of stimulation by INS 26. For example, ICD 16 may sense cardiac activity via electrodes of leads 18, 20, 22. Example responses of heart 14 include, for example, proarrhythmic effects. The therapy program may be analyzed based on a positive or negative response of heart 14 or other portions of the cardiovascular system to the delivery of stimulation by INS 26. The therapy program may be selected for storage in INS 26, e.g., for chronic therapy delivery if the test stimulation via the therapy program evoked a positive response by heart 14 and/or other portions of the patient's cardiovascular system.

Stimulation delivered by INS 26 may have a carryover effect on patient 12. A carryover effect generally refers to a physiological effect generated in response to the delivery of an electrical stimulation signal, where the effect persists after termination of the stimulation signal. The carryover effect may be at least partially attributable to, for example, neurochemicals that are by the patient's body that have an ongoing effect on the patient's physiological condition after the termination of a stimulation signal. Neurochemicals may provide the benefits of electrical stimulation therapy that continue for a period of time, such as seconds, minutes, hours or days, after the delivery of a stimulation signal by INS 26. If INS 26 delivers electrical stimulation to one or more nerves of patient 12, the carryover effect may also be at least partially attributable to nerves maintaining a self-stimulating mode following the delivery of a stimulation signal by INS 26. Nerves may continue to fire after the termination of a stimulation signal, which may also provide on-going benefits of INS 26 to patient 12 that continue for a period of time, such as seconds, minutes, hours or days, following the termination of a stimulation signal.

In some examples, the stimulation schedule or therapy program (e.g., frequency of stimulation signals) for INS 26 may be selected based on the carryover effect of the stimulation delivery by INS 26 on patient 12. For example, the interval at which INS 26 delivers stimulation signals to patient 12 may be substantially equal to or less than a duration of a carryover effect from the delivery of a stimulation signal. The carryover effect may differ between patients and/or based on the type of stimulation signals, and, thus, a clinician may test patient 12 to determine the duration of a carryover effect. For example, if delivery of electrical stimulation therapy by INS 26 causes paresthesia that patient 12 perceives, the clinician may control INS 26 to deliver a stimulation signal and then measure the duration of time required for the paresthesia to dissipate. This duration of time may be substantially equal to a duration of a carryover effect for that particular stimulation signal.

In some cases, ICD 16 may sense electrical noise and interpret the electrical noise as electrical cardiac signals (e.g., an electrocardiogram (ECG) or electrogram (EGM) signal). The misinterpretation of electrical noise may cause ICD 16 to oversense cardiac signals, and, in some cases, erroneously detect an arrhythmia. For example, a processor of ICD 16 may interpret electrical noise as a heart rhythm, and detect the presence of a tachyarrhythmia episode or event (e.g., a heart cycle measured between successive R-waves that has a duration less than a threshold value) based on the electrical noise. A tachyarrhythmia episode may include more than one tachyarrhythmia event. Depending on the source of the electrical noise, the electrical noise may present itself as a relatively fast rhythm, which the processor may interpret as one or more tachyarrhythmia events, which may then be used to detect a tachyarrhythmia episode. ICD 16 may detect the presence of a tachyarrhythmia episode by determining whether a certain number of intervals of a particular number of total intervals have a certain duration, e.g., whether a certain number of intervals are considered tachyarrhythmia events.

Oversensing heart rhythms may result in inappropriate withholding or delivery of electrical stimulation to heart 14. For example, oversensing may cause ICD 16 to detect a tachycardia or fibrillation episode when heart 14 is in a normal sinus rhythm, which may result in the inappropriate delivery of a high voltage defibrillation shock. Thus, oversensing of heart rhythms by ICD 16 is generally undesirable.

Electrical noise that ICD 16 characterizes as heart rhythms may be attributable to different sources. In some cases, ICD 16 may sense the electrical stimulation signals (or "neurostimulation signals") generated by and delivered to target tissue site 40 by INS 26. The electrical stimulation signals generated by INS 26 and sensed by ICD 16 may be referred to as "electrical noise" or "interference," and the presence of electrical noise between INS 26 and ICD 16 may be referred to as "crosstalk." As previously indicated, ICD 16 may control the delivery of electrical stimulation to heart 14 based on electrical cardiac signals (e.g., EGM signals) sensed within heart 14. A sensing integrity issue may arise when ICD 16 senses the electrical stimulation signals generated by INS 26 and mischaracterizes the stimulation signals as cardiac signals. For example, if ICD 16 detects an arrhythmia of heart 14 based on electrical signals generated by INS 26 rather than true electrical cardiac signals, ICD 16 may unnecessarily deliver electrical stimulation (e.g., pacing pulses or defibrillation/cardioversion shocks) to heart 14.

Therapy system 10 may implement various techniques described herein to reduce the amount of crosstalk between INS 26 and ICD 16. In some examples, one or more therapy parameter values of the electrical stimulation delivered by INS 26 may be modified in order to minimize the possibility that the electrical stimulation delivered by INS 26 and sensed by ICD 16 mimics cardiac signals, thereby minimizing the possibility that ICD 16 mischaracterizes the electrical stimulation delivered by INS 26 as cardiac signals. Modifying the one or more therapy parameter values with which INS 26 generates electrical stimulation signals may help modify one or more signal characteristics of the noise sensed by ICD 16, such as the signal amplitude or frequency.

As described in further detail below with reference to FIGS. 9-11D, in some examples, if ICD 16 detects an arrhythmia via electrodes of one or more leads 18, 20, 22 or a housing of ICD 16, ICD 16 may determine whether the arrhythmia was detected based on noise attributable to the electrical stimulation delivered by INS 26. ICD 16 may, for example, instruct INS 26 to temporarily stop delivery of electrical stimulation or reduce an intensity of stimulation, and ICD 16 may determine, while INS 26 is not delivering stimulation or delivering stimulation with a lower intensity, whether sensed cardiac signals still indicate an arrhythmia.

An intensity of stimulation may be adjusted by modifying one or more stimulation parameter values, such as the current or voltage amplitude of the stimulation signal, the frequency, slew rate, duty cycle, and, if the stimulation signal comprises stimulation pulses, the pulse width and pulse rate.

If the cardiac signals detected within the suspend period of the INS 26, i.e., the period during which INS 26 does not deliver electrical stimulation or during which INS 26 delivers electrical stimulation having a lower intensity, indicate that an arrhythmia is not present, ICD 16 may determine that the arrhythmia was detected based on noise from electrical stimulation delivered by INS 26. In some examples, ICD 16 may control INS 26 to modify one or more stimulation parameter values in order to change the stimulation signal that is detected by ICD 16 and reduce the possibility that ICD 16 senses the stimulation signals generated by INS 26 and mischaracterizes the sensed stimulation signals as cardiac signals.

As described with reference to FIGS. 12A and 12B, ICD 16 may control INS 26 to modify one or more stimulation parameter values by switching therapy programs. For example, INS 26 may switch from therapy delivery according to a first therapy program to therapy delivery according to a second therapy program upon detection of an arrhythmia by ICD 16. The therapy programs may define electrical stimulation parameter values with which INS 26 may generate electrical stimulation signals. Therapy delivery by INS 26 according to the second therapy program may result in the generation and delivery of electrical signals that are not mischaracterized by ICD 16 as cardiac signals. For example, the second therapy program may define electrical stimulation signals that have a waveform that differs from a cardiac signal in at least one respect, such that ICD 16 does not mischaracterize the electrical stimulation delivered by INS 26 according to the second therapy program as cardiac signals. In other examples, INS 26 may switch from therapy delivery according to a first therapy program group to therapy delivery according to a second therapy program group upon detection of an arrhythmia by ICD 16. The therapy program groups may include one or more therapy programs.

Programmer 24 may include a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display.

A user, such as a physician, technician, or other clinician, may interact with programmer 24 to communicate with ICD 16 and/or INS 26. For example, the user may interact with programmer 24 to retrieve physiological or diagnostic information from ICD 16 and/or INS 26. A user may also interact with programmer 24 to program ICD 16 and INS 26, e.g., select values for operational parameters of ICD 16 and INS 26, respectively.

For example, the user may use programmer 24 to retrieve information from ICD 16 regarding the rhythm of heart 14, trends therein over time, or tachyarrhythmia episodes. As another example, the user may use programmer 24 to retrieve information from ICD 16 regarding other sensed physiological parameters of patient 12, such as electrical depolarization/repolarization signals from the heart (referred to as "electrogram" or EGM), intracardiac or intravascular pressure, activity, posture, respiration, heart sounds, or thoracic impedance. As another example, the user may use programmer 24 to retrieve information from ICD 16 regarding the performance or integrity of ICD 16 or other components of system 10, such as leads 18, 20, and 22, or a power source of ICD 16.

The user may use programmer 24 to program a therapy progression, select electrodes used to deliver defibrillation pulses, select waveforms for the defibrillation pulse, or select or configure a fibrillation detection algorithm for ICD 16. The user may also use programmer 24 to program aspects of other therapies provided by ICD 16, such as cardioversion or pacing therapies. In some examples, the user may activate certain features of ICD 16 by entering a single command via programmer 24, such as depression of a single key or combination of keys of a keypad or a single point-and-select action with a pointing device.

The user may also use programmer 24 to retrieve information from INS 26 regarding the performance or integrity of INS 26 or leads 28, 29 (if INS 26 is connected to more than one lead) or a power source of INS 26. In addition, the user may use programmer 24 to program INS 26. For example, with the aid of programmer 24 or another computing device, a user may select values for therapy parameters for controlling therapy delivery by INS 26. The values for the therapy parameters may be organized into a group of parameter values referred to as a "therapy program" or "therapy parameter set." "Therapy program" and "therapy parameter set" are used interchangeably herein.

In the case of electrical stimulation, the therapy parameters for INS 26 may include an electrode combination, and an amplitude, which may be a current or voltage amplitude, and, if INS 26 delivers electrical pulses, a pulse width, and a pulse rate for stimulation signals to be delivered to patient 12. An electrode combination may include a selected subset of one or more electrodes located on implantable lead 28 coupled to INS 26. By selecting particular electrode combinations, a clinician may target particular anatomic structures within patient 12. In addition, by selecting values for amplitude, pulse width, and pulse rate, the physician can attempt to generate an efficacious therapy for patient 12 that is delivered via the selected electrode subset.

Programmer 24 may communicate with ICD 16 and INS 26 via wireless communication using any techniques known in the art. Examples of communication techniques may include, for example, low frequency or RF telemetry, but other techniques are also contemplated. In some examples, programmer 24 may include a programming head that may be placed proximate to the patient's body near the ICD 16 and INS 26 implant sites in order to improve the quality or security of communication between ICD 16 or INS 26, respectively, and programmer 24.

Figure 3:
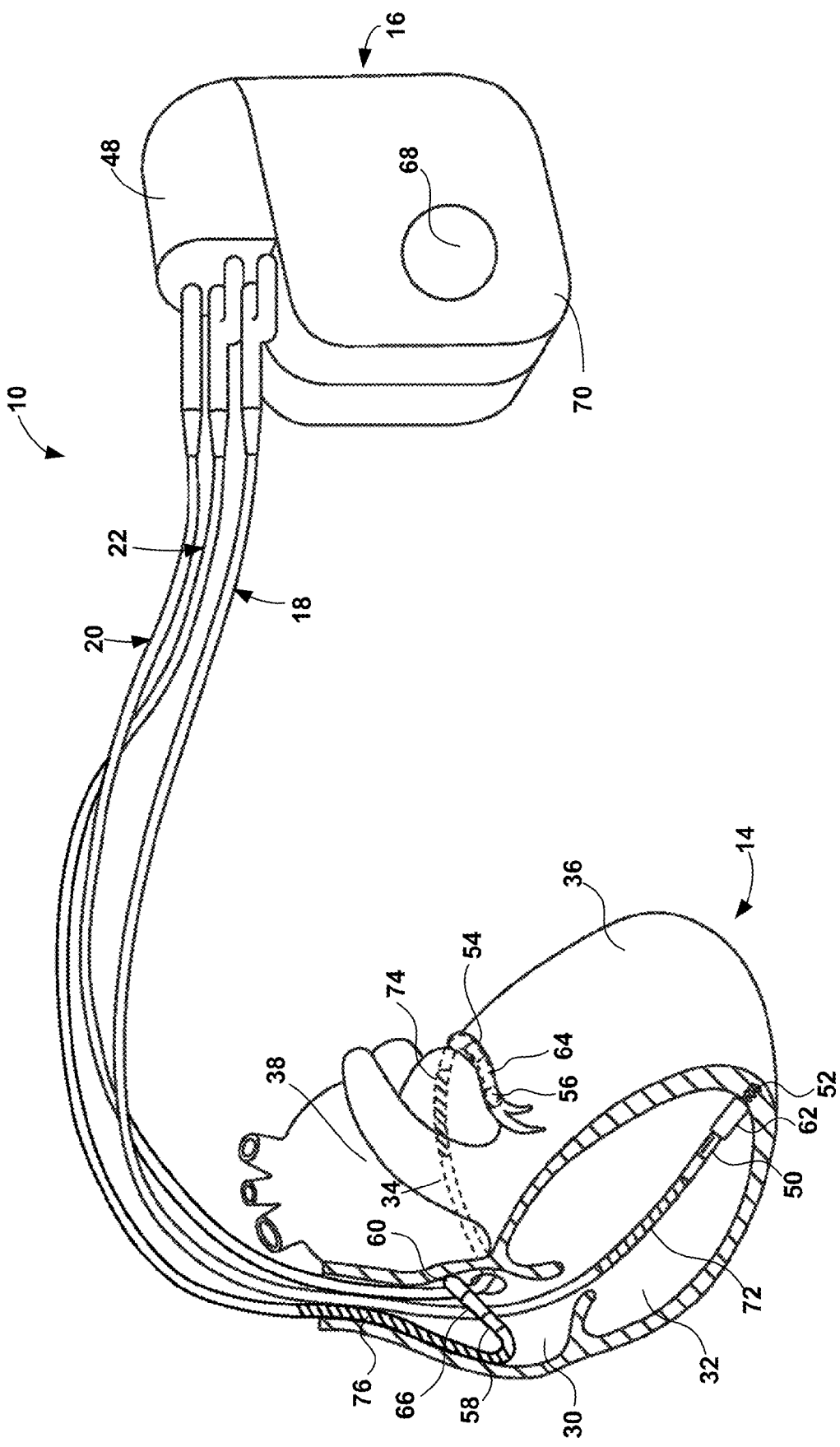
FIG. 3 is a conceptual diagram illustrating the ICD of FIGS. 1 and 2 and the respective leads in greater detail.

FIG. 3 is a conceptual diagram illustrating ICD 16 and leads 18, 20, 22 of therapy system 10 in greater detail. Leads 18, 20, 22 may be electrically coupled to a stimulation generator, a sensing module, or other modules ICD 16 via connector block 48. In some examples, proximal ends of leads 18, 20, 22 may include electrical contacts that electrically couple to respective electrical contacts within connector block 48. In addition, in some examples, leads 18, 20, 22 may be mechanically coupled to connector block 48 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. Other lead configurations are also contemplated, such as configurations that do not include coiled conductors. In the illustrated example, bipolar electrodes 50 and 52 are located proximate to a distal end of lead 18. In addition, bipolar electrodes 54 and 56 are located proximate to a distal end of lead 20 and bipolar electrodes 58 and 60 are located proximate to a distal end of lead 22.

Electrodes 50, 54, and 58 may take the form of ring electrodes, and electrodes 52, 56, and 60 may take the form of extendable helix tip electrodes mounted retractably within insulative electrode heads 62, 64, and 66, respectively. Each of the electrodes 50, 52, 54, 56, 58, and 60 may be electrically coupled to a respective one of the conductors within the lead body of its associated lead 18, 20, 22, and thereby coupled to respective ones of the electrical contacts on the proximal end of leads 18, 20 and 22.

Electrodes 50, 52, 54, 56, 58, and 60 may sense electrical signals attendant to the depolarization and repolarization of heart 14. The electrical signals are conducted to ICD 16 via the respective leads 18, 20, 22. In some examples, ICD 16 also delivers pacing pulses via electrodes 50, 52, 54, 56, 58, and 60 to cause depolarization of cardiac tissue of heart 14. In some examples, as illustrated in FIG. 2, ICD 16 includes one or more housing electrodes, such as housing electrode 68, which may be formed integrally with an outer surface of hermetically-sealed housing 70 of ICD 16 or otherwise coupled to housing 70. In some examples, housing electrode 68 is defined by an uninsulated portion of an outward facing portion of housing 70 of ICD 16. Divisions between insulated and uninsulated portions of housing 70 may be employed to define two or more housing electrodes. In some examples, housing electrode 68 comprises substantially all of housing 70. Any of the electrodes 50, 52, 54, 56, 58, and 60 may be used for unipolar sensing or pacing in combination with housing electrode 68. As described in further detail with reference to FIG. 6, housing 70 may enclose a stimulation generator that generates cardiac pacing pulses and defibrillation or cardioversion shocks, as well as a sensing module for monitoring the patient's heart rhythm.

Leads 18, 20, 22 also include elongated electrodes 72, 74, 76, respectively, which may take the form of a coil. ICD 16 may deliver defibrillation pulses to heart 14 via any combination of elongated electrodes 72, 74, 76, and housing electrode 68. Electrodes 68, 72, 74, 76 may also be used to deliver cardioversion pulses to heart 14. Electrodes 72, 74, 76 may be fabricated from any suitable electrically conductive material, such as, but not limited to, platinum, platinum alloy or other materials known to be usable in implantable defibrillation electrodes.

The configurations of therapy system 10 illustrated in FIGS. 1-3 are merely examples. In other examples, a therapy system may include epicardial leads and/or patch electrodes instead of or in addition to the transvenous leads 18, 20, 22 illustrated in FIG. 1. Further, ICD 16 and INS 26 need not be implanted within patient 12. In examples in which ICD 16 is not implanted in patient 12, ICD 16 may deliver defibrillation pulses and other therapies to heart 14 via percutaneous leads that extend through the skin of patient 12 to a variety of positions within or outside of heart 14 or via external patch electrodes. In examples in which INS 26 is not implanted in patient 12, INS 26 may deliver electrical stimulation to target tissue sites within patient 12 via external electrodes or via percutaneous leads that extend through the skin of patient 12.

In other examples of therapy systems that provide electrical stimulation therapy to heart 14, a therapy system may include any suitable number of leads coupled to ICD 16, and each of the leads may extend to any location within or proximate to heart 14. Other examples of therapy systems may include three transvenous leads located as illustrated in FIGS. 1-3, and an additional lead located within or proximate to left atrium 38. Other examples of therapy systems may include a single lead that extends from ICD 16 into right atrium 30 or right ventricle 32, or two leads that extend into a respective one of the right ventricle 32 and right atrium 30. An example of this type of therapy system is shown in FIG. 4.

Figure 4:
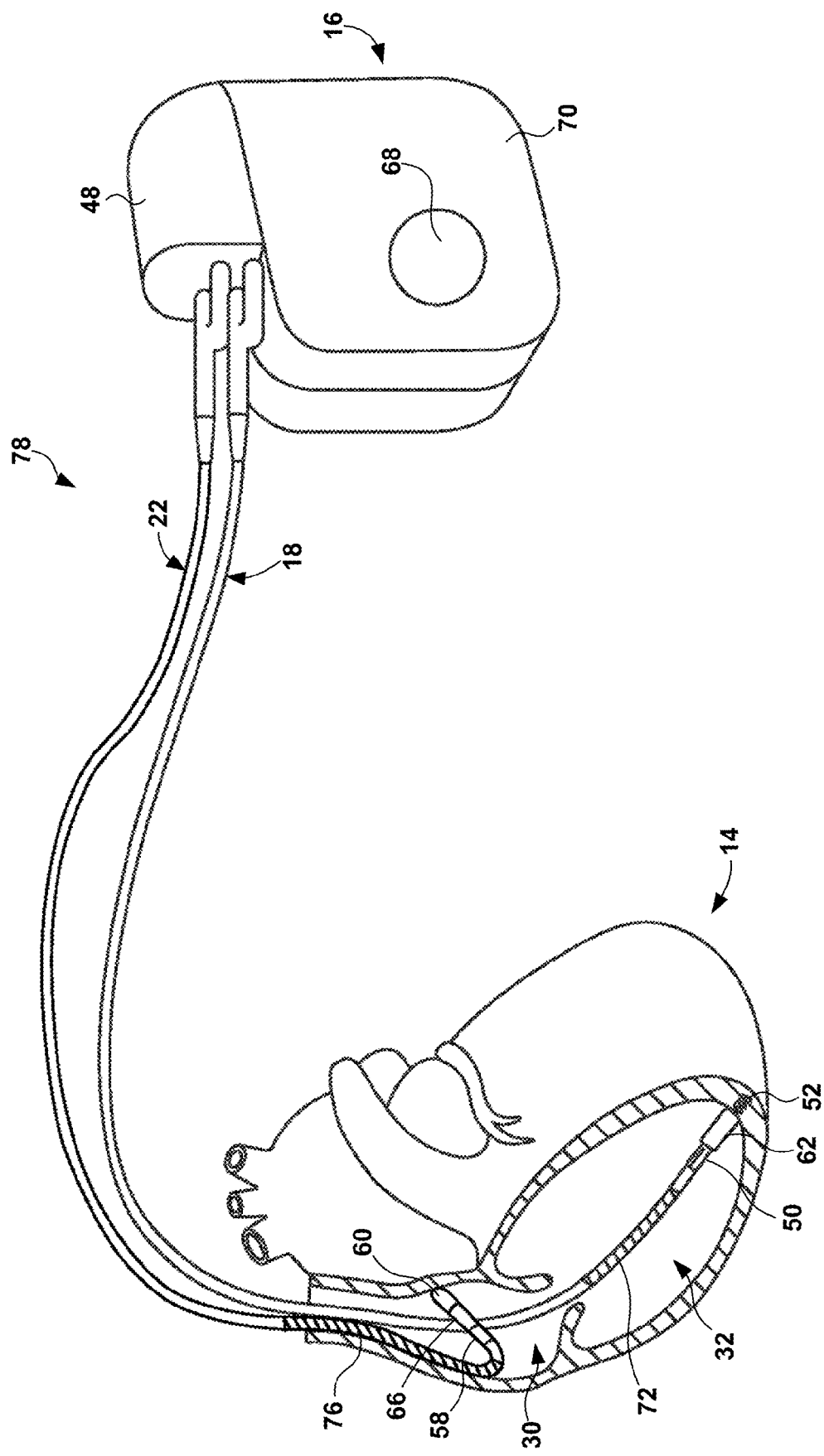
FIG. 4 is a conceptual diagram illustrating another example of the ICD of FIGS. 1 and 2 and the respective leads in greater detail.

FIG. 4 is a conceptual diagram illustrating another example of therapy system 78, which includes ICD 16 connected to two leads 18, 22, rather than three leads as shown in FIGS. 1-3. Leads 18, 22 are implanted within right ventricle 32 and right atrium 30, respectively. Therapy system 78 shown in FIG. 4 may be useful for providing defibrillation and pacing pulses to heart 14. Therapy system 78 may further include INS 26 (not shown in FIG. 4), which is configured to deliver electrical stimulation therapy to modulate an autonomic nervous system of patient 12, (e.g., via stimulation of a vagus nerve or within spinal cord 44) in order to help prevent or mitigate an arrhythmia of patient 12.

Figure 5:
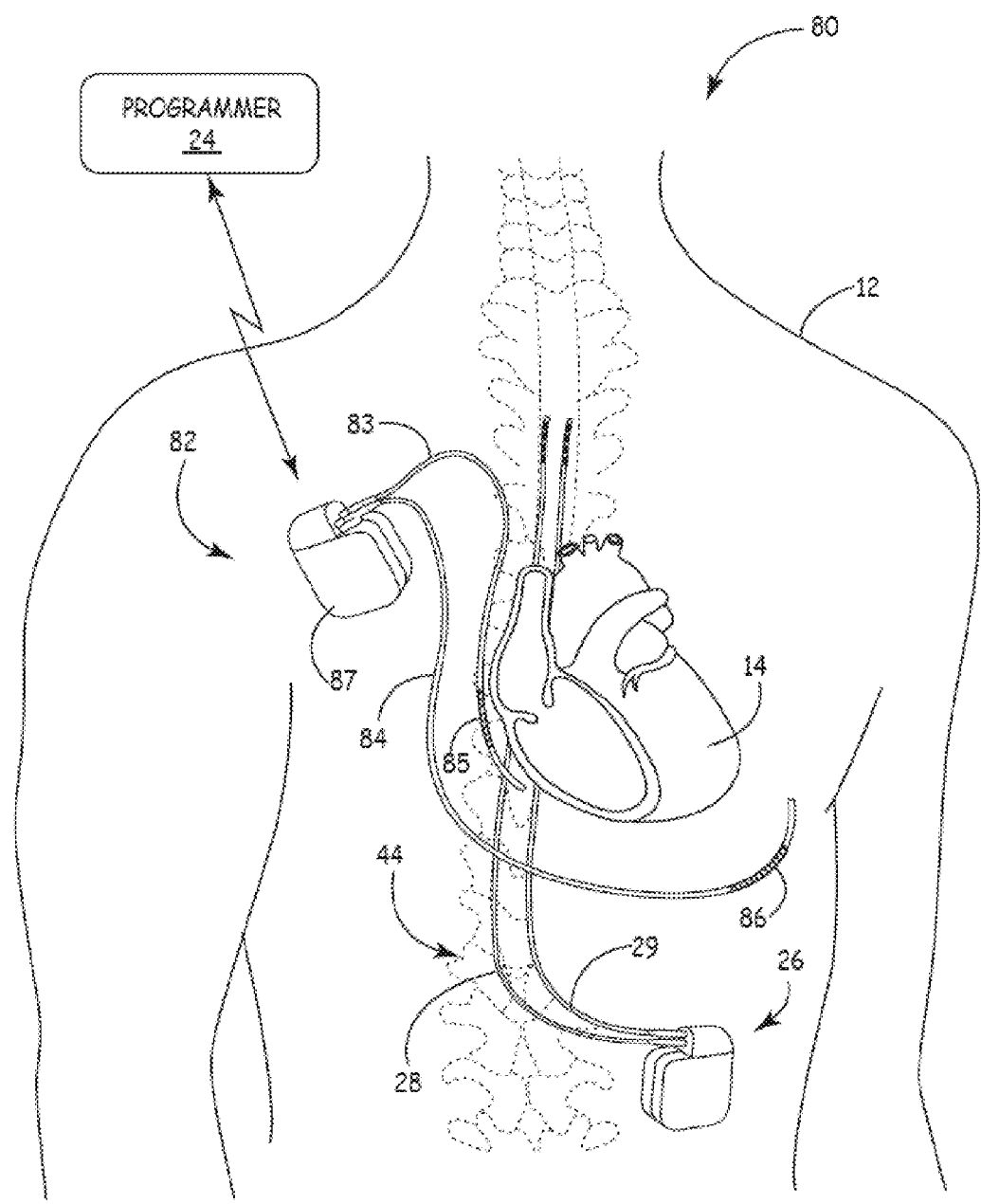
FIG. 5 is a conceptual diagram illustrating another example therapy system that includes an ICD and an INS.

FIG. 5 is a conceptual diagram of another example therapy system 80 that includes two medical devices to provide therapy to patient 12. In addition to INS 26, therapy system 80 includes ICD 82, which delivers electrical stimulation to heart 14 without intravascular leads. ICD 82 is coupled to extravascular leads 83, 84, which each include at least one electrode 85, 86, respectively. Electrodes 85, 86 may be subcutaneous coil electrodes, which may be positioned within a subcutaneous tissue layer of patient 12. In other examples, electrodes 85, 86 may comprise any other suitable type of extravascular electrode. For example, electrodes 85, 86 may include any other type of subcutaneous electrode, such as subcutaneous ring electrodes, subcutaneous plate electrodes, subcutaneous patch or pad electrodes, or any other type of extrathoracic electrode, such as a submuscular electrode, an epicardial electrode or an intramural electrode.

Electrodes 85 may be located within the thoracic cavity of patient 12 proximate to right ventricle 32 (FIG. 1), on the patient's side or back, or any other portion of the body appropriate for providing electrical stimulation to heart 14. Electrode 86 may be located within the thoracic cavity of patient 12 proximate left ventricle 36 (FIG. 1), on the patient's side or back, or any other portion of the body appropriate for providing electrical stimulation to the heart. Similar extravascular electrodes are disclosed in commonly-assigned U.S. Pat. No. 5,261,400 to Bardy, which is entitled "DEFIBRILLATOR EMPLOYING TRANSVENOUS AND SUBCUTANEOUS ELECTRODES AND METHOD OF USE" and issued Nov. 16, 1993, and U.S. Pat. No. 5,292,338 to Bardy, which is entitled "ATRIAL DEFIBRILLATOR EMPLOYING TRANSVENOUS AND SUBCUTANEOUS ELECTRODES AND METHOD OF USE" and issued Mar. 8, 1994. U.S. Pat. Nos. 5,261,400 and 5,292,338 are incorporated herein by reference in their entireties.

Leads 83, 84 may be electrically coupled to stimulation modules, and, in some cases, sensing modules, that are enclosed within housing 87 of ICD 82. As with housing 70 of ICD 16 (FIG. 3), housing 87 may comprise a hermetic housing that substantially encloses the components of ICD 16, such as a sensing module, stimulation generator, processor and the like. Components of an example ICD 16 or ICD 82 are described with respect to FIG. 6. ICD 82 may deliver electrical stimulation (e.g., pacing, cardioversion or defibrillation pulses) to heart 14 between electrodes 85, 86 e.g., in a bipolar configuration. In other examples, ICD 82 may deliver electrical stimulation to heart 14 between electrodes 85 and housing 87 (or an electrode attached to an outer surface of housing 87), or between electrode 86 and housing 87, e.g., in a unipolar configuration.

Just as with ICD 16 (FIG. 1) that delivers stimulation to heart 14 via intravascular electrodes, the delivery of electrical stimulation by INS 26 may interfere with the ability of ICD 82 to sense cardiac signals and deliver appropriate therapy upon the detection of an arrhythmia. ICD 82 may include a sensing module similar to that of ICD 16. In some cases, the sensing module may sense the electrical stimulation delivered by INS 26 and mischaracterize the signals as cardiac signals, which may cause ICD 82 to deliver inappropriate therapy to heart 14 of patient 12.

While the disclosure primarily refers to therapy system 10 including ICD 16 (FIG. 1) and INS 26, the description of the techniques, systems, and devices herein are also applicable to therapy system 80 including ICD 82 and INS 26.

Figure 6:
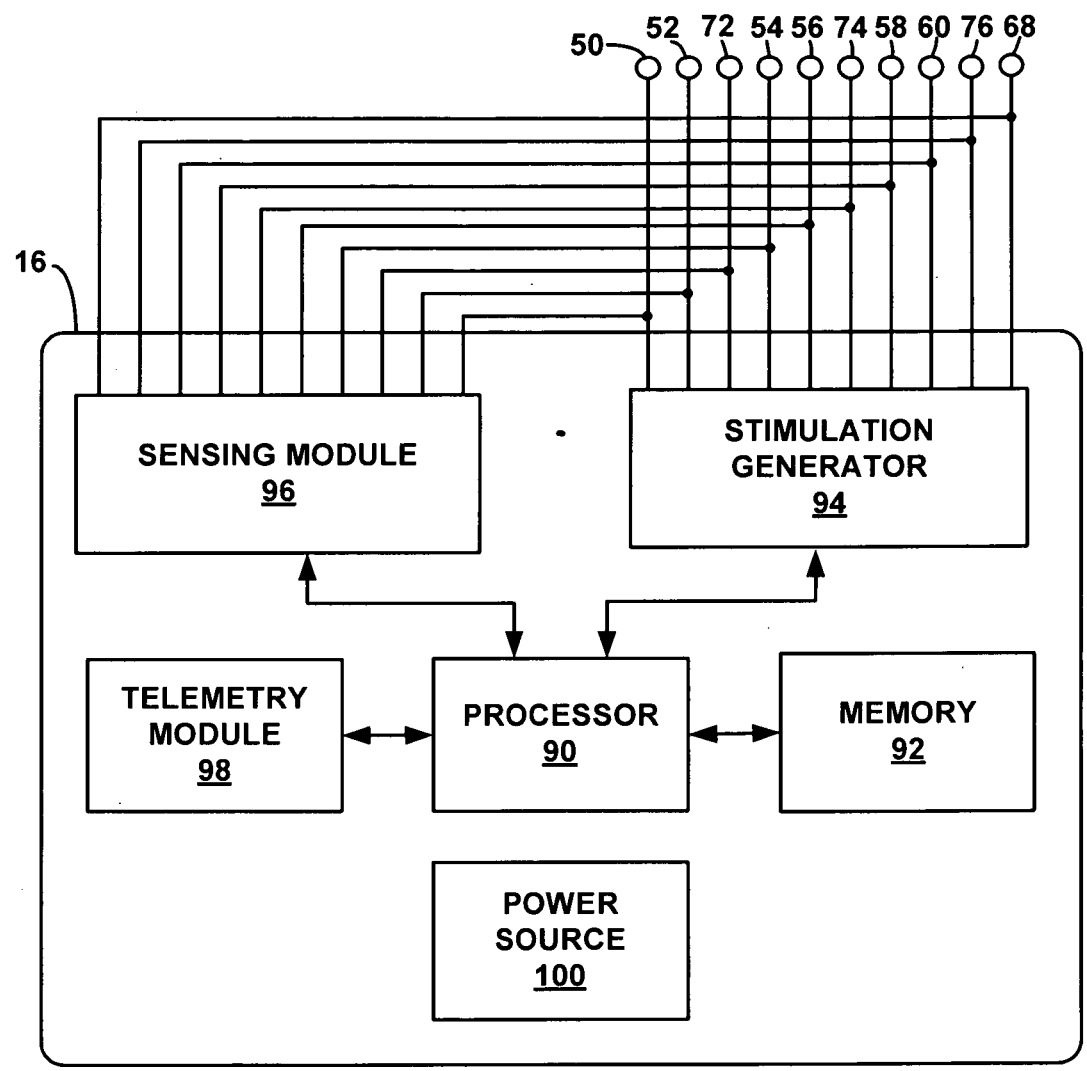
FIG. 6 is a functional block diagram of an example ICD that generates and delivers electrical stimulation to a heart of a patient.

FIG. 6 is a functional block diagram of an example configuration of ICD 16 (FIG. 1), which includes processor 90, memory 92, stimulation generator 94, sensing module 96, telemetry module 98, and power source 100. The block diagram shown in FIG. 6 may also illustrate an example configuration of ICD 82 (FIG. 5). Memory 92 includes computer-readable instructions that, when executed by processor 90, cause ICD 16 and processor 90 to perform various functions attributed to ICD 16 and processor 90 herein. Memory 92 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 90 may include any one or more of a microprocessor, a controller, a digital signal processor (DSP), an application specific integrated circuit (ASIC), a field-programmable gate array (FPGA), or equivalent discrete or integrated logic circuitry. In some examples, processor 90 may include multiple components, such as any combination of one or more microprocessors, one or more controllers, one or more DSPs, one or more ASICs, or one or more FPGAs, as well as other discrete or integrated logic circuitry. The functions attributed to processor 90 herein may be embodied as software, firmware, hardware or any combination thereof. Processor 90 controls stimulation generator 94 to deliver stimulation therapy to heart 14 according to a selected one or more of therapy programs, which may be stored in memory 92. Specifically, processor 44 may control stimulation generator 94 to deliver electrical pulses with the amplitudes, pulse widths, frequency, or electrode polarities specified by the selected one or more therapy programs.

Stimulation generator 94 is electrically coupled to electrodes 50, 52, 54, 56, 58, 60, 68, 72, 74, and 76, e.g., via conductors of the respective lead 18, 20, 22, or, in the case of housing electrode 68, via an electrical conductor disposed within housing 70 of ICD 16. Stimulation generator 94 is configured to generate and deliver electrical stimulation therapy to heart 14 to manage a rhythm of heart 14. For example, stimulation generator 94 may deliver defibrillation shocks to heart 14 via at least two electrodes 68, 72, 74, 76. Stimulation generator 94 may deliver pacing pulses via ring electrodes 50, 54, 58 coupled to leads 18, 20, and 22, respectively, helical electrodes 52, 56, and 60 of leads 18, 20, and 22, respectively, and/or housing electrode 68. In some examples, stimulation generator 94 delivers pacing, cardioversion or defibrillation therapy in the form of electrical pulses. In other examples, stimulation generator 94 may deliver one or more of these types of therapy in the form of other signals, such as sine waves, square waves, or other substantially continuous time signals.

In some examples, stimulation generator 94 may include a switch module (not shown in FIG. 6) and processor 90 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes. In other examples, however, stimulation generator 94 may independently deliver stimulation to electrodes 50, 52, 54, 56, 58, 60, 68, 72, 74, and 76 or selectively sense via one or more of electrodes 50, 52, 54, 56, 58, 60, 68, 72, 74, and 76 without a switch matrix.

Sensing module 96 monitors signals from at least one of electrodes 50, 52, 54, 56, 58, 60, 68, 72, 74, and 76 in order to monitor electrical activity of heart 14, e.g., via an EGM signal. Sensing module 96 may also include a switch module (not shown in FIG. 6) to select a particular subset of available electrodes to sense the heart activity. In some examples, processor 90 may select the electrodes that function as sense electrodes via the switch module within sensing module 96, e.g., by providing signals via a data/address bus. In some examples, sensing module 96 includes one or more sensing channels, each of which may comprise an amplifier. In response to the signals from processor 90, the switch module of sensing module 96 may couple the outputs from the selected electrodes to one of the sensing channels.

In some examples, sensing module 96 may include a plurality of channels. One channel of sensing module 96 may include an R-wave amplifier that receives signals from electrodes 50 and 52, which are used for pacing and sensing in right ventricle 32 of heart 14. Another channel may include another R-wave amplifier that receives signals from electrodes 54 and 56, which are used for pacing and sensing proximate to left ventricle 36 of heart 14. In some examples, in one operating mode of sensing module 96, the R-wave amplifiers may take the form of an automatic gain controlled amplifier that provides an adjustable sensing threshold as a function of the measured R-wave amplitude of the heart rhythm.

In addition, in some examples, one channel of sensing module 96 may include a P-wave amplifier that receives signals from electrodes 58 and 60, which are used for pacing and sensing in right atrium 30 of heart 14. In some examples, in one operating mode of sensing module 96, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 96 may be selectively coupled to housing electrode 68, or elongated electrodes 72, 74, or 76, with or instead of one or more of electrodes 50, 52, 54, 56, 58 or 60, e.g., for unipolar sensing of R-waves or P-waves in any of chambers 30, 32, or 36 of heart 14.

In some examples, sensing module 96 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 92 as an EGM. In some examples, the storage of such EGMs in memory 92 may be under the control of a direct memory access circuit. Processor 90 may employ digital signal analysis techniques to characterize the digitized signals stored in memory 92 to detect and classify the patient's heart rhythm from the electrical signals. Processor 90 may detect and classify the heart rhythm of patient 12 by employing any of the numerous signal processing methodologies known in the art.

If ICD 16 is configured to generate and deliver pacing pulses to heart 14, processor 90 may include pacer timing and control module, which may be embodied as hardware, firmware, software, or any combination thereof. The pacer timing and control module may comprise a dedicated hardware circuit, such as an ASIC, separate from other processor 90 components, such as a microprocessor, or a software module executed by a component of processor 90, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided. When a pacing code includes "D" as the third letter in the code, it may indicate that the sensed signal is used for tracking purposes.

Intervals defined by the pacer timing and control module within processor 90 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals from sensing module 96 to blank one or more channels, e.g., amplifiers, for a period during and after delivery of electrical stimulation to heart 14. The durations of these intervals may be determined by processor 90 in response to stored data in memory 92. The pacer timing and control module of processor 90 may also determine the amplitude of the cardiac pacing pulses.

During pacing, escape interval counters within the pacer timing/control module of processor 90 may be reset upon sensing of R-waves and P-waves. Stimulation generator 94 may include pacer output circuits that are coupled, e.g., selectively by a switching module, to any combination of electrodes 50, 52, 54, 56, 58, 60, 68, 72, 74, and 76 appropriate for delivery of a bipolar or unipolar pacing pulse to one of the chambers of heart 14. Processor 90 may reset the escape interval counters upon the generation of pacing pulses by stimulation generator 94, and thereby control the basic timing of cardiac pacing functions, including anti-tachyarrhythmia pacing.

The value of the count present in the escape interval counters when reset by sensed R-waves and P-waves may be used by processor 90 to measure the durations of R-R intervals, P-P intervals, P-R intervals and R-P intervals, which are measurements that may be stored in memory 92. Processor 90 may use the count in the interval counters to detect a tachyarrhythmia event, such as ventricular fibrillation event or ventricular tachycardia event. Upon detecting a threshold number of tachyarrhythmia events, processor 90 may identify the presence of a tachyarrhythmia episode, such as a ventricular fibrillation episode, a ventricular tachycardia episode, or a non-sustained tachycardia (NST) episode. Examples of tachyarrhythmia episodes that may qualify for delivery of responsive therapy include a ventricular fibrillation episode or a ventricular tachyarrhythmia episode. In the case of a NST, however, the count in the interval counters may not meet the requirements for triggering a therapeutic response.

In some examples, processor 90 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 90 and any updating of the values or intervals controlled by the pacer timing and control module of processor 90 may take place following such interrupts. A portion of memory 92 may be configured as a plurality of recirculating buffers, capable of holding series of measured intervals, which may be analyzed by processor 90 in response to the occurrence of a pace or sense interrupt to determine whether heart 14 of patient 12 is presently exhibiting atrial or ventricular tachyarrhythmia.

In some examples, an arrhythmia detection method may include any suitable tachyarrhythmia detection algorithms. In one example, processor 90 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 90 in other examples.

In the examples described herein, processor 90 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 92 of ICD 16. In addition, the number of tachyarrhythmia events that are detected to confirm the presence of a tachyarrhythmia episode may be stored as a number of intervals to detect (NID) threshold value in memory 92. In some examples, processor 90 may also identify the presence of the tachyarrhythmia episode by detecting a variability of the intervals between tachycardia events. For example, if the interval between successive tachyarrhythmia events varies by a particular percentage or the differences between the coupling intervals are higher than a given threshold over a predetermined number of successive cycles, processor 90 may determine that the tachyarrhythmia is present.

If processor 90 detects an atrial or ventricular tachyarrhythmia based on signals from sensing module 96, and an anti-tachyarrhythmia pacing regimen is desired, timing intervals for controlling the generation of anti-tachyarrhythmia pacing therapies by stimulation generator 94 may be loaded by processor 90 into the pacer timing and control module to control the operation of the escape interval counters therein and to define refractory periods during which detection of R-waves and P-waves is ineffective to restart the escape interval counters.

If ICD 16 is configured to generate and deliver defibrillation pulses to heart 14, stimulation generator 94 may include a high voltage charge circuit and a high voltage output circuit. In the event that generation of a cardioversion or defibrillation pulse is required, processor 90 may employ the escape interval counter to control timing of such cardioversion and defibrillation pulses, as well as associated refractory periods. In response to the detection of atrial or ventricular fibrillation or tachyarrhythmia requiring a cardioversion pulse, processor 90 may activate a cardioversion/defibrillation control module, which may, like pacer timing and control module, be a hardware component of processor 90 and/or a firmware or software module executed by one or more hardware components of processor 90. The cardioversion/defibrillation control module may initiate charging of the high voltage capacitors of the high voltage charge circuit of stimulation generator 94 under control of a high voltage charging control line.

Processor 90 may monitor the voltage on the high voltage capacitor, e.g., via a voltage charging and potential (VCAP) line. In response to the voltage on the high voltage capacitor reaching a predetermined value set by processor 90, processor 90 may generate a logic signal that terminates charging. Thereafter, timing of the delivery of the defibrillation or cardioversion pulse by stimulation generator 94 is controlled by the cardioversion/defibrillation control module of processor 90. Following delivery of the fibrillation or tachycardia therapy, processor 90 may return stimulation generator 94 to a cardiac pacing function and await the next successive interrupt due to pacing or the occurrence of a sensed atrial or ventricular depolarization.

Stimulation generator 94 may deliver cardioversion or defibrillation pulses with the aid of an output circuit that determines whether a monophasic or biphasic pulse is delivered, whether housing electrode 68 serves as cathode or anode, and which electrodes are involved in delivery of the cardioversion or defibrillation pulses. Such functionality may be provided by one or more switches or a switching module of stimulation generator 94.

Telemetry module 98 includes any suitable hardware, firmware, software or any combination thereof for communicating with another device, such as INS 26 or programmer 24 (FIG. 1). Under the control of processor 90, telemetry module 98 may receive downlink telemetry from and send uplink telemetry to programmer 24 with the aid of an antenna, which may be internal and/or external. Processor 90 may provide the data to be uplinked to programmer 24 and the control signals for the telemetry circuit within telemetry module 98, e.g., via an address/data bus. In some examples, telemetry module 98 may provide received data to processor 90 via a multiplexer.

In some examples, processor 90 may transmit atrial and ventricular heart signals (e.g., ECG signals) produced by atrial and ventricular sense amp circuits within sensing module 96 to programmer 24. Programmer 24 may interrogate ICD 16 to receive the heart signals. Processor 90 may store heart signals within memory 92, and retrieve stored heart signals from memory 92. Processor 90 may also generate and store marker codes indicative of different cardiac episodes that sensing module 96 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of ICD 16 are coupled to power source 100, which may include a rechargeable or non-rechargeable battery. A non-rechargeable battery may be selected to last for several years, while a rechargeable battery may be inductively charged from an external device, e.g., on a daily or weekly basis. Examples of a rechargeable battery include, but are not limited to, a lithium ion battery, a lithium polymer battery or a supercapacitor.

In some examples, data from sensing module 96 may be uploaded to a remote server, from which a clinician or another user may access the data to determine whether a potential sensing integrity issue exists. An example of a remote server includes the CareLink Network, available from Medtronic, Inc. of Minneapolis, Minn. An example of a system that includes an external device, such as a server, and one or more computing devices that are coupled to ICD 16 and programmer 24 via a network is described below with respect to FIG. 32.

Figure 7:
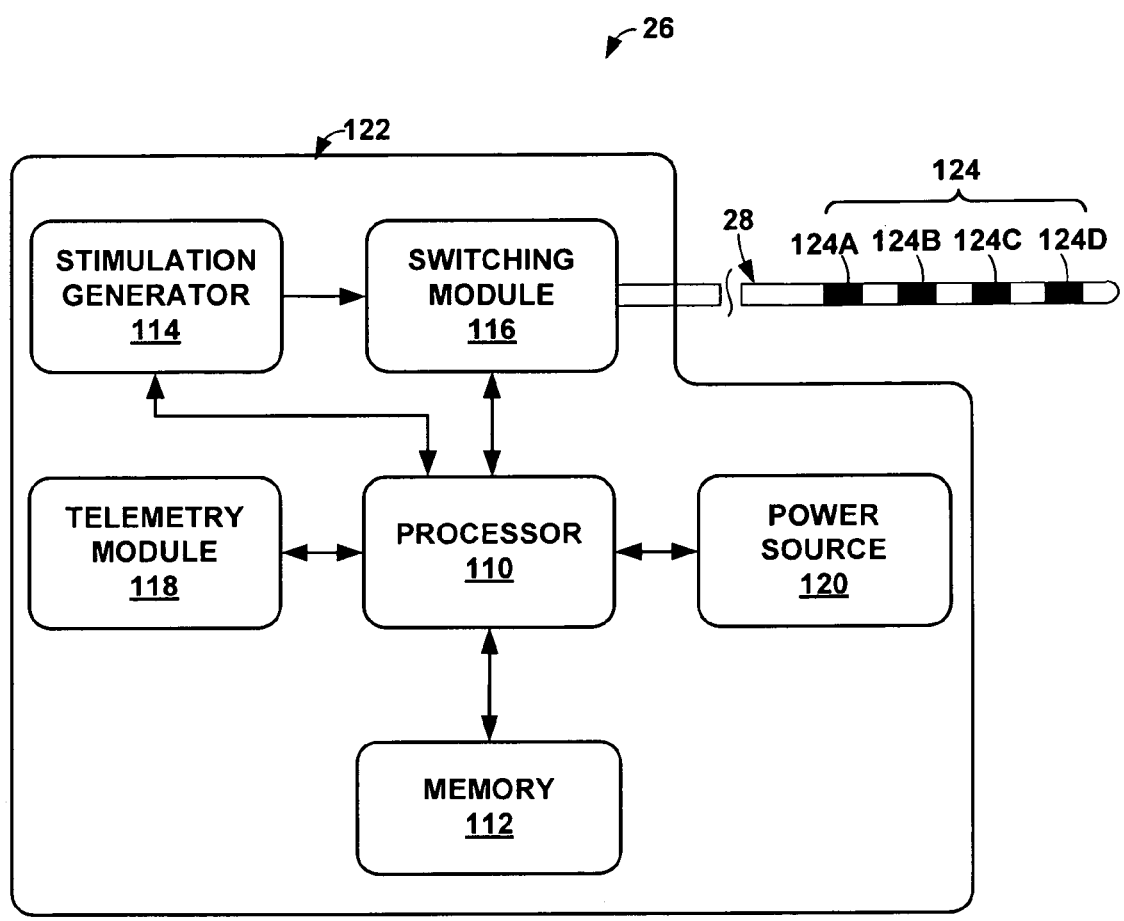
FIG. 7 is a functional block diagram of an example INS that generates and delivers electrical stimulation signals to a tissue site within the patient.

Telemetry module 98 may also be useful for communicating with INS 26, which may also include a telemetry module as described with respect to FIG. 7. In some examples, INS 26 and ICD 16 may communicate with each other by way of RF communication techniques supported by the respective telemetry modules. In addition to or instead of the RF communication techniques, INS 26 and ICD 16 may communicate with each other by generating electrical communication signals that are sensed via the other device. For example, as described in U.S. Provisional Patent Application No. 61/110,117 by Burnes et al., which is entitled, "INTERDEVICE IMPEDANCE" and was filed on Oct. 31, 2008, and U.S. patent application Ser. No. 12/362,895 by Burnes et al., which is entitled "INTERDEVICE IMPEDANCE," was filed on Jan. 30, 2009, and published as U.S. Patent Application Publication No. 2010/0114204 on May 6, 2010, in order to transmit information to INS 26, ICD 16 may generate an electrical signal between two or more electrodes 50, 52, 54, 56, 58, 60, 68, 72, 74, 76 electrically connected to ICD 16, and INS 26 may sense the electrical signal and retrieve information from the sensed electrical signal. The electrical signal may or may not provide therapeutic benefits to patient 12. The entire contents of U.S. Provisional Patent Application No. 61/110,117 by Burnes et al. and U.S. patent application Ser. No. 12/362,895 by Burnes et al. are incorporated herein by reference.

As another example, as described in U.S. patent application Ser. No. 12/362,895 by Burnes et al. in order to transmit information to ICD 16, INS 26 may generate an electrical signal between two or more electrodes 124 electrically connected to INS 26 and INS 26 may sense the electrical signal and retrieve information therefrom. Again, the electrical signal may or may not provide therapeutic benefits to patient 12. In either example, ICD 16 or INS 26 may modulate one or more characteristics of the electrical signal (e.g., an amplitude of frequency of the signal) in order to exchange information with the other device INS 26 or ICD 16, respectively.

FIG. 7 is a functional block diagram of an example INS 26. INS 26 includes processor 110, memory 112, stimulation generator 114, switching module 116, telemetry module 118, and power source 120. In the example shown in FIG. 7, processor 110, memory 112, stimulation generator 114, switching module 116, telemetry module 118, and power source 120 are enclosed within housing 122, which may be, for example a hermetic housing. As shown in FIG. 7, stimulation generator 114 is coupled to lead 28 either directly or indirectly (e.g., via a lead extension). Alternatively, stimulation generator 114 may be coupled to more than one lead directly or indirectly (e.g., via a lead extension, such as a bifurcating lead extension that may electrically and mechanically couple to two leads) as needed to provide neurostimulation therapy to patient 12.

In the example illustrated in FIG. 7, lead 28 includes electrodes 124A-124D (collectively referred to as "electrodes 124"). Electrodes 124 may comprise ring electrodes. In other examples, electrodes 124 may be arranged in a complex electrode array that includes multiple non-contiguous electrodes at different angular positions about the outer circumference of lead 28, as well as different levels of electrodes spaced along a longitudinal axis of lead 28. The configuration, type, and number of electrodes 124 illustrated in FIG. 7 are merely exemplary. In other examples, INS 26 may be coupled to any suitable number of leads with any suitable number and configuration of electrodes. Moreover, lead 28 may comprise a shape other than a cylindrical shape. As an example, lead 28 may comprise a paddle-shaped portion that carries electrodes 124.

Memory 112 includes computer-readable instructions that, when executed by processor 110, cause INS 26 to perform various functions. Memory 112 may include any volatile, non-volatile, magnetic, optical, or electrical media, such as a RAM, ROM, NVRAM, EEPROM, flash memory, or any other digital media. Memory 112 may store therapy programs, which may be stored in therapy program groups, and operating instructions. The therapy programs may define a particular program of therapy in terms of respective values for electrical stimulation parameters, such as electrode combination, electrode polarity, current or voltage amplitude, pulse width and pulse rate. A program group may comprise a plurality of therapy programs that may be delivered together on an overlapping or non-overlapping basis. The stored operating instructions may guide the general operation of INS 26 under control of processor 110, and may include instructions for measuring the impedance of electrodes 124.

Stimulation generator 114 generates stimulation signals, which may be pulses as primarily described herein, or continuous signals, such as sine waves, for delivery to patient 12 via selected combinations of electrodes 124. Processor 110 controls stimulation generator 114 according to stored therapy programs and/or program groups in memory 112 to apply particular stimulation parameter values specified by one or more of programs, such as amplitude, pulse width, and pulse rate. Processor 110 may include any one or more microprocessors, controllers, a DSPs, ASICs, FPGAs, or equivalent discrete or integrated digital or analog logic circuitry, and the functions attributed to processor 110 herein may be embodied as software, firmware, hardware or any combination thereof.

Processor 110 may also control switching module 116 to apply the stimulation signals generated by stimulation generator 114 to selected combinations of electrodes 124. In particular, switching module 116 couples stimulation signals to selected conductors within lead 28 which, in turn, deliver the stimulation signals across selected electrodes 124. Switching module 116 may be a switch array, switch matrix, multiplexer, or any other type of switching device suitable to selectively couple stimulation energy to selected electrodes. Hence, stimulation generator 114 is coupled to electrodes 124 via switching module 116 and conductors within lead 28. In some examples, INS 26 does not include switching module 116.

Stimulation generator 114 may be a single or multi-channel stimulation generator. In particular, stimulation generator 114 may be capable of delivering a single stimulation pulse, multiple stimulation pulses, or a continuous signal at a given time via a single electrode combination or multiple stimulation pulses at a given time via multiple electrode combinations. In some examples, however, stimulation generator 114 and switching module 116 may be configured to deliver multiple channels on a time-interleaved basis. In this case, switching module 116 serves to time division multiplex the output of stimulation generator 114 across different electrode combinations at different times to deliver multiple programs or channels of stimulation energy to patient 12.

Telemetry module 118 supports wireless communication between INS 26 and an external programmer 24 (FIG. 1) or another computing device, and, in some examples, between INS 26 and ICD 16 under the control of processor 110. Processor 110 of INS 26 may receive, as updates to programs, values for various stimulation parameters such as amplitude and electrode combination, from programmer 24 via telemetry module 118. The updates to the therapy programs may be stored within memory 112.

The various components of INS 26 are coupled to power source 120, which may include a rechargeable or non-rechargeable battery. A non-rechargeable battery may be selected to last for several years, while a rechargeable battery may be inductively charged from an external device, e.g., on a daily or weekly basis. In other examples, power source 120 may be powered by proximal inductive interaction with an external power source carried by patient 12.

Figure 8:
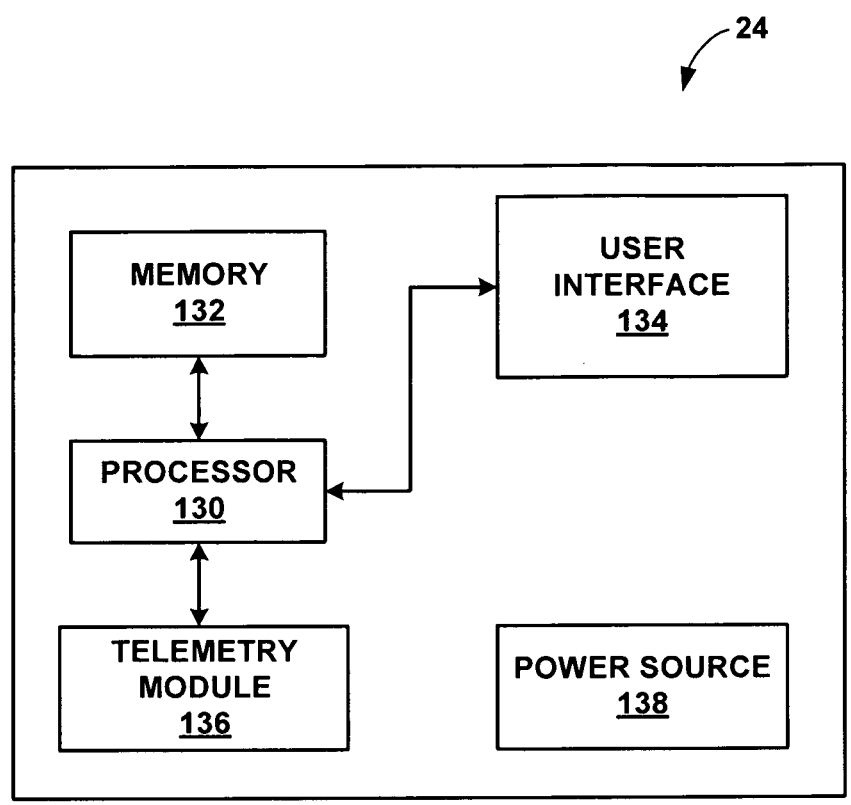
FIG. 8 is a functional block diagram of an example medical device programmer.

FIG. 8 is block diagram of an example programmer 24. As shown in FIG. 6, programmer 24 includes processor 130, memory 132, user interface 134, telemetry module 136, and power source 138. Programmer 24 may be a dedicated hardware device with dedicated software for programming of ICD 16 and INS 26. Alternatively, programmer 24 may be an off-the-shelf computing device running an application that enables programmer 24 to program ICD 16 and INS 26. In some examples, separate programmers may be used to program ICD 16 and INS 26. However, a common programmer 24 that is configured to program both ICD 16 and INS 26 may provide a more streamlined programming process for a user, such as a clinician or patient 12.

A user may use programmer 24 to select therapy programs (e.g., sets of stimulation parameters), generate new therapy programs, modify therapy programs through individual or global adjustments or transmit the new programs to a medical device, such as ICD 16 or INS 26 (FIG. 1). The clinician may interact with programmer 24 via user interface 134, which may include display to present graphical user interface to a user, and a keypad or another mechanism for receiving input from a user.

Processor 130 can take the form one or more microprocessors, DSPs, ASICs, FPGAs, programmable logic circuitry, or the like, and the functions attributed to processor 102 herein may be embodied as hardware, firmware, software or any combination thereof. Memory 132 may store instructions that cause processor 130 to provide the functionality ascribed to programmer 24 herein, and information used by processor 130 to provide the functionality ascribed to programmer 24 herein. Memory 132 may include any fixed or removable magnetic, optical, or electrical media, such as RAM, ROM, CD-ROM, hard or floppy magnetic disks, EEPROM, or the like. Memory 132 may also include a removable memory portion that may be used to provide memory updates or increases in memory capacities. A removable memory may also allow patient data to be easily transferred to another computing device, or to be removed before programmer 24 is used to program therapy for another patient. Memory 132 may also store information that controls therapy delivery by ICD 16 and INS 26, such as stimulation parameter values.

Programmer 24 may communicate wirelessly with ICD 16 and INS 24, such as using RF communication or proximal inductive interaction. This wireless communication is possible through the use of telemetry module 136, which may be coupled to an internal antenna or an external antenna. An external antenna that is coupled to programmer 24 may correspond to the programming head that may be placed over heart 14, as described above with reference to FIG. 1. Telemetry module 136 may be similar to telemetry module 98 of ICD 16 (FIG. 6) or telemetry module 118 of INS 26 (FIG. 7).

Telemetry module 136 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 138 delivers operating power to the components of programmer 24. Power source 138 may include a battery and a power generation circuit to produce the operating power. In some examples, the battery may be rechargeable to allow extended operation. Recharging may be accomplished by electrically coupling power source 138 to a cradle or plug that is connected to an alternating current (AC) outlet. In addition or alternatively, recharging may be accomplished through proximal inductive interaction between an external charger and an inductive charging coil within programmer 24. In other examples, traditional batteries (e.g., nickel cadmium or lithium ion batteries) may be used. In addition, programmer 24 may be directly coupled to an alternating current outlet to power programmer 24. Power source 138 may include circuitry to monitor power remaining within a battery. In this manner, user interface 134 may provide a current battery level indicator or low battery level indicator when the battery needs to be replaced or recharged. In some cases, power source 138 may be capable of estimating the remaining time of operation using the current battery.

Figure 9:
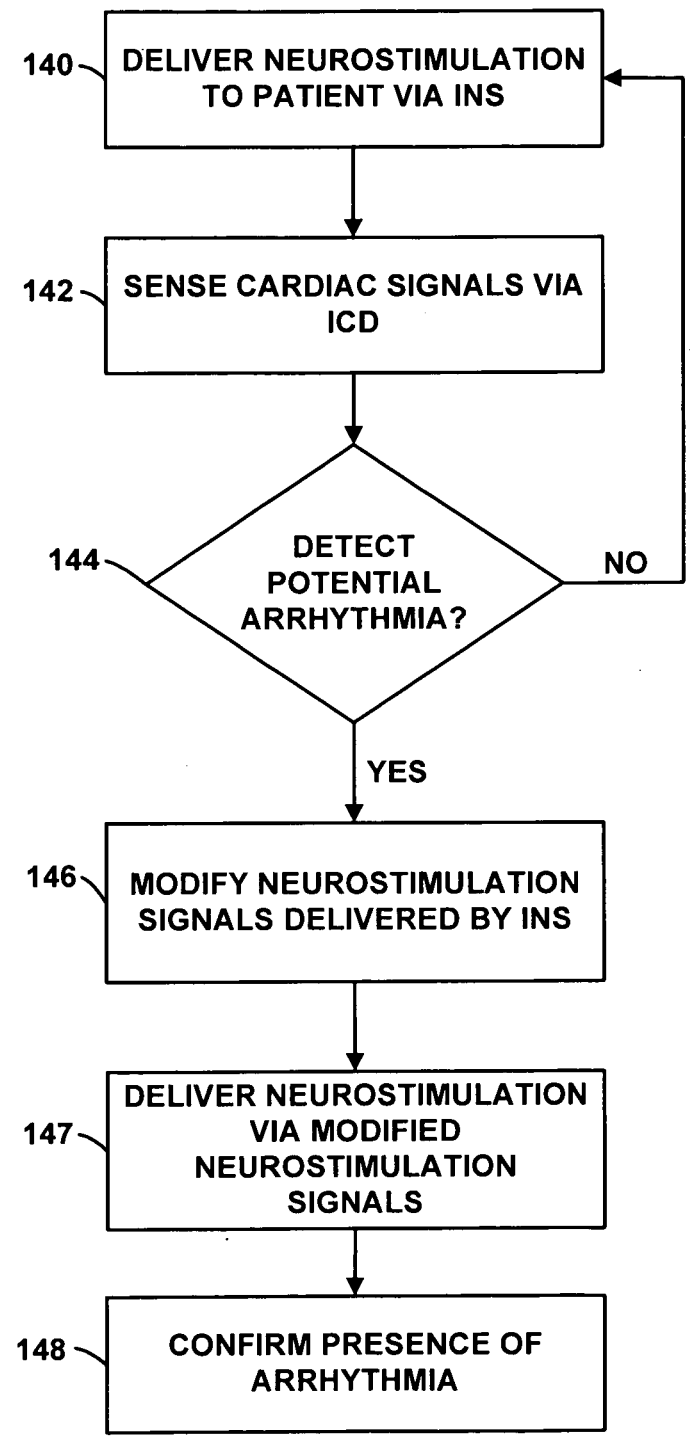
FIG. 9 is a flow diagram illustrating an example technique for modifying electrical stimulation therapy delivered by an INS.

As previously indicated, in some cases, electrical stimulation signals generated and delivered to patient 12 by INS 26 may be sensed by ICD 16 and ICD 16 may mischaracterize the sensed electrical stimulation signals as cardiac signals. FIG. 9 is a flow diagram illustrating an example technique that therapy system 10 may implement in order to minimize the possibility that ICD 16 delivers electrical stimulation to heart 14 in response to detecting electrical signals generated by INS 26 that resemble an arrhythmic cardiac signal. While the techniques shown in FIGS. 9-12B, 16, 19-21, and 23-30 are primarily described as being performed by one or more of processors 90, 110, 130 of ICD 16, INS 26, and programmer 24, respectively, any one or more parts of the techniques described herein may be implemented by a processor of one of the devices 16, 24, 26, alone or in combination with each other.

INS 26 may deliver neurostimulation to patient 12 (140) and ICD 16 may sense cardiac signals (142). As described above, stimulation generator 114 of INS 26 (FIG. 7) may generate electrical stimulation signals according to therapy parameter values defined by a therapy program or a therapy program group, and deliver the signals to patient 12 via a selected subset of electrodes 124 (FIG. 7) of lead 28. ICD 16 may sense cardiac signals of heart 14 via any subset of electrodes 50, 52, 54, 56, 58, and 60 of leads 18, 20, 22 (FIGS. 2 and 3) and electrode 68 of housing 70. True electrical cardiac signals are generated as heart 14 depolarizes and repolarizes.

Processor 90 of ICD 16 may detect a potential arrhythmia based on the sensed cardiac signals (144). The potential arrhythmia may be, for example, a suspected bradycardia or a suspected tachyarrhythmia. The cardiac signals sensed by ICD 16 may appear to indicate that heart 14 of patient 12 is in an arrhythmia, but, as described herein, ICD 16 may sense noise from delivery of stimulation by INS 26 in addition to the true cardiac signals. The noise (also referred to as crosstalk) may mask the true cardiac activity of heart 14, and, therefore, the detected arrhythmia may be referred to as a potential arrhythmia.

Processor 90 may implement any suitable technique to detect a potential arrhythmia of heart 14 (144). Processor 90 of ICD 16 may detect a potential arrhythmia by detecting a threshold number of arrhythmia events or an arrhythmia episode, which includes a predetermined number of arrhythmia events. In some examples, an arrhythmia event may comprise a tachyarrhythmia event, which includes a cardiac cycle that has an R-R interval that is less than a predetermined threshold value. If desired, processor 90 may characterize the arrhythmia event as a ventricular fibrillation event, a ventricular tachycardia event or a fast ventricular tachycardia event, where different threshold values may be used to characterize the cardiac cycle as the different types of events, e.g., based on the duration of the cardiac cycles. In other examples, the arrhythmia event may comprise a bradycardia event, which includes a cardiac cycle that has an R-R interval that is greater than a predetermined threshold.

The threshold duration values for determining whether an R-R interval qualifies a cardiac cycle as an arrhythmia event may be stored by memory 92 of ICD 16 (FIG. 6). In addition, the threshold number of arrhythmia events that are characterized as a potential arrhythmia or the number of arrhythmia events that constitute an arrhythmia episode may be stored by memory 92 of ICD 16 (FIG. 6) or a memory of another device (e.g., INS 26 or programmer 24). In some examples, the threshold number may be about two to about five arrhythmia events, such that processor 90 may detect a potential arrhythmia after about two to about five arrhythmia events are detected. However, processor 90 may use any suitable threshold number of arrhythmia events to detect a potential arrhythmia. In other examples, other techniques for detecting a potential arrhythmia may be used.

If processor 90 of ICD 16 does not detect a potential arrhythmia (144), processor 90 may not take any action to modify INS 26 and INS 26 may continue delivering electrical stimulation therapy to patient 12 (140) according to the current therapy program or program group. On the other hand, if processor 90 of ICD 16 detects a potential arrhythmia based on the sensed cardiac signals (144), processor 90 may determine that modification to the neurostimulation signals delivered by INS 26 are desirable in order to, for example, reduce the crosstalk between ICD 16 and INS 26. Thus, processor 90 may initiate the modification to the neurostimulation signals delivered by INS 26 (146).

In some examples, processor 90 of ICD 16 initiates the modification to the electrical stimulation signals generated and delivered by INS 26. For example, processor 90 of ICD 16 may provide INS 26 with a control signal via the respective telemetry modules 98, 118, where the control signal causes processor 110 of INS 26 to modify one or more electrical stimulation parameter values of the electrical stimulation generated and delivered by INS 26. In other examples, processor 90 of ICD 16 may modify the one or more electrical stimulation parameter values and transmit the modified parameter values to INS 26. The stimulation parameter values that may be modified include, but are not limited to, a current amplitude, a voltage amplitude, a pulse width, a slew rate, a pulse rate, a continuous waveform frequency, a duty cycle, an electrode combination, a timing of the delivery of the electrical stimulation relative to a cardiac cycle of the heart of the patient, a waveform shape, and a signal envelope of the electrical stimulation signal.

Modifying the one or more electrical stimulation parameter values that define the electrical stimulation signals generated and delivered by INS 26 may help change the characteristics of the electrical signal delivered by INS 26 and sensed by ICD 16. The modified neurostimulation signal generated and delivered by INS 26 may no longer resemble cardiac signals, thereby minimizing the possibility that ICD 16 senses the neurostimulation signals and mischaracterizes the signals as cardiac signals. For example, the modified neurostimulation signal may have a frequency component that falls outside of a sensing bandpass filter used by ICD 16 to sense cardiac signals. In this way, ICD 16 may "ignore" the modified neurostimulation signals.

The current or voltage amplitude or the frequency of the electrical signal that ICD 16 senses may change after the electrical stimulation parameter values for INS 26 are modified (146). As an example, if the current or voltage amplitude of the electrical stimulation signals delivered by INS 26 is modified, the current or voltage amplitude of the modified neurostimulation signals may no longer resemble cardiac signals and ICD 16 may no longer sense the electrical stimulation signals or mischaracterize the electrical stimulation signals as cardiac signals. As another example, the current or voltage amplitude of the modified neurostimulation signals may below the current or voltage amplitude threshold used by ICD 16 to identify cardiac signals. As another example, if the frequency of the electrical stimulation signal delivered by INS 26 is modified, the frequency of the signal sensed by ICD 16 may no longer have the required frequency or morphology to resemble an arrhythmic cardiac signal (e.g., the neurostimulation signals may no longer resemble a cardiac signal having short R-R intervals that characterize the signals as ventricular fibrillation cardiac signals).

In some examples, processor 110 of INS 26 may modify the combination of electrodes that INS 26 uses to deliver stimulation to patient 12. That is, processor 110 may select a different subset of electrodes 124 of lead 28 (FIG. 7) that are activated or modify the polarity of the selected electrodes. Modifying the electrode combination that is used to deliver neurostimulation may help reduce the amount of noise detected by ICD 16 from the delivery of electrical stimulation by INS 26. For example, modifying the electrode combination with which INS 26 delivers electrical stimulation signals may help steer the stimulation field away from the sensing field of ICD 16 or at least reduce the amount of stimulation field that is sensed by ICD 16.

In addition, modifying the electrode combination that is used to deliver neurostimulation may help reduce the amount of noise detected by ICD 16 by changing the nature of the noise detected by ICD 16. For example, modifying the neurostimulation electrode combination may change the vector between the electrodes with which the neurostimulation signal is delivered to tissue of patient 12 and the sensing electrodes of ICD 16 that are used to sense a cardiac signal. Changing the relative vector with which the sensing electrodes of ICD 16 may sense electrical signals delivered by INS 26 may help change the characteristics of the electrical signals delivered by INS 26 and sensed by ICD 16, such as the current or voltage amplitude of the neurostimulation signals sensed by ICD 16, the frequency of the signals, and the like. Other types of modifications to the neurostimulation signals generated and delivered by INS 26 are also contemplated.

After modifying the one or more electrical stimulation parameter values that define the electrical stimulation signals generated and delivered by INS 26 (146), INS 26 may deliver stimulation to patient 12 via the modified electrical stimulation parameter values (147). After INS 26 begins delivering stimulation to patient 12 with the modified electrical stimulation signals, processor 90 of ICD 16 may confirm the presence of the arrhythmia (148). Processor 90 may confirm the presence of the arrhythmia using any suitable technique, such as the techniques that were used to detect the arrhythmia (144). In some examples, if processor 90 confirms that the arrhythmia is present, processor 90 of ICD 16 or processor 110 of INS 26 may modify the neurostimulation signals generated and delivered by INS 26 at least one more time in an attempt to reduce the electrical noise attributable to 26 (144).

In other examples, if, after modifying the neurostimulation signals delivered by INS 26, processor 90 confirms that the arrhythmia is present, processor 90 of ICD 16 may determine that the arrhythmia is a true arrhythmia. In response, processor 90 may characterize a type of true arrhythmia detected. For example, based on the R-R interval of the sensed cardiac signals upon which the true arrhythmia was detected, processor 90 may determine whether the arrhythmia is a ventricular fibrillation, a bradycardia event, a supraventricular tachycardia, and the like. The type of true arrhythmia may be identified in order to select the appropriate cardiac rhythm therapy. Processor 90 may select a therapy program from memory 92 (FIG. 6) of ICD 16 or a memory of another device based on the type of true arrhythmia that is detected. For example, a plurality of therapy programs for a plurality of different types of arrhythmia may be stored by memory 92. After selecting a cardiac rhythm therapy based upon the type of true arrhythmia that is detected, processor 90 may control stimulation generator 94 (FIG. 6) to deliver electrical stimulation to heart 14 based on the selected therapy in order to terminate the arrhythmia.

In some examples, INS 26 may deliver electrical stimulation therapy to patient 12 according to the modified neurostimulation signals (147) for a finite period of time (rather than substantially indefinitely) and then revert back to the prior electrical stimulation parameter values after the finite period of time. In some examples, the finite period of time may be selected by a clinician and stored by memory 92 of ICD 16 or a memory of another device, such as INS 26.

In some examples of the technique shown in FIG. 9, as well as the other techniques described herein for modifying therapy delivery by INS 26 to minimize crosstalk with ICD 16 (e.g., FIGS. 10 and 11A-11D), INS 26 may deliver neurostimulation to patient 12 (140) for a test period of time, e.g., for a certain number of cardiac cycles of patient 12, and processor 90 of INS 26 may determine if the arrhythmia is detected during the delivery of electrical stimulation by INS 26. For example, INS 26 may deliver stimulation to patient 12 for about ten to about twenty cardiac cycles (e.g., as indicated by heart beats), and during that time, ICD 16 may sense cardiac signals (142) and processor 90 may determine whether a potential arrhythmia is detected (144). The test electrical stimulation delivered by INS 26 may provide therapeutic benefits to patient 12. In some examples, if the potential arrhythmia is detected during the delivery of the test neurostimulation to patient 12, processor 90 may determine that the neurostimulation may be interfering with the detection of true cardiac signals by ICD 16. Thus, in some examples, processor 90 may initiate the modification to the neurostimulation signals delivered by IND 26 (146), as described above with respect to FIG. 9.

Figure 10:
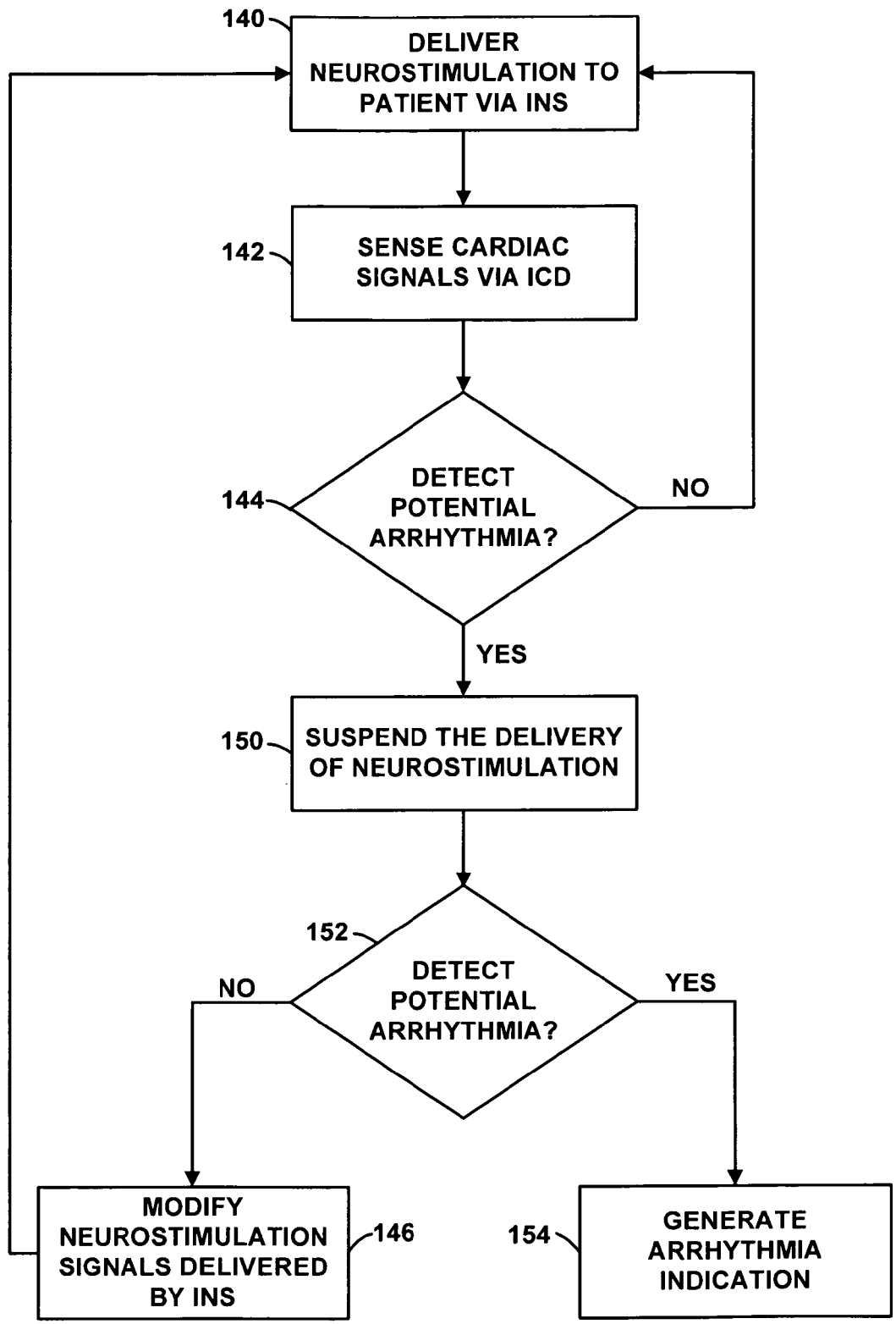
FIG. 10 is a flow diagram illustrating another example technique for modifying electrical stimulation therapy delivered by an INS.

FIG. 10 is a flow diagram of an example technique that may be implemented to determine whether an arrhythmia detected by ICD 16, INS 26 or another device may have been attributable to noise from neurostimulation delivered by INS 26. According to the example technique shown in FIG. 10, INS 26 may deliver neurostimulation to a nonmyocardial tissue site (e.g., proximate a nerve) within patient 12 according to a therapy program or therapy program group (140) and ICD 16 may sense cardiac signals (142). Processor 90 of ICD 16 may detect a potential arrhythmia based on the sensed cardiac signals using any suitable technique, such as the techniques described above with respect to FIG. 9 (144). If processor 90 does not detect a potential arrhythmia, INS 26 may continue delivering neurostimulation to patient 12 according to the therapy program or therapy program group (140).

If processor 90 of ICD 16 detects a potential arrhythmia (144), processor 90 may adjust the delivery of neurostimulation by INS 26 (150). In one example, processor 90 of ICD 16 may generate and deliver a control signal to INS 26 via the respective telemetry modules 98, 118. Upon receiving the control signal, processor 110 of INS 26 may temporarily adjust the delivery of stimulation, such as by suspending the active delivery of electrical stimulation to patient 12 or reducing an intensity of a stimulation signal delivered to patient 12. The control signal may indicate how long INS 26 should deliver therapy according to the adjusted parameters or may only indicate that INS 26 should adjust the delivery of neurostimulation. For example, the control signal may indicate how long INS 26 should suspend the delivery of neurostimulation. In some examples, processor 110 of INS 26 may refer to instructions stored within memory 112 of INS 26 that indicate the duration of time for which INS 26 should suspend or otherwise adjust the delivery of neurostimulation in response to receiving the control signal from ICD 16. The stored instructions may also indicate other operating parameters for the suspension period. For examples, in some cases, rather than deactivating all electrical stimulation signals delivered by INS 26, processor 110 may control stimulation generator 114 to deliver stimulation to patient 12 according to a different set of therapy parameters, such as a therapy program that defines electrical stimulation having a lower intensity (e.g., a lower amplitude or frequency).

After INS 26 suspends or otherwise adjusts the delivery of neurostimulation (150), processor 90 of ICD 16 may sense cardiac signals and determine whether the cardiac signals indicate a potential arrhythmia (152). If the cardiac signals indicate a potential arrhythmia after neurostimulation is suspended or otherwise adjusted, processor 90 of ICD 16 may determine that the arrhythmia was not detected based on crosstalk from the delivery of neurostimulation by INS 26. Processor 90 may, for example, determine that the arrhythmia was detected based on true cardiac signals and that a true arrhythmia may be present. Thus, in the technique shown in FIG. 10, processor may generate an arrhythmia indication if the cardiac signals indicate a potential arrhythmia after neurostimulation is suspended or otherwise adjusted (154). The arrhythmia indication may be a value, flag, or signal that is stored or transmitted to indicate the detection of an arrhythmia.

The arrhythmia indication may be used to control different aspects of therapy system 10. In some examples, processor 90 may control stimulation generator 94 (FIG. 6) to generate and deliver at least one of pacing, cardioversion or defibrillation therapy to heart 14 upon the generation of the arrhythmia indication. In other examples, processor 90 may confirm the detection of the arrhythmia using physiological parameter of patient 12 other than electrical cardiac signals upon the generation of the arrhythmia indication. For example, processor 90 may confirm the detection of the arrhythmia based on pressure within heart 14, as described in U.S. patent application Ser. No. 12/180,160 by Mayotte, which is entitled, "SENSING INTEGRITY DETERMINATION BASED ON CARDIOVASULAR PRESSURE," was filed on Jul. 25, 2008, and published as U.S. Patent Application Publication No. 2009/0026201 on Jan. 29, 2009.

In other examples, processor 90 may confirm the detection of the arrhythmia based on relative tissue perfusion values, blood oxygen saturation levels, blood pressure, heart sounds, cardiovascular pressure, respiratory rate, intrathoracic impedance, cardiac mechanical activity, body temperature, acoustic signals indicative of cardiac mechanical activity, and the like. A decrease in tissue perfusion or blood oxygen saturation levels may indicate the presence of an arrhythmia for which therapy delivery to heart 14 is desirable. For example, processor 90 may discriminate between hemodynamically tolerated arrhythmias and arrhythmias for which therapy delivery is desirable based on the blood oxygen saturation level associated with the detected arrhythmia. Processor 90 may also store the arrhythmia indication in memory 92 of ICD 16 or a memory of another device, such as programmer 24 (FIG. 1) for later analysis by a clinician.

If the cardiac signals sensed by ICD 16 do not indicate a potential arrhythmia after neurostimulation is suspended or otherwise adjusted, processor 90 of ICD 16 may determine that the previous arrhythmia detection (144) was based on crosstalk from the delivery of neurostimulation by INS 26. Accordingly, processor 90 may initiate the modification of the neurostimulation (146), as described with respect to FIG. 9. After the neurostimulation signal is modified, e.g., via modifying one or more stimulation parameter values, INS 26 may deliver neurostimulation to patient 12 via the modified neurostimulation signal and processor 90 may continue controlling sensing module 96 (FIG. 6) of ICD 16 to sense cardiac signals (142). The technique shown in FIG. 10 may then be repeated as necessary.

FIGS. 11A-11D are flow diagrams illustrating a technique that may be implemented to modify the electrical stimulation signals generated and delivered by INS 26 in order to reduce the crosstalk between ICD 16 and INS 26. Crosstalk may refer to the phenomenon in which an electrical stimulation signal generated and delivered by INS 26 interferes with the ability of ICD 16 to deliver cardiac therapy to heart 14 of patient 12 (FIG. 1). For example, the technique shown in FIGS. 11A-11D may be used to minimize the possibility that ICD 16 detects the neurostimulation signals and mischaracterizes the signals as cardiac signals by modifying one or more characteristics of the neurostimulation signal (e.g., the signal frequency, signal amplitude, slew rate, duty cycle, electrode combination, waveform shape, signal envelope, pulse width, and the like).

Processor 90 of ICD 16 may receive cardiac signals sensed via any of electrodes 50, 52, 54, 56, 58, 60, 68, 72, 74, and 76 (FIG. 3) of leads 18, 20, 22 or housing 70 of ICD 16. Processor 90 may detect a potential arrhythmia based on the sensed cardiac signals (160). For example, as described above with respect to FIG. 9, processor 90 may detect an arrhythmia event or an arrhythmia episode, which includes a predetermined number of arrhythmia events. In some examples, the arrhythmia event may comprise a tachyarrhythmia event, which includes a cardiac cycle that has an R-R interval that is less than a predetermined threshold value. The threshold value may be stored within memory 92 of ICD 16 (FIG. 6). In other examples, the arrhythmia event may comprise a bradycardia event, which includes a cardiac cycle that has an R-R interval that is greater than a predetermined threshold value, which may also be stored in memory 92 of ICD 16. The predetermined threshold number of arrhythmia events that processor 90 detects prior to determining that an arrhythmia episode is detected may be stored in memory 92 of ICD 16 (FIG. 6) or a memory of another device.

Upon detecting the potential arrhythmia (160), processor 90 of ICD 16 may temporarily cause INS 26 to suspend or otherwise adjust the delivery of neurostimulation signals to patient 12, e.g., by decreasing the intensity of stimulation (150), as described with respect to FIG. 10. If processor 90 detects the potential arrhythmia after INS 26 suspends or otherwise adjusts the delivery of stimulation signals to patient 12, processor 90 may determine that the sensed cardiac arrhythmia is a true cardiac arrhythmia. Thus, processor 90 may control stimulation generator 94 (FIG. 6) of ICD 16 to deliver cardiac therapy to patient 12 in order to try to terminate the arrhythmia (162). The cardiac therapy may be selected based on the type of arrhythmia that is detected. For example, if processor 90 detects a ventricular fibrillation, processor 90 may control stimulation generator 94 to generate and deliver defibrillation shocks electrical stimulation to heart 14 until the ventricular fibrillation of heart 14 is stopped. In other examples, processor 90 may confirm the cardiac arrhythmia based on physiological parameters of patient 12 other than sensed electrical cardiac signals, such as based on vascular pressure, prior to delivering the cardiac therapy to terminate the arrhythmia.

If processor 90 does not detect the potential arrhythmia after INS 26 stops actively delivering stimulation signals to patient 12, processor 90 may determine that the arrhythmia may have been detected based on electrical stimulation signals delivered to tissue of patient 12 by INS 26. That is, processor 90 may determine that the electrodes 50, 52, 54, 56, 58, 60, 68, 72, 74, and 76 (FIG. 3) that were used to sense the electrical cardiac signals sensed the neurostimulation signals and processor 90 mischaracterized the sensed neurostimulation signals as electrical cardiac signals. This may indicate that the amount of crosstalk between ICD 16 and INS 26 exceeds an acceptable amount. Accordingly, either processor 90 of ICD 16 or processor 110 of INS 110 may modify a stimulation parameter value used by INS 26 to generate the neurostimulation signals in order to help reduce the amount of crosstalk.

As previously indicated, modifying at least one stimulation parameter value that defines the electrical stimulation therapy provided by INS 26 may help change at least one characteristic of the electrical stimulation signal delivered by INS 26, such that ICD 16 either ignores the signal (i.e., does not sense the signal) or senses the electrical stimulation signal delivered by INS 26 and recognizes that the sensed signal is not a true cardiac signal.

In the example shown in FIGS. 11A-11D, processor 110 of INS 26 modifies one stimulation parameter value at a time. For example, processor 110 may modify the stimulation parameter value that least affects the efficacy of therapy delivery to patient 12 by INS 26 and/or most likely reduces the possibility that ICD 16 will mischaracterize the neurostimulation signal as a cardiac signal. In other examples, processor 110 may modify the stimulation parameter values in any order or may modify more than one stimulation parameter value at a time. While the description of FIGS. 11A-11D states that processor 110 of INS 26 modifies the stimulation parameter values of INS 26, in other examples, processor 90 of ICD 16 or a processor of another device (e.g., programmer 24) may modify the stimulation parameter values and provide the modified values to processor 110 of INS 26 or processor 110 of INS 26 may otherwise act under the direction of processor 90 of ICD 16.

Figure 11A:
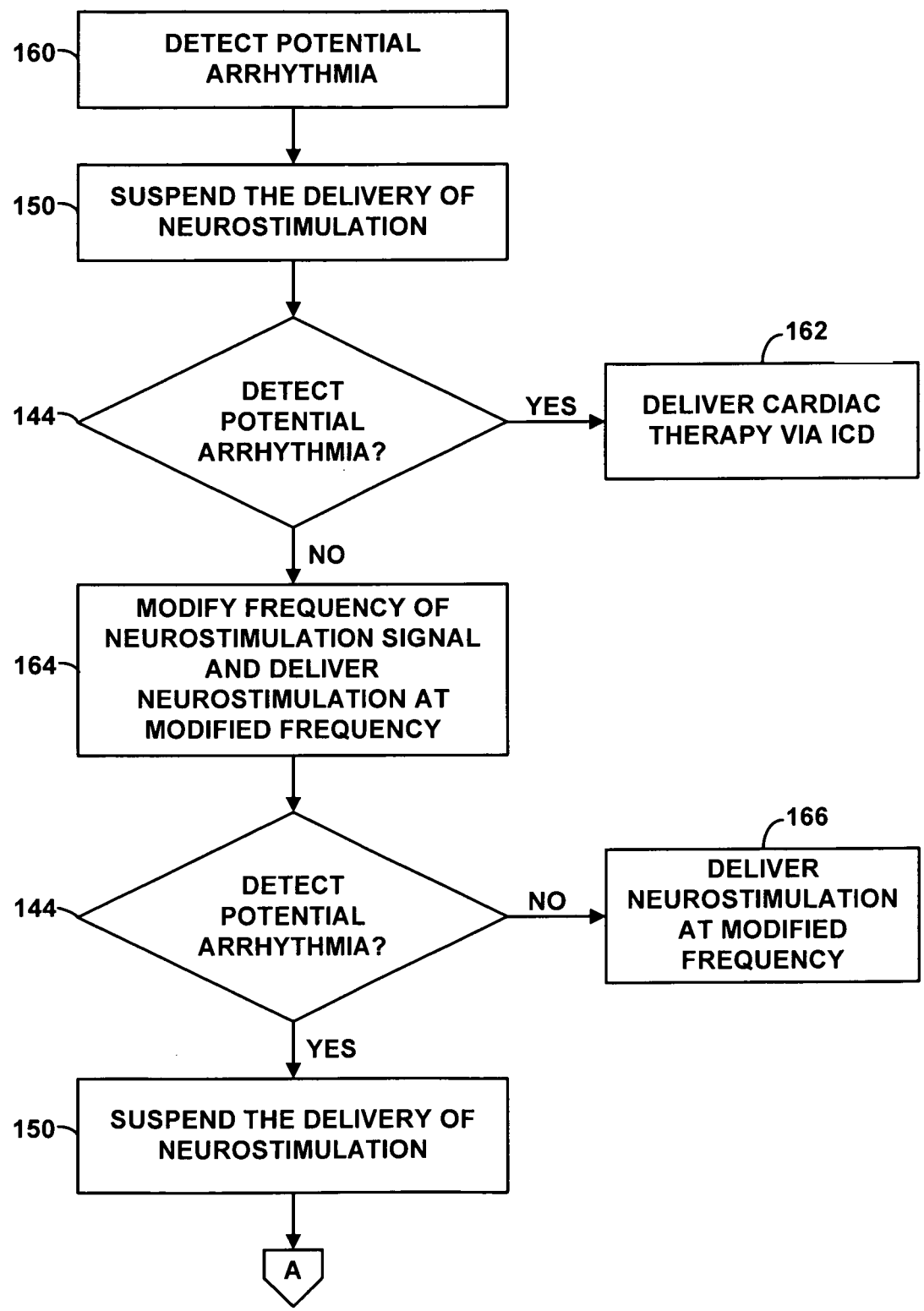
FIGS. 11A-11D are flow diagrams illustrating another example technique for modifying electrical stimulation therapy delivered by an INS.

In the example shown in FIG. 11A, processor 110 may modify a stimulation parameter value by modifying a frequency of the neurostimulation signal and processor 110 may subsequently controls stimulation generator 114 of INS 26 (FIG. 7) to generate and deliver electrical signals having the modified frequency (164). In some examples, processor 110 may store the modified frequency in memory 112 as a therapy program.

In some examples, processor 110 may modify the frequency based on a set of rules that are stored in memory 112 of INS 26 or another device, such as ICD 16 or programmer 24. The rules may, for example, provide a range of frequency values that provide efficacious therapy to patient 12 and the increments with which processor 110 may modify the frequency (164). The range of frequency values that provide efficacious therapy to patient 12 may indicate the maximum frequency and the minimum frequency of stimulation signals that provide efficacious therapy to patient 12. Thus, in some examples, the rules may prohibit processor 110 from modifying the frequency outside of the range of stored frequency values in order to prevent processor 110 from modifying the electrical stimulation therapy delivery provided by INS 26 such that the therapy does not provide therapeutic benefits to patient 12.

In some examples, the rules may indicate the type of modification processor 110 may make to the stimulation parameter based on the type of arrhythmia that was detected by ICD 16. For example, the rules may indicate that if a tachyarrhythmia is detected, the frequency of the neurostimulation signal generated by INS 26 should be decreased by a particular increment. Decreasing the frequency of the neurostimulation signal may decrease the possibility that ICD 16 will sense the stimulation signal and mischaracterize the neurostimulation signal as a cardiac signal. In some examples, decreasing the frequency of a neurostimulation signal may result in electrical noise that does not meet the requirements of a tachyarrhythmia (e.g., does not appear to have an R-R interval that is less than a predetermined threshold value). As another example, the rules may indicate that if a bradycardia is detected, the frequency of the neurostimulation signal generated by INS 26 should be increased by a particular increment. The neurostimulation signal having the increased frequency may no longer resemble a cardiac signal, or at least may no longer resemble a cardiac signal that indicates a bradycardia (e.g., does not appear to have an R-R interval that is greater than a predetermined threshold value).

After processor 110 of INS 26 modifies the frequency of the neurostimulation signal, processor 90 of ICD 16 may sense cardiac signals and determine whether an arrhythmia is still detected based on the sensed cardiac signals (144). If the arrhythmia is no longer detected, processor 90 of ICD 16 may determine that the prior-detected arrhythmia was detected based on neurostimulation signals delivered by INS 26 and that the modification to the frequency (164) successfully reduced the amount of crosstalk between INS 26 and ICD 16. Thus, if the arrhythmia is no longer detected after modifying the frequency of the neurostimulation, processor 110 may not take any further action to modify the neurostimulation delivered by stimulation generator 114. Stimulation generator 114 may continue generating and delivering neurostimulation to patient 12 at the modified frequency (166).

On the other hand, if processor 90 of ICD 16 detects a cardiac arrhythmia after the frequency of the neurostimulation signal was modified, processor 90 of ICD 16 may control INS 26 to temporarily suspends or adjusts the delivery of neurostimulation signals to patient 12 (150), as described with respect to FIG. 10. If processor 90 detects the potential arrhythmia after INS 26 suspends or otherwise adjusts the delivery of stimulation signals to patient 12, processor 90 may determine that the detected arrhythmia was a true arrhythmia and control stimulation generator 94 (FIG. 6) of ICD 16 to deliver cardiac therapy (e.g., at least one of pacing, cardioversion or defibrillation pulses) to patient 12 in order to try to terminate the arrhythmia (162). Again, in some examples, processor 90 may confirm the presence of the arrhythmia based on a physiological parameter of patient 12 other than the electrical cardiac signals prior to delivering the cardiac therapy.

If processor 90 does not detect the arrhythmia after INS 26 stops delivering neurostimulation to patient 12, processor 90 may determine that the arrhythmia was detected based on noise, rather than true cardiac signals. The noise may be at least partially attributable to the crosstalk from INS 26. Thus, if processor 90 does not detect the arrhythmia after INS 26 stops delivering neurostimulation to patient 12, processor 90 may determine that the prior modification to the frequency of neurostimulation delivered by INS 26 was insufficient to reduce the noise and that ICD 16 is still sensing the neurostimulation signals and mischaracterizing the signals as cardiac signals. Accordingly, processor 110 of INS 26 may modify at least one more stimulation parameter value that defines the neurostimulation therapy delivered by INS 26.

Figure 11B:
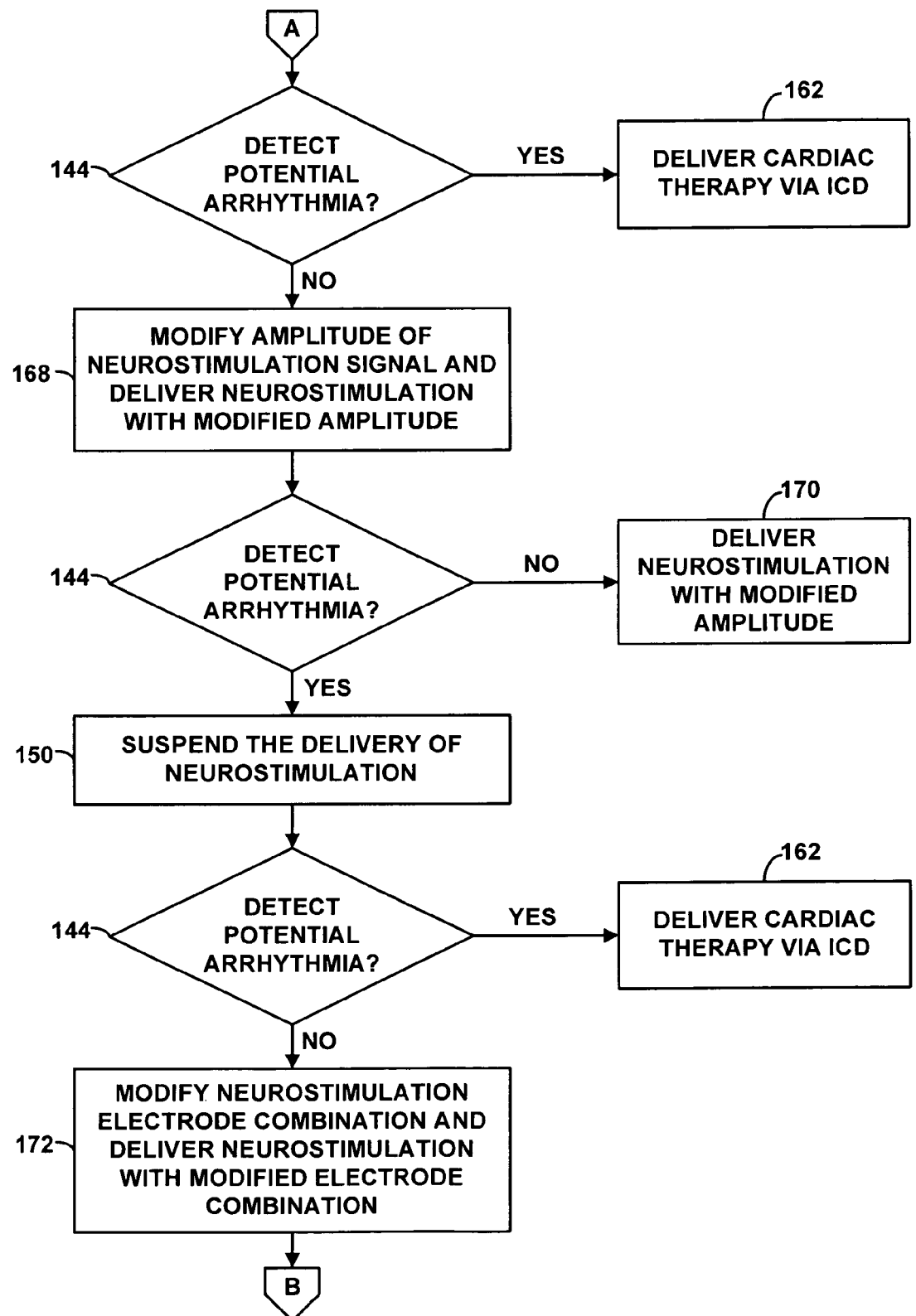
Figure 11C:
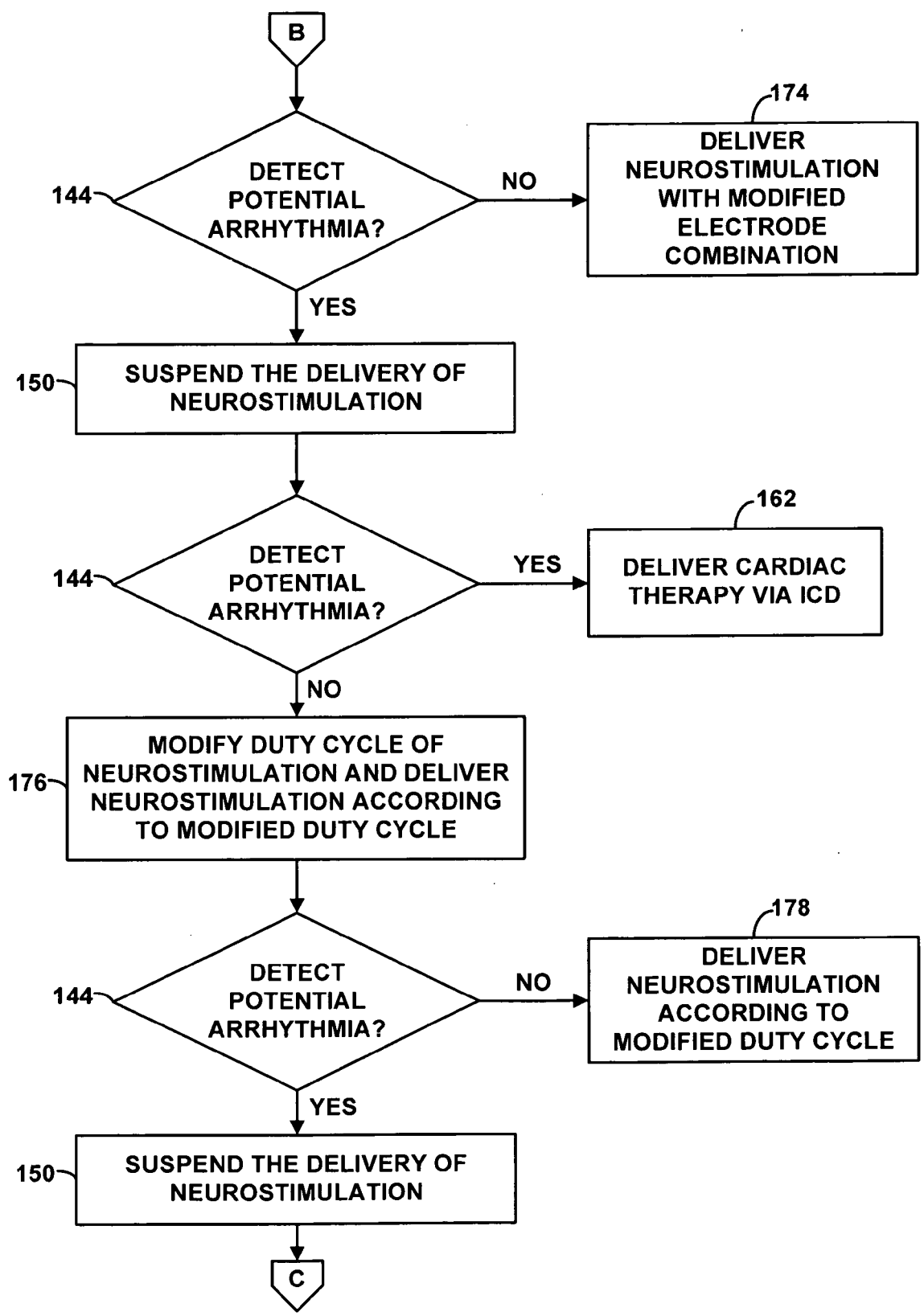
Figure 11D:
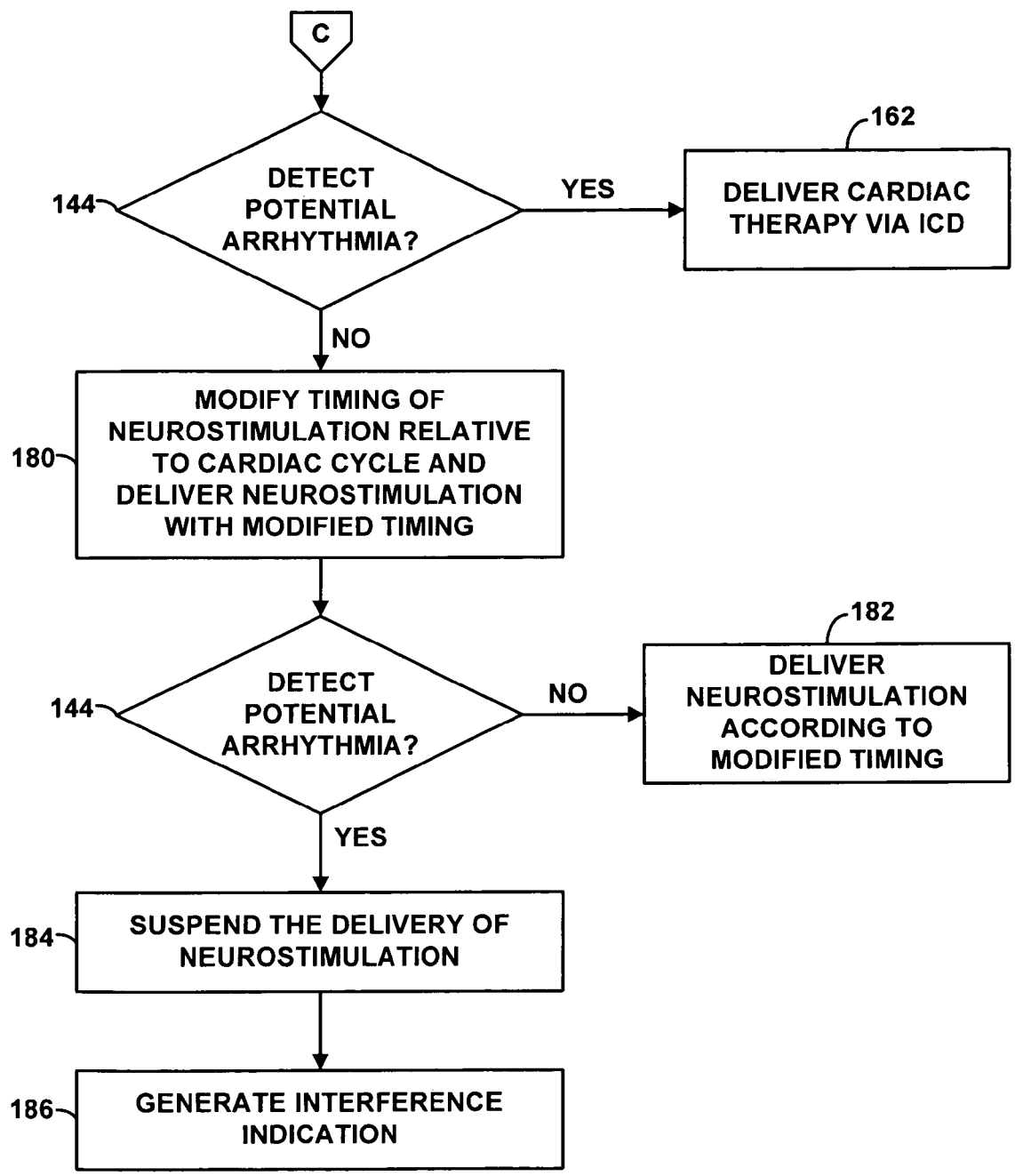

In the example shown in FIG. 11B, processor 110 modifies an amplitude of the neurostimulation signal and delivers neurostimulation according to the modified amplitude (168). In other examples, processor 110 may modify one or more other types of stimulation parameter values, including the frequency of the neurostimulation signal. The amplitude that is modified may be a current amplitude or a voltage amplitude and may depend on, for example, the type of amplitude that is defined by the therapy program currently implemented by INS 26. In some examples, processor 110 may modify the amplitude of the neurostimulation signal by modifying the amplitude or pulse width value of the therapy program used by stimulation generator 114 to generate the neurostimulation signals. In other examples, as described with respect to FIGS. 12A and 12B, processor 110 may select a different therapy program from memory 112 in order to modify the amplitude.

As previously indicated, modifying an amplitude of the neurostimulation signal may result in a stimulation signal waveform that differs from a cardiac signal. For example, decreasing or increasing the amplitude of the neurostimulation signal may result in a signal that falls outside of the range of threshold amplitude values that INS 26 uses to detect a cardiac signal. Just as with the modification to the frequency (164), in some examples, processor 110 may modify the amplitude of the neurostimulation signal based on a set of rules that are stored in memory 112 of INS 26. The rules may provide a range of amplitude values that provide efficacious therapy to patient 12 and the increments with which processor 110 may modify the neurostimulation signal amplitude (168). In some examples, the rules may control processor 110 to modify the amplitude values within the stored range of values and prevent processor 110 from selecting an amplitude value that falls outside of the stored range of efficacious amplitude values. In addition, as indicated above, in some examples, the rules may indicate the type of modification processor 110 may make to the amplitude based on the type of arrhythmia that was detected by ICD 16.

After modifying the amplitude of the neurostimulation signal generated and delivered by INS 26, processor 90 of ICD 16 may sense cardiac signals and determine whether an arrhythmia is detected (144). If the arrhythmia is no longer detected, processor 90 of ICD 16 may determine that the prior detected arrhythmia was detected based on neurostimulation signals delivered by INS 26 and sensed by ICD 16, and that the modification to the neurostimulation signal amplitude (168) successfully changed a characteristic of the neurostimulation signal so that it no longer resembles a cardiac signal. Thus, if the arrhythmia is no longer detected after modifying the amplitude of the neurostimulation signal, processor 110 may not take any further action to modify the neurostimulation delivered by stimulation generator 114. Stimulation generator 114 may continue generating and delivering neurostimulation to patient 12 at the modified frequency and the modified amplitude (170).

On the other hand, if processor 90 of ICD 16 detects a cardiac arrhythmia after the frequency and amplitude of the neurostimulation signal were modified, processor 90 of ICD 16 may cause INS 26 to temporarily stop delivering neurostimulation signals to patient 12 (150). If processor 90 detects the potential arrhythmia after INS 26 suspends or otherwise adjusts the delivery of stimulation signals to patient 12, processor 90 may determine that the detected arrhythmia was a true arrhythmia and control stimulation generator 94 (FIG. 6) of ICD 16 to deliver cardiac therapy to patient 12 in order to try to terminate the arrhythmia (162).

If processor 90 does not detect the arrhythmia after INS 26 suspends or otherwise adjusts the delivery of neurostimulation to patient 12, processor 90 may determine that the arrhythmia was detected based on noise (e.g., from INS crosstalk), rather than true cardiac signals. Processor 90 may determine that the prior modifications to the frequency and amplitude of the neurostimulation signal generated and delivered by INS 26 were insufficient to reduce the crosstalk between ICD 16 and INS 26. That is, processor 90 may determine that ICD 16 is still sensing the neurostimulation signals and mischaracterizing the signals as cardiac signals. Accordingly, processor 110 of INS 26 may modify another parameter of the neurostimulation signal, e.g., in response to a control signal transmitted to INS 26 from processor 90 of ICD 16. In the example shown in FIG. 11B, processor 110 may modify an electrode combination that is used to deliver the neurostimulation signal to patient 12 and deliver neurostimulation with the modified electrode combination (172). The electrode combination may be defined by a therapy program used by INS 26 to generate the neurostimulation signals. Processor 110 may modify the electrode combination by modifying the therapy program currently implemented by INS 26 or by selecting a second therapy program from memory 112, whereby the second therapy program defines a different electrode combination.

An electrode combination defines the subset of electrodes 124 of lead 28 (FIG. 7) coupled to INS 26 that are used to deliver stimulation therapy to patient 12. The electrode combination may also refer to the polarities of the electrodes in the selected subset. Modifying the subset of electrodes 124 that are used to deliver stimulation therapy to patient 12 may change the amount of crosstalk between INS 26 and ICD 16 by changing the vector between the neurostimulation signal delivered by INS 26 and the electrodes 50, 52, 54, 56, 58, 60, 68, 72, 74, and/or 76 (FIG. 3) coupled to ICD 16 that are used to sense cardiac signals. For example, delivering the neurostimulation with a different subset of electrodes 124 may steer the electrical field generated by the delivery of neurostimulation to the patient's tissue in a different direction, which may change the intensity of the neurostimulation signal that is transmitted through the patient's body to the sense electrodes of ICD 16. This may help reduce the possibility that ICD 16 senses the neurostimulation signal and mischaracterizes the signal as a cardiac signal. For example, delivering the neurostimulation with a different subset of electrodes 124 may change the amplitude or frequency of the neurostimulation signal that is sensed by ICD 16, such that ICD 16 does not mischaracterize the neurostimulation signal as a cardiac signal.

Processor 110 may modify the electrode combination by, for example, modifying the quantity of electrodes that are selected to deliver neurostimulation to patient 12, modifying the location of the selected electrodes, and/or modifying the spacing between the selected electrodes. In addition to or instead of the aforementioned modifications to the electrode combination, processor 110 may increase the size of a ground reference electrode area, such as by increasing the number of ground electrodes. In some examples, the ground electrode may comprise an anode electrode, while in other examples the ground electrode may comprise one or more cathode electrodes. By reducing the resistance of the one or more grounded electrodes, the noise sensed by ICD 16 from the neurostimulation may be reduced by reducing the common mode noise.

In some examples, lead 28 coupled to INS 26 may comprise segmented electrodes or partial ring electrodes that do not extend around the entire outer circumference of lead 28. Segmented electrodes may be useful for directing neurostimulation in a specific direction to enhance therapy efficacy. In examples in which lead 28 comprises segmented or partial ring electrodes, processor 110 may modify the electrode combination by selecting segmented electrodes to deliver the neurostimulation in a different direction, such as a direction away from ICD 16 and its associated electrodes. Processor 110 may modify the direction of stimulation via the segmented electrodes in order to minimize the far field neurostimulation signal sensed by ICD 16.

In some examples, processor 110 may modify the electrode combination used to deliver the neurostimulation signal based on a set of rules or a predetermined set of electrode combinations that are stored in memory 112 of INS 26. The rules may indicate which electrodes may be activated or deactivated, and the order in which the activation and deactivation of particular electrodes may take place. For example, the delivery of stimulation via certain electrodes 124 (FIG. 7) may substantially increase or decrease the efficacy of neurostimulation therapy. Thus, in some examples, the stored rules may indicate that some electrodes should not be deactivated, or at least should be deactivated after other electrodes are deactivated, and other electrodes are not preferred electrodes for delivering electrical stimulation to patient 12.

In some examples, the rules may indicate the type of modifications processor 110 may make to the electrode combination, as well as the order in which the types of modifications may be made. For example, the rules may set forth a hierarchy of modifications, whereby the processor 110 may first modify the quantity of selected electrodes, followed by the selected electrodes, followed by the space between the selected electrodes.

After modifying the electrode combination used to deliver a neurostimulation signal by INS 26, processor 90 of ICD 16 may sense cardiac signals and determine whether an arrhythmia is detected (144). If the arrhythmia is no longer detected, processor 90 of ICD 16 may determine that the prior detected arrhythmia was detected based on neurostimulation signals delivered by INS 26 and sensed by ICD 16, and that the modification to the electrode combination (172) successfully reduced the crosstalk between INS 26 and ICD 16. Thus, if the arrhythmia is no longer detected after modifying the electrode combination used to deliver the neurostimulation signal, processor 110 may not take any further action to modify the neurostimulation delivered by stimulation generator 114. Stimulation generator 114 may continue generating and delivering neurostimulation signals having the modified frequency and amplitude with the modified electrode combination (174).

On the other hand, if processor 90 of ICD 16 detects a cardiac arrhythmia after the electrode combination used to deliver the neurostimulation signal was modified, processor 90 of ICD 16 may cause INS 26 to temporarily stop delivering neurostimulation signals to patient 12 (150). If processor 90 detects the potential arrhythmia after INS 26 suspends or otherwise adjusts the delivery of stimulation signals to patient 12, processor 90 may determine that the detected arrhythmia was a true arrhythmia and control stimulation generator 94 (FIG. 6) of ICD 16 to deliver cardiac therapy to patient 12 in order to try to terminate the arrhythmia (162), or may confirm the arrhythmia based on other physiological parameters of patient 12.

If processor 90 does not detect the arrhythmia after INS 26 suspends or otherwise adjusts the delivery of neurostimulation via the modified electrode combination to patient 12, processor 90 may determine that the arrhythmia was detected based on noise, rather than true cardiac signals. Processor 90 may determine that the prior modifications to the frequency and amplitude of the neurostimulation signal and the modification to the electrode combination used to deliver the neurostimulation signals were insufficient to reduce the crosstalk between ICD 16 and INS 26. Accordingly, processor 110 of INS 26 may modify another parameter of the neurostimulation signal. In the example shown in FIG. 11C, processor 110 may modify a duty cycle of the neurostimulation, and deliver neurostimulation with the modified duty cycle (176).

A duty cycle of neurostimulation may refer to the proportion of time during which a neurostimulation signal is actively delivered to patient 12. For example, INS 26 may deliver electrical stimulation to patient 12 in a regular duty cycle, whereby the stimulation is delivered for a first duration of time (e.g., in a single pulse or signal or a burst of multiple pulses or signals) and off for a second duration of time, followed by the stimulation delivery for the first duration of time and so forth. The duty cycle may indicate the ratio between the first duration of time and the total cycle time (the first duration plus the second duration of time). Modifying the duty cycle of the neurostimulation may help reduce the duration of the neurostimulation, such that even if crosstalk between ICD 16 and INS 26 is present due to the delivery of neurostimulation by INS 26, the neurostimulation signals may not achieve the required duration of a cardiac signal indicative of an arrhythmia. That is, as described above, processor 90 of ICD 16 may detect a potential arrhythmia by detecting a threshold number of arrhythmia events. If the duration of the neurostimulation is minimized by modifying the duty cycle of the neurostimulation, the neurostimulation signal may not resemble a cardiac signal comprising the threshold number of arrhythmia events. Thus, even if the neurostimulation signal resembles a potential arrhythmia event, processor 90 may not detect the threshold number of potential arrhythmia events based on the neurostimulation signals.

In some examples, processor 110 may modify the duty cycle of the neurostimulation signals based on a set of rules or by switching to another therapy program stored in memory 112 of INS 26. The rules may indicate maximum and minimum duty cycle values for the neurostimulation therapy, where the maximum and minimum may define a range of duty cycle values that may be selected without adversely affecting the efficacy of neurostimulation therapy. In some examples in which stimulation generator 114 delivers electrical stimulation pulses to patient 12, processor 110 may modify the pulse width of the pulses instead of or in addition to modifying the duty cycle of the neurostimulation.

After modifying the duty cycle of the neurostimulation signal delivered by INS 26, processor 90 of ICD 16 may sense cardiac signals and determine whether an arrhythmia is detected (144). If the arrhythmia is no longer detected, processor 90 of ICD 16 may determine that the prior detected arrhythmia was detected based on neurostimulation signals delivered by INS 26 and sensed by ICD 16, and that the modification to the duty cycle (176) successfully changed a characteristic of the neurostimulation signal so that it no longer resembles a cardiac signal. Thus, if the arrhythmia is no longer detected after modifying the electrode combination used to deliver the neurostimulation signal, processor 110 may not take any further action to modify the neurostimulation delivered by stimulation generator 114. Stimulation generator 114 may continue generating and delivering electrical stimulation signals having the modified frequency, amplitude, and duty cycle, and with the modified electrode combination (178).

On the other hand, if processor 90 of ICD 16 detects a cardiac arrhythmia after the duty cycle of the neurostimulation signal was modified, processor 90 of ICD 16 may cause INS 26 to temporarily suspend delivering neurostimulation signals to patient 12 or otherwise reduce the intensity of stimulation (150). If processor 90 detects the potential arrhythmia after INS 26 suspends or otherwise adjusts the delivery of stimulation signals to patient 12, processor 90 may determine that the detected arrhythmia was a true arrhythmia and control stimulation generator 94 (FIG. 6) of ICD 16 to deliver cardiac therapy to patient 12 in order to try to terminate the arrhythmia or may confirm the arrhythmia based on other physiological parameters of patient 12 (162).

If processor 90 does not detect the arrhythmia after INS 26 suspends or otherwise adjusts the delivery of neurostimulation having the modified duty cycle, processor 90 may determine that the arrhythmia was detected based on noise, rather than true cardiac signals. Processor 90 may determine that the prior modification to the frequency, amplitude, and duty cycle of the neurostimulation signal and the modification to the electrode combination used to deliver the neurostimulation signals were insufficient to reduce the crosstalk between ICD 16 and INS 26, such that ICD 16 is still sensing the neurostimulation signals and mischaracterizing the signals as cardiac signals. Accordingly, processor 110 of INS 26 may modify another therapy parameter of the neurostimulation therapy. In the example shown in FIG. 11D, processor 110 may modify the timing between the delivery of neurostimulation signals relative to the cardiac cycle of heart 14 of patient 12 (180). Processor 110 may then control stimulation generator 114 to deliver neurostimulation signals to patient 12 at the modified times (180).

In some examples, processor 110 controls stimulation generator 114 to deliver neurostimulation signals to patient 12 during a blanking period of sensing module 96 of ICD 16, and to withhold the delivery of neurostimulation signals outside of the blanking period. In other examples, processor 110 may control stimulation generator 114 to deliver neurostimulation signals to patient 12 during a blanking period of sensing module 96 and for a relatively short amount of time after the blanking period. The relatively short amount of time may include, for example, about 1 millisecond (ms) to about 100 ms, although other time ranges are contemplated. The blanking period may refer to a period of time during which sensing module 96 does not sense any cardiac signals. Therefore, sensing module 96 of ICD 16 may not inadvertently sense neurostimulation signals that are delivered during the blanking period. In some examples, the blanking period may be about 120 ms, although other blanking periods are contemplated.

In addition, in some examples, processor 110 may control stimulation generator 114 to deliver neurostimulation signals to patient 12 outside of the blanking period, but relatively early in a cardiac cycle. In some examples, sensing module 96 (FIG. 6) of ICD 16 may include an automatically adjusting sense amplifier threshold. In some examples, INS 26 may deliver stimulation to patient 12 early in the automatic adjustment period of the sensing module 96 amplifier because the sense amplifier may be less sensitive to noise from delivery of neurostimulation by INS 26 early in the automatic adjustment period of the sensing module 96 amplifier, which may help decrease oversensing.

Processor 110 of INS 26 may time the delivery of neurostimulation signals during the blanking period of sensing module 96 using any suitable technique. In some examples, processor 90 of ICD 16 may notify INS 26 at the beginning of each blanking period, and, in some cases, the end of each blanking period. The notification may be in the form of a flag or another format that may be transmitted to INS 26 via a wired or wireless signal. In other examples, ICD 16 and INS 26 have substantially synchronized clocks and memory 112 (FIG. 7) of INS 26 may store information that details the timing of the blanking period of sensing module 96. In addition, in some examples, ICD 16 and INS 26 may periodically synchronize their respective internal clocks, e.g., by via the respective telemetry modules 98, 118. For example, ICD 16 may instruct INS 26 to synchronize its clock to the clock of ICD 16, or INS 26 may instruct ICD 16 to synchronize its clock to the clock of INS 26. Synchronizing clocks may be useful for coordinating stimulation activity. In some examples, ICD 16 and INS 26 may each include a crystal controlled clock, with counters or other means to provide collaborative clocking or strobe or synchronizing of circuits.

After modifying the timing of neurostimulation such that it is delivered during a blanking period of sensing module 96 of ICD 16 (180), processor 90 of ICD 16 may sense cardiac signals and determine whether an arrhythmia is detected (144). If the arrhythmia is no longer detected, processor 90 of ICD 16 may determine that the prior detected arrhythmia was detected based on neurostimulation signals delivered by INS 26 and sensed by ICD 16, and that the modification to the timing of the neurostimulation signal relative to the cardiac signal sufficiently reduced the crosstalk between INS 26 and ICD 16. Thus, if the arrhythmia is no longer detected after modifying the timing of the delivery of the neurostimulation signals, processor 110 may not take any further action to modify the neurostimulation delivered by stimulation generator 114. Stimulation generator 114 may continue generating and delivering neurostimulation to patient 12 via the modified timing (182).

On the other hand, if processor 90 of ICD 16 detects a cardiac arrhythmia after the timing of the neurostimulation delivery was modified, processor 90 of ICD 16 may control INS 26 to indefinitely suspend the delivery of electrical stimulation signals to patient 12 or deliver electrical stimulation signals according to the adjusted stimulation parameters (184). Either processor 90 of ICD 16 or processor 110 of INS 26 may generate an interference indication (186) and transmit the indication to programmer 24 (FIG. 1) or store the interference indication in the respective memory 92, 112. The interference indication may indicate that the crosstalk between INS 26 and ICD 16 was not reducible by modifying one or more stimulation parameter values of INS 26. The clinician may later retrieve the stored interference indication and determine whether other measures may be taken in order to reduce the crosstalk between INS 26 and ICD 16. For example, the clinician may determine whether repositioning lead 28 coupled to INS 26 within patient 12 may help reduce the crosstalk.

In some examples, other types of therapy parameter values may be modified in accordance with the technique described with reference to FIGS. 11A-11D. For example, in other examples of the technique shown in FIGS. 11A-11D, processor 110 may modify the waveform shape of the neurostimulation signal, the signal envelope (e.g., by adjusting the stimulation start and stop times), and the like.

For each of the adjustments to the therapy parameter values of INS 26 described above with reference to FIGS. 11A-11D, the adjustments may be occur over several steps, rather than one step as described above. For example, the adjustments to the frequency of the neurostimulation signal may be made in several increments until a predetermined limit is reached. For example, processor 110 of INS 26 may modify the frequency in 5 Hz increments until the frequency is increased by a total of 50 Hz. Other increment and total limit values are contemplated. In some examples, a range of parameter values for a particular stimulation parameter may be implemented by processor 110 prior to modifying a different type of stimulation parameter value.

In addition, in some examples, two or more therapy parameter values of INS 26 may be adjusted in a single step, e.g., upon detecting a potential arrhythmia, rather than adjusting independent stimulation parameters in different steps as described above with reference to FIGS. 11A-11D. For example, upon detecting a potential arrhythmia, processor 110 of INS 26 may modify both the frequency and amplitude of a neurostimulation signal. Other combinations of therapy parameter values may also be modified together.

In some examples, processor 110 of INS 26 may generate electrical stimulation signals according to a different therapy program (or program group) in order to modify one or more stimulation parameter values. For example, processor 110 may control stimulation generator 114 to generate electrical stimulation signals according to a first therapy program, and, upon the detection of an arrhythmia, processor 110 may control stimulation generator 114 to generate electrical stimulation signals according to a second therapy program that has at least one different stimulation parameter value than the first therapy program. The first and second therapy programs, as well as any number of other therapy programs may be stored in memory 112 of INS 26 or a memory of another device, such as ICD 16.

As previously indicated, if ICD 16 detects an arrhythmia based on the electrical stimulation signals delivered by INS 26, switching therapy programs with which INS 26 generates stimulation signals may change the characteristics of the neurostimulation signals, which may reduce the possibility that ICD 16 detects the arrhythmia based on the electrical signals from INS 26. Thus, in some cases, if ICD 16 detects an arrhythmia after a therapy program of INS 26 is modified, ICD 16 may determine that the arrhythmia is a true arrhythmia or at least not detected based on electrical noise from the delivery of electrical stimulation signals by INS 26.

Figure 12A:
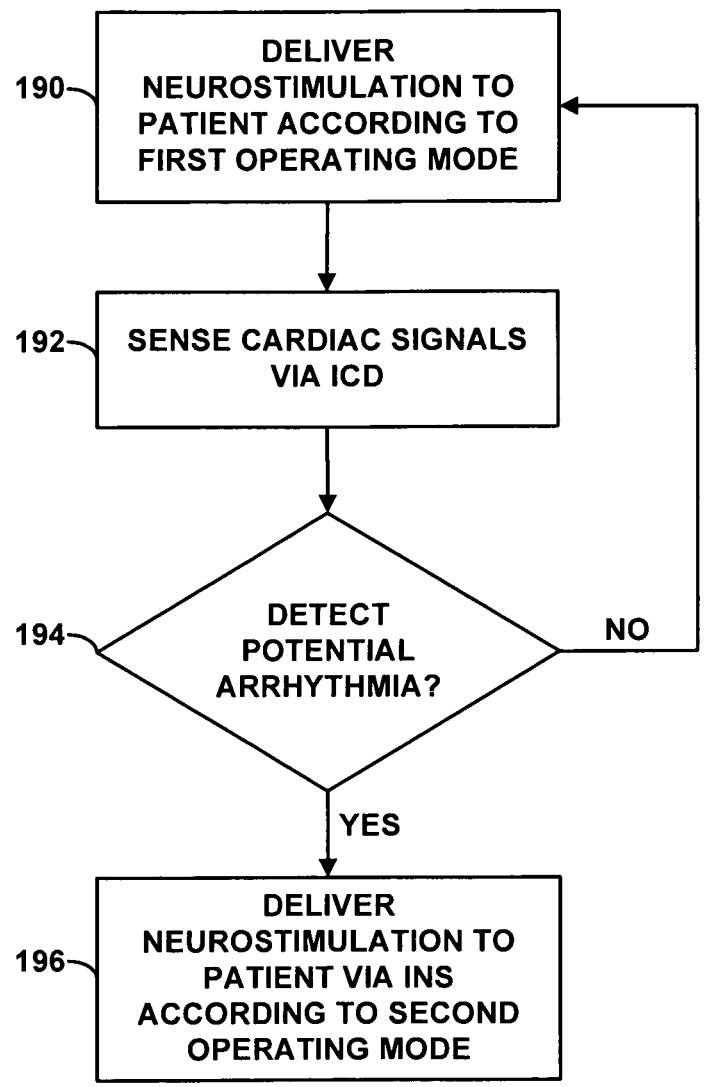
FIGS. 12A and 12B are flow diagrams illustrating example techniques for delivering electrical stimulation therapy to a patient.

FIG. 12A is a flow diagram of an operating mode of therapy system 10 including ICD 16 and INS 26. Processor 110 of INS 26 may control stimulation generator 114 to generate and deliver electrical stimulation according to a first operating mode to modulate a nerve of patient 12 or deliver electrical stimulation to a nonmyocardial tissue site of patient 12 that is not proximate a nerve (190). In the examples described herein, the first operating mode is defined by a first therapy program. As previously indicated, a therapy program defines values for the therapy parameters that define the electrical stimulation delivered by INS 26. In the case of electrical stimulation, the therapy parameters may include an electrode combination, and an amplitude, which may be a current or voltage amplitude, and, if INS 26 delivers electrical pulses, a pulse width for stimulation signals. The therapy program may also indicate the timing of the stimulation signals relative to, e.g., cardiac signals.

ICD 16 may sense cardiac signals via at least one or more of electrodes 50, 52, 54, 56, 58, 60, 68, 72, 74, and/or 76 (192). ICD 16 may determine whether the sensed cardiac signals, and, in some examples, one or more other physiological parameter values of patient 12 indicate an arrhythmia of heart 14 (194). If ICD 16 does not detect an arrhythmia (194), processor 110 of INS 26 may continue controlling stimulation generator 114 to generate and deliver neurostimulation to patient 12 according to the first operating mode. On the other hand, if ICD 16 detects an arrhythmia (194), processor 110 of INS 26 may control stimulation generator 114 of INS 26 to generate and deliver stimulation therapy according to a second operating mode that is different than the first operating mode (196). In the examples described herein, the second operating mode is defined by a second therapy program that is different than the first therapy program. The second therapy program may comprise at least one stimulation parameter value that differs from the first therapy program. In some examples, processor 90 of ICD 16 or another device (e.g., programmer 24) may instruct processor 110 of INS 26 to switch operating modes (e.g., switch therapy programs). In addition, in some examples, processor 90 of ICD 16 or another device may transmit the therapy parameter values of the second operating mode to INS 26.

The therapy parameter values of the first therapy program may be selected to provide patient 12 with efficacious neurostimulation therapy. In some cases, the therapy parameter values of the first therapy program may be selected with little or no regard as to the impact of the crosstalk from the neurostimulation on the sensing of cardiac signals by ICD 16. The second therapy program, on the other hand, may define therapy parameter values that minimize the possibility that ICD 16 senses the neurostimulation signals delivered by INS 26 and mischaracterizes the neurostimulation signals as cardiac signals. For example, the second therapy program may define a different frequency, current or voltage amplitude, pulse width or duty cycle than the first therapy program.

In some examples, the second therapy program defines a stimulation signal comprising a different waveform than the first therapy program. For example, processor 110 of INS 26 may select a second therapy program that defines a waveform that has a voltage or current amplitude that ramps up in amplitude and ramps down in amplitude over a longer period of time than a true cardiac signal (e.g., an EGM signal), such that ICD 16 does not mischaracterize the neurostimulation signal as a cardiac signal. The ramping up and down of a stimulation signal waveform may help reduce the amount of artifact imposed on the signal sensed by ICD 16 because the rise time of the neurostimulation signal may be less abrupt than a rise time of a true cardiac signal. In some examples, the waveforms defined by the second therapy program may comprise nonrectangular waveforms that gradually ramp up and gradually ramp down in amplitude over time. Example waveforms for stimulation signals defined by the second therapy program are shown and described with respect to FIGS. 13A-13I.

Processor 110 of INS 26 may generate and deliver electrical stimulation signals according to the second therapy program for a limited period of time, which may be preset by a clinician or another individual, or may be based on a sensed physiological parameter of patient 12. For example, processor 110 of INS 26 may generate and deliver electrical stimulation signals according to the second therapy program until ICD 16 no longer detects an arrhythmia or a predetermined amount of time following the detection of an arrhythmia, such as about thirty seconds to about ten minutes following the detection of an arrhythmia. In some examples, processor 110 of INS 26 may generate and deliver electrical stimulation signals according to the second therapy program until ICD 16 indicates that the detected arrhythmia has been terminated. ICD 16 may, for example, communicate with INS 26 via wireless communication techniques, as previously described.

Figure 12B:
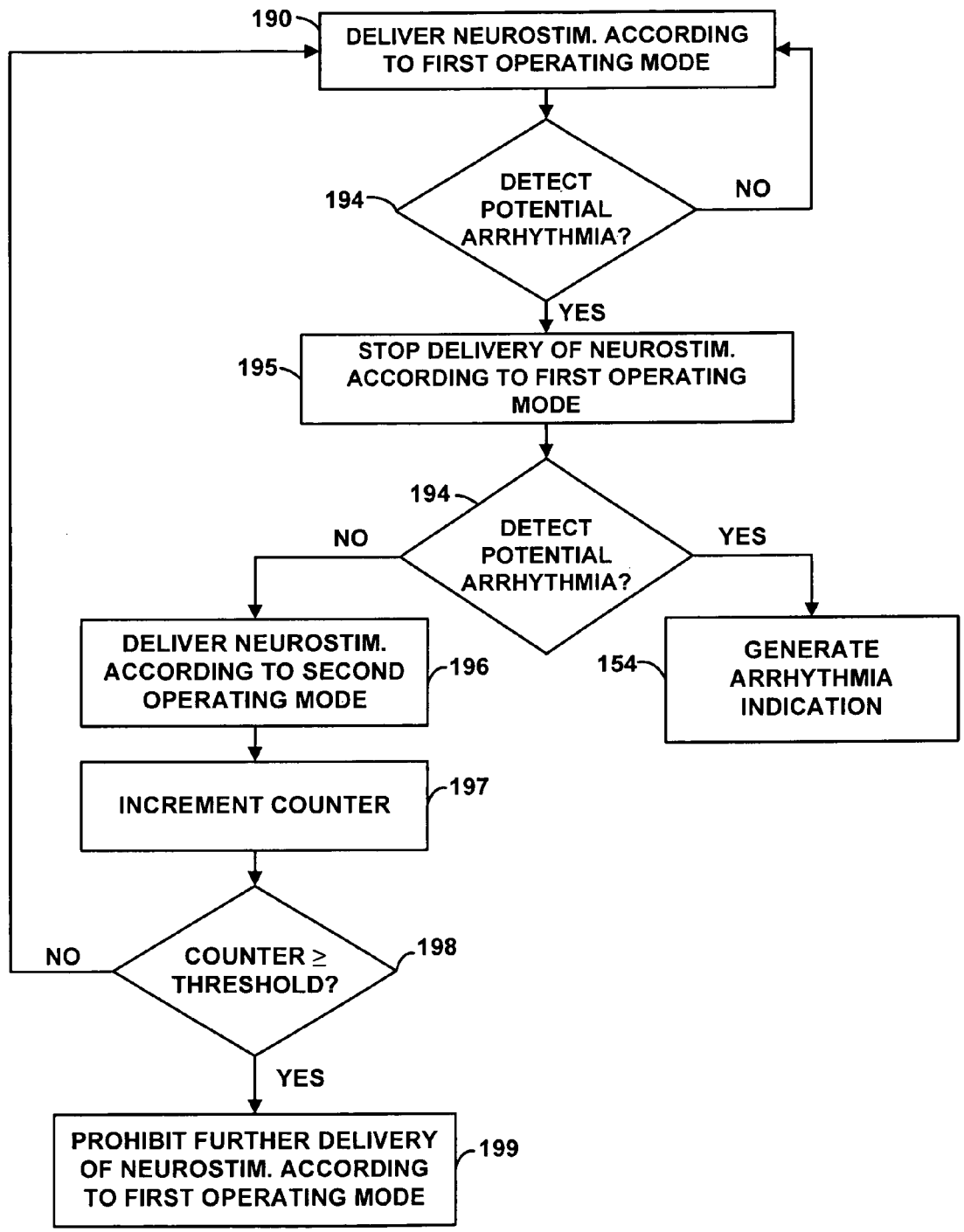

FIG. 12B is a flow diagram of another example technique that processor 110 may implement to control stimulation generator 114 of INS 26. Just as in the technique shown in FIG. 12A, processor 110 may control stimulation generator 114 to generate and deliver neurostimulation to a nonmyocardial tissue site of patient 12 according to a first operating mode (190). The first operating mode may be characterized by a first therapy program that defines a first set of stimulation parameter values with which stimulation generator 114 (FIG. 7) of INS 26 generates electrical stimulation signals. ICD 16 may sense electrical cardiac signals of patient 12 via at least one or more of electrodes 50, 52, 54, 56, 58, 60, 68, 72, 74, and/or 76 and determine whether the sensed electrical cardiac signals, and, in some examples, one or more other physiological parameter values of patient 12 indicate an arrhythmia of heart 14 (194). If ICD 16 does not detect an arrhythmia (194), processor 110 of INS 26 may continue controlling stimulation generator 114 to generate and deliver neurostimulation to patient 12 according to the first operating mode.

On the other hand, if ICD 16 detects a potential arrhythmia (194), processor 110 of INS 26 may control stimulation generator 114 of INS 26 to adjust the generation and delivery of electrical stimulation signals according to the first therapy mode (195). Processor 110 may adjust the delivery of electrical stimulation to patient 12 by suspending the delivery of stimulation or by decreasing the intensity of stimulation (e.g., modifying an amplitude, frequency, duty cycle, waveform, or another stimulation parameter). If, upon suspending or otherwise adjusting the generation and delivery of electrical stimulation signals according to the first therapy mode, processor 110 of INS 26 either detects a potential arrhythmia (e.g., based on sensed physiological signals or by receiving an indication that indicates a potential arrhythmia is detected) (194), processor 110 may determine that the potential arrhythmia was not detected based on the electrical stimulation signals from INS 26. Accordingly, processor 110 of INS 26 or processor 90 of ICD 16 may generate an arrhythmia indication (154), as described with respect to FIG. 10.

If, upon suspending or otherwise adjusting the generation and delivery of electrical stimulation signals according to the first operating mode, processor 110 of INS 26 does not detect a potential arrhythmia or receive an indication that an arrhythmia is detected (194), processor 110 may determine that the arrhythmia may have been detected based on noise resulting from electrical signals delivered by INS 26, rather than true cardiac signals. In order to mitigate the crosstalk between INS 26 and ICD 16 while still maintaining therapeutic benefits that may be provided by INS 26, processor 110 may control stimulation generator 114 to generate and deliver electrical stimulation signals according to a second operating mode, e.g., a second therapy program (196).

In some examples, the second operating mode may define a therapy program in which no neurostimulation is delivered to patient 12. Thus, when processor 110 controls stimulation generator 114 to generate and deliver electrical stimulation signals to patient 12 according to a second operating mode, INS 26 may suspend the delivery of stimulation to patient 12.

Processor 110 of INS 26 may control stimulation generator 114 to deliver therapy to patient 12 according to the second operating mode for a predetermined period of time following the switch from the first operating mode to the second operating mode. After the period of time has expired, processor 110 may control stimulation generator 114 to switch therapy delivery from therapy according to the second operating mode to therapy according to the first operating mode. The period of time may be stored in memory 112 of INS 26 or a memory of another device. The period of time may be selected by a clinician, e.g., based on how much the clinician wishes to mitigate the possibility of inadvertent cardiac rhythm therapy by ICD 16. In some examples, the period of time with which INS 26 delivers therapy to patient 12 according to the second operating mode is in a range of about 100 ms to about 24 hours or more.

Processor 110 of INS 26 may prohibit further delivery of therapy according to the first operating mode (e.g., first therapy program) based upon a number of times therapy delivery by INS 26 is switched from therapy according to the first operating mode to therapy according to the second operating mode. In some examples, processor 110 may prohibit stimulation generator 114 from delivering therapy according to the first operating mode if the therapy delivery is switched from the first to the second operating modes a threshold number of times within a predetermined period of time. The threshold number of therapy switches and predetermined period of time may be stored in memory 112 of INS 26 or a memory of another device (e.g., ICD 16 or programmer 24).

In the example shown in FIG. 12B, processor 110 may track the number of times therapy delivery by INS 26 is switched from therapy according to the first operating mode to therapy according to the second operating mode with a counter. For example, upon switching operating modes (e.g., by switching therapy programs) of INS 26 in response to the detected arrhythmia, processor 110 of INS 26 may increment a counter (197) and determine whether the value of the counter is greater than or equal to a threshold value (198). The value of the counter may indicate the number of times that processor 110 switched operating modes in response to a detected arrhythmia event. In some examples, the counter may track the number of detected arrhythmias for a particular period of time, which may be programmed by a clinician and stored in memory 112. After the period of time expires, processor 110 may reset the counter.

The threshold value may indicate the number of operating mode switches that are acceptable. The threshold value may be stored within memory 112 of INS 26 or a memory of another device, such as ICD 16 or programmer 24. In some examples, the threshold value may be about two to about ten, such as about three, and a time period for tracking the number of operating mode switches may be about one hour to about one day, although other threshold values and time periods are contemplated.

In some examples, processor 110 may increment the counter by a number that is selected based on the type of arrhythmia that is detected. For example, if a ventricular tachyarrhythmia is detected (194), processor 110 may increment the counter by a greater number (e.g., two counts) than if a nonsustained tachyarrhythmia is detected. A nonsustained tachyarrhythmia may comprise fewer arrhythmia events (e.g., R-R intervals less than a threshold value) than the ventricular tachyarrhythmia. In addition, in some examples, ICD 16 may not deliver cardiac rhythm therapy to heart 14 if a nonsustained tachyarrhythmia is detected, but may deliver therapy if a ventricular tachyarrhythmia is detected.

If the number of times that processor 110 switched operating modes, i.e., the count, is not greater than or equal to the threshold value, processor 110 may continue delivering therapy according to first and second operating modes of INS 26, as described with respect to FIG. 12A. However, if the number of times that processor 110 switched operating modes is equal to or exceeds the threshold value, processor 110 may determine that the delivery of electrical stimulation according to the first operating mode results in excessive interference with the proper detection of cardiac signals by ICD 16. Thus, if the number of times that processor 110 switched operating modes is greater than or equal to the threshold value, processor 110 may prohibit any further delivery of electrical stimulation signals generated according to the first therapy program (199). That is, processor 110 may indefinitely switch to the second operating mode of INS 26. For example, processor 110 may control stimulation generator 114 to generate and deliver electrical stimulation therapy to patient 12 according to a second therapy program indefinitely, rather than continuing to switch between first and second therapy programs.

Processor 110 may prohibit the generation and delivery of electrical stimulation according to the first operating mode until user intervention is received, e.g., to assess the extent of crosstalk. The user intervention may comprise, for example, input from patient 12 or the clinician resetting the counter, such that INS 26 may deliver stimulation signals that are generated in accordance with the first therapy program. The input may be received via user interface 134 (FIG. 8) of programmer 24 or a user interface of another computing device, which may transmit the user input to processor 110 via the respective telemetry modules 136 (FIG. 8), 118 (FIG. 7). In addition, in some examples, the user input may be received from a clinician at a remote location, e.g., via the system including a network that is described with respect to FIG. 32.

In some cases, processor 110 may generate an interference indication that is transmitted to patient 12 or a clinician, e.g., via programmer 24. For example, processor 110 may transmit the interference indication to programmer 24 via telemetry module 118 (FIG. 7) and programmer 24 may receive the indication via telemetry module 136 (FIG. 8) and generate an interference indication to notify patient 12 or another person that clinician intervention may be necessary to mitigate crosstalk between ICD 16 and INS 26. Processor 110 may generate the interference indication in response to the mode switch counter value exceeding the threshold.

Figure 13A:
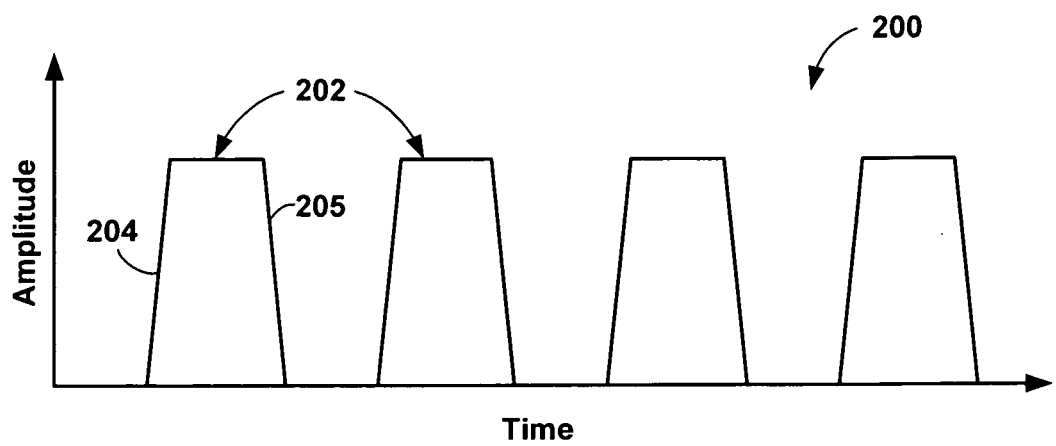
FIGS. 13A-13I are conceptual illustrations of example waveforms for electrical stimulation therapy.

FIGS. 13A-13I are conceptual illustrations of example non-rectangular waveforms that may be defined by a second operating mode implemented by INS 26 to generate neurostimulation signals after the detection of an arrhythmia. FIG. 13A illustrates a ramped square waveform 200, which includes a plurality of waves 202. Each wave 202 includes a leading edge 204 that gradually increases in amplitude over time and a trailing edge 205 that follows the leading ledge 204 and gradually decreases in time. In some examples, leading edge 204 exhibits a substantially continuous increase in amplitude, such that leading edge 204 has a different amplitude at subsequent points in time. Similarly, trailing edge 205 may exhibit a substantially continuous decrease in amplitude, such that trailing edge 205 has a different amplitude at subsequent points in time. Although leading edge 204 and trailing edge 205 are illustrated as having substantially equal, but opposite slopes, in other examples, leading edge 204 and trailing edge 205 may have slopes of different magnitude.

In some examples, stimulation generator 114 of INS 26 may generate the ramped square wave by generating a square wave stimulation signal and modulating the amplitude by a relatively slow sine wave. For example, stimulation generator 114 may generate square wave signals having a frequency of about 80 Hz and a pulse duration of about 300 µs duration pulses, and modulate the amplitude of the square wave from about 0% to about 100% by an approximately 3 Hz sine wave. The resulting square wave signal may have a frequency of about 80 Hz and a signal envelope of about 3 Hz.

Figure 13B:
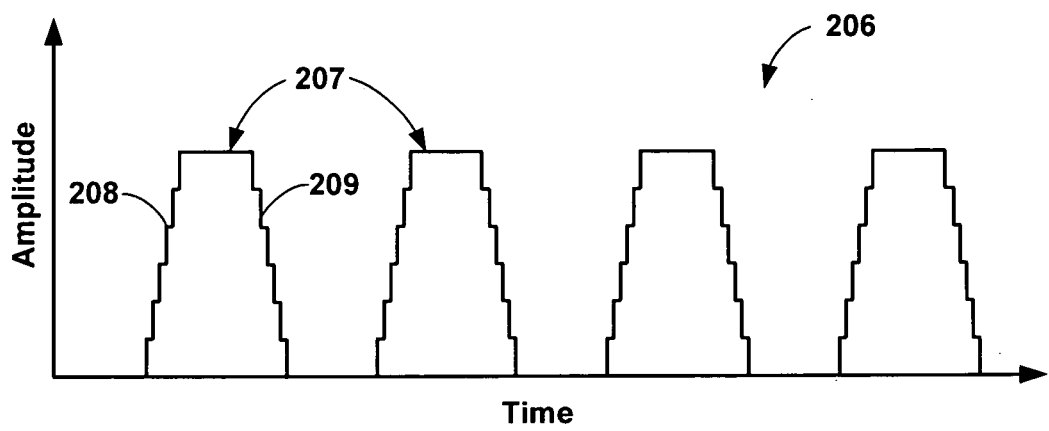

FIG. 13B illustrates a stair step square waveform 206, which includes a plurality of waves 207. Each wave 207 includes a leading edge 208 and a trailing edge 209. The lead edge 208 includes stepwise increases in amplitude over time, whereas the trailing edge 209 includes stepwise decreases in amplitude over time. Although FIG. 13B illustrates waves 207 in which leading edge 208 and trailing edge 209 increase and decrease, respectively, in substantially equal increments of amplitude, in other examples each step of leading edge 208 and trailing edge 209 may increase and decrease, respectively, in amplitude by different magnitudes. Moreover, the rising edge of each step in leading edge 208 may have a different absolute magnitude than other steps in leading edge 208, such that some steps of leading edge 208 are larger than others. Similarly, each step of trailing edge 209 may have a different absolute magnitude than other steps in trailing edge 209.

Figure 13C:
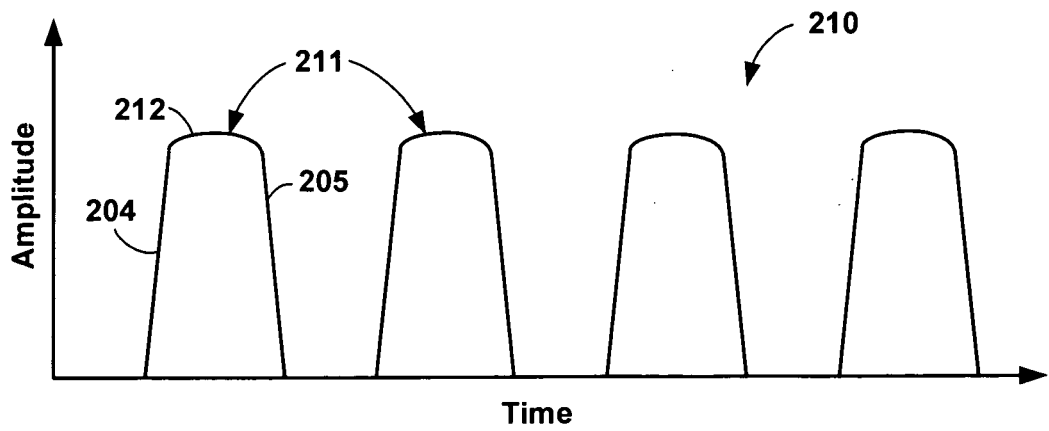

FIG. 13C illustrates rounded square waveform 210, which includes a plurality of waves 211. Each wave 211 defines a leading edge 204 that gradually increases in amplitude over time and a trailing edge 205 that gradually decreases in time, as described with respect to ramped square waveform 200 in FIG. 13A. In addition, waves 211 of rounded square waveform 210 includes rounded portion 212 between leading edge 204 and trailing edge 205. Rounded portion 212 may help further distinguish neurostimulation waveform 210 from a sinus rhythm of heart 14 (FIG. 1) because of the gradual increase and decrease in amplitude. In contrast, the sinus rhythm of heart 14 may exhibit a sharper increase and decrease in amplitude.

In some examples, stimulation generator 114 may generate rounded square waveform 210 shown in FIG. 13C by passing a square wave signal or a substantially square wave signal through a resistor-capacitor (RC) low pass filter with a cutoff frequency in a range of about 20 Hz to about 100 Hz, such as about 60 Hz. The RC low pass filter may help eliminate the relatively rapid rise time of the square wave, which may help reduce the stimulation signal artifact imposed on ICD 16 because the resulting rounded square wave may no longer resemble a true electrical cardiac signal, which may comprise a relatively rapid rise time.

Figure 13D:
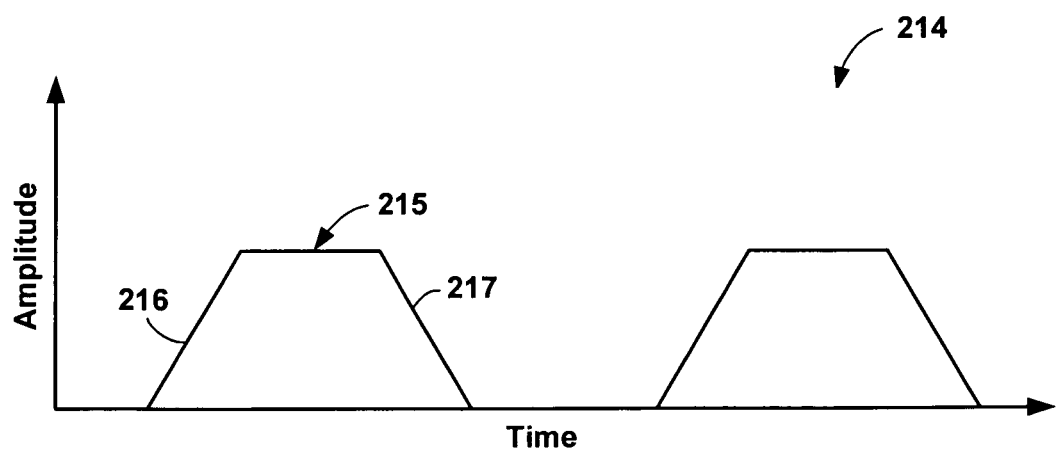

FIG. 13D illustrates trapezoidal waveform 214, which includes a plurality of waves 215 comprising a substantially trapezoidal shape. Each trapezoidal wave 215 comprises leading edge 216 and trailing edge 217, which follows leading edge 216 in time. Leading edge 216 may comprise a greater slope compared to lead edge 204 of ramped square wave 202 (FIG. 13A). Similarly, trailing edge 217 may comprise a smaller slope (or a greater absolute slope value) compared to trailing edge 205 of ramped square wave 202 (FIG. 13A). Although leading edge 216 and trailing edge 217 are illustrated as having substantially equal, but opposite slopes, such that the waves 215 define isosceles trapezoids, in other examples, leading edge 216 and trailing edge 217 may have slopes of different magnitude.

Figure 13E:
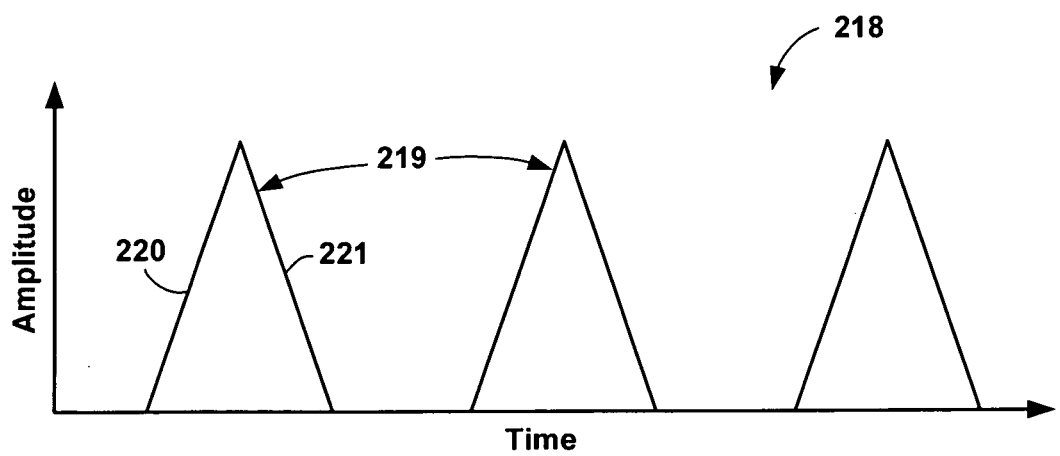

FIG. 13E illustrates triangular waveform 218, which includes a plurality of waves 219 defining a substantially triangular shape. Waves 219 each comprise leading edge 220 and trailing edge 221, which follows leading edge 220 in time. Leading edge 220 and trailing edge 221 of each wave 219 may have slopes of substantially equal magnitude, or may have different slopes. In some examples, upon the detection of an arrhythmia, processor 110 of INS 26 may control stimulation generator 114 to generate and deliver electrical stimulation signals comprising a stair-step triangular waveform. Just as with the stair step square wave shown in FIG. 13B, a leading edge of the stair step triangular wave may define stepwise increases in amplitude over time, and a trailing edge of the waveform may define stepwise decreases in amplitude over time.

Figure 13F:
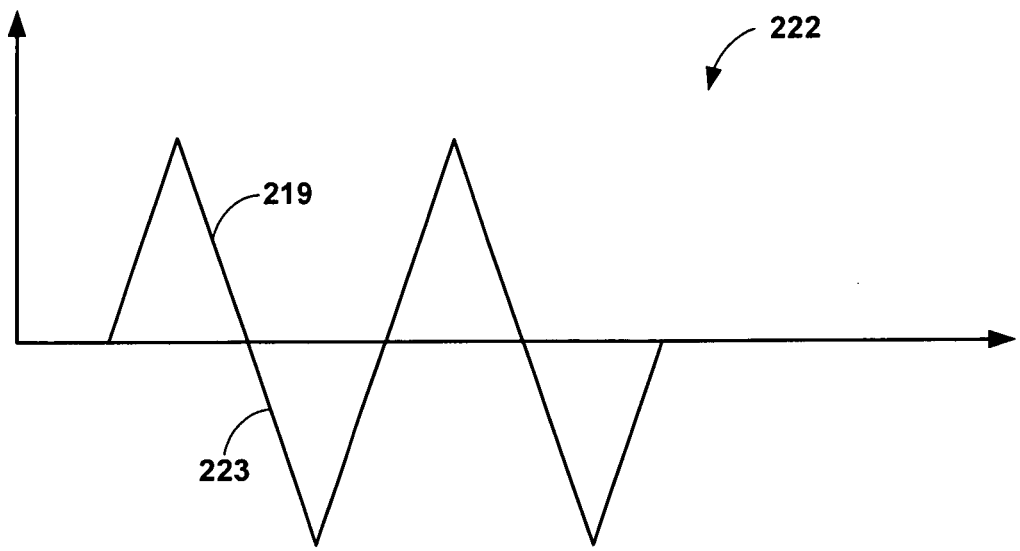

In some examples, stimulation generator 114 of INS 26 may generate and deliver biphasic stimulation signals, as shown in FIG. 13F. FIG. 13F illustrates biphasic triangular waveform 222, which includes triangular waves 219 having a positive amplitude and triangular waves 223 having a negative amplitude. Biphasic triangular waveform 222 may include alternating positive amplitude triangular waves 219 and negative amplitude triangular waves 223. Biphasic waveforms may also help distinguish neurostimulation signals from cardiac signals. Other types of biphasic waveforms are also contemplated, such as biphasic square waves.

Figure 13G:
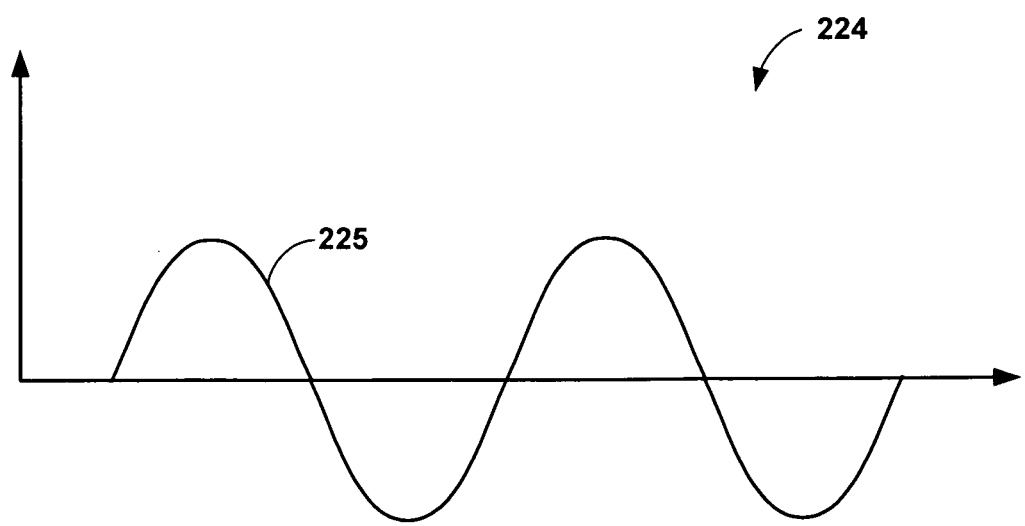
Figure 13H:
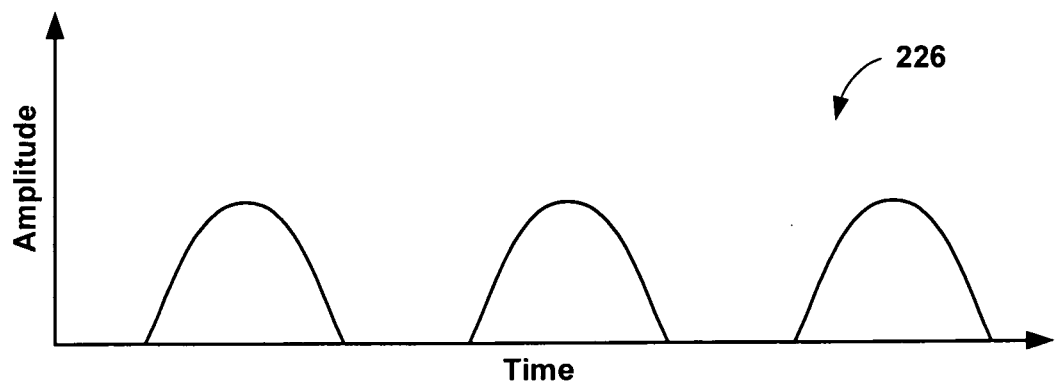
Figure 13I:
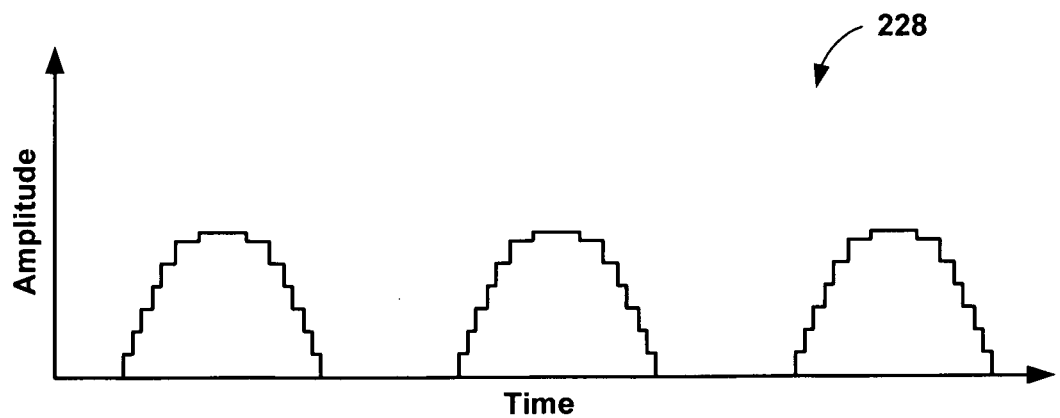

Stimulation generator 114 of INS 26 may also generate and deliver neurostimulation to patient 12 via a sine waveform. FIG. 13G illustrates sine waveform 224, which includes a periodic wave 225 defined by a sine function. In some examples, as shown in FIG. 13H, stimulation generator 114 may also generate and deliver neurostimulation signals having a half sine waveform 226, such as the positive half of a sine wave or a rectified sine wave. The half sine wave may have a duration of approximately 200 microseconds (μs), although other signal durations are contemplated. In other examples, stimulation generator 114 of INS 26 may generate and deliver neurostimulation signals comprising a stepwise half sine waveform 228, as shown in FIG. 13I.

Figure 14A:
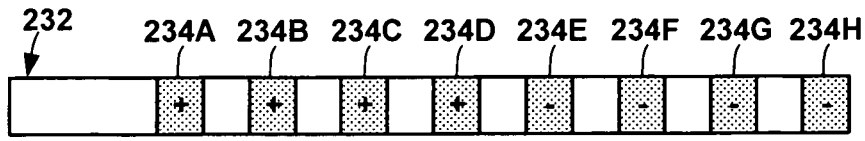
FIGS. 14A and 14B are conceptual illustrations of example electrode combinations that may be used to deliver a biphasic stimulation signal.
Figure 14B:
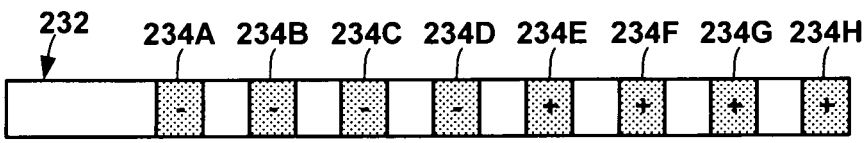

As previously described with respect to biphasic triangular waveform 222 in FIG. 13F, in some examples, the second therapy program implemented by processor 110 of INS 26 after the detection of an arrhythmia may define a biphasic signal. That is, processor 110 may control stimulation generator 114 to deliver stimulation signals to selected electrodes 124 (FIG. 7) of lead 28 such that the selected electrodes reverse polarity with each subsequent pulse or, in examples in which continuous wave signals are delivered, each subsequent half wave. FIGS. 14A and 14B provide a conceptual illustration of a configuration of electrode polarities that may be employed in order to for INS 26 to deliver a biphasic neurostimulation signal to patient 12 in the second operating mode. FIGS. 13F and 13G illustrate examples of biphasic waveforms that may be generated and delivered to patient 12.

FIGS. 14A and 14B illustrate lead 232 comprising a plurality of electrodes 234A-234H, which may comprise ring electrodes, partial ring electrodes or segmented electrodes that extend around less than the full outer perimeter of lead 232. In the example shown in FIGS. 14A and 14B, lead 232 may comprise a cylindrical lead body with a circular cross-section (when the cross-section is take in a direction substantially orthogonal to a longitudinal axis of lead 232). Lead 232 may be coupled to stimulation generator 114 of INS 26 instead of or in addition to lead 28 and/or lead 29 (FIG. 2). Although eight electrodes 234A-234H are shown in FIGS. 14A and 14B, in other examples, lead 232 may comprise any suitable number of electrodes, which may be greater than or fewer than eight.

FIG. 14A illustrates a first example electrode combination that may be defined by a second therapy program that processor 110 of INS 26 may implement upon the detection of an arrhythmia. In the electrode configuration shown in FIG. 14A, electrodes 234A-234D are selected to be anodes and electrodes 234E-234H are selected to be cathodes. Stimulation generator 114 may generate a first stimulation pulse or another type of stimulation signal and transmit the stimulation pulse or signal to electrodes 234A-234H via the conductors within lead 232. An electrical field may be generated through the patient's tissue as the electrical signal flows between the anode electrodes 234A-234D and the cathode electrodes 234E-234H. In other examples, a subset of electrodes 234A-234H may be selected as part of the electrode combination.

FIG. 14B illustrates a second electrode combination defined by the second therapy program in which electrodes 234A-234D are selected to be cathodes and electrodes 234E-234H are selected to be anodes. Thus, compared to the first electrode combination shown in FIG. 14A, electrodes 234A-234H have reversed polarity. Stimulation generator 114 may utilize the electrode combination shown in FIG. 14B to deliver a subsequent stimulation pulse or wave, i.e., subsequent to the pulse or wave delivered with the electrode combination shown in FIG. 14A. An electrical field may be generated through the patient's tissue as the electrical signal flows between the anode electrodes 234E-234H and the cathode electrodes 234A-234D.

In accordance with an example of the second operating mode of INS 26, stimulation generator 114, e.g., with the aid of switching module 116 (FIG. 7) may continue delivering alternating pulses with the electrode combinations shown in FIGS. 14A and 14B. In some examples, stimulation generator 114 may deliver neurostimulation to patient 12 with the same electrode combination (e.g., the same polarity configuration) for two or more pulses or stimulation waves in a row and subsequently deliver neurostimulation to patient 12 to an electrode combination having reversed polarities. For example, in other examples, stimulation generator 114 may deliver two or more pulses with the electrode combination shown in FIG. 14A followed by two or more pulses with the electrode combination shown in FIG. 14B. In addition, in other examples, INS 26 may deliver a biphasic neurostimulation signal to patient 12 using the electrodes of two or more leads, rather than one lead as shown in FIGS. 14A and 14B.

Delivering neurostimulation signals to patient 12 via a biphasic signal (e.g., via electrode combinations with alternating polarity) may help reduce the neurostimulation artifact impact on ICD 16 or another physiological parameter monitoring device. The stimulation output net energy artifact effect sensed by ICD 16 may be approximately zero due to the rapid encounter of alternate polarity artifact that may cancel out the neurostimulation signal. In addition, delivering neurostimulation signals to patient 12 via a biphasic signal may help limit the bandwidth of the transmitted neurostimulation signal, and limiting the bandwidth may help increase the possibility that ICD 16 may filter out the neurostimulation signal, e.g., via a bandpass filter. Further, in some examples, sensing module 98 of ICD 16 may be configured to disregard or attenuate the alternating polarity neurostimulation signals. Thus, if INS 26 delivers biphasic neurostimulation signals, ICD 16 may not sense the neurostimulation signals and if ICD 16 senses the neurostimulation signals, ICD 16 may not mischaracterize the neurostimulation signals as cardiac signals.

In either or both the first and second operating modes of INS 26, INS 26 may deliver electrical stimulation signals to patient 12 with an electrode combination that reduces the extent of the energy and/or electrical field that leaves the target tissue site 40, thereby reducing the intensity of neurostimulation signal that traverses through the patient's body and is sensed by ICD 16. The anodes and cathodes of the electrode combination may be selected such that the stimulation field generated by the delivery of neurostimulation via the anodes and cathodes (i.e., the selected electrodes) may be relatively focused within target tissue site 40 (FIG. 1).

FIGS. 15A-15F illustrate different examples of electrode combinations that may be used to deliver neurostimulation therapy to patient 12. In the electrode combinations shown in FIGS. 15A-15F, the anodes and cathodes of the electrode combination are positioned relative to each other to help reduce the extent of the size of the electrical field (or stimulation field) that is generated as a result of the delivery of neurostimulation signals by INS 26. In some examples, the electrode combinations shown in FIGS. 15A-15F may be used to deliver a plurality of stimulation pulses with an interval of time between each pulse, or a plurality of bursts of electrical stimulation that are separated by an interval of time, where each burst includes a plurality of stimulation pulses.

In some examples, during a programming session in which a clinician selects the one or more electrode combinations for a second operating mode of INS 26, the clinician may utilize a user interface that graphically represents the stimulation field generated by stimulation delivery with a particular subset of electrodes of the one or more leads coupled to INS 26. An example of a user interface that may be used to select an electrode combination for the delivery of neurostimulation is described in commonly-assigned U.S. patent application Ser. No. 11/999,722 by Goetz et al., entitled, "USER INTERFACE WITH TOOLBAR FOR PROGRAMMING ELECTRICAL STIMULATION THERAPY," which was filed on Dec. 6, 2007 and is incorporated herein by reference in its entirety. U.S. patent application Ser. No. 11/999/722 by Goetz et al. published as U.S. Patent Application Publication No. 2008/0215118 on Sep. 4, 2008.

As described in U.S. patent application Ser. No. 11/999, 722 by Goetz et al., a user interface may display a representation of implanted electrical leads in conjunction with at least one menu with icons that the user can use to adjust the stimulation field of the stimulation therapy with one or more field shape groups. For example, one menu may be a field shape selection menu that provides field shapes to indicate the resulting stimulation field according to initial stimulation parameters. Another menu may be a manipulation tool menu that allows a user to perform certain actions on the field shapes to adjust the stimulation therapy. The user interface may be useful for selecting an electrode combination and other stimulation parameter values that focus the stimulation field within target tissue site 40 (FIG. 1). Focusing the neurostimulation within the desired target tissue site 40 may help minimize the extent of the stimulation field that falls outside of target tissue site 40, particularly in a direction towards heart 14 (FIG. 1), and decrease the extent to which the stimulation field may be sensed by ICD 16.

Figure 15A:
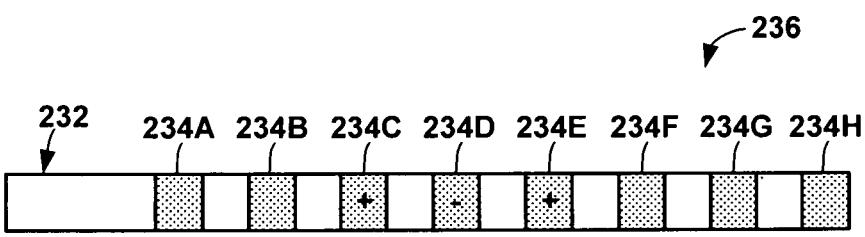
FIGS. 15A-15F are conceptual illustrations of example electrode combinations that may be used to help focus a stimulation field generated by the delivery of electrical stimulation by an INS.

FIG. 15A illustrates an example of a guarded cathode electrode combination 236 that may be selected during the second operating mode of INS 26 in order to help focus the neurostimulation delivered to patient 12. In a guarded cathode arrangement, two or more anodes are positioned around a cathode of the electrode combination. In FIG. 15A, electrode 234D of lead 232 is selected as a cathode of the electrode combination and electrodes 234C and 234E are selected as anodes. In the example shown in FIG. 15A, the anode electrodes 234C, 234E and cathode electrode 234D are substantially linearly aligned along a longitudinal axis of lead 232. The anode electrodes 234C and 234E surrounding the cathode electrode 234D may be useful for focusing a stimulation field generated by the delivery of electrical stimulation via electrode combination 236. In particular positioning anode electrodes 234C and 234E on opposite sides of cathode electrode 235D may help limit the size of the stimulation field resulting from the delivery of stimulation via the electrode combination 236.

Figure 15B:
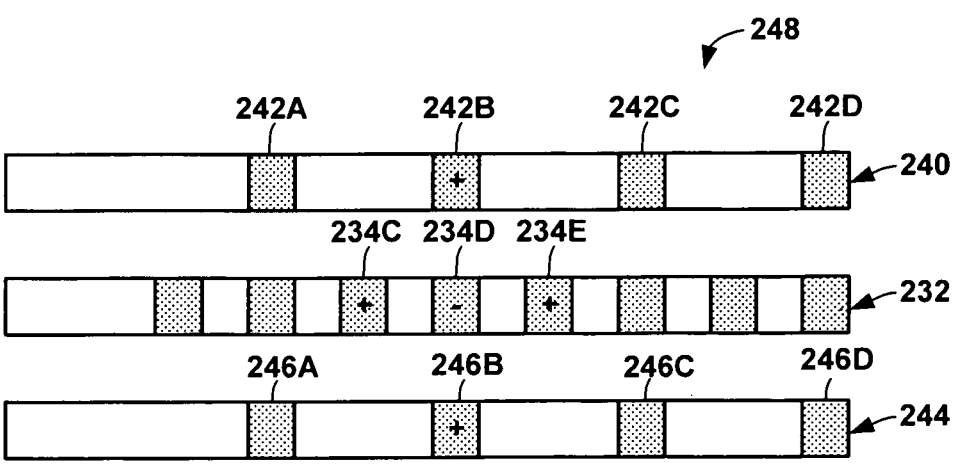

In some examples, INS 26 may be coupled to two or more leads, directly or via one or more lead extensions, such as a bifurcated lead extension. FIG. 15B illustrates a configuration in which INS 26 is coupled to lead 232 including eight electrodes 234A-234H, lead 240 including four electrodes 242A-242D, and lead 244 including four electrodes 246A-246D. Electrodes 232A-232H, 242A-242D, 246A-246D of leads 232, 240, 244 may define a three-lead full guard electrode configuration. The three-lead full guard electrode combination utilizes electrodes on all three leads implanted within patient 12. In the example shown in FIG. 15B, electrode combination 248 includes cathode electrode 234D on a middle lead 232, where the cathode electrode 234D is surrounded by two anode electrodes 234C, 234E on the same lead 232 and anode electrodes 242B, 246B on leads 240, 244 on either side of cathode electrode 234D. Anode electrodes 234C, 234E, 242B, 246B of electrode combination 248 may define a stimulation field that activates only the tissue around cathode electrode 235D while inhibiting the tissue on all sides of cathode electrode 235D.

Figure 15C:
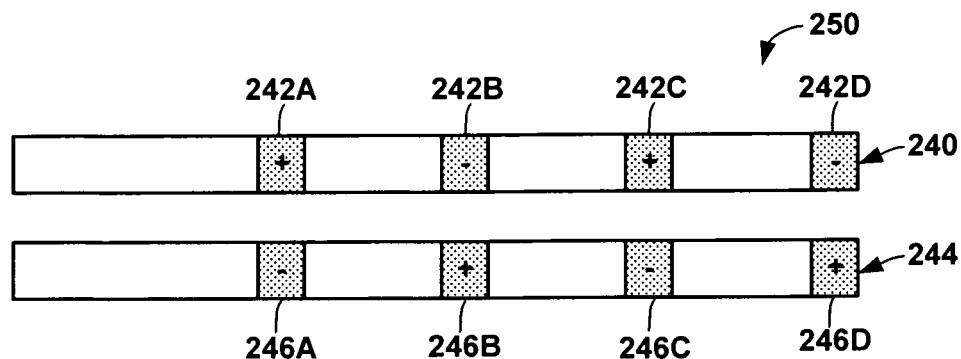

FIG. 15C illustrates another example electrode combination 250 that processor 110 of INS 26 may select during the second operating mode of INS 26 in order to help focus the neurostimulation delivered to patient 12. Electrode combination 250 is defined by electrodes 242A-242D and 246A-246D of two leads 240, 244, respectively. In the example shown in FIG. 15C, electrodes 242A, 242C, 246B, 246D are anode electrodes and electrodes 242B, 242D, 246A, 246D are cathode electrodes. By substantially surrounding cathode electrodes 242B, 242D, 246A, 246C with anode electrodes 242A, 242C, 246B, 246D, electrode combination 250 may shape a stimulation field that focuses stimulation to the area proximate leads 240, 244.

Figure 15D:
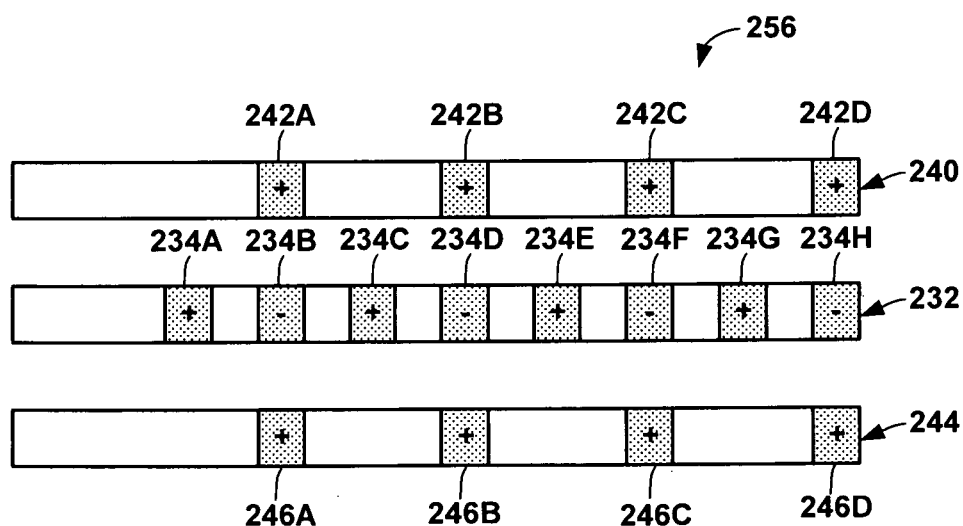

FIG. 15D illustrates another example electrode combination 256 that is defined by selected electrodes 242A-242D, 232A-232H, 246A-246D of three leads 240, 232, 244, respectively. In the example shown in FIG. 15D, electrodes 242A-242D, 246A-246D, 234A, 234C, 234E, 234G are anode electrodes and electrodes 234B, 234D, 234F, 234H are cathode electrodes. Anode electrodes 242A-242D, 246A-246D on leads 240, 244 adjacent to lead 232, which includes cathode electrodes 234B, 234D, 234F, 234H, are positioned to help limit the size of the stimulation field generated by the delivery of electrical stimulation via electrode combination 256. By placing the cathode electrodes 234B, 234D, 234F, 234H along a center lead 232, the stimulation field may be focused to the region of tissue proximate leads 232, 240, 244.

Anode electrodes 242A-242D, 246A-246D, 234B, 234D, 234F, 234H may act as guard band electrodes that help focus a stimulation field to the region of tissue proximate leads 232, 240, 244. In some examples, anode electrodes 242A-242D may define a substantially continuous and contiguous anode electrode, rather than a plurality of discrete electrodes, as shown in FIG. 15D. Similarly, in some examples, anode electrodes 246A-246D may define a substantially continuous and contiguous anode electrode, rather than a plurality of discrete electrodes, as shown in FIG. 15D. Anode electrodes 242A-242D, 246A-246D on opposing sides of cathode electrodes 234B, 234D, 234F, 234H may serve as a guard band that reduce the projection of a stimulation field beyond leads 240, 246, which may help reduce the amount of the neurostimulation signal that reaches the sense electrodes coupled to ICD 16. This may help reduce the stimulation artifact on the sensing of cardiac signals by ICD 16.

Figure 15E:
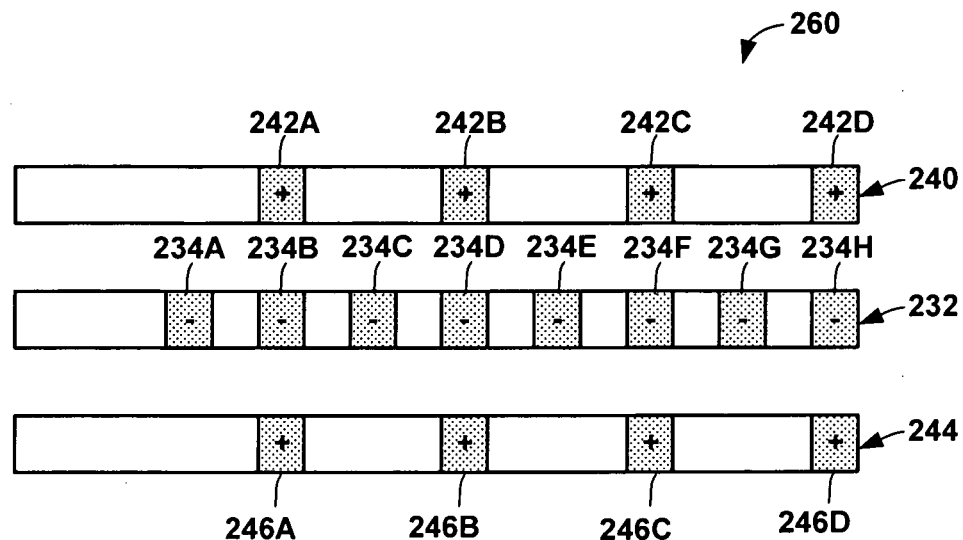

FIG. 15E illustrates another example electrode combination 260 that is defined by electrodes 242A-242D, 232A-232H, 246A-246D on three leads 240, 232, 244, respectively. In particular, cathode electrodes 234A-234H are located on the middle (or central) lead 232, and anode electrodes 242A-242D, 246-246D are positioned on leads 240, 244 on opposing sides of center lead 232, which, in some examples, may be spatially centered between leads 240, 244. Again, in some examples, anode electrodes 242A-242D may define a substantially continuous and contiguous anode electrode and anode electrodes 246A-246D may define a substantially continuous and contiguous anode electrode.

Anode electrodes 242A-242D, 246A-246D on opposing sides of cathode electrodes 234A-234H may serve as a guard band that reduce the projection of a stimulation field beyond leads 240, 246, which may help reduce the amount of the neurostimulation signal that reaches the sense electrodes coupled to ICD 16. This may help reduce the stimulation artifact on the sensing of cardiac signals by ICD 16.

Figure 15F:
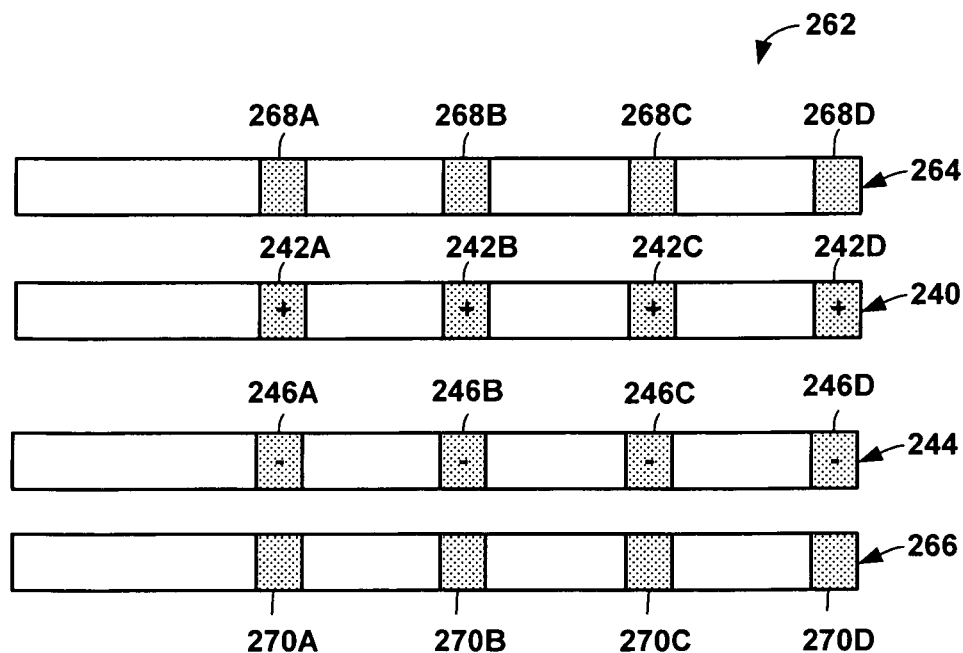

FIG. 15F illustrates another example electrode combination 262 that is defined by electrodes positioned on four leads 240, 244, 264, 266 that are coupled to INS 26, either directly or indirectly with a lead extension (e.g., a bifurcated lead extension). Electrodes 242A-242D of lead 240 may be anode electrodes and electrodes 246A-246D of lead 244 may be cathode electrodes. Electrodes 268A-268D of lead 264 and electrodes 270A-270D of lead 266 may be neutral, or inactive, electrodes. For example, electrodes 268A-268D may be electrically connected, e.g., shorted, to electrodes 270A-270D. Electrodes 268A-268D, 270A-270D may limit the size (e.g., breadth) of the stimulation field generated by therapy delivery according to electrodes 242A-242D, 246A-246D, e.g., by absorbing energy from the stimulation field. Minimizing the size of the stimulation field may help limit the extent to which ICD 16 senses the stimulation field, and, therefore, may help minimize crosstalk between INS 26 and ICD 16.

Figure 16:
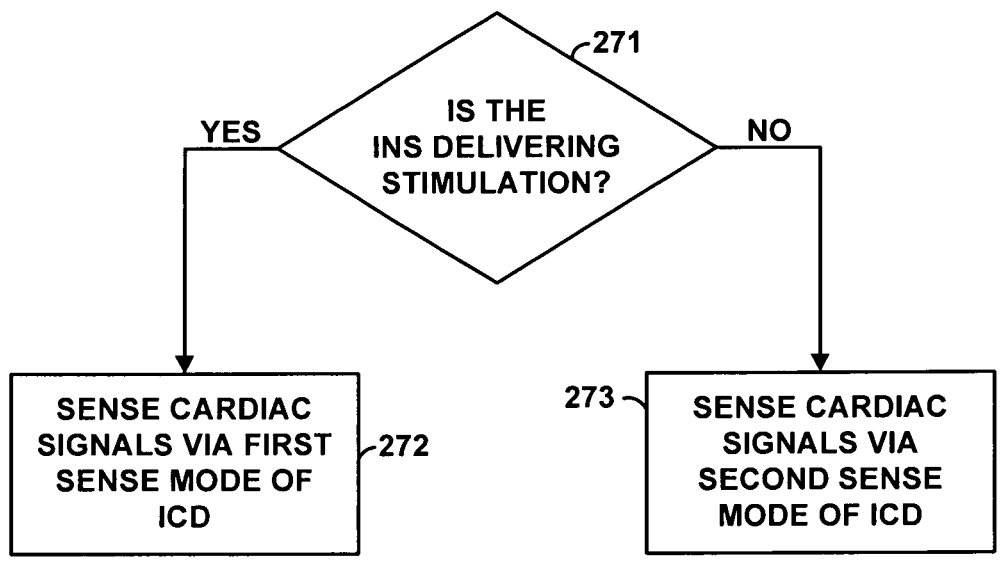
FIG. 16 is a flow diagram illustrating an example technique that an ICD may implement in order to detect an arrhythmia while an INS is delivering electrical stimulation.

In addition to or instead of modifying one or more operating parameters of INS 26, one or more operating parameters (e.g., sensing parameters) of ICD 16 may be modified in order to help prevent the inappropriate delivery of stimulation by ICD 16 based on a neurostimulation signal artifact present in a signal sensed by that ICD 16. Modifying the sensing parameters of ICD 16 may help minimize the possibility that ICD 16 mischaracterizes a neurostimulation signal as an electrophysiological cardiac signal. FIG. 16 is a flow diagram illustrating an example technique that ICD 16 may implement in order to detect an arrhythmia while INS 26 is delivering electrical stimulation to a tissue site 40 (FIG. 1) within patient 12.

Processor 90 of ICD 16 may determine whether INS 26 is delivering stimulation to the nonmyocardial tissue site 40 (271). In some examples, INS 26 may transmit a signal to ICD 16 to notify ICD 16 that INS 26 is actively delivering electrical stimulation to patient 12, i.e., the delivery of stimulation by INS 26 is not in a suspended state. For example, INS 26 may transmit a signal with predetermined characteristics to ICD 16 via the respective telemetry modules 118, 98 prior to or substantially at the same time that INS 26 delivers a stimulation signal to patient 12 or at the beginning of a stimulation pulse train including more than one stimulation pulse.

As another example, ICD 16 may determine when INS 26 is delivering stimulation based on a known stimulation schedule. As previously indicated, in some examples, ICD 16 and INS 26 have substantially synchronized clocks. Memory 92 (FIG. 6) of ICD 16 may store information that indicates when INS 26 is expected to be delivering stimulation to patient 12. For example, ICD 16 may store a stimulation schedule for INS 26, where the stimulation schedule indicates the times of day at which INS 26 is programmed to actively deliver stimulation to patient 12.

If INS 26 is delivering stimulation to patient 12, processor 90 of ICD 16 may implement a first sense mode in order to monitor cardiac activity of patient 12 (272). The first sense mode may define a first sensing threshold that is used by processor 90 (or sensing module 96, in some examples) to detect a cardiac signal. ICD 16 may filter sensed signals with the aid of the sensing threshold voltage in order to discriminate cardiac signals from noise, which may be attributable to many external sources. Sensing module 96 may sense electrical signals via two or more of the electrodes 50, 52, 54, 56, 58, 60, 68, 72, 74, 76 connected to sensing module 96. Processor 90 may only identify sensed signals that have a voltage amplitude greater than the sensing threshold value as electrical cardiac activity. For example, sensing module 96 may only transmit EGM signals above the sensing threshold value to processor 90 for timing analysis. As previously indicated, the timing analysis may include an analysis of the sensed EGM signal for R-R intervals, P-P intervals, and so forth.

If INS 26 is not delivering stimulation to patient 12, e.g., because the delivery of stimulation by INS 26 is currently suspended, processor 90 may implement a second sense mode in order to sense cardiac signals (273). The second sense mode may define a second sensing threshold that is used by processor 90 (or sensing module 96, in some examples) to detect a cardiac signal. In some examples, the second sensing threshold may be lower than the first sensing threshold defined by the first sense mode. In this way, the second sense mode may be more sensitive to electrical cardiac signals than the first sense mode.

In some examples, the first and second sense modes may also define different amplifier gains used by the sensing amplifiers of sensing module 96 to sense electrical cardiac signals. The first sense mode may have a lower amplifier gain than the second sense mode, which may result in less sensitivity to cardiac signals.

While the first sense mode of ICD 16 may be less sensitive to electrical cardiac signals of patient 12, ICD 16 may monitor other physiological parameters of patient in order to detect an arrhythmia, thereby at least partially compensating for the decreased sensitivity to electrical cardiac signals. That is, in the first sense mode, in addition to sensing electrophysiological cardiac signals (e.g., EGM or ECG signals) of patient 12, processor 90 may detect an arrhythmia based on other non-electrophysiological parameters that are indicative of cardiac activity of patient in order to detect an arrhythmia. In contrast, in the second sense mode, sensing module 96 may not detect an arrhythmia based on non-electrophysiological parameters of patient 12 or may detect an arrhythmia based on fewer non-electrophysiological parameters of patient 12 compared to the second sense mode.

Examples of non-electrophysiological parameters of patient 12 that may be indicative of an arrhythmia include, but are not limited to, cardiovascular pressure, tissue perfusion, blood oxygen saturation levels, heart sound signals, respiratory rate, thoracic impedance, cardiac mechanical activity (e.g., muscle movement monitored via an accelerometer), body temperature (e.g., metabolic rate may change with decreased cardiac function, which may affect body temperature), acoustic signals indicative of cardiac mechanical activity or other blood flow information. Sensing a greater number of non-electrophysiological parameters of patient 12 in the first sense mode may help prevent underdetecting an arrhythmia of patient 12 despite the less sensitive sensing threshold utilized to sense cardiac signals.

Cardiovascular pressure may include intracardiac pressure (i.e., pressure within a chamber of heart 14) or extravascular pressure sensed outside of the patient's vasculature. One or more characteristics of sensed cardiovascular pressure in either the time domain or frequency domain may indicate whether a detected arrhythmia is a true arrhythmia. Cardiovascular pressure may vary based on the mechanical contraction and relaxation of heart 14. Thus, changes in cardiovascular pressure may indicate whether heart 14 is mechanically contracting and relaxing in a normal manner and, therefore, may indicate the presence of an arrhythmia. For example, an arrhythmia may be detected if the time domain cardiovascular pressure data indicates that the pressure within right ventricle 32 (FIG. 3) of heart 14 has decreased by at least a particular amount or decreased below a threshold amount. As another examples, processor 90 of ICD 16 may detect an arrhythmia using the first sense mode of ICD 16 if the pressure within right ventricle 32 (FIG. 3) or another chamber is less than its expected physiologic range.

Intracardiac pressure may be monitored with the aid of a pressure sensor coupled to at least one of leads 18, 20, 22. Extravascular pressure may be monitored with the aid of a pressure sensor located outside of heart 14. The pressure sensor may be mechanically coupled to or physically separate from ICD 16 and INS 26. If physically separate from ICD 16 and INS 26, the pressure sensor may transmit a signal indicative of pressure to ICD 16 and INS 26 via a wired or wireless connection. The sensed pressure may be, for example, a systolic pressure, diastolic pressure, a pulse pressure, a maximum and minimum derivative of sensed pressure(s), or any combination thereof.

Tissue perfusion and blood oxygen saturation levels of patient 12 may also vary based on the mechanical contraction and relaxation of heart 14. Thus, changes in tissue perfusion or blood oxygen saturation levels or a decreasing trend in blood oxygen saturation or tissue perfusion may indicate that heart 14 is not mechanically contracting and relaxing in a normal manner and, therefore, may indicate the presence of an arrhythmia. Tissue perfusion and blood oxygen saturation levels of patient 12 may be with the aid of an optical sensor, which may or may not be mechanically coupled to ICD 16 or INS 26.

As described in U.S. Pat. No. 7,787,947 to Bhunia et al., entitled, "METHOD AND APPARATUS FOR USING AN OPTICAL HEMODYNAMIC SENSOR TO IDENTIFY AN UNSTABLE ARRHYTHMIA," which issued on Aug. 31, 2010 and is incorporated herein by reference in its entirety, an optical perfusion sensor may include a red light emitting diode (LED) and an infrared (IR) LED as light sources, and a detector. An increase in a red optical signal sensed by the detector, which may indicate the amount of red light from the red LED that was reflected by blood in the tissue proximate to the optical perfusion sensor, and a decrease in an IR signal sensed by the detector, which may indicate the amount of IR light form the IR LED that was reflected by blood in the tissue in blood-perfused tissue, may indicate the occurrence of a cardiac arrhythmia. According to U.S. Pat.

No. 7,787,947 to Bhunia et al., electrical signals generated by the detector of the optical perfusion sensor may experience a significant change in value following a hemodynamically unstable ventricular fibrillation. This change may be detected by sensing module 96 or a separate optical sensor in the second sense mode of sensing module 96 in order to detect an arrhythmia.

Another non-electrophysiological parameter of patient 12 that processor 90 may use to detect an arrhythmia in the first sense mode includes heart sound signals or acoustic signals indicative of mechanical contractions of heart 14. Heart sounds or other acoustic signals may be sensed with a sensor, which may or may not be coupled to ICD 16 or INS 26, such as an accelerometer or acoustic transducer. The heart sounds or acoustic vibrations may be generated as the heart valves open and close during a cardiac cycle or by turbulent flow during the fill phases in diastole. Changes in the heart sounds or acoustic vibrations, such as the lack of heart sounds or acoustic vibrations or a decrease in the frequency of the heart sounds or acoustic vibrations may indicate the presence of an arrhythmia.

In some examples, in either or both the first and second sense modes, sensing module 96 or processor 90 may filter out the neurostimulation signals from sensed electrical signals. For example, sensing module 96 may implement a front-end filter to filter out the neurostimulation signals delivered by INS 26 or processor 90 may implement digital signal processing to filter out the neurostimulation signals. Because the source of the artifact from the electrical signals generated and delivered by INS 26 is known, and the characteristics of the electrical signals are known, it may be relatively easy for processor 90 to filter out the electrical signals generated and delivered by INS 26. For example, sensing module 96 may filter sensed signals on the basis of frequency content and eliminate frequency components of a sensed signal that falls outside of the range. The neurostimulation signal delivered by INS 26 may have a known signature, in terms of the signal frequency, duty cycle, signal envelope, and so forth.

ICD 16 may store the known signature in memory 92 or INS 26 may periodically provide the neurostimulation signal information to ICD 16. For example, INS 26 may periodically transmit the therapy program defining the stimulation parameter values with which INS 26 generates electrical stimulation signals. In some examples, ICD 16 may sense cardiac signals while INS 26 is delivering stimulation signals to patient 12, and processor 90 may determine the characteristics (e.g., patterns, amplitude, frequency, and the like) of the neurostimulation signal artifact present in the sensed signal. This may be done, for example, after ICD 16 and INS 26 are implanted within patient 12, e.g., in the same session. In this way, processor 90 of ICD 16 may learn the characteristics of the neurostimulation signal artifact that may be present in a sensed signal.

Processor 90 of ICD 16 may use these known characteristics of the neurostimulation signal to filter the signal out of the electrical signals sensed by sensing module 96. In some examples, processor 90 or sensing module 96 may include a notch filter to filter the neurostimulation signals generated by INS 26. The notch filter may comprise a band-stop filter (or a band rejection filter) that attenuates frequencies in a specific frequency range. The frequency range of the notch filter may be selected based on the known frequency range of the neurostimulation signals generated and delivered by INS 26. The notch filter may be dynamically adjustable based on, for example, the therapy program with which INS 26 generates the electrical stimulation signals.

In some examples, sensing module 96 of ICD 16 may apply different filters to sensed electrical signals in the first and second sense modes. In addition, in some examples, processor 90 of ICD 16 may apply different arrhythmia detection algorithms based on whether the first or second sense modes are applied by ICD 16. The arrhythmia detection algorithms may define the rules with which processor 90 identifies a potential arrhythmia. For example, the arrhythmia detection algorithms may define the number of arrhythmia events that define an arrhythmia episode, or the R-R interval duration that defines an arrhythmia event.

Modifying the type of arrhythmia detection algorithms based on whether INS 26 is delivering stimulation to patient 12 may help compensate for the decrease in sensitivity to electrical cardiac signals in the first sense mode of ICD 16 compared to the second sense mode. For example, when ICD 16 is applying the first sense mode to sense electrical cardiac signals, processor 90 of ICD 16 may determine that an arrhythmia episode is observed when a fewer number of R-R intervals having a duration less than a stored threshold are detected compared to arrhythmia detection algorithm implemented during the second sense mode. In this way, processor 90 may compensate for the decrease in sensitivity to electrical cardiac signals by increasing the sensitivity to arrhythmia detection.

In some examples, the segment of an electrical cardiac signal that is observed to detect the arrhythmia may differ based on whether ICD 16 is applying the first or second sense modes. For example, in the first sense mode, processor 90 of ICD 16 may detect arrhythmia events based on a duration of an S-T segment of a sensed EGM, and in the second sense mode, processor 90 may detect arrhythmia events based on a different segment of a sensed EGM (e.g., the R-R segment or P-P segment).

Figure 17A:
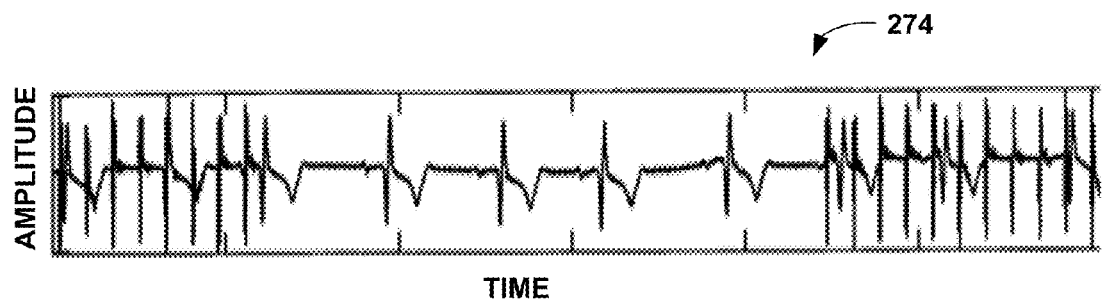
FIGS. 17A and 17B are conceptual illustrations of sensed electrocardiogram (ECG) signals prior to and after a neurostimulation signal artifact is at least partially removed from the sensed ECG signal.
Figure 17B:
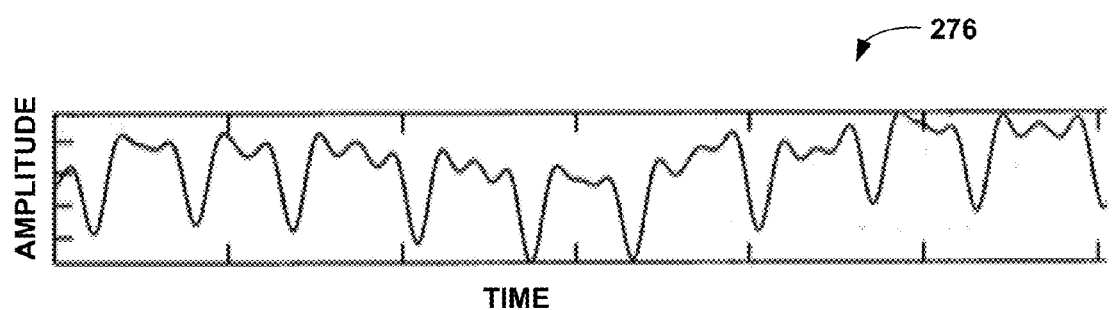

FIG. 17A provides a conceptual illustration of an ECG signal 274 sensed by a sensing device via subcutaneous electrodes on left and right sides of a human subject. ECG signal is an example of an electrical signal that is sensed prior to the application of a filter by a processor (e.g., processor 90 of ICD 16). FIG. 17B provides a conceptual illustration of filtered ECG signal 276 after a processor applies a filter to sensed ECG signal 274. An artifact from delivery of neurostimulation is present in ECG signal 274. As FIG. 17B demonstrates, sensed ECG signal 274 comprising the neurostimulation signal artifact exhibits a relatively fast heart rhythm, e.g., about 260 beats per minute. Signal processing ECG signal 274, e.g., by applying a filter to ECG signal 274, may help remove the relatively high frequency neurostimulation signal artifact from sensed ECG signal 274. As FIG. 17B illustrates, the processed ECG signal 276 exhibits a relatively slower heart rhythm, such as about 92 beats per minute.

The processed ECG signal may be a more accurate and precise representation of true cardiac signals of the human subject. For example, while the heart rhythms indicated by signal 274 may indicate a ventricular tachycardia events, the processed signal 276 indicates a slower heart rhythm, which may not be associated with a ventricular tachycardia events. Accordingly, it may be useful for processor 90 to apply one or more filters or implement other signal processing techniques to a sensed signal in order to minimize the possibility of delivering inappropriate therapy to patient 12.

Figure 18A:
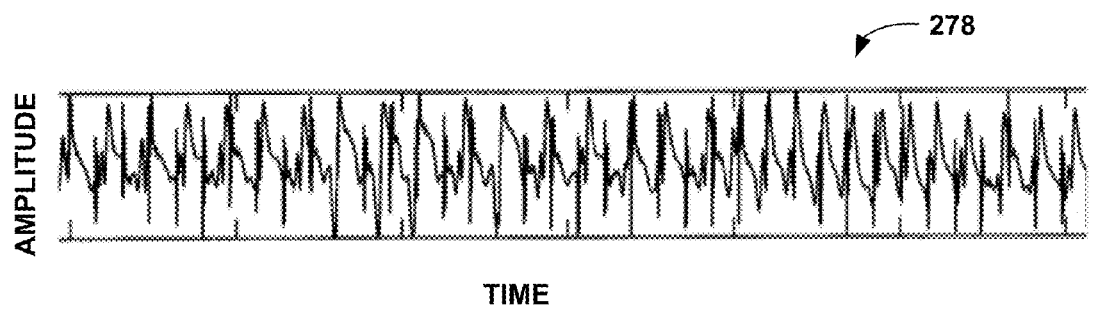
FIGS. 18A and 18B are conceptual illustrations of sensed ECG during a ventricular tachycardia prior to and after a neurostimulation signal artifact is at least partially removed from the sensed ECG signal.
Figure 18B:
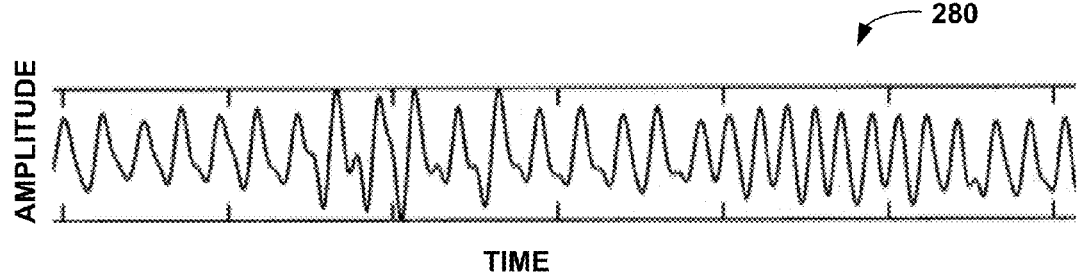

FIG. 18A provides a conceptual illustration of an ECG signal 278 sensed by a sensing device via subcutaneous electrodes on left and right sides of a human subject. An ischemia-inducted ventricular tachycardia was induced in the human subject. FIG. 18B provides a conceptual illustration of filtered ECG signal 280 after a processor applies a filter to sensed ECG signal 278. An artifact from delivery of neurostimulation is present in ECG signal 278. As FIG. 18A demonstrates, sensed ECG signal 278 comprising the neurostimulation signal artifact exhibits a relatively fast heart rhythm, e.g., about 470 beats per minute. Signal processing ECG signal 278, e.g., by applying a filter to ECG signal 278, may help remove the relatively high frequency neurostimulation signal artifact from sensed ECG signal 278. As FIG. 18B illustrates, the processed ECG signal 280 exhibits a relatively slower heart rhythm, such as about 280 beats per minute. FIGS. 18A and 18B further demonstrate that a processed ECG signal 280 may be a more accurate and precise representation of true cardiac signals of the human subject. As FIGS. 18A and 18B demonstrate, at least partially filtering the neurostimulation signal artifact from a sensed electrical signal may be useful for determining a true heart rate, such as a true ventricular tachycardia rate.

Figure 19A:
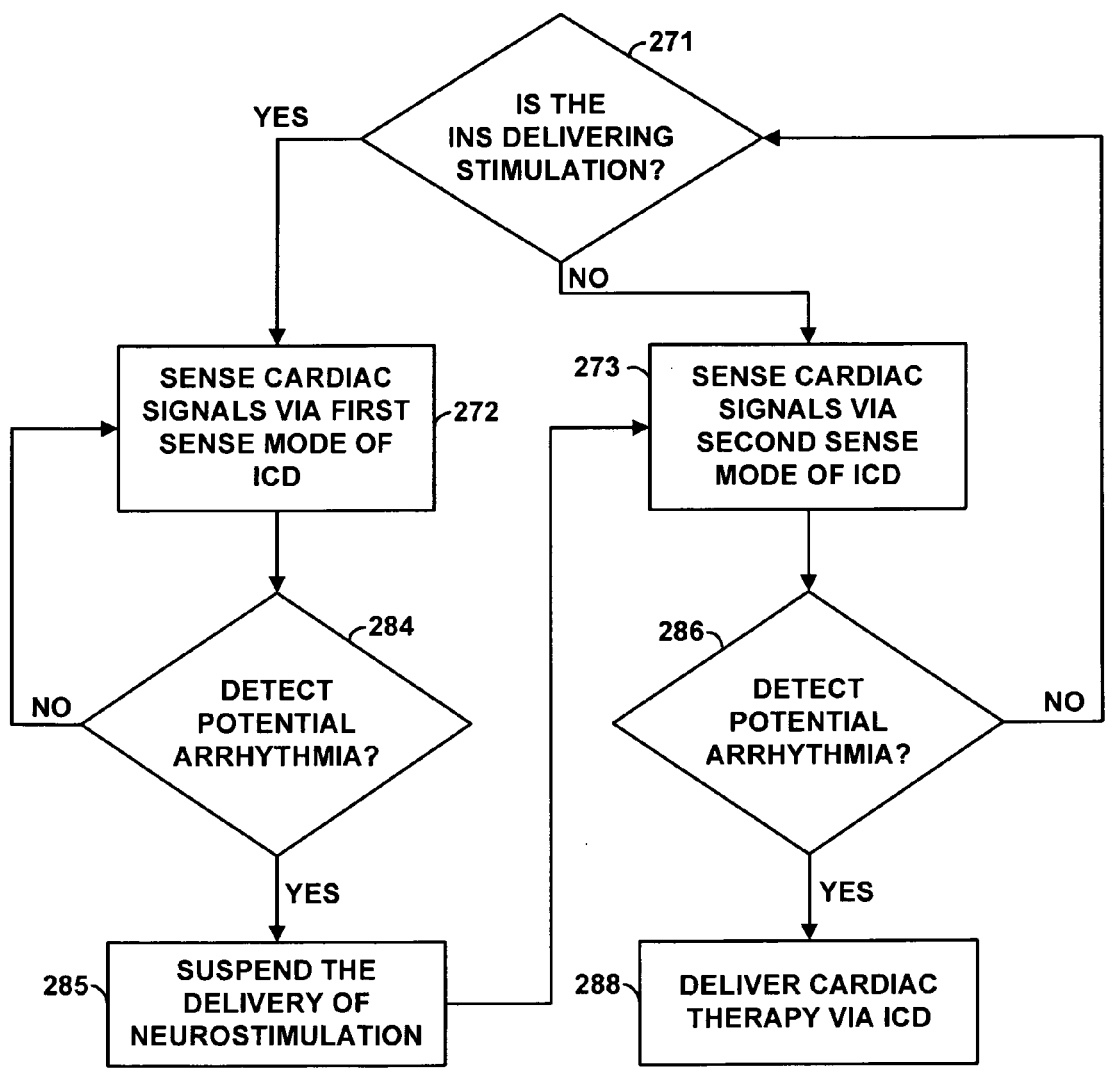
FIGS. 19A and 19B are flow diagrams illustrating example techniques that an ICD may implement in order to detect an arrhythmia while an INS is delivering electrical stimulation.

FIG. 19A is a flow diagram illustrating another example technique that processor 90 of ICD 16 may implement in order to change a cardiac signal sense mode based on whether INS 26 is actively delivering electrical stimulation. As with the technique shown in FIG. 16, processor 90 may determine whether INS 26 is delivering stimulation to patient 12 (271). If INS 26 is currently delivering stimulation to patient 12, processor 90 may control sensing module 96 to sense cardiac signals via a first sense mode (272). On the other hand, if INS 26 is not delivering stimulation to patient 12, e.g., because the delivery of stimulation by INS 26 is currently suspended, processor 90 may implement a second sense mode in order to sense cardiac signals (273), where the second sense mode comprises at least one different sensing parameter than the first sense mode. In addition, if processor 90 (or sensing module 96 under the control of processor 90) detects an arrhythmia via the first sense mode (284), processor 90 may control INS 26 to suspend the delivery of therapy to patient 12 (285) and processor 90 may control sensing module 96 to sense according to the second sense mode (273).

If processor 90 detects an arrhythmia while sensing cardiac activity via the second sensing mode (286), processor 90 may control stimulation generator 94 (FIG. 6) to deliver the appropriate stimulation therapy to heart 14 (288), which may be, for example, any one or more of pacing, cardioversion or defibrillation pulses. As shown in FIG. 19A, the second sense mode of ICD 16 may be used to confirm the detection of an arrhythmia detected via the first sense mode. The second sense mode of ICD 16 may be more specific to appropriately detecting electrical cardiac signals than the first sense mode, e.g., may be more likely to detect a cardiac arrhythmia based on the electrical cardiac signals compared to the first sense mode. This may be attributable to, for example, the lower cardiac signal sensing threshold defined by the second sense mode and/or the higher amplifier gain used to sense the signals. By decreasing the sensing threshold or increasing the amplifier gain, the sensitivity of ICD 16 to heart signals may increase because sensing module 96 may characterize more electrical signals as cardiac signals, and, therefore decrease the possibility of undersensing cardiac signals.

As previously indicated, although the first sense mode is less sensitive to cardiac signals, the first sense mode detects an arrhythmia based on other physiological parameters of patient. Detecting a potential arrhythmia based on physiological parameters in addition to electrical cardiac signals may compensate for the decrease in sensitivity to cardiac signals.

As shown in FIG. 19A, the second sense mode may be a default sense mode when INS 26 is not actively delivering stimulation therapy to patient because crosstalk between ICD 16 and INS 26 may be negligible. Thus, the possibility that sensing module 96 may oversense cardiac signals in the second sense mode is reduced when INS 26 is not actively delivering stimulation therapy to patient 12.

In some examples, the first and second sense modes may comprise different sense vectors. A sense vector may be defined by the subset of electrodes 50, 52, 54, 56, 58, 60, 70, 72, 74, and 76 electrically coupled to ICD 16 that are used by sensing module 96 to sense electrical cardiac signals. A sensing vector may be modified by switching the electrodes with which sensing module 96 senses intracardiac electrical signals. ICD 16 may sense electrical cardiac signals via one or more external electrodes. In some examples, ICD 16 may sense electrical cardiac signals via external electrodes in the first sense mode and sense electrical cardiac signals via implanted electrodes in the second sense mode.

As another example of how a sensing vector may be modified by selecting different electrode, if sensing module 96 senses an intracardiac electrical signal via electrodes 50, 52 of lead 18, which are positioned in right ventricle 32 (FIG. 3), and processor 90 detects an arrhythmia (284) based on the sensed signals, processor 90 may control sensing module 96 to switch sense modes, and, therefore, switch sensing vectors and sense intracardiac electrical signals via electrodes 54, 56 of lead 20, which is positioned in left ventricle 36 (FIG. 3).

In some examples, sensing module 96 of ICD 16 may sense electrical cardiac signals within left ventricle 36 (FIG. 3) and outside of right ventricle 32 (FIG. 3) of heart 14 in the first sense mode. That is, in the first sense mode, sensing module 96 may not sense electrical cardiac signals via electrodes 50, 52, 72 (FIG. 3) positioned within right ventricle 32. In addition, in some examples, sensing module 96 of ICD 16 may sense electrical cardiac signals within right ventricle 32 and outside of left ventricle 36 of heart 14 in the first sense mode. That is, in the first sense mode, sensing module 96 may not sense electrical cardiac signals via electrodes 54, 56, 74 (FIG. 3) positioned within left ventricle 36.

As another example of how ICD 16 may switch sense vectors with which electrical cardiac signals of heart 14 of patient 12 are sensed, in the first sense mode, ICD 16 may sense electrical cardiac signals via two electrodes of one of leads 18, 20, 22 (FIG. 3), and in the second sense mode, ICD 16 may sense electrical cardiac signals via at least one electrode carried by a lead 18, 20 and/or 22 and housing electrode 68 (FIG. 3). In this way, in the second sense mode, ICD 16 may sense electrical cardiac signals across a greater span of heart 14 than in the first sense mode.

In some examples, in at least the first sense mode, ICD 16 may sense electrical cardiac signals via each of a plurality of sense vectors. If ICD 16 senses electrical cardiac signals via each of a plurality of sense vectors in the second sense modes, the sense vectors defined by the second sense mode may be different than the sense vectors defined by the first sense mode. Crosstalk from therapy delivery by INS 26 may have different strengths, depending on the vector with which ICD 16 senses electrical signals. Thus, sensing electrical cardiac signals with a plurality of sense vectors may help increase the possibility that ICD 16 senses a true electrical cardiac signal or at least an electrical cardiac signal that that does not have a large signal artifact from INS crosstalk.

In addition, if ICD 16 senses electrical cardiac signals via each of a plurality of sense vectors, ICD 16 may determine cardiac function of patient 12 based on a weighted sum of the electrical cardiac signals or at least based on a correlation of the electrical cardiac signals sensed via two or more sense vectors. In one example of weighing the electrical signals sensed by each of a plurality of sensing vectors, processor 90 may individually gain and sum the signals and determine whether the summed signal indicates the presence of a cardiac episode or event (e.g., a tachyarrhythmia). In another example, processor 90 may sum the absolute value of each sensed signal to generate a summed signal that is evaluated to detect cardiac function (e.g., the presence of an arrhythmia). In general, processor 90 sums the different sensed signals in order to combine the sensing information and attempt to filter out crosstalk noise, which may only be affecting only one or two of the sensing vectors.

In some examples, the electrical signals sensed via each of the sense vectors are each used to determine the timing of the R-waves or other signal characteristics, e.g., to detect an arrhythmia. Processor 90 of ICD 16 may determine whether the R-waves sensed via different sense vectors indicate that an arrhythmia is detected. If, for example, a threshold number (e.g., two or more) of the electrical signals sensed via different sense vectors indicate different R-R intervals, processor 90 may determine that the sensed electrical cardiac signals are not true electrical cardiac signals, but are at least partially attributable to delivery of electrical stimulation by INS 26.

If processor 90 detects a potential arrhythmia based on intracardiac electrical signals sensed via a first sensing vector defined by the first sense mode (284), processor 90 may determine whether an arrhythmia is detected based on the intracardiac electrical signals sensed via a second sensing vector defined by the second sense mode (273, 284). The first and second sensing vectors may be defined by respective subsets of electrodes 50, 52, 54, 56, 58, 60, 70, 72, 74, and 76, where the first and second sensing vectors may include at least one different electrode. If processor 90 detects the potential arrhythmia based on the signals sensed via the new sensing vector, processor 90 may confirm the presence of the arrhythmia and, therefore, determine whether the detected arrhythmia was based on true cardiac signals, or at least not based on electrical stimulation signals from INS 26.

In some cases, switching the sensing vector may help decrease the crosstalk that ICD 16 senses by, for example, changing the relative vector between the stimulation electrodes 124 connected to INS 26 and the sensing vector used by ICD 16 to sense cardiac signals. Thus, in some cases, the crosstalk sensed by the new sensing vector may change characteristics compared to the initial sensing vector, and, as a result, processor 90 may not mischaracterize the artifact generated by the delivery of electrical stimulation by INS 26 as true cardiac signals.

If the potential arrhythmia is not detected (286) when ICD 16 is sensing in the second sense mode, processor 90 may determine that the potential arrhythmia detected via the cardiac signals sensed via the first sense mode (284) was a false detection based on noise from INS 26, rather than true cardiac signals. Thus, processor 90 may not provide any therapy to patient 12, and processor 90 of ICD 16 may determine whether INS 26 is delivering electrical stimulation to patient 12 (271) and control sensing module 96 to sense electrical cardiac signals of patient 12 via the first sense mode (272) if INS 26 is delivering stimulation to patient 12 and control sensing module 96 to sense electrical cardiac signals of patient 12 via the second sense mode if INS 26 is not delivering stimulation to patient 12 (273).

Figure 19B:
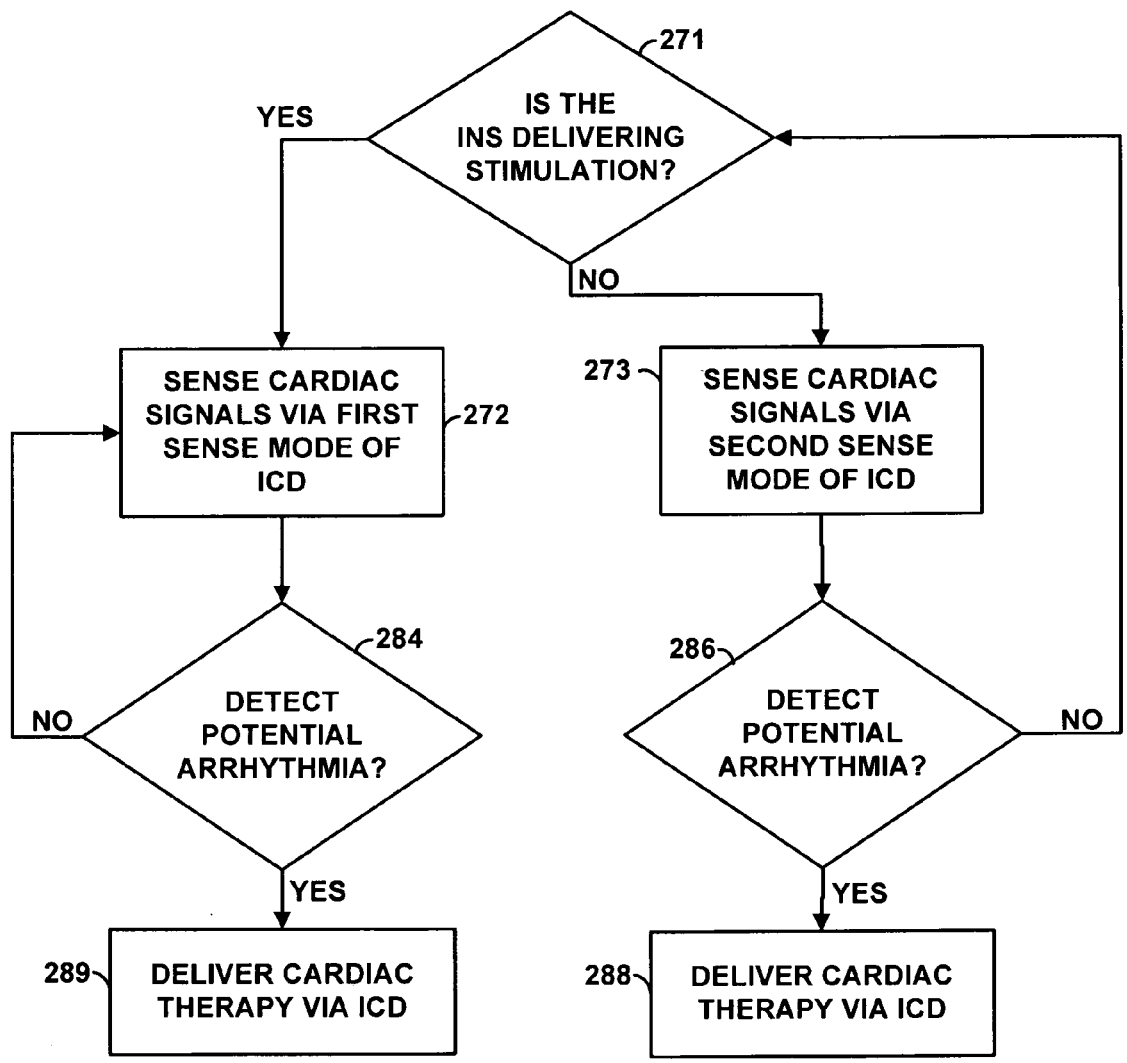

FIG. 19B is a flow diagram illustrating another example technique that processor 90 of ICD 16 may implement in order to change a cardiac signal sense mode based on whether INS 26 is actively delivering electrical stimulation. The technique shown in FIG. 19B is similar to that shown in FIG. 19A. However, in the example shown in FIG. 19B, if processor 90 (or sensing module 96 under the control of processor 90) detects an arrhythmia via the first sense mode (284), in the example shown in FIG. 19B, processor 90 may control stimulation generator 94 (FIG. 6) to deliver the appropriate stimulation therapy to heart 14 (289). In contrast, in the example shown in FIG. 19A, processor 90 controlled INS 26 to suspend or otherwise adjust the delivery of stimulation to patient 12 (285) and then determined whether the potential arrhythmia was also detected when the patient's condition was sensed via the second sense mode of ICD 16 (273, 286).

In some cases, it may be desirable to evaluate the extent of the crosstalk between INS 26 and ICD 16. For example, it may be desirable to evaluate the strength of the electrical stimulation signal generated by INS 26 and sensed by ICD 16, i.e., evaluate one or more characteristics of an artifact present in a signal sensed by ICD 16 when INS 26 is delivering stimulation to patient 12. The artifact may be referred to as a neurostimulation artifact, although the artifact may also be attributable to the delivery of stimulation other than neurostimulation by INS 26. A clinician or patient 12 may evaluate the crosstalk between INS 26 and ICD 16 in order to determine if the crosstalk is excessive at various times, such as after implantation of ICD 16 and INS 26 in patient 12, after programming the electrical stimulation parameters or sensing parameters of either ICD 16 or INS 26 or periodically throughout the use of therapy system 10.

Crosstalk may be excessive if it hinders the intended operation of ICD 16, such as the sensing of true cardiac signals by ICD 16. As previously described, in some examples, ICD 16 may sense the electrical stimulation signal generated and delivered by INS 26 and mischaracterize the electrical stimulation signal as a cardiac signal. This mischaracterization of the electrical stimulation signal as a cardiac signal may result in a detection of a cardiac arrhythmia, which may result in the inappropriate delivery of a defibrillation shock or other electrical stimulation to heart 14. In this way, the crosstalk between INS 26 and ICD 16 may affect the intended operation of ICD 16.

In some examples, the crosstalk between INS 26 and ICD 16 may be excessive if a characteristic of a signal sensed by the ICD 16 while electrical stimulation is being delivered by INS 26 differs from a characteristic of a baseline signal by a threshold value. As described in further detail below, the characteristic of the electrical signals may be an amplitude value or a power level (or energy level) in one or more frequency bands. For example, the characteristic of the electrical signals may be an absolute amplitude value or a root mean square amplitude value. In addition, the amplitude value may comprise a mean or median amplitude value over a period of time or a maximum amplitude or an amplitude in a particular percentile of the maximum (e.g., an amplitude value that represents 95% of the maximum amplitude value). In some examples, as described in further detail below, the threshold value may be a percentage of a sensing threshold with which ICD 16 senses electrical cardiac signals.

If the crosstalk between INS 26 and ICD 16 is determined to be excessive, a clinician or a device (e.g., INS 26, ICD 16 or programmer 24) may attempt to reduce the extent of the crosstalk. For example, ICD 16 or INS 26 may modify one or more stimulation parameter values of INS 26, as described with respect to FIGS. 9-12B and/or modify one or more sensing parameter values of ICD 16, as described with respect to FIGS. 16, 19A, and 19B.

In some examples, an external device, such as medical device programmer 24 (FIG. 1) may be used to evaluate the extent of crosstalk between INS 26 and ICD 16. While programmer 24 is primarily referred to throughout the description of FIG. 20, in other examples, another device may be used to measure the amount of crosstalk between INS 26 and ICD 16. The device may be an external device, such as multifunction computing device or may be a device dedicated to measuring the amount of crosstalk between INS 26 and ICD 16, or one of the implanted medical devices 16, 26. In addition, in some examples, ICD 16, INS 26 or another implanted device may measure the amount of crosstalk between ICD 16 and INS 26. The implanted device may store the information indicative of the amount of crosstalk between ICD 16 and INS 26 or may transmit information to an external device, such as programmer 24.

Figure 20:
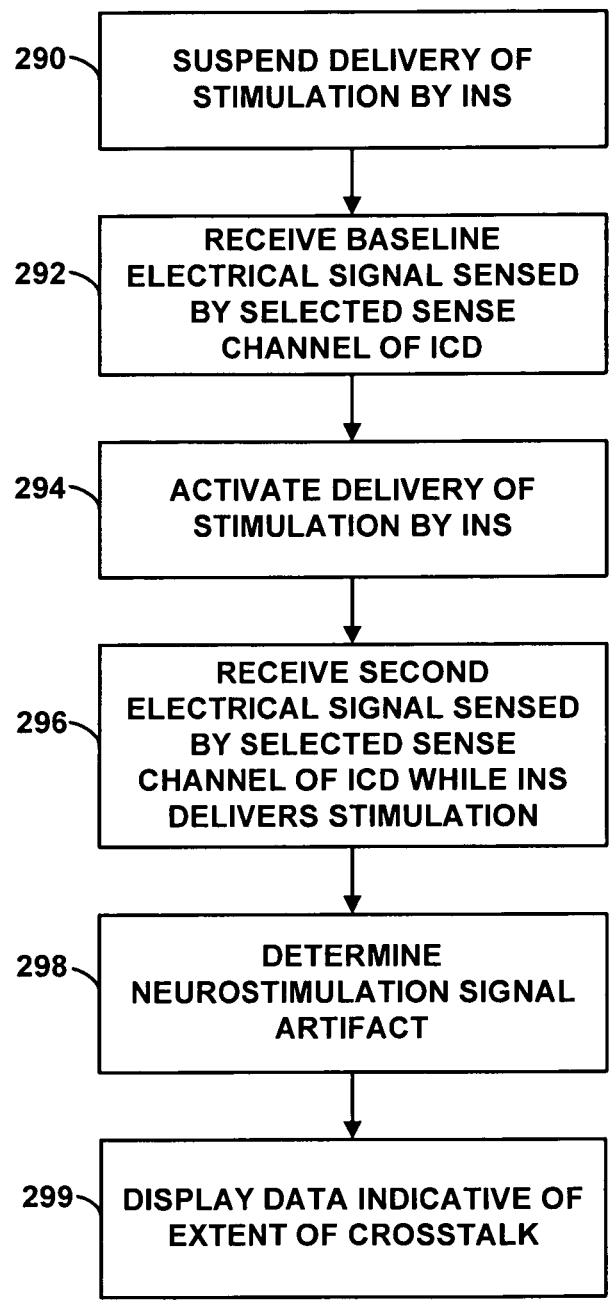
FIG. 20 is a flow diagram illustrating an example technique for evaluating the crosstalk between an INS and an ICD implanted within a patient.

FIG. 20 is a flow diagram illustrating an example technique for evaluating crosstalk between ICD 16 and INS 26. The technique shown in FIG. 20 may be implemented in order to determine a status of the electrical noise sensed by ICD 16 due to the delivery of stimulation by INS 26. The status determination may be used to, for example, modify an stimulation parameter of INS 26 or a sensing parameter of ICD 16, e.g., in accordance with the techniques described above with respect to FIGS. 9-12, 16, 19A, and 19B.

As shown in FIG. 20, processor 130 of programmer 24 (FIG. 8) may evaluate one or more characteristics of a signal sensed by ICD 16 when the neurostimulation artifact is present under the direction of a clinician or automatically, e.g., based on a schedule determined by a clinician. The schedule may define an evaluation frequency with processor 130 evaluates the neurostimulation signal artifact sensed by ICD 16. For example, the artifact evaluation frequency may be in a range of about one to about ten times per minute, once per hour, or once per day, although other frequency ranges are contemplated.

In order to measure the magnitude of the neurostimulation artifact (or "crosstalk") present in the electrical cardiac signal sensed by ICD 16, processor 130 of programmer 24 may instruct processor 110 of INS 26 to suspend or otherwise adjust the delivery of neurostimulation (290). For example, processor 130 of programmer 24 may transmit a control signal to processor 110 via the respective telemetry modules 136 (FIG. 8), 118 (FIG. 7). The control signal may not only indicate whether INS 26 should suspend or otherwise adjust the delivery of neurostimulation to patient 12, but, in some examples, may indicate how long INS 26 should suspend neurostimulation or deliver therapy according to the adjust parameters. In other examples, memory 112 (FIG. 7) of INS 26 may store instructions for suspending or otherwise adjusting neurostimulation when processor 110 of INS 26 receives the control signal from processor 130 of programmer 24. As another example, INS 26 may suspend or otherwise adjust delivery of stimulation without intervention from programmer 24, e.g., according to schedule stored by memory 112.

During the time in which neurostimulation is suspended or adjusted, processor 130 of programmer 24 may receive an electrical signal sensed by ICD 16 from ICD 16 (292). This electrical signal may represent a baseline artifact level present in the cardiac signal sensed by ICD 16. Artifacts from sources other than the neurostimulation signals delivered by INS 26 may be present in the signal sensed by ICD 16, such as from electromagnetic interference from electronics or electrical outlets in the patient's surroundings. The baseline electrical signal may indicate these other artifacts present in the signal sensed by ICD 16.

In some examples, processor 130 of programmer 24 may instruct processor 90 of ICD 16 to sense a baseline electrical signal via a selected sensing channel of sensing module 96 (FIG. 6) of ICD 16. As described with respect to FIG. 6, in some examples, sensing module 96 may include a plurality of sensing channels, which may each include an amplifier. For example, sensing module 96 may include a sensing channel including an R-wave amplifier to sense R-waves within right ventricle 32 of heart 14 (FIG. 3), a sensing channel including an R-wave amplifier to sense R-waves within left ventricle 36 of heart 14 (FIG. 3), a sensing channel including a P-wave amplifier to sense P-waves within right atrium 30 of heart 14 (FIG. 3), and/or a sensing channel including a wide band amplifier in order to generate an EGM representing the electrical activity of heart 14. Processor 90 of ICD 16 may transmit the electrical signal sensed on the selected sensing channel of sensing module 96 to processor 130 of programmer 24 via the respective telemetry modules 98 (FIG. 6), 136 (FIG. 8).

After processor 130 of programmer 24 receives the baseline electrical signal from ICD 16 (292), processor 130 may control processor 110 of INS 26 to activate the delivery of electrical stimulation (294). For example, processor 130 may generate a control signal that is transmitted to processor 110 of INS 26 via the respective telemetry modules 136 (FIG. 8), 118 (FIG. 7). Upon receiving the control signal, processor 110 of INS 26 may control stimulation generator 114 to begin generating and delivering neurostimulation therapy, e.g., in accordance with a first operating mode of INS 26. As described with respect to FIG. 12A, a first operating mode may be defined by a therapy program that defines one or more stimulation parameter values for the electrical stimulation signals generated and delivered by INS 26. In other examples, processor 110 of INS 26 may begin generating and delivering neurostimulation therapy based on a predetermined schedule that indicates the times at which processor 110 should suspend the delivery of neurostimulation and initiate the delivery of stimulation.

After INS 26 commences the delivery of neurostimulation to patient 12, processor 130 of programmer 24 may receive an electrical signal sensed by the selected channel of sensing module 96 of ICD 16 (FIG. 6) (296). This electrical signal that is sensed on the selected sensing channel during the delivery of neurostimulation by INS 26 may be referred to as a "second electrical signal" to distinguish it from the baseline electrical signal. Processor 130 of programmer 24 may receive the baseline electrical signal and the second electrical signal, for example, by periodically interrogating ICD 16. In other examples, ICD 16 may periodically transmit the baseline electrical signal and second electrical signal to processor 130 of programmer 24 without being interrogated by programmer 24.

Processor 130 of programmer 24 may determine the neurostimulation signal artifact on the selected sensing channel of ICD 16 based on the baseline electrical signal and the second electrical signal that was sensed while INS 26 was actively delivering neurostimulation to patient 12 (298). In some examples, processor 130 of programmer 24 may determine the neurostimulation signal artifact that is present on more than one sensing channel of sensing module 96 of ICD 16. In addition, in some examples, processor 90 of ICD 16 may sense the neurostimulation signal artifact present in the signal sensed via one or more selected sensing channels during a quiet segment of the cardiac cycle. The quiet segment of a cardiac cycle may be when the intrinsic electrical signal of heart 14 is least active, such as during the S-T segment of a sinus rhythm of heart 14.

In some examples, processor 130 of programmer 24 may determine the neurostimulation signal artifact on the selected sensing channel by determining a difference between one or more signal characteristics of the baseline electrical signal and the second electrical signal. In some examples, the signal characteristic may comprise a current or a voltage amplitude of the signal waveforms. For example, processor 130 of programmer 24 may determine a difference in the amplitude of the baseline electrical signal and a sensing threshold of sensing module 96 (FIG. 6) of ICD 16. This value may be referred to as the "first value" for ease of description. The amplitude may be a mean or median amplitude (e.g., a peak-to-peak amplitude), a highest amplitude (e.g., a peak-to-peak amplitude), a root means square (RMS) amplitude, an amplitude that is equal to a certain percentage (e.g., about 95%) of the highest amplitude, and the like. A sensing threshold may indicate a threshold amplitude value above which processor 90 of ICD 16 characterizes a sensed electrical signal as an electrical cardiac signal.

Processor 130 may also determine a second value indicative of the difference in the amplitude of the second electrical signal and a sensing threshold of sensing module 96. The amplitude may be a mean or median amplitude, a highest amplitude, a RMS amplitude, an amplitude that is equal to a certain percentage (e.g., about 95%) of the highest amplitude, and the like. In order to determine the neurostimulation signal artifact on the selected sensing channel, processor 130 of programmer 24 may determine a difference between the first and second values. If the difference is greater than or equal to a stored threshold value, which may be based on the sensing threshold amplitude of ICD 16, processor 130 may determine that the crosstalk between ICD 16 and INS 26 due to the delivery of neurostimulation by INS 26 is unacceptable. On the other hand, if the difference between the first and second values is less than the stored threshold value, processor 130 may determine that the crosstalk between ICD 16 and INS 26 due to the delivery of neurostimulation by INS 26 is within acceptable ranges. In this way, processor 130 may evaluate the extent of the crosstalk between ICD 16 and INS 26 due to the delivery of neurostimulation by INS 26. The threshold value may be, for example, selected by a clinician and stored by programmer 24, ICD 16, INS 26 or another device.

As another example, the signal characteristic may comprise a power level within a particular frequency band of an electrical signal. Processor 130 may determine the neurostimulation signal artifact by determining a first value indicative of the difference in energy levels in the selected frequency band of the baseline electrical signal and a stored energy level, and a second value indicative of the difference in energy levels in the selected frequency band of the second electrical signal and the stored energy level. The difference between the first and second values may be indicative of noise on a sensing channel of ICD 16 due to the delivery of neurostimulation by INS 26.

Figure 21:
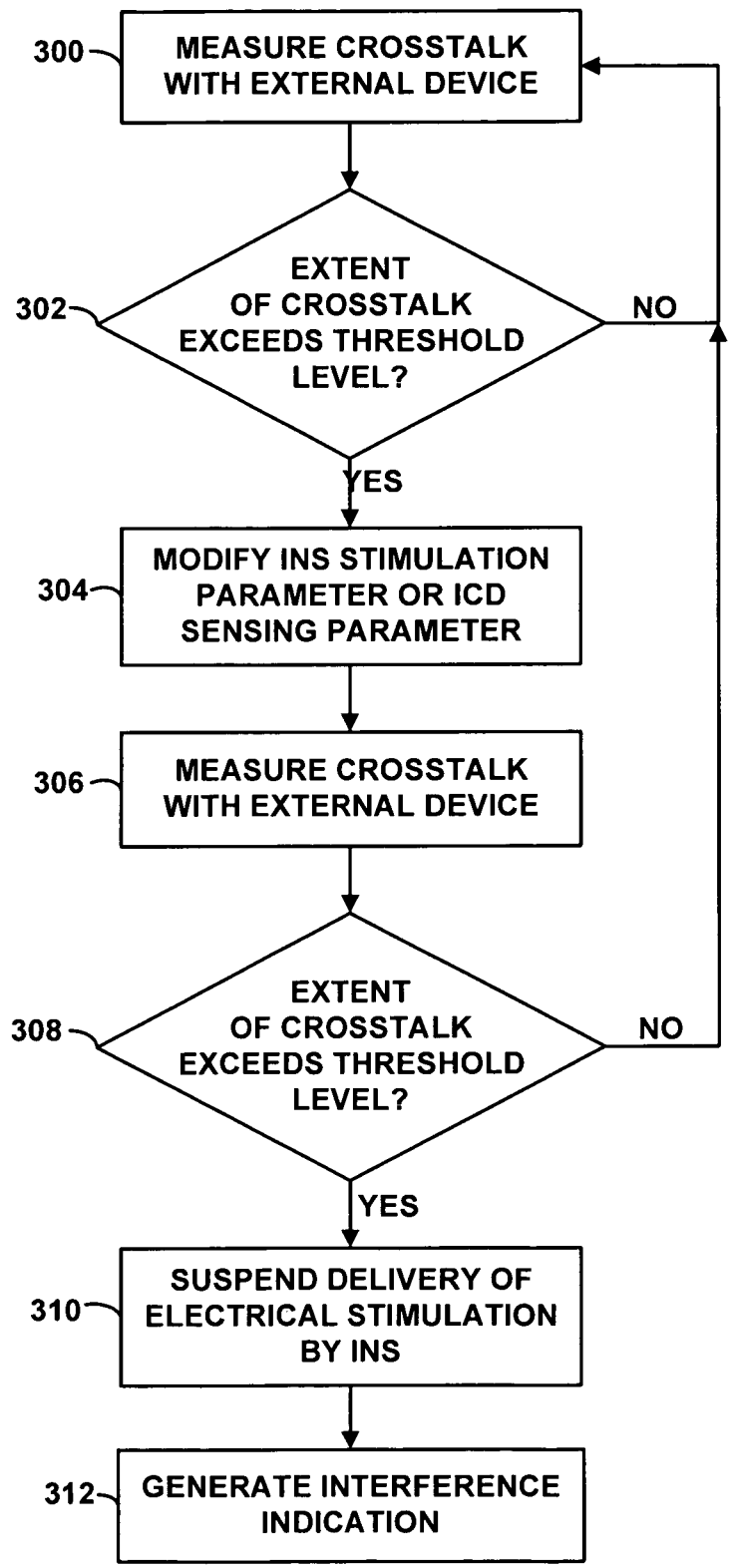
FIG. 21 is a flow diagram illustrating an example technique that may be used to evaluate the extent of the crosstalk between an INS and ICD implanted within a patient and minimize the crosstalk if the crosstalk exceeds a threshold level.

Processor 130 of programmer 24 may display data indicative of the extent of crosstalk between ICD 16 and INS 26 on a display of user interface 134 (FIG. 8) (299). For example, the data may include a graphical display of the waveform of the baseline electrical signal or a waveform of the second electrical signal. An example of a graphical display of different types of waveforms indicative of the crosstalk between ICD 16 and INS 26 is shown in FIG. 21, which is described below.

As patient 12 changes posture and/or activity level, the one or more leads 28, 29 (FIGS. 1 and 2) connected to INS 26 may move within patient 12. For example, in the example shown in FIG. 2, as patient 12 changes posture, leads 28, 29 may move relative to ICD 16 as spinal cord 44 moves. The amount of neurostimulation artifact that ICD 16 senses may change as a function of the position of leads 28, 29 within patient 12. For example, in some patient postures, at least one of the leads 28, 29 may be closer to the sense electrodes coupled to ICD 16, and, as a result, ICD 16 may sense a stronger neurostimulation signal. That is, as leads 28, 29 move closer to ICD 16, the extent of crosstalk between INS 26 and ICD 16 may increase. Similarly, for increased levels of patient activity, leads 28, 29 may undergo more movement within patient 12, which may also result in at least one of the leads 28, 29 moving closer to heart 14.

In some examples, in order to better evaluate the neurostimulation artifact present in a signal sensed by ICD 16 when INS 26 is actively delivering stimulation, processor 130 of programmer 24 may evaluate the neurostimulation artifact while patient 12 is in different postures and/or activity levels. This may help processor 130 and/or the clinician evaluate the spectrum of crosstalk that may be present between ICD 16 and INS 26. In some examples, processor 130 may present a display on user interface 134 (FIG. 8) of programmer 24 that prompts patient 12 to undertake different postures or activities. The different patient postures may include, for example, standing, sitting, a prone position, bending forward while standing or bending backward at the waist while standing, and the like. Processor 130 may then evaluate the amount of crosstalk between INS 26 and ICD 16 while patient 12 is in each of the different postures or activities, e.g., using the technique shown in FIG. 20. For example, while patient 12 is in each of the different postures or activities, processor 130 of programmer 24 may receive and record both a baseline and a second electrical signal sensed by ICD 16.

In other examples, processor 90 of ICD 16, rather than processor 130 of programmer 24, may determine the neurostimulation signal artifact on the selected sensing channel of ICD 16 based on the baseline electrical signal and the second electrical signal that was sensed while INS 26 was actively delivering neurostimulation to patient 12. In this way, ICD 16 may provide real-time detection of crosstalk and switch sensing modes at a useful time, e.g., before inappropriately delivering a shock to patient 12, or communicate to the INS 26 to adjust therapy delivery (e.g., adjust a stimulation parameter value or suspend neurostimulation).

FIG. 21 is a flow diagram illustrating an example technique that may be used to evaluate the extent of the crosstalk between INS 26 and ICD 16 and minimize the crosstalk if the crosstalk exceeds a threshold level. Processor 130 of programmer 24 may measure the crosstalk (300), e.g., using the technique described with respect to FIG. 20. Processor 130 may determine whether the extent of crosstalk exceeds a threshold level (302). In some examples, processor 130 may determine whether the extent of crosstalk exceeds the threshold level by determining whether the values of one or more signal characteristics (e.g., a voltage amplitude) of the second electrical signal differs from the respective signal characteristic values of the baseline electrical signal. The threshold level may indicate a percentage change or an absolute value change in the one or more signal characteristics. As discussed with respect to FIG. 20, the baseline electrical signal may represent the amount of artifact present on a selected sensing channel of ICD 16 when the delivery of neurostimulation by INS 26 is suspended and the second electrical signal may represent the amount of artifact present on the selected sensing channel when INS 26 is delivering neurostimulation therapy, e.g., in the ordinary course of neurostimulation therapy. The threshold level may be stored within memory 132 of programmer 24 (FIG. 8), memory 92 of ICD 16, memory 112 of INS 26 or a memory of another device.

In some examples, processor 130 may determine whether the extent of crosstalk exceeds a threshold level (302) by comparing a first value indicative of the difference between a voltage amplitude of the baseline electrical signal and a sensing threshold of sensing module 96 (FIG. 6) of ICD 16 and a second value indicative of the difference between a voltage amplitude of the second electrical signal and a sensing threshold of sensing module 96. The relevant voltage amplitudes of the baseline and second electrical signals may be the average or median amplitudes over a particular range of time, the amplitudes at a particular point in time, such as a greatest amplitude over a particular range of time or a percentage of the greatest amplitude. In addition, in some examples, the voltage amplitude may also comprise an absolute amplitude value or a root mean square voltage amplitude. In some examples, the sensing threshold may be the sensing threshold of sensing module 96 (FIG. 6) of ICD 16 at the most sensitive setting or at the least sensitive setting.

If the first and second values do not differ from each other by at least the threshold value (or threshold level), processor 130 of programmer 24 may determine that the extent of the crosstalk between INS 26 and ICD 16 is within an acceptable range. That is, if the difference between the first and second is less than or equal to the threshold value, processor 130 of programmer 24 may determine that the possibility that ICD 16 may sense the neurostimulation signals delivered by INS 26 and mischaracterize the neurostimulation signals as cardiac signals is relatively low. Processor 130 may then determine that modifications to the operating parameters of INS 26 or the sensing parameters of ICD 16 are not necessary. Processor 130 of programmer 24 may then continue measuring crosstalk (300) and comparing it to a threshold value (302).

On the other hand, if the first and second values differ from each other by at least the threshold value (or threshold level), processor 130 of programmer 24 may determine that the crosstalk between INS 26 and ICD 16 exceeds an acceptable level. In some examples, the threshold level may be up to about 100% of the sensing threshold of ICD 16, such as about 25% to about 50% of the sensing threshold. As previously indicated, the sensing threshold may be the sensing threshold of sensing module 96 (FIG. 6) of ICD 16 at the most sensitive setting or at the least sensitive setting. Thus, in some examples, if the difference between the first and second values is greater than the sensing threshold of ICD 16, processor 130 may determine that the crosstalk between INS 26 and ICD 16 exceeds an acceptable level. Other percentages or absolute value changes in voltage amplitudes that indicate an unacceptable level of neurostimulation signal artifact are contemplated.

In other examples, processor 130 may determine whether the extent of crosstalk exceeds a threshold level (302) by comparing the spectral content of the baseline electrical signal and the second electrical signal. For example, processor 130 may implement a fast Fourier transform algorithm in order to extract the frequency components of the baseline electrical signal and the second electrical signal. Processor 130 may compare one or more frequency components of the baseline electrical signal and the second electrical signal. The one or more frequency components may include, for example, a power level within one or more frequency bands, a trend in the power level within one or more frequency bands over time, a ratio of power levels between one or more frequency bands, and the like. Different frequency bands may be more revealing of the extent to which the second electrical signal includes an unacceptable level of neurostimulation signal artifact. A clinician may determine the revealing frequency bands during a trial phase in which INS 26 and ICD 16 are tested to determine the frequency bands are relatively revealing of a neurostimulation artifact that adversely affects the sensing of cardiac signals by ICD 16.

If processor 130 of programmer 24 determines that the extent of the crosstalk between INS 26 and ICD 16 exceeds an acceptable level, processor 130 may initiate the modification to one or more stimulation parameter values with which stimulation generator 114 of INS 26 generates and delivers neurostimulation therapy to patient 12 or one or more sensing parameter values of ICD 16 (304). Processor 130 may initiate the modification to the one or more stimulation parameter values of INS 26 using any suitable technique. In one example, processor 130 may transmit a control signal to processor 110 of INS 26, and processor 110 may initiate the modification to the one or more stimulation parameter values upon receiving the control signal from processor 130 of programmer 24. For example, processor 110 may modify the one or more stimulation parameter values using a set of rules stored in memory 112, as described with respect to FIGS. 11A-11D. Examples of stimulation parameter values that processor 110 may modify include, but are not limited to, an electrode combination, voltage amplitude, current amplitude, pulse rate, pulse duration, and the like. As another example, processor 110 may modify the one or more stimulation parameter values by switching therapy programs, as described with respect to FIGS. 12A and 12B.

In other examples, processor 130 of programmer 24 may provide processor 110 of INS 26 with a new therapy program defining one or more stimulation parameter values or provide processor 110 with specific instructions for modifying the one or more stimulation parameter values. For example, the instructions may indicate that processor 110 of INS 26 should decrease the frequency of the neurostimulation signal by a certain percentage or to a specific value. Other types of therapy parameter value modification instructions are contemplated. In other examples, processor 130 of programmer 24 may instruct processor 110 of INS 26 to modify one or more stimulation parameter values by switching therapy programs, as described with respect to FIG. 12A.

Processor 130 may initiate the modification to the one or more sensing parameters of ICD 16 using any suitable technique. In one example, processor 130 may transmit a control signal to processor 90 of ICD 16, and processor 90 may initiate the modification to the one or more sensing parameters upon receiving the control signal from processor 130 of programmer 24. For example, processor 90 may modify the one or more sensing parameter values by switching sense modes, as described with respect to FIGS. 16, 19A, and 19B. Examples of sensing parameters values that processor 90 may modify include, but are not limited to, a sensing threshold value, an amplifier gain, a sensing vector, and a type of filter used by sensing module 96 or processor 90 to filter noise out of a sensed signal.

After the one or more neurostimulation parameter values or ICD 16 sensing parameters are modified (304), processor 130 of programmer 24 may measure the crosstalk (306) and determine whether the extent of the crosstalk exceeds a threshold level (308), e.g., using the techniques described above. If processor 130 determines that the extent of the crosstalk does not exceed the threshold level, processor 130 may not take any further action to modify the one or more neurostimulation parameter values of INS 26. Processor 130 may then continue periodically or continuously measuring the crosstalk (300) until a condition in which the crosstalk exceeds a threshold level (302) is detected.

On the other hand, if processor 130 determines that the extent of the crosstalk exceeds the threshold level (308), processor 130 may suspend the delivery of neurostimulation by INS 26 (310). In other examples, prior to suspending the delivery of neurostimulation, processor 130 may initiate the modification to one or more stimulation parameter values of INS 26 or sensing parameters of ICD 16 in an attempt to minimize the neurostimulation artifact on the signal sensed by ICD 16. Processor 130 may repeat the steps shown in blocks 304, 306, and 308 to attempt to reduce the neurostimulation artifact. The one or more stimulation parameter values or sensing parameters may be modified for one or more iterations prior to suspending the delivery of neurostimulation by INS 26. As described with the technique shown in FIGS. 11A-11D, in some examples, processor 130 may modify a different stimulation parameter value or sensing parameter during each iteration of the stimulation parameter value modification (304), may modify the same stimulation parameter or sensing parameter for at least two consecutive or nonconsecutive iterations or may modify more than one type of stimulation parameter value in the same iteration of INS 26 modification.

Processor 130 of programmer 24 may generate an interference indication if the extent of the crosstalk between INS 26 and ICD 16 exceeds a threshold level, despite the modification to one or more stimulation parameter values (312). Processor 130 may present the interference indication to a user (e.g., a clinician or patient 12) via a display user interface 134 or processor 130 may generate an audible or a somatosensory alert (e.g., a pulse vibration of programmer 24) via programmer 24. In this way, programmer 24 may present a real-time interference alert to a user to notify the user that the stimulation delivered by INS 26 may be interfering with the sensing of cardiac signals by ICD 16.

In some examples, a characteristic of the visual, auditory or somatosensory alert may change in response to the amount of crosstalk determined to exist between ICD 16 and INS 26. For example, if the visual alert includes displaying a colored display, the color of the display may change or change intensity as a function of the amount of crosstalk determined to exist between ICD 16 and INS 26. As another example, if the interference indication comprises an audible alert, the tone, frequency, volume or another characteristic of the audible sound may change as a function of the amount of crosstalk determined to exist between ICD 16 and INS 26. The amount of crosstalk determined to exist between ICD 16 and INS 26 may be based on a difference between the first and second values, where the first value is indicative of the difference between the characteristic of the baseline electrical signal and the sensing threshold of ICD 16 and the second value is indicative of the difference between the characteristic of the second electrical signal and the sensing threshold of ICD 16. For example, processor 130 may determine that the greater the difference between the first and second values, the more crosstalk is present between ICD 16 and INS 26.

The interference indication may also indicate that the delivery of neurostimulation by INS 26 was adjusted (e.g., suspended or the intensity of neurostimulation was reduced) and or that patient 12 should seek medical attention. As previously indicated, the tonal frequency of the audible alert or the pulse rate or intensity of the somatosensory alert may change as a function of the relative level of crosstalk between INS 26 and ICD 16. For example, the intensity of the somatosensory alert or the pitch of the audible alert may change with the strength of the neurostimulation artifact present in the signal sensed by ICD 16.

Figure 32:
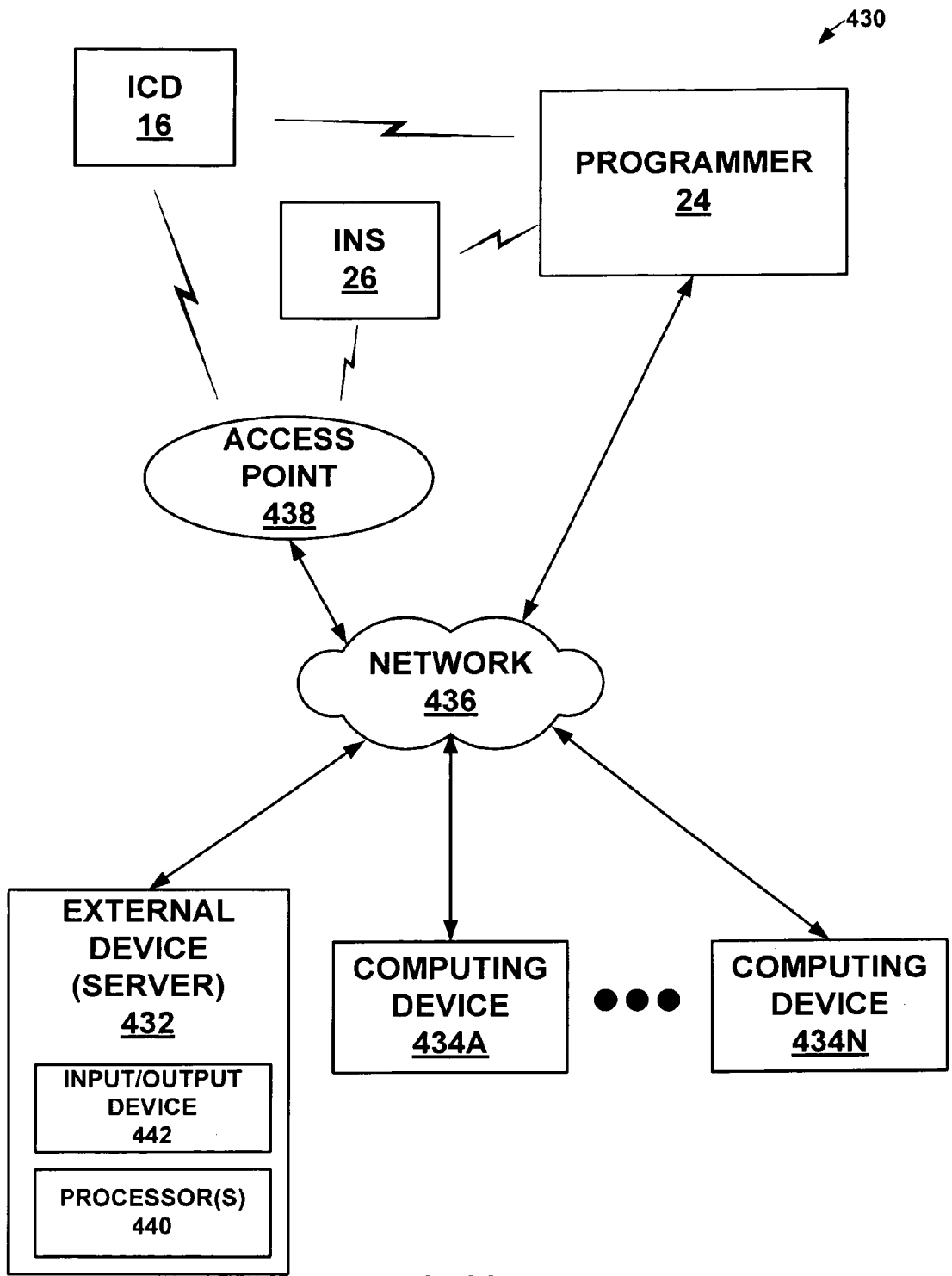
FIG. 32 is a block diagram illustrating an example system that includes an external device, such as a server, and one or more computing devices that are coupled to the INS, ICD, and programmer shown in FIG. 1 via a network.

In some examples, processor 130 may transmit the interference indication to a remote site, such as a remote clinician's office, via a network, as described with respect to FIG. 32. In addition, in some examples, processor 130 may also store the interference indication in memory 132. The interference indication may indicate, e.g., to a clinician, that the crosstalk between INS 26 and ICD 16 was not reducible by modifying one or more stimulation parameter of INS 26 or one or more sensing parameters of ICD 16. After receiving the interference indication, the clinician may determine whether other measures may be taken in order to reduce the crosstalk between INS 26 and ICD 16. For example, the clinician may determine whether repositioning lead 28 coupled to INS 26 within patient 12 may help reduce the crosstalk.

Figure 23:
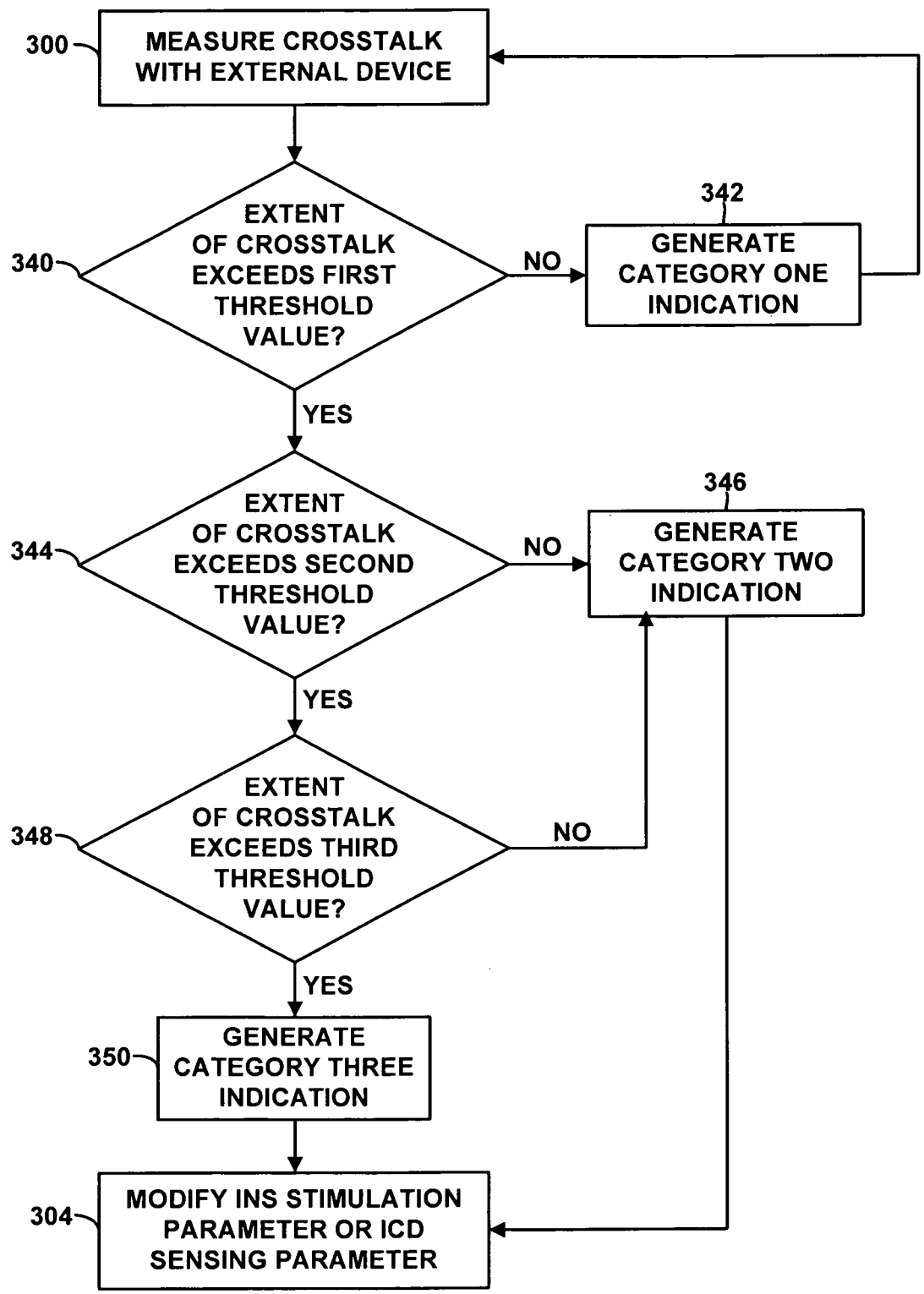
FIG. 23 is a flow diagram of an example technique for categorizing sensed crosstalk between ICD and INS into different categories.
Figure 24:
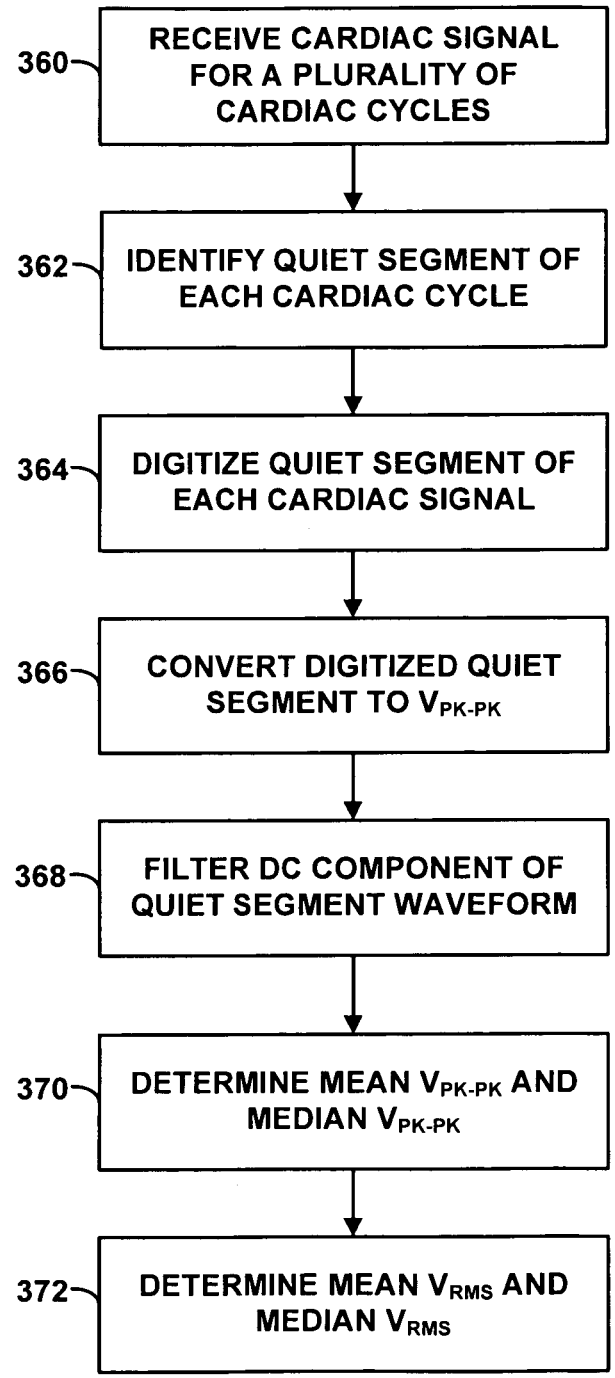
FIG. 24 is a flow diagram of an example technique for extracting data from a waveform of an artifact present in an electrical signal sensed by an ICD.

In other examples of the technique shown in FIG. 21, as well as FIGS. 23 and 24, processor 90 of ICD 16 or processor 110 of INS 26 may perform any part of the technique shown in FIG. 21 in addition to or instead of processor 130 of programmer 24.

In other examples of the technique shown in FIG. 21, processor 130 may evaluate the extent of crosstalk between ICD 16 and INS 26 based only on the second electrical signal, which is sensed by ICD 16 during delivery of neurostimulation by INS 26. For example, rather than comparing the baseline and second electrical signals to determine whether the extent of crosstalk exceeds an acceptable level (302), processor 130 may determine that if the difference between an amplitude of the second electrical signal and a sensing threshold of sensing module 96 during a quiet segment of cardiac cycle of heart 14 (FIG. 1) of patient 12 is greater than or equal to a stored value, the noise on the sensing channel of sensing module 96 is greater than an acceptable level. The amplitude may be a mean or median amplitude, a highest amplitude, a RMS amplitude, an amplitude that is equal to a certain percentage (e.g., about 95%) of the highest amplitude, and the like. The stored value may be a percentage of the sensing threshold of sensing module 96 of ICD 16. For example, the stored value may be about 10% to about 50%, such as about 25% of the sensing threshold voltage.

The noise on the sensing channel of sensing module 96 may be at least partially attributable to the delivery of neurostimulation by INS 26. In this way, a comparison of a stored value and the difference between an amplitude of the second electrical signal and a sensing threshold of sensing module 96 may indicate whether the extent of crosstalk between ICD 16 and INS 26 is undesirable.

Figure 22:
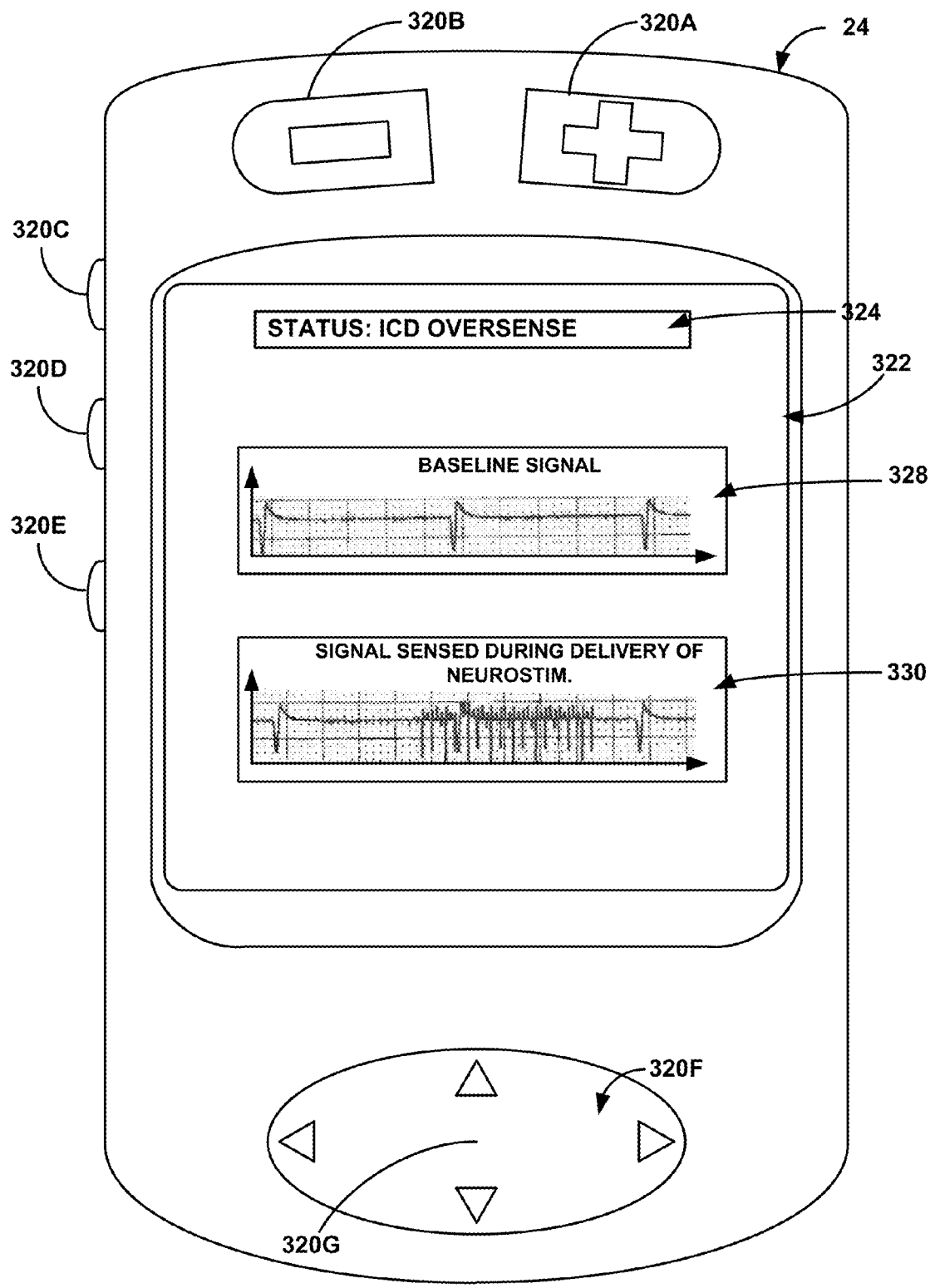
FIG. 22 is a conceptual illustration of a programmer, which may display various signals indicative of the extent of crosstalk between an ICD and an INS implanted within a patient.

FIG. 22 is a conceptual illustration of programmer 24, which may display a status level of the INS 26 and ICD 16 interference. The interference status may be referred to as, for example, an electrical noise status or crosstalk status. In the example shown in FIG. 22, programmer 24 includes user input mechanisms 320A-320G (collectively "user input mechanisms 320") and display 322. A user (e.g., patient 12 or a clinician) may interact with user input mechanisms 320 to input information into programmer 24, and, in some cases, control aspects of therapy delivered by ICD 16 and/or INS 26 within the limits programmed by a clinician. User input mechanisms 320 include buttons 320A and 320B, which may be used to increase or decrease the therapy intensity delivered by INS 26, if allowed, and may perform other functions. An intensity of therapy may be modified by, for example, modifying a therapy parameter value, such as the current or voltage amplitude of stimulation signals, the frequency of stimulation signals, the shape of a stimulation signal or the electrode combination used to deliver the stimulation signal. In some examples, user input mechanisms 320C, 320D may be used to decrease or increase the contrast of display 322, and user input mechanism 320E may be used to power programmer 24 on and off.

Multi-directional controller 320F may allow a user to navigate through menus displayed by display 322, and may include a button 320G that is actuated when the center of multi-directional controller 320F is pressed. Display 322 may comprise any suitable type of display, such as an LCD display, LED display or a touch screen display. Display 322 may present graphical user interface screens for presenting information to the user, such as information related to the sensed level of neurostimulation signal artifact on a selected sense channel of ICD 16. In the example shown in FIG. 21, display 322 presents first screen 324 that indicates crosstalk status, a second screen 328 that illustrates a waveform of a baseline electrical signal that is sensed on the selected sense channel of ICD 16 when INS 26 is not delivering electrical stimulation to patient 12, and a third screen 330 that illustrates a waveform of a second electrical signal that is sensed on the selected sense channel of ICD 16 when INS 26 is delivering electrical stimulation to patient 12.

The user may review the different waveforms present in screens 328, 330 in order to visually ascertain the extent to which the neurostimulation artifact on the selected sensing channel of ICD 16 may be affecting the detection of true cardiac signals. Status screen 324 presents an indication of whether the neurostimulation signal artifact exceeds a threshold level or whether the stimulation signal artifact is sufficiently low, such that the neurostimulation signal delivered by INS 26 does not adversely affect the sensing of cardiac signals by ICD 16. In the example shown in FIG. 22, status screen 324 provides an indication that ICD 16 may be oversensing cardiac signals, i.e., the neurostimulation artifact on the selected sensing channel of sensing module 96 of ICD 16 exceeds a threshold level.

In other examples, programmer 24 may present other types of displays to provide information to a user regarding the neurostimulation signal artifact on one or more sensing channels of ICD 16. For example, in some examples, processor 130 of programmer 24 may categorize a neurostimulation signal artifact based on the probability that the artifact will affect the sensing of true cardiac signals by ICD 16. The categorization of the neurostimulation signal artifact maybe useful for providing a relatively quick and easy way to ascertain the extent of crosstalk between INS 26 and ICD 16.

FIG. 23 is a flow diagram illustrating an example technique for categorizing a neurostimulation signal artifact. Processor 130 of programmer 24 may measure the extent of the crosstalk between INS 26 and ICD 16 (300), e.g., by determining a difference between a characteristic of a baseline electrical signal and a respective characteristic of the second electrical signal sensed by ICD 16 while INS 26 is delivering stimulation, as described with respect to FIG. 21. Processor 130 may determine a difference between the characteristics of the baseline and second electrical signals using any suitable technique. In some examples, processor 130 determines a difference between the characteristics of the baseline and second electrical signals by determining a difference between a first value indicative of the difference between an amplitude of the baseline electrical signal and a sensing threshold value of sensing module 96 (FIG. 6) of ICD 16 and a second value indicative of the difference between an amplitude of the second electrical signal and the sensing threshold value of sensing module 96.

Processor 130 may determine whether the characteristics of baseline and second electrical signals differ by a first threshold value (340). As discussed with respect to FIG. 21, in some examples, the threshold value may be based on the sensing threshold of ICD 16, e.g., may be less than the sensing threshold, such as about 1% to about 99% of the sensing threshold or about 25% to about 50% of the sensing threshold amplitude. In the example shown in FIG. 23, memory 132 of programmer 24 stores a plurality of threshold values (or threshold levels) that are each associated with a different neurostimulation signal artifact category. The different categories may represent the relative intensity of the neurostimulation artifact on a selected sense channel of ICD 16. The threshold values may be adjustable. For example, a clinician may program the threshold values into programmer 24, ICD 16, INS 26 or another device. The threshold values may be specific to a particular patient.

If processor 130 determines that the characteristics of baseline and second electrical signals do not differ by at least the first threshold value, processor 130 may determine that the extent of the crosstalk between INS 26 and ICD 16 falls within a first category, and processor 130 may generate a category one indication (342). The first category of crosstalk may be associated with a crosstalk level in which crosstalk between INS 26 and ICD 16 is present, but the extent of the crosstalk is relatively low. Processor 130 may determine that modifications to one or more stimulation parameters of INS 26 or one or more sense parameters of ICD 16 are not necessary when a category one indication is generated.

If processor 130 determines that the characteristics of the baseline and second electrical signals differ by at least the first threshold value, processor 130 may determine whether the characteristics of the baseline and second electrical signals differ by a second threshold level that is different than the first threshold level (344). In some examples, the second threshold level may be associated with a greater artifact intensity than the first threshold level. For example, the first threshold value may include a first voltage amplitude value or a first percentage that indicates a percentages change of a voltage amplitude of the second electrical signal relative to a baseline electrical signal. The second threshold level may include a second voltage amplitude value or a second percentage, where the second voltage amplitude value or percentage are greater than the first voltage amplitude value or percentage, respectively.

If processor 130 determines that the characteristics of the baseline and second electrical signals do not differ by at least the second threshold value, processor 130 may determine that the extent of the crosstalk between INS 26 and ICD 16 is within a second category, and processor 130 may generate a category two indication (346). In some examples, the second category of crosstalk may be associated with a crosstalk level in which crosstalk between INS 26 and ICD 16 exceeds an acceptable level. Thus, as shown in FIG. 23, upon generating the category two indication, processor 130 may initiate the modification to one or more stimulation parameter values of INS 26 or one or more sensing parameters of ICD 16 (304).

If processor 130 determines that the characteristics of the baseline and second electrical signals differ by at least the second threshold level, processor 130 may determine whether the characteristics of the baseline and second electrical signals differ by a third threshold value that is different than the first and second threshold values (348). In some examples, the third threshold value may be associated with a greater artifact intensity than the first and second threshold levels. For example, the third threshold level may include a third voltage amplitude value or a third percentage, where the third voltage amplitude value or percentage are greater than the first and second voltage amplitude values or percentages, respectively.

If processor 130 determines that the characteristics of the baseline and second electrical signals do not differ by at least the third threshold value, processor 130 may determine that the extent of the crosstalk between INS 26 and ICD 16 is within the second category, and processor 130 may generate a category two indication (346). On the other hand, if processor 130 determines that the characteristics of the baseline and second electrical signals differ by at least the third threshold value (348), processor 130 may generate a category three indication (350). In some examples, the third category of crosstalk may be associated with a crosstalk level in which crosstalk between INS 26 and ICD 16 exceeds an acceptable level. Thus, as shown in FIG. 23, upon generating the category three indication, processor 130 may initiate the modification to one or more stimulation parameter values of INS 26 or one or more sensing parameters of ICD 16 (304). These modifications may be the same or different as the modifications made in response to the generation of a category two indication (346). In addition, in some examples, the modification to the one or more stimulation parameter values of INS 26 may result in the suspension of the delivery of neurostimulation by INS 26 upon generation of the category three indication.

In some examples, processor 130 of programmer 24 or a processor of another device may evaluate the extent of crosstalk between ICD 16 and INS 26 based on the difference between one or more characteristics of the baseline and second electrical signals during a quiet segment of a cardiac cycle of heart 14. As previously indicated the second electrical signal may be the electrical signal sensed by ICD 16 on a particular sense channel while INS 26 delivers neurostimulation signals to patient 12. The quiet segment of a cardiac cycle may be when the intrinsic electrical signal of heart 14 is least active, such as during the T-P segment of a sinus rhythm of heart 14. Because the absolute value of a voltage amplitude of a true cardiac signal may be the lowest during the quiet segment, determining a voltage amplitude of a second electrical signal sensed by ICD 16 on a particular sensing channel during the quiet segment may provide a more useful indication of the artifact present on the sensing channel of ICD 16. The difference in voltage amplitudes between a baseline signal and a second electrical signal during the quiet segment may be more pronounced and, therefore, more revealing of the crosstalk between ICD 16 and INS 26.

FIG. 24 is a flow diagram illustrating an example technique for parsing data from a baseline electrical signal and the second electrical signal that is sensed by the selected sense channel of ICD 16 during active delivery of stimulation by INS 26. The parsed data may indicate the voltage amplitude of the baseline signal or the second electrical signal sensed by ICD 16 during a quiet segment of a cardiac cycle of heart 14. Processor 130 of programmer 24 may receive a cardiac signal that includes a plurality of cardiac cycles (360), such as about 10 cardiac cycles to about 20 cardiac cycles. A cardiac cycle may be defined by, for example, a sinus rhythm including a QRST segment.

Processor 130 may identify the portion of the received electrical cardiac signals that correspond to the quiet segment of each cardiac cycle (362). As previously indicated, in some examples, the quiet segment may include the T-P segment of a sinus rhythm. Processor 130 may digitize the portions of the cardiac signals corresponding to the quiet segments (364), e.g., defining each quiet segment as about six points, although any suitable number of digitized points may be used.

Processor 130 may convert the digitized quiet segment portions of the cardiac cycles into a waveform in order to determine the peak-to-peak voltage amplitude ($V_{PK-PK}$) (366). Processor 130 may filter the direct current (DC) component out of the waveform in order to remove low-frequency artifact prior to determining the root mean square (RMS) amplitude of the waveform indicative of the quiet segment (368). Processor 130 may determine the mean and median peak-to-peak voltage amplitudes ($V_{PK-PK}$) (370), and determine the mean and median root mean square amplitudes ($V_{RMS}$) of the waveform indicative of the quiet segment of the cardiac signal based on the mean and median peak-to-peak voltage amplitudes (372). For example, processor 130 may determine the mean root mean square amplitude by determining the square root of the square of the mean peak-to-peak voltage amplitudes.

In order to evaluate the extent of crosstalk between ICD 16 and INS 26, processor 130 may compare the RMS voltage amplitudes of the baseline and second electrical signals and determine whether the RMS amplitudes differ by one or more threshold values, as generally described with respect to FIG. 21.

In some examples, the extent of the crosstalk between INS 26 and ICD 16 may be evaluated based on one or more characteristics of an electrical signal that is sensed by ICD 16 when INS 26 is delivering an electrical signal that does not provide any therapeutic benefits to patient 12. For example, INS 26 may generate and deliver a test electrical signal that does not provide stimulation therapy to patient 12, and ICD 16 may sense electrical cardiac signals while INS 26 is delivering the test signals. In some examples, patient 12 does not perceive the test electrical signal, due to, for example, the intensity of the test signal and/or the timing of delivery of the test signal. For example, test electrical signal may comprise a sub-threshold amplitude signal that does not capture or otherwise activate tissue (e.g., neurons within the tissue) of patient 12. An intensity of stimulation may be modified by modifying the current or voltage amplitude of a stimulation signal, a frequency of the stimulation signal, and, if the signal comprises a pulse, a pulse width or pulse shape of the stimulation signal.

Figure 25:
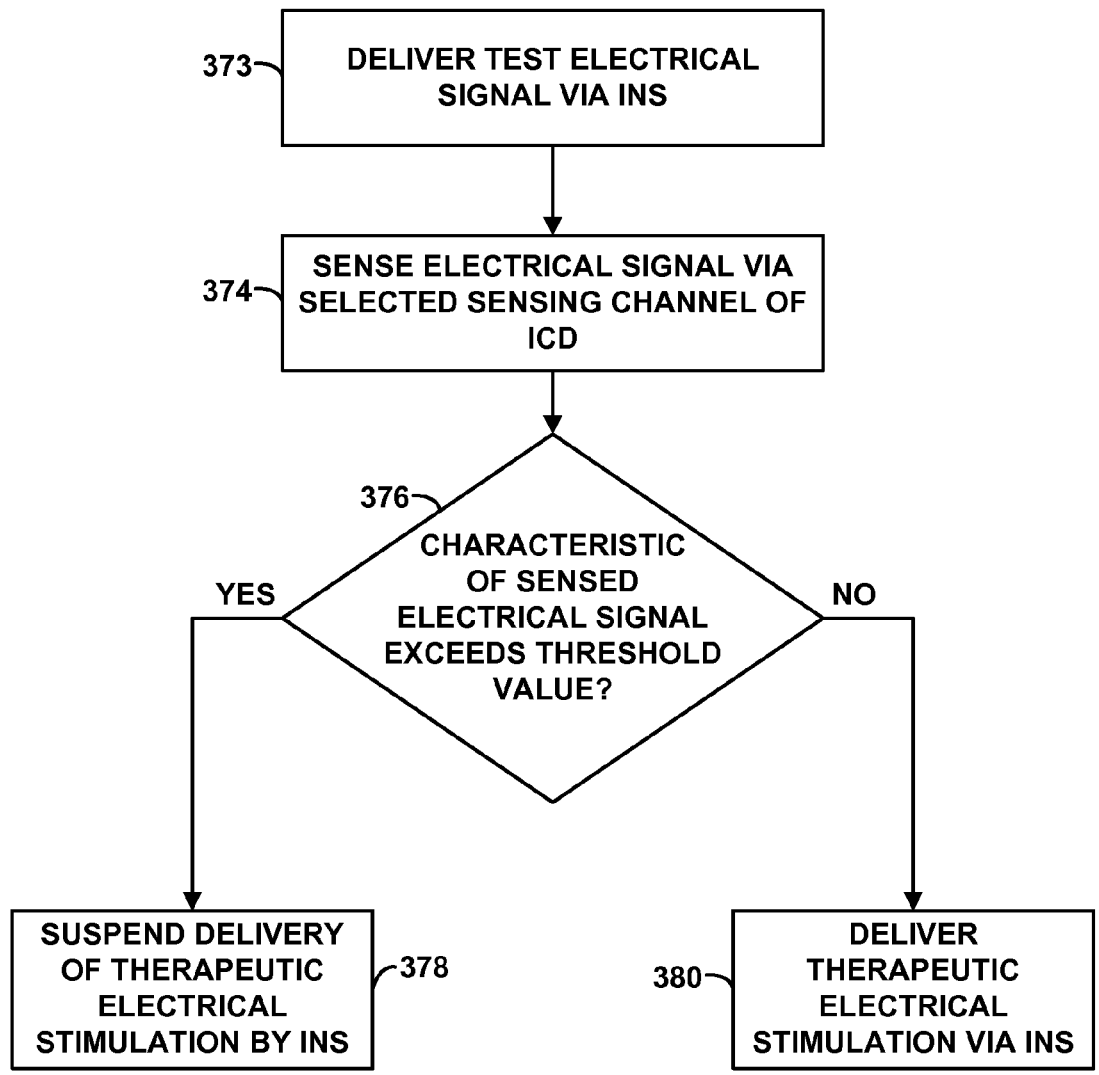
FIG. 25 is a flow diagram illustrating an example technique that may be used to evaluate the extent of the crosstalk between an INS and an ICD.

FIG. 25 is a flow diagram illustrating an example technique for determining an extent of crosstalk between INS 26 and ICD 16 with a test signal that does not provides little to no therapeutic benefits to patient 12. In the example shown in FIG. 25, processor 110 of INS 26 may control signal generator 114 to generate and deliver a test signal to patient 12 (373). The test signal may be nontherapeutic, e.g., does not provide efficacious therapy to patient 12 or provides minimally efficacious therapy to patient 12. In contrast, a therapeutic electrical stimulation signals delivered by INS 26 may have a greater voltage amplitude, current amplitude, frequency or a different burst pattern than the test signal delivered by INS 26. Memory 112 of INS 26, memory 132 of programmer 24 or a memory of another device may store a therapy program that defines the signal parameter values for the test signal. In addition, in some examples, the test signal may comprise an amplitude that is less than an activation threshold of tissue, such that the patient's tissue is not substantially affected by the delivery of the test signal. Furthermore, in some examples, the test signal may comprise an amplitude that is less than a perception threshold of patient 12, such that patient 12 does not perceive the delivery of the test signal by INS 26.

As INS 26 generates and delivers the test signal, sensing module 96 (FIG. 6) of ICD 16 may sense an electrical signal via a selected sensing channel (374), although more than one sensing channel may also be used in other examples. Processor 90 of ICD 16 may determine whether a characteristic of the sensed electrical signal exceeds a threshold value (376). The threshold value may indicate an amplitude value at which the electrical signal sensed by the selected sensing channel of ICD 16 indicates that the extent of crosstalk between INS 26 and ICD 16 may exceed an acceptable level if INS 26 delivers neurostimulation signals in an ordinary course, e.g., according to a therapy program defining therapeutic neurostimulation signals. While the delivery of the test signal by INS 26 may not result in an unacceptable level of crosstalk between INS 26 and ICD 16, one or more characteristics of the signal that is sensed by ICD 16 during the delivery of the test signal by INS 26 may be represent a neurostimulation artifact that may result if INS 26 delivers neurostimulation signals in an ordinary course.

A clinician may determine the threshold value using any suitable technique. In one example, the clinician may detect when there is an unacceptable level of crosstalk between INS 26 and ICD 16, e.g., based on actual signals sensed by ICD 16 when INS 26 delivers therapeutic neurostimulation signals to patient 12. Shortly thereafter, e.g., while leads 28, 29 are likely in the same position as when the unacceptable level of crosstalk was detected, the clinician may control INS 26 to deliver the test signal to patient 12. The electrical signal that is sensed by ICD 16 while INS 26 delivers the test signal to patient 12 may be indicative of the unacceptable level of crosstalk between INS 26 and ICD 16. Thus, one or more characteristics of the electrical signal that is sensed by ICD 16 while INS 26 delivers the test signal to patient 12 may be stored as a threshold value, e.g., in memory 92 of ICD 16 or memory 112 of INS 26.

Determining the extent of potential crosstalk between INS 26 and ICD 16 prior to delivering therapeutic neurostimulation therapy to patient 12 may be useful for confirming that the extent of crosstalk between INS 26 and ICD 16 is within an acceptable range in advance of delivering the neurostimulation therapy. This may help mitigate the possibility that the delivery of neurostimulation by INS 26 interferes with the sensing of cardiac signals by ICD 16.

If processor 90 of ICD 16 determines that one or more characteristics of the sensed electrical signal is greater than or equal to the threshold value (376), processor 90 may suspend the delivery of therapeutic electrical stimulation by INS 26 (378). If processor 90 of ICD 16 determines that the sensed electrical signal does not exceed the threshold value (376), processor 90 may determine that the relative level of crosstalk between INS 26 and ICD 16 is within an acceptable level. Processor 90 may then provide INS 26 with a controls signal that indicates that INS 26 may generate and deliver therapeutic electrical stimulation to patient 12 (380).

The technique shown in FIG. 25 may be implemented to evaluate the extent of crosstalk between INS 26 and ICD 16 at any suitable evaluation frequency. In some examples, INS 26 may deliver the test signal to patient 12 (373) at a test frequency of about one to about ten times per minute, although more frequent (e.g., about 1 Hz to about 100 Hz) or less frequent testing frequencies are contemplated. INS 26 may notify ICD 16 prior to sending the test signal or ICD 16 and INS 26 may have synchronized clocks such that ICD 16 senses the electrical signal on a selected sensing channel (374) at substantially the same time that INS 26 delivers the test signal.

In some cases, the one or more characteristics of the electrical signal sensed by ICD 16 while INS 26 is delivering the non-therapeutic test signal may also indicate an intensity of stimulation signals that INS 26 may deliver without adversely affecting the sensing of cardiac signals by ICD 16. For example, the one or more characteristics of the electrical signal (e.g., a voltage or current amplitude) may be associated with a specific therapy program or instructions for modifying a therapy program in memory 132 (FIG. 8) of programmer 24, memory 112 (FIG. 7) of INS 26 or memory 92 (FIG. 6) of ICD 16.

Processor 130 of programmer 24 or another device may determine the one or more characteristics of the electrical signal sensed by ICD 16 while INS 26 is delivering the non-therapeutic test signal to patient 12. If the one or more characteristics of the signal are less than the threshold value (376), thereby indicating that the crosstalk between ICD 16 and INS 26 is acceptable, processor 130 may determine an acceptable stimulation therapy program for INS 26. For example, processor 130 may reference a data structure stored in memory 112 to determine the therapy program or instructions for modifying a therapy program. Processor 130 may then instruct processor 110 of INS 26 to deliver therapy to patient 12 in accordance with the therapy program associated with the one or more characteristics of the electrical signal or in accordance with therapy parameters modified based on the instructions associated with the one or more characteristics of the electrical signal.

The therapy programs or instructions for modifying a therapy program based on the one or more characteristics of the electrical signal sensed by ICD 16 while INS 26 is delivering the non-therapeutic test signal to patient 12 may be determined during a programming session with a clinician. The clinician may determine a characteristic of an electrical signal sensed by ICD 16 while INS 26 is delivering the non-therapeutic test signal to patient 12, and determine the therapy parameter values that provide efficacious therapy to patient 12 without interfering with the sensing of cardiac signals by ICD 16. These therapy parameter values may then be associated with the signal characteristic in memory 132 (or a memory of another device) as a therapy program or an instruction for modifying a baseline therapy program.

The delivery of electrical stimulation by INS 26 may change an amplitude of an electrical cardiac signal (e.g., an EGM) sensed by ICD 16. Thus, in some examples, the crosstalk status of a therapy system including ICD 16 and INS 26 may be evaluated based on a change in amplitude of an electrical cardiac signal sensed while INS 26 is not actively delivering stimulation to patient 12 and an electrical cardiac signal sensed while INS 26 is delivering stimulation to patient 12.

Figure 26:
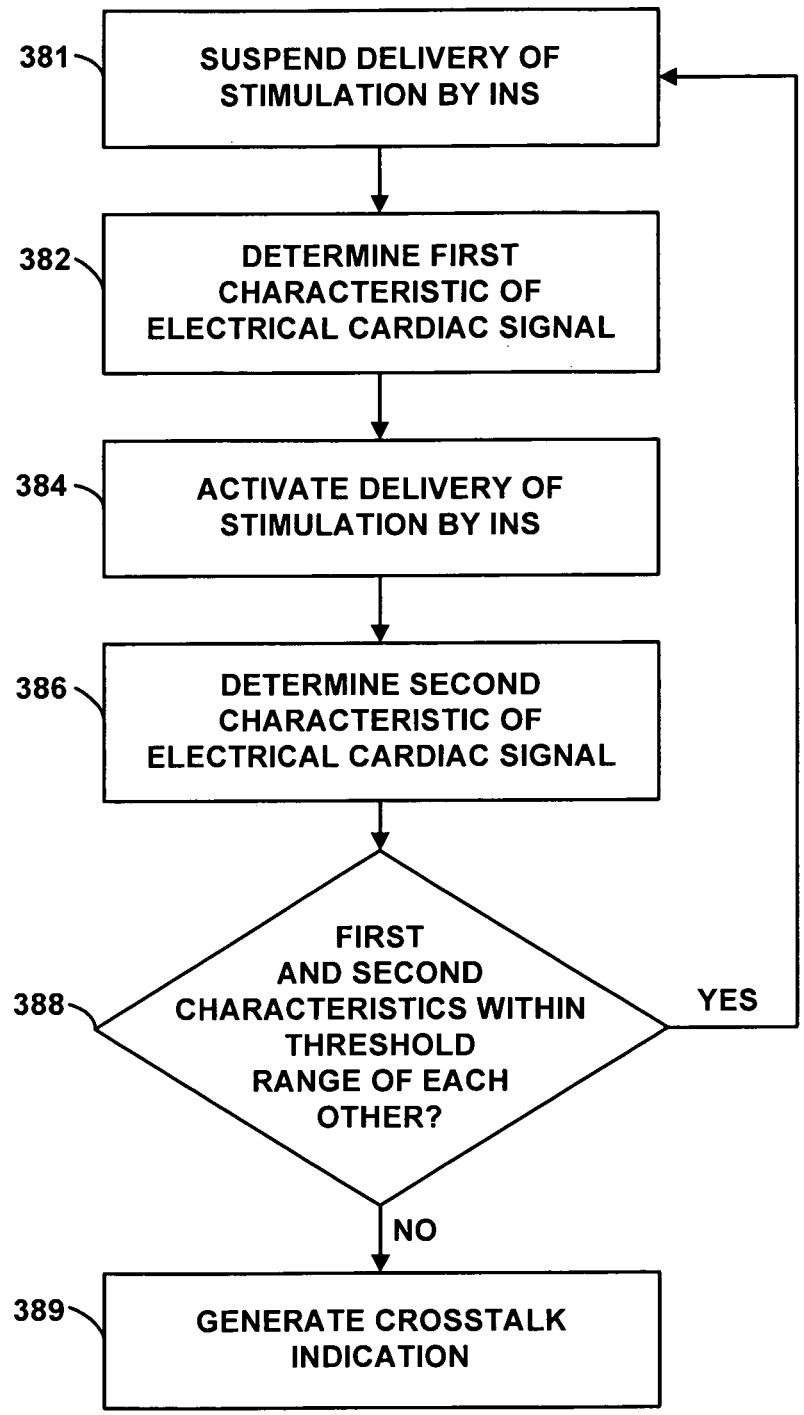
FIG. 26 is a flow diagram illustrating another example technique that may be used to evaluate the extent of the crosstalk between an INS and an ICD.

FIG. 26 illustrates a flow diagram of an example technique for determining a crosstalk status (or an electrical noise status) of therapy system 10. In the technique shown in FIG. 26 Processor 90 of ICD 16 may instruct processor 110 of INS 26 to suspend or otherwise adjust the delivery of neurostimulation (381). For example, processor 90 may transmit a control signal to processor 110 via the respective telemetry modules 98 (FIG. 6), 118 (FIG. 7). The control signal may not only indicate whether INS 26 should suspend or otherwise adjust the delivery of neurostimulation to patient 12, but, in some examples, may indicate how long INS 26 should suspend neurostimulation or deliver therapy according to the adjusted parameters. In other examples, memory 112 (FIG. 7) of INS 26 may store instructions for suspending or otherwise adjusting neurostimulation when processor 110 of INS 26 receives the control signal from processor 90 of ICD 16. As another example, INS 26 may suspend or otherwise adjust delivery of stimulation without intervention from ICD 16, e.g., according to schedule stored by memory 112.

During the time in which neurostimulation is suspended or adjusted, sensing module 96 (FIG. 6) of ICD 16 may sense a first electrical cardiac signal and processor 90 may determine a first characteristic of the first electrical cardiac signal (382). In some examples, the first characteristic may be a mean or median P-wave or R-wave amplitude over a predetermined period of time. Processor 90 of ICD 16 may then activate the delivery of stimulation by INS 26 (384). For example, processor 90 may generate a control signal that is transmitted to processor 110 of INS 26 via the respective telemetry modules 98 (FIG. 6), 118 (FIG. 7). Upon receiving the control signal, processor 110 of INS 26 may control stimulation generator 114 to begin generating and delivering neurostimulation therapy. In other examples, processor 110 of INS 26 may begin generating and delivering neurostimulation therapy based on a predetermined schedule that indicates the times at which processor 110 should suspend the delivery of neurostimulation and initiate the delivery of stimulation.

After INS 26 commences the delivery of neurostimulation to patient 12, processor 90 may control sensing module 96 to sense a second electrical cardiac signal of heart 14 of patient 12. Processor 90 may determine a second characteristic of the second electrical cardiac signal (386). In some examples, the first and second characteristics may be similar characteristics. For example, the first and second characteristics may be a mean or median P-wave or R-wave amplitude of the first and second electrical cardiac signals, respectively, over a predetermined period of time.

Processor 90 may determine whether the first and second characteristics are within a threshold range of each other (388). In general, if the first and second characteristics are similar, e.g., within a threshold range of each other, the crosstalk status of the therapy system including ICD 16 and INS 26 may be relatively low. The threshold range may be, for example, about 20% of the value of the first characteristic, such as about 5% to about 20%, about 10% to about 15%, or substantially equal. Thus, in some examples, if the difference between the first and second characteristics is less than about 20% of the value of the first characteristic, processor 90 may determine that the first and second characteristics are within a threshold range of each other.

First and second characteristics that are within a threshold range of each other may indicate that the delivery of neurostimulation by INS 26 has a minimal affect on the electrical cardiac signal sensed by ICD 16, such that the possibility that ICD 16 may sense the neurostimulation signal and mischaracterize the signal as an electrical cardiac signal is relatively low. In such a situation, the crosstalk status may be acceptable.

If the first and second characteristics are within a threshold range of each other, processor 90 may continue comparing the first and second characteristics of subsequently sensed electrical cardiac signals in accordance with the technique shown in FIG. 26. On the other hand, if the first and second characteristics are not within a threshold range of each other, processor 90 may determine that the extent of crosstalk between ICD 16 and INS 26 is unacceptable, e.g., that the crosstalk status is unacceptable. Accordingly, processor 90 may generate a crosstalk indication (389) if the first and second characteristics are not within a threshold range of each other. The crosstalk indication may be a value, flag, or signal that is stored or transmitted to indicate the unacceptable crosstalk status. In some examples, processor 90 or 110 may transmit the crosstalk indication to programmer 24 or another external device, including remote devices, e.g., using a system described with respect to FIG. 32. In some examples, programmer 24 may present a notification to a user via user interface 134 (FIG. 8) to indicate an unacceptable level of crosstalk was detected.

While FIG. 26 is described with respect to processor 90 of ICD 16, in other examples, processor 130 of programmer 24 or processor 110 of INS 26 or another device may perform any part of the technique shown in FIG. 26. For example, a clinician may evaluate the crosstalk status between ICD 16 and INS 26 with the aid of programmer 24. Processor 130 of programmer 24 may perform any part of the technique shown in FIG. 26. For example, processor 130 may determine the first and second characteristics (382, 386) based on electrical cardiac signals sensed by ICD 16 and transmitted to programmer 24 by ICD 16.

In some examples, ICD 16 and/or INS 26 may periodically check the impedance of one or more electrical paths, each path comprising two or more implanted electrodes on one or more implanted leads. For example, processor 90 of ICD 16 may initiate a check of the impedance of an electrical path comprising lead 18 (FIG. 3) and electrodes 50, 52, 72. ICD 16 and/or INS 26 may, for example, check the impedance of one or more electrical paths comprising an electrode prior to delivering electrical stimulation to patient 12 in order to confirm that electrical interference or lead-related conditions that may affect the efficacy of the delivery of stimulation to patient 12 are not present.

The impedance measurements may be used to detect lead-related conditions, such as short circuits, open circuits or significant changes in impedance that may adversely affect the performance of therapy delivery by ICD 16 or INS 26 or sensing by ICD 16 or INS 26. Changes in impedance of an electrical path that is electrically connected to ICD 16 or INS 26 may increase the amount of crosstalk observed by ICD 16 by, for example, effectively widening a stimulation dipole of INS 26 or a sensing dipole of ICD 16 by creating a leakage path due to a lead-related condition, such as a lead fracture. A lead-related condition my often cause noise on a sensing channel of ICD 16. Thus, the technique shown in FIG. 25 may be useful for identifying a lead-related condition.

In some examples, lead integrity testing may also involve comparing the measured impedance to a threshold in order to determine whether the lead(s) have a lead-related condition. This integrity testing may be performed periodically, e.g., while patient 12 is sleeping or as patient 12 moves and subjects any of the leads 18, 20, 22, 28, 29 coupled to ICD 16 or INS 26 to mechanical stresses.

ICD 16 and INS 26 may measure impedance by determining an electrical parameter value indicative of the impedance. In some examples, ICD 16 or INS 26 may perform an impedance measurement by delivering, from the respective stimulation generator 94, 114, an electrical signal having a constant voltage between at least two electrodes, and measuring a resulting current of the signal that is sensed by two or more electrodes. The respective processor 90, 110 may determine a resistance based upon the voltage amplitude of the electrical signal and the measured amplitude of the resulting current. The current of the sensed signal or the determined resistance may be electrical parameter values indicative of the impedance path comprising the electrodes.

In other examples, ICD 16 or INS 26 may perform impedance measurement by delivering, from the respective stimulation generator 94, 114, a current pulse across at least two electrodes, and measuring a resulting voltage of a signal that is sensed by two or more electrodes. The respective processor 90, 110 may determine a resistance based upon the current amplitude of the pulse and the measured amplitude of the resulting voltage. The voltage of the sensed signal or the determined resistance may be electrical parameter values indicative of the impedance path comprising the electrodes.

Sensing module 96 of ICD 16 and a sensing module of INS 26 may include circuitry for measuring amplitudes of resulting currents or voltages, such as sample and hold circuitry. ICD 16 and INS 26 may use defined or predetermined pulse amplitudes, widths, frequencies, or electrode polarities for the pulses delivered for these various impedance measurements. In these examples, stimulation generators 94, 114 may deliver electrical signals that do not necessarily deliver stimulation therapy to patient 12, due to, for example, the amplitudes of such signals and/or the timing of delivery of such signals. For example, these signals may comprise sub-threshold amplitude signals that may not stimulate tissue, e.g., below a threshold necessary to capture or otherwise activate tissue. In the case of ICD 16, the electrical signals for measuring impedance of an electrical path may be delivered during a refractory period, in which case they also may not stimulate heart 14.

In certain cases, ICD 16 and INS 26 may collect electrical parameter values that include both a resistive and a reactive (i.e., phase) component. In such cases, ICD 16 and INS 26 may measure impedance during delivery of a sinusoidal or other time varying signal by the respective stimulation generator 94, 114. Thus, as used herein, the term "impedance" is used in a broad sense to indicate any collected, measured, and/or determined value that may include one or both of resistive and reactive components. Impedance data may include electrical parameter values that can be used to determine impedance (such as current and/or voltage values).

Crosstalk between INS 26 and ICD 16 may adversely affect the impedance measurements take by ICD 16 and INS 26. For example, the electrical stimulation signals generated and delivered by INS 26 may be sensed by ICD 16 during a bipolar, tripolar or quadrapolar impedance measurement. Similarly, the electrical stimulation signals (e.g., pacing pulses or defibrillation pulses) generated and delivered by ICD 16 may be sensed by INS 26 during a bipolar, tripolar or quadrapolar impedance measurement. Inaccurate impedance measurements by either INS 26 or ICD 16 may adversely affect the system integrity checks performed by INS 26 or ICD 16, such as by causing ICD 16 or INS 26 to over-sense or under-sense a system integrity issue. Over-sensing a system integrity issue may be undesirable because of, for example, the time required for patient 12 to resolve a false-positive system integrity issue. Undersensing a system integrity issue may also be undesirable because a system integrity issue may affect the efficacy of therapy delivery by ICD 16 and INS 26, and, therefore, it may be desirable for system integrity issues to be addressed by qualified individual as soon as possible.

Figure 27:
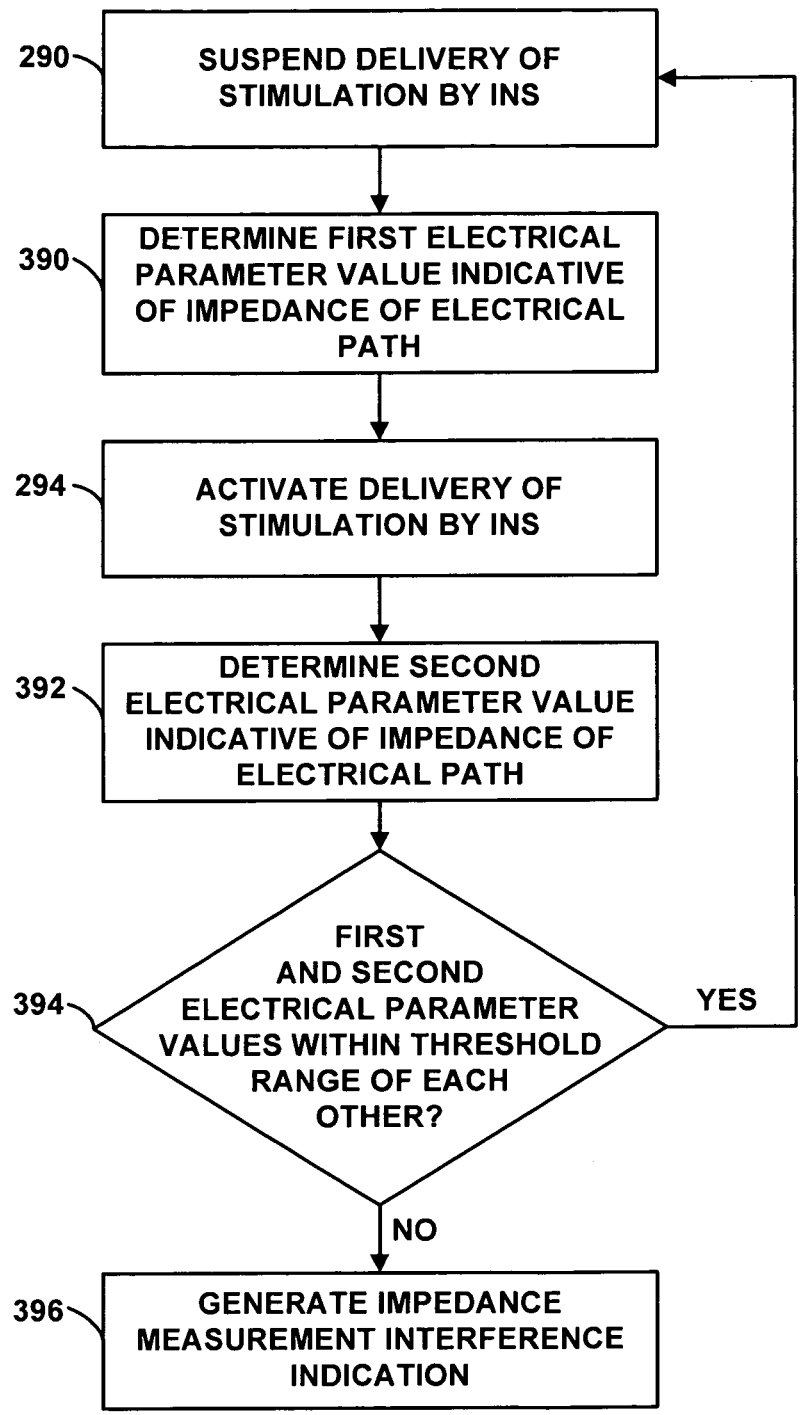
FIG. 27 is a flow diagram of an example technique for determining whether the crosstalk between an ICD and an INS may be adversely affecting the impedance measurements taken by the ICD.

FIG. 27 is a flow diagram of an example technique that may be implemented in order to determine whether the crosstalk between ICD 16 and INS 26 may be adversely affecting the impedance measurements taken by ICD 16. Processor 90 of ICD 16 may control INS 26 to suspend or otherwise adjust (e.g., decrease the intensity) the delivery of neurostimulation (290), as described above with respect to FIG. 20. Processor 90 may determine a first electrical parameter value indicative of an impedance of an electrical path (390), e.g., by delivering a voltage pulse or a current pulse and determining a resulting current or voltage, respectively. Thereafter, processor 90 may activate the delivery of neurostimulation signals by INS 26, e.g., as described above with respect to FIG. 20 (294).

While INS 26 is delivering neurostimulation signals to patient 12, processor 90 of ICD 16 may determine a second electrical parameter value indicative of the impedance of the electrical path (392). Processor 90 may compare the first and second electrical parameter values (394). If the first and second determined impedance values are within a threshold range, e.g., within about 20% or less of each other, such as about 5% to about 20%, about 10% to about 15%, or substantially equal, processor 90 may determine that the delivery of neurostimulation by INS 26 does not adversely affect the impedance measurement by ICD 16. Processor 90 may periodically perform the technique shown in FIG. 27, such as at an impedance sampling frequency of about 1 Hz to about 100 Hz. Other frequencies are contemplated, such as a frequency of about one to about ten times per minute. In other examples, processor 90 may compare the first and second electrical parameter values indicative of impedance by, for example, comparing the difference between the first and second electrical parameter values to a threshold value.

If the difference exceeds a threshold value or falls outside of a threshold range of values, processor 90 may determine that the first and second electrical parameter values are not within the threshold range of each other. If the first and second determined impedance values are not within the threshold range of each other (394), processor 90 may generate an impedance measurement interference indication (396). The impedance measurement interference indication may be a value, flag, or signal that is stored in memory 92 of ICD 16 or transmitted to another device (e.g., programmer 24 or INS 26) to indicate that the delivery of neurostimulation by INS 26 may potentially be interfering with the accurate and precise impedance measurements of one or more electrical paths coupled to ICD 16. In some cases, the change in impedance after INS 26 begins delivering stimulation to patient 12 may also indicate that a therapy system integrity issue is present, such as a lead-related condition (e.g., a lead fracture). The lead-related condition may be related to the integrity of one or more of the leads 18, 20, 22 (FIG. 3) electrically connected to ICD 16 or one or more of the leads 28, 29 (FIG. 5) electrically connected to ICD 16.

Figure 28:
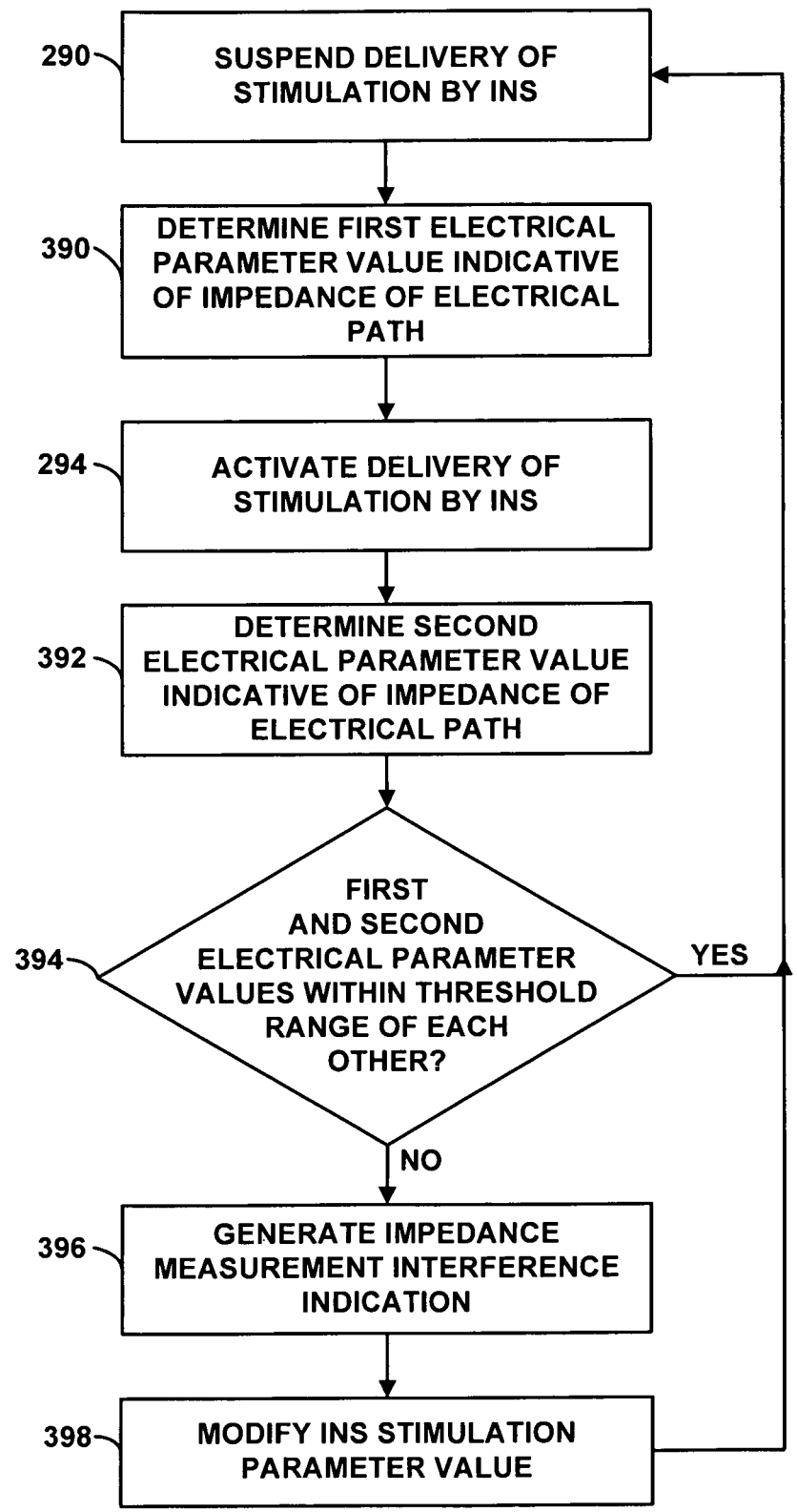
FIG. 28 is a flow diagram illustrating an example technique for modifying an electrical stimulation signal generated and delivered by an INS to mitigate the affect on impedance measurements of electrical paths taken by an ICD.

In some examples, processor 90 may initiate the modification to one or more stimulation parameter values that define the neurostimulation delivered by INS 26 or suspend the delivery of neurostimulation by INS 26 if an impedance measurement interference indication determination is generated. FIG. 28 is a flow diagram illustrating an example technique that may be implemented to modify the neurostimulation signal delivered by INS 26 in an attempt to mitigate the effect on impedance measurements of electrical paths taken by ICD 16. The example technique shown in FIG. 28 is substantially similar to the technique shown in FIG. 27. However, after generating the impedance measurement interference indication (396), processor 90 of ICD 16 may initiate the modification to one or more one or more neurostimulation parameter values (398). For example, processor 90 may instruct processor 110 of INS 26 to modify the one or more stimulation parameter values or switch therapy programs, or processor 90 of ICD 16 may transmit the modified stimulation parameter values to INS 26.

After the one or more stimulation parameter values are modified, processor 90 may suspend or otherwise adjust the delivery of neurostimulation by INS 26 (290), determine a first electrical parameter value indicative of an impedance an electrical path (390), activate the delivery of neurostimulation by INS 26 (294), determine a second electrical parameter value indicative of the impedance of the electrical path (392), and determine whether the first and second electrical parameter values are within an threshold range of each other (394). Processor 90 of ICD 16 or processor 110 of INS 26 may continue modifying the INS 26 stimulation parameter values until processor 90 determines that the impedance measurement by ICD 16 is not substantially affected by the delivery of neurostimulation by INS 26 or until no further neurostimulation parameter values may be modified, i.e., all permissible neurostimulation modifications have been exhausted. The permissible neurostimulation modifications may set forth ranges for the different stimulation parameter values that provide efficacious therapy to patient 12. Thus, modifying the neurostimulation parameters such that the values fall outside of the ranges may result in neurostimulation signals that do not provide efficacious therapy to patient 12.

Figure 29:
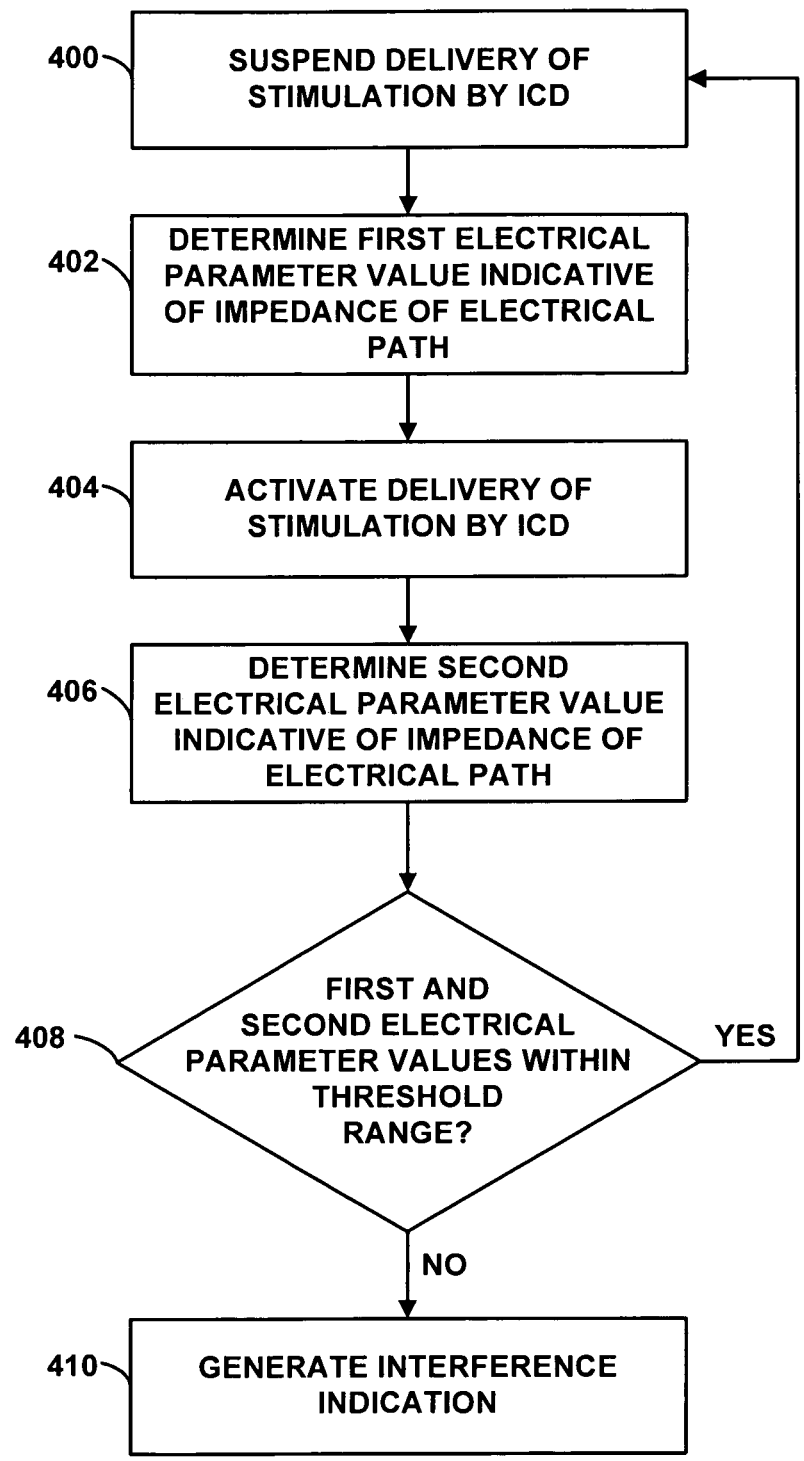
FIG. 29 is a flow diagram of an example technique for determining whether the crosstalk between an ICD and an INS may be adversely affecting the impedance measurements taken by the INS.

In some examples, the delivery of electrical stimulation, e.g., pacing pulses or defibrillation pulses, by ICD 16 may adversely affect impedance determinations by INS 26. FIG. 29 is a flow diagram illustrating an example technique for determining whether the delivery of electrical stimulation by ICD 16 adversely affects impedance determinations by INS 26. The technique shown in FIG. 29 is similar to the technique that may be implemented by ICD 16 and shown in FIG. 27.

Processor 110 of INS 26 may cause ICD 16 to suspend or otherwise adjust the delivery of stimulation (400), which may include, for example, a cardiac rhythm therapy. For example, processor 110 may transmit a control signal to processor 90 of ICD 16 via the respective telemetry modules 118 (FIG. 7), 98 (FIG. 6). The control signal may not only indicate whether ICD 16 should suspend the delivery of stimulation to patient 12, but, in some examples, may indicate how long ICD 16 should suspend stimulation. In other examples, memory 92 of ICD 16 may store instructions for suspending stimulation when processor 90 receives the control signal from processor 110 of INS 26. As another example, ICD 16 may suspend delivery of stimulation without intervention from INS 26, e.g., according to schedule stored by memory 92, where the schedule may indicate the times at which INS 26 takes impedance measurements.

Processor 110 may determine a first electrical parameter value indicative of an impedance of an electrical path (402), e.g., by generating and delivering a constant voltage signal or a constant current signal and measuring a resulting current or voltage, respectively, of a sensed signal, respectively. The electrical path may comprise, for example, a path between stimulation generator 114 and electrodes 124 (FIG. 7) of lead 28. Thereafter, processor 90 may activate the delivery of stimulation signals by ICD 16 (404). For example, processor 90 of ICD 16 may control stimulation generator 94 to generate and deliver stimulation upon the detection of an arrhythmia or at regular intervals, e.g., to pace heart 14.

While ICD 16 is delivering stimulation signals to patient 12, processor 110 of INS 26 may determine a second electrical parameter value indicative of the impedance of the electrical path (406). Processor 110 may compare the first and second determined impedance values (408). If the first and second determined impedance values are within a threshold range, e.g., within about 20% or less of each other, such as about 10% or substantially equal, processor 110 may determine that the delivery of stimulation by ICD 16 does not adversely affect the impedance determination by INS 26. Processor 90 may periodically perform the technique shown in FIG. 27, such as at an impedance sampling frequency of about 1 Hz to about 100 Hz or about one to about ten times per minute.

On the other hand, if the first and second determined impedance values are not within the threshold range of each other (408), processor 110 may generate an impedance measurement interference indication (410). The impedance measurement interference indication may be a value, flag, or signal that is stored in memory 112 of INS 26 or transmitted to another device (e.g., programmer 24 or ICD 16) to indicate that the delivery of stimulation by ICD 16 may potentially be interfering with the accurate and precise impedance measurements of one or more electrical paths coupled to INS 26.

In other examples, any part of the techniques shown in FIGS. 27-29 may be performed by processor 130 of programmer 24 or another device.

In some cases, processor 90 of ICD 16, processor 110 of INS 26 or another device may evaluate a change in the difference between the first and second electrical parameter values over time to evaluate the integrity of therapy system 10 (FIG. 1). As indicated above, the first electrical parameter value may be indicative of an impedance of an electrical path electrically connected to ICD 16 or INS 26 while INS 26 or ICD 16, respectively, is not actively delivering stimulation to patient 12, and the second electrical parameter value may be indicative of the impedance of the electrical path while INS 26 or ICD 16, respectively, is delivering stimulation to patient 12.

Figure 30:
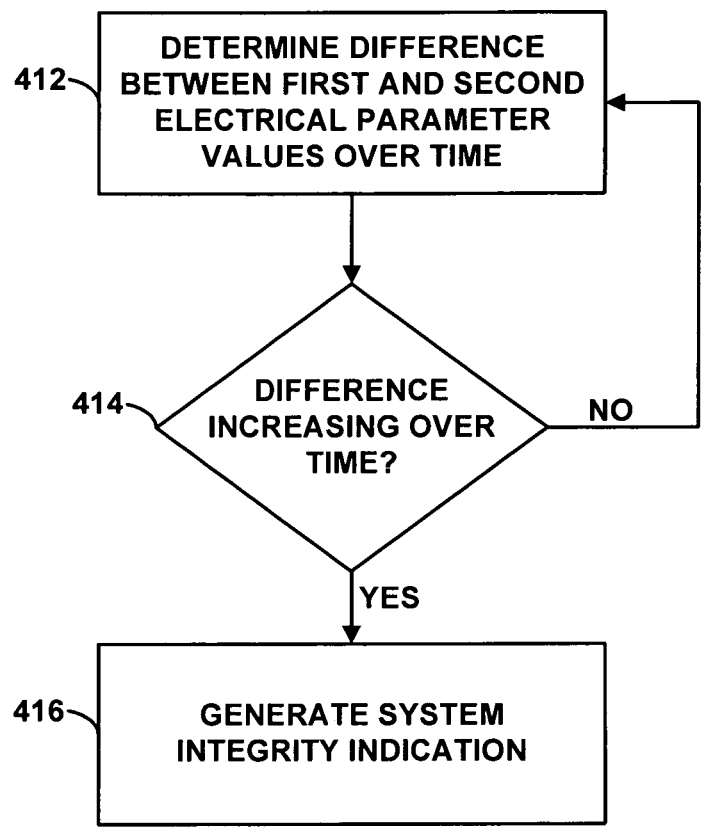
FIG. 30 is a flow diagram illustrating an example technique for evaluating the integrity of a therapy system.

FIG. 30 is a flow diagram illustrating an example technique for evaluating the integrity of therapy system 10 based on the difference between the first and second electrical parameter values over time. Processor 90 of ICD 16 or processor 110 of INS 26 may determine the difference between the first and second electrical parameter values over time (412). For example, for each impedance determination, e.g., as described above with respect to FIG. 27, processor 90 or processor 110 may determine the difference between the first and second electrical parameter values and store the value indicative of the difference in memory 92 (FIG. 6). In other examples, processor 90 or processor 110 may determine the difference between the first and second electrical parameter values less frequently than the frequency with which the first and second electrical parameter values are determined. For example, processor 90 or processor 110 may determine the difference between the first and second electrical parameter values once for every two times the first and second electrical parameter values are determined. Other frequencies with which processor 90 or processor 110 the difference between the first and second electrical parameter values are contemplated.

Processor 90 or processor 110 may determine whether the difference between the first and second electrical parameter values is increasing over time (414). That is, processor 90 or processor 110 may determine a trend in a difference between the impedance of the electrical path electrically connected to ICD 16 that is determined while INS 26 is delivering stimulation begins to differ from the impedance that is determined while INS 26 is not actively delivering stimulation to patient 12. This trend may indicate, for example, whether the crosstalk between ICD 16 and INS 26 is increasing over time. In addition, the trend may indicate whether another system integrity issue, such as a lead-related condition, may be present.

If the difference between first and second electrical parameter values remains substantially constant over time (e.g., stays within a particular range, such as less than about 25% of a mean or median difference value), processor 90 or processor 110 may determine that a system integrity issue is not present. Processor 90 or processor 110 may then continue monitoring the difference between the first and second electrical parameter values over time (412).

On the other hand, if the difference between first and second electrical parameter values increases over time, processor 90 or processor 110 may determine that a therapy system integrity issue is present. Accordingly, processor 90 or processor 110 may generate a system integrity indication (416). The system integrity indication may be a value, flag, or signal that is stored or transmitted to indicate that clinician attention is desirable. The clinician attention may be desirable to, for example, assess the integrity of leads 18, 20, 22, 28, 29 that may be implanted within patient 12. In some examples, processor 90 or 110 may transmit the system integrity indication to programmer 24 or another external device, including remote devices, e.g., using a system described with respect to FIG. 32.

In some examples, processor 90 or processor 110 may generate the system integrity indication if the difference between the first and second electrical parameter values increases over time by a predetermined rate, which may be stored in memory 92 or 112 of ICD 16 or INS 26, respectively. In other examples, processor 90 or processor 110 may generate the system integrity indication if the difference between the first and second electrical parameter values at a particular point in time exceeds the mean or median difference by a threshold value. The mean or median difference may be determined based on the mean or median value of the difference between the first and second electrical parameter values over a particular range of time preceding the current determination of the difference between the first and second electrical parameter values.

The techniques described herein, such as the techniques described with respect to FIGS. 9-12B for modifying one or more operating parameters of INS 26 in order to minimize crosstalk between INS 26 and ICD 16, with respect to FIGS. 16, 19A, and 19B for modifying one or more sensing parameters of ICD 16 in order to minimize crosstalk between INS 26 and ICD 16, with respect to FIGS. 20, 21, 23-30 for determining the extent of crosstalk between INS 26 and ICD 16, may also be implemented for determining the extent of crosstalk in a device comprising the functionality of INS 26 and ICD 16 in a common housing.

Figure 31:
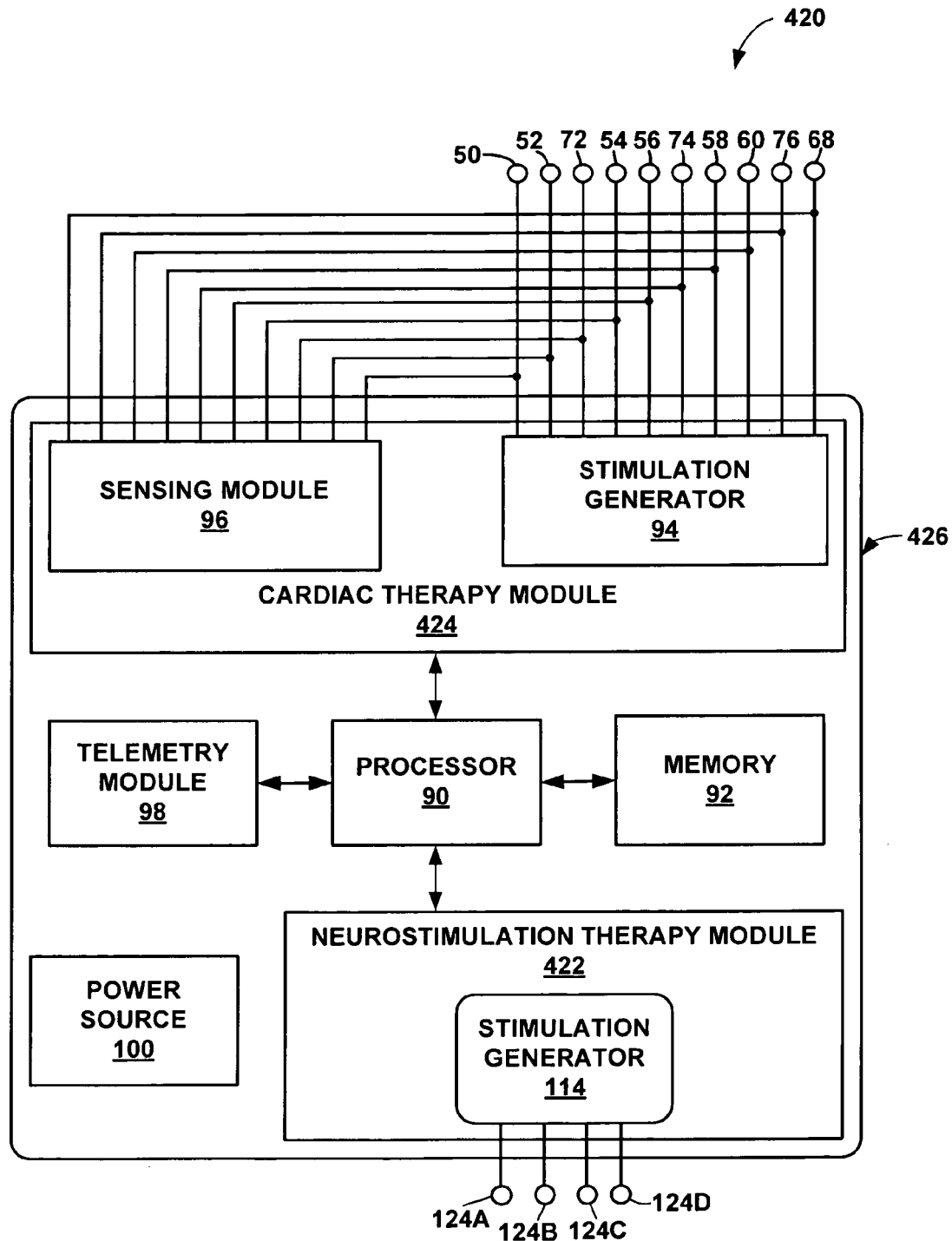
FIG. 31 is a functional block diagram of an example implantable medical device that includes a neurostimulation module that generates and delivers electrical stimulation to a tissue site within a patient and a cardiac therapy module that generates and delivers electrical stimulation to a heart of the patient.

FIG. 31 is a functional block diagram illustrating an example IMD 420 that includes a neurostimulation module 422 and a cardiac therapy module 424 in a common housing 426. Neurostimulation therapy module 422 includes stimulation generator 114, which is described above with respect to FIG. 7. Similarly, cardiac therapy module 424 includes stimulation generator 94 and sensing module 96, which are described above with respect to FIG. 6. IMD 420 also includes processor 90, memory 92, telemetry module 98, and power source 100, which are described above with respect to FIG. 6.

Neurostimulation therapy module 422 may deliver electrical stimulation to a tissue site proximate to a nerve. As previously discussed with respect to INS 26, the stimulation may be delivered to the nerve via an intravascular lead or an extravascular lead. In other examples, neurostimulation therapy module 422 may deliver electrical stimulation to a nonmyocardial tissue site that may or may not be proximate a nerve. Cardiac therapy module 424 may sense electrical cardiac signals of patient 12 and deliver cardiac rhythm management therapy to heart 14, such as pacing, cardioversion or defibrillation therapy.

Processor 90 may control neurostimulation therapy module 422 and cardiac therapy module 424 according to any of the techniques described above to minimize the possibility that cardiac therapy module 424 delivers electrical stimulation to heart 14 in response to detecting electrical signals generated and delivered by neurostimulation therapy module 422 that resemble an arrhythmic cardiac signal. For example, with respect to the technique shown in FIG. 9, processor 90 may control neurostimulation therapy module 422 to deliver stimulation therapy to patient 12 (140). In addition, processor 90 may control sensing module 96 to sense electrical cardiac signals (142).

If processor 90 detects a potential arrhythmia based on the sensed electrical cardiac signals (144), processor may modify the stimulation signals delivered by neurostimulation therapy module 422 (146). For example, processor 90 may modify one or more therapy parameter values with which neurostimulation therapy module 422 generates electrical stimulation signals, e.g., using the techniques described with respect to FIGS. 11A-11D. As another example, processor 90 may switch the therapy programs with which neurostimulation therapy module 422 generates the electrical stimulation signals, e.g., using the techniques described with respect to FIGS. 12A and 12B.

Processor 90 of the IMD 420 including both neurostimulation therapy module 422 and cardiac therapy module 424 may also modify one or more sensing parameters of sensing module 96 if neurostimulation therapy module 422 is delivering electrical stimulation therapy to patient 12, e.g., as described with respect to FIGS. 16, 19A, and 19B.

Programmer 24 or another device may also evaluate the crosstalk between neurostimulation therapy module 422 and cardiac therapy module 424 using any of the techniques described herein, e.g., the techniques described with reference to FIGS. 20, 21, and 23-26. However, instead of controlling ICD 16 and INS 26 or receiving information from separate devices 16, 26, programmer 24 may control neurostimulation therapy module 422 and cardiac therapy module 424 of a common IMD 420, and receive information from a single IMD 420. In addition, the techniques shown in FIGS. 27-30 may also be implemented by processor 90 in order to determine whether the delivery of electrical stimulation by neurostimulation therapy module 422 or cardiac therapy module 424 interferes with impedance measurements taken by processor 90.

FIG. 32 is a block diagram illustrating a system 430 that includes an external device 432, such as a server, and one or more computing devices 434A-434N that are coupled to ICD 16, INS 26, and programmer 24 shown in FIG. 1 via a network 436, according to one example. In this example, ICD 16 and INS 26 uses their respective telemetry modules 98 (FIG. 6) and 118 (FIG. 7) to communicate with programmer 24 via a first wireless connection, and to communicate with an access point 438 via a second wireless connection. In the example of FIG. 11, access point 438, programmer 24, external device 432, and computing devices 434A-434N are interconnected, and able to communicate with each other, through network 436.

In some cases, one or more of access point 438, programmer 24, external device 432, and computing devices 434A-434N may be coupled to network 436 through one or more wireless connections. ICD 16, INS 26, programmer 24, external device 432, and computing devices 434A-434N may each comprise one or more processors, such as one or more microprocessors, DSPs, ASICs, FPGAs, programmable logic circuitry, or the like, that may perform various functions and operations, such as those described herein.

Access point 438 may comprise a device that connects to network 436 via any of a variety of connections, such as telephone dial-up, digital subscriber line (DSL), or cable modem connections. In other examples, access point 438 may be coupled to network 436 through different forms of connections, including wired or wireless connections. In some examples, access point 438 may communicate with programmer 24, ICD 16, and/or INS 26. Access point 438 may be co-located with patient 12 (e.g., within the same room or within the same site as patient 12) or may be remotely located from patient 12. For example, access point 438 may be a home monitor that is located in the patient's home or is portable for carrying with patient 12.

During operation, ICD 16 and/or INS 26 may collect, measure, and store various forms of diagnostic data. For example, as described previously, ICD 16 or INS 26 may collect electrical parameter values indicative of an impedance of an electrical path. In certain cases, ICD 16 or INS 26 may directly analyze collected diagnostic data and generate any corresponding reports or alerts. In some cases, however, ICD 16 or INS 26 may send diagnostic data to programmer 24, access point 438, and/or external device 432, either wirelessly or via access point 438 and network 436, for remote processing and analysis.

For example, ICD 16 or INS 26 may send programmer 24 collected electrical parameter values indicative of the impedance of various electrical paths of therapy system 10 (FIG. 1), arrhythmia indications that indicate an arrhythmia was detected (e.g., as discussed with respect to FIG. 10), interference indications that indicate modification to the stimulation or sensing parameters of ICD 16 or INS 26 failed to reduce detected crosstalk between ICD 16 and INS 26 (e.g., as discussed with respect to FIGS. 11A-11D), interference indications that indicate the determined interference between ICD 16 and INS 26 or otherwise detected exceeds a certain level (e.g., as discussed with respect to FIGS. 21 and 23), and impedance measurement interference indications that indicate that stimulation delivery by ICD 16 or INS 26 may be interfering with the measurement of the impedance of various electrical paths of therapy system 10 (e.g., as discussed with respect to FIGS. 27-29).

Processor 24 may analyze the received electrical parameter values and/or indications. Programmer 24 may generate reports or alerts after analyzing the information from ICD 16 or INS 26 and determine whether the values and indications indicate that patient 12 requires medical attention, e.g., based on ICD 16 and INS 26 crosstalk that exceeds an acceptable level. In some cases, ICD 16, INS 26, and/or programmer 24 may combine all of the diagnostic data into a single displayable report, which may be displayed on programmer 24. The report may contain information concerning the impedance measurements or indications, the time of day at which the measurements were taken or at which the indications were generated, and identify any patterns in the impedance measurements or arrhythmia or interference indications.

In another example, ICD 16 or INS 26 may provide external device 432 with collected impedance data via access point 438 and network 436. External device 432 includes one or more processors 440. In some cases, external device 432 may request collected impedance data and stored indications, and in some cases, ICD 16 or INS 26 may automatically or periodically provide such data to external device 432. Upon receipt of the impedance data and indication data via input/output device 442, external device 432 is capable of analyzing the data and generating reports or alerts upon determination that the impedance data indicates a lead integrity issue or upon determination that additional clinician assistance is necessary to decrease the crosstalk between ICD 16 and INS 26. In some examples, ICD 16 or INS 26 may analyze the data and generate reports or alerts, which may be transmitted to external device 432 via network 436. In addition, in some examples, a therapy system may not include programmer 24 to evaluate crosstalk, but, may instead rely on external device 432 or other devices to evaluate crosstalk between ICD 16 and INS 26.

In one example, external device 432 may combine the diagnostic data into an report. One or more of computing devices 434A-434N may access the report through network 436 and display the report to users of computing devices 434A-434N. In some cases, external device 432 may automatically send the report via input/output device 442 to one or more of computing devices 434A-434N as an alert, such as an audio or visual alert. In some cases, external device 432 may send the report to another device, such as programmer 24, either automatically or upon request. In some cases, external device 432 may display the report to a user via input/output device 442.

In one example, external device 432 may comprise a secure storage site for diagnostic information that has been collected from ICD 16, INS 26, and/or programmer 24. In this example, network 436 may comprise an Internet network, and trained professionals, such as clinicians, may use computing devices 434A-434N to securely access stored diagnostic data on external device 432. For example, the trained professionals may need to enter usernames and passwords to access the stored information on external device 432. In one example, external device 432 may be a CareLink server provided by Medtronic, Inc., of Minneapolis, Minn.

The examples therapy systems described herein include one ICD 16 and one INS 26. In other examples, the techniques described herein may also apply to therapy systems that include more than one ICD 16 and/or more than one INS 26. For example, the techniques shown in FIGS. 9-11D for modifying one or more electrical stimulation parameter values of an INS may be applicable to modifying one or more electrical stimulation parameter values for more than one INS. Some therapy systems may include more than one INS. For example, some therapy systems may include multiple microstimulators that each delivers electrical stimulation therapy to patient 12. A microstimulator may include a substantially self-contained electrical stimulation device that includes electrodes on a housing of the microstimulator, rather than being coupled to electrodes via one or more leads that extend from the housing. However, the microstimulator may be coupled to electrodes of leads in some examples. The multiple implanted microstimulators or other INS' may be distributed throughout the patient's body. In some examples, the microstimulators may communicate with each other to coordinate therapy delivery to patient 12. In addition, in some examples, the microstimulators may communicate with a master microstimulator or ICD 16, either of which may control the delivery of electrical stimulation by one or more of the other implanted microstimulators. Delivery of electrical stimulation signals by any one of the INS' may generate crosstalk with ICD 16. Thus, the techniques described herein may be used to minimize the crosstalk between one or more of the implanted INS' and ICD 16, evaluate the crosstalk between one or more of the implanted INS' and ICD 16, and the like.

The techniques described in this disclosure, including those attributed to ICD 16, INS 26, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 90 of ICD 16, processor 110 of INS 26, and/or processor 130 of programmer 24, any one or more parts of the techniques described herein may be implemented by a processor of one of the devices 16, 26, programmer 24 or another computing device, alone or in combination with ICD 16, INS 26 or programmer 24.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described in the disclosure. These and other examples are within the scope of the following example statements.

The invention claimed is:

1. A method comprising:
    determining whether a therapy module is delivering electrical stimulation to a tissue site within a patient;
    sensing electrical cardiac signals according to a first sense mode when the therapy module is delivering electrical stimulation to the tissue site; and
    sensing electrical cardiac signals according to a second sense mode when the therapy module is not delivering electrical stimulation to the tissue site, wherein the first and second sense modes define different sense vectors for sensing the electrical cardiac signals.

2. The method of claim 1, wherein the tissue site comprises at least one of a nonmyocardial tissue site or a nonvascular cardiac tissue site.

3. The method of claim 1, wherein the tissue site comprises at least one of an extravascular tissue site or the tissue site proximate to a nerve of the patient.

4. The method of claim 1, wherein sensing electrical cardiac signals according to the first sense mode comprises sensing electrical cardiac signals within a left ventricle of a heart of the patient and outside of a right ventricle of the heart, and wherein sensing electrical cardiac signals according to the second sense mode comprises sensing electrical cardiac signals within the right ventricle of the heart of the patient and outside of the left ventricle of the heart.

5. The method of claim 1, wherein sensing electrical cardiac signals according to the first sense mode comprises sensing electrical cardiac signals via at least two electrodes of a lead electrically connected to a sensing module, and wherein sensing electrical cardiac signals according to the second sense mode comprises sensing electrical cardiac signals via at least one electrode of the lead electrically connected to the sensing module and a housing electrode of a medical device comprising the sensing module.

6. The method of claim 1, wherein sensing electrical cardiac signals according to the first sense mode comprises sensing electrical cardiac signals via each of a plurality of sensing vectors.

7. The method of claim 6, further comprising:
    determining a weighted sum of the electrical cardiac signals sensed via each of the plurality of sensing vectors; and
    determining cardiac function of the patient based on the weighted sum of the electrical cardiac signals sensed via each of the plurality of sensing vectors.

8. The method of claim 6, further comprising:
    determining a difference between the electrical cardiac signals sensed via each of the plurality of sensing vectors; and
    determining cardiac function of the patient based on the difference between the electrical cardiac signals sensed via each of the plurality of sensing vectors.

9. The method of claim 1, wherein sensing electrical cardiac signals according to the first sense mode comprises sensing electrical cardiac signals via external electrodes, and sensing electrical cardiac signals according to the second sense mode comprises sensing electrical cardiac signals via implanted electrodes.

10. The method of claim 1, wherein sensing electrical cardiac signals according to the first and second modes comprises sensing electrical cardiac signals via a sensing module, and wherein the first sense mode defines a first sense vector comprising a first subset of electrodes electrically connected to the sensing module and the second sense mode defines a second sense vector comprising a second subset of electrodes electrically connected to the sensing module, the first and second subsets of electrodes comprising at least one different electrode.

11. The method of claim 1, further comprising:
    detecting a potential arrhythmia of a heart of the patient based on the electrical cardiac signals sensed according to the first sense mode; and sensing the electrical cardiac signals according to the second sense mode in response to detecting the potential arrhythmia.

12. The method of claim 11, wherein detecting the potential arrhythmia based on the electrical cardiac signals sensed according to the first sense mode comprises detecting the potential arrhythmia based on the electrical cardiac signals and a non-electrophysiological parameter of the patient indicative of cardiac function.

13. The method of claim 12, wherein the non-electrophysiological parameter comprises at least one of cardiovascular pressure, tissue perfusion, blood oxygen saturation levels, heart sound signals, respiratory rate, intrathoracic impedance, cardiac mechanical activity, muscle movement, ultrasonic signals, heart rate, body temperature, or acoustic signals indicative of cardiac mechanical activity.

14. The method of claim 12, further comprising sensing the non-electrophysiological parameter of the patient indicative of cardiac function with at least one of an external or an implanted sensor.

15. The method of claim 11, wherein the therapy module comprises a first therapy module and the potential arrhythmia comprises a first potential arrhythmia, the method further comprising:
in response to detecting the first potential arrhythmia based on the electrical cardiac signals sensed according to the first sense mode, determining whether a second potential arrhythmia is detected based on the electrical cardiac signals sensed according to the second sense mode; and
delivering at least one of a pacing, cardioversion or defibrillation electrical signal to the heart of the patient with a second therapy module in response to determining the second potential arrhythmia is detected based on the electrical cardiac signals sensed according to the second sense mode.

16. . The method of claim 15, wherein detecting the first potential arrhythmia based on the electrical cardiac signals sensed according to the first sense mode comprises detecting the first potential arrhythmia based on the electrical cardiac signals and a plurality of non-electrophysiological parameters of the patient indicative of cardiac function, and wherein determining whether the second potential arrhythmia is detected comprises detecting the second potential arrhythmia of the patient based on the electrical cardiac signals sensed according to the second sense mode and a fewer number of non-electrophysiological parameters of the patient than the first sense mode.

17. The method of claim 15, wherein the first and second therapy modules are enclosed in a common housing.

18. The method of claim 15, wherein the first therapy module is enclosed in a first housing of a first implantable medical device and the second therapy module is enclosed in a second housing of a second implantable medical device that is physically separate from the first implantable medical device.

19. The method of claim 11, further comprising:
determining whether the potential arrhythmia is detected based on the electrical cardiac signals sensed according to the second sense mode; and
sensing electrical cardiac signals according to the first sense mode if the potential arrhythmia is not detected based on the electrical cardiac signals sensed according to the second sense mode.

20. The method of claim 1, wherein the first and second sense modes define at least one of different sensing threshold levels or different amplifier gains for sensing the electrical cardiac signals.

21. The method of claim 1, wherein the first and second sense modes comprise different filters that are applied to the sensed electrical cardiac signals.

22. The method of claim 1, wherein the first and second sense modes comprise different potential arrhythmia event detection algorithms.

23. The method of claim 22, wherein the first sense mode defines an arrhythmia event detection algorithm that detects a potential arrhythmia based on a duration of an S-T segment of a sensed electrical cardiac signal.

24. The method of claim 1, wherein determining whether the therapy module is delivering electrical stimulation comprises at least one of receiving an indication from the therapy module or determining the therapy module is delivering stimulation based on known schedule.

25. A system comprising:
a therapy module that delivers electrical stimulation to a tissue site within a patient;
a sensing module that senses electrical cardiac signals of the patient; and
a processor that determines whether the therapy module is delivering electrical stimulation to the tissue site, controls the sensing module to sense electrical cardiac signals according to a first sense mode when the therapy module is delivering electrical stimulation to the tissue site, and controls the sensing module to sense electrical cardiac signals according to a second sense mode when the therapy module is not delivering electrical stimulation to the tissue site, wherein the first and second sense modes define different sense vectors for sensing the electrical cardiac signals.

26. The system of claim 25, wherein the tissue site comprises at least one of a nonmyocardial tissue site or a nonvascular cardiac tissue site.

27. The system of claim 25, wherein the tissue site comprises at least one of an extravascular tissue site or the tissue site proximate to a nerve of the patient.

28. The system of claim 25, wherein in the first sense mode, the sensing module senses electrical cardiac signals within a left ventricle of a heart of the patient and outside of a right ventricle of the heart, and in the second sense mode, the sensing module senses electrical cardiac signals within the right ventricle of the heart of the patient and outside of the left ventricle of the heart.

29. The system of claim 25, wherein in the first sense mode, the sensing module senses electrical cardiac signals via at least two electrodes of a lead electrically connected to a sensing module, and in the second sense mode, the sensing module senses electrical cardiac signals via at least one electrode of the lead and a housing electrode of a medical device comprising the sensing module.

30. The system of claim 25, wherein in the first sense mode, the sensing module senses electrical cardiac signals via each of a plurality of sensing vectors.

31. The system of claim 25, wherein in the first sense mode, the sensing module senses electrical cardiac signals via external electrodes, and in the second sense mode, the sensing module senses electrical cardiac signals via implanted electrodes.

32. The system of claim 25, further comprising a plurality of electrodes coupled to the sensing module, wherein the first sense mode defines a first sense vector comprising a first subset of electrodes of the plurality of electrodes and the second sense mode defines a second sense vector comprising a second subset of electrodes of the plurality of electrodes, the first and second subsets of electrodes comprising at least one different electrode.

33. The system of claim 25, wherein the processor detects a potential arrhythmia of the patient based on the electrical cardiac signals sensed by the sensing module according to the first sense mode, and controls the sensing module to sense the electrical cardiac signals according to the second sense mode upon detecting the potential arrhythmia.

34. The system of claim 33, wherein the sensing module comprises a first sensing module, the system further comprising a second sensing module that senses a non-electrophysiological parameter of the patient indicative of cardiac function, wherein the processor detects the potential arrhythmia of the patient based on the electrical cardiac signals sensed by the first sensing module according to the first sense mode and the non-electrophysiological parameter sensed by the second sensing module.

35. The system of claim 34, wherein the second sensing module is implanted within the patient.

36. The system of claim 34, wherein the second sensing module is external to the patient.

37. The system of claim 34, wherein the non-electrophysiological parameter of the patient comprises at least one of cardiovascular pressure, tissue perfusion, blood oxygen saturation levels, heart sound signals, respiratory rate, intrathoracic impedance, cardiac mechanical activity, muscle movement, ultrasonic signals, heart rate, body temperature, or acoustic signals indicative of cardiac mechanical activity.

38. The system of claim 33, wherein the therapy module comprises a first therapy module and the potential arrhythmia comprises a first potential arrhythmia, the system further comprising a second therapy module that delivers at least one of a pacing, cardioversion or defibrillation electrical signal to a heart of the patient, wherein, in response to detecting the first potential arrhythmia based on the electrical cardiac signals sensed according to the first sense mode, the processor determines whether a second potential arrhythmia is detected based on the electrical cardiac signals sensed by the sensing module according to the second sense mode and controls the second therapy module to deliver the at least one of a pacing, cardioversion or defibrillation electrical signal to the heart of the patient in response to determining the second potential arrhythmia is detected based on the electrical cardiac signals sensed according to the second sense mode.

39. The system of claim 38, wherein the sensing module comprises a first sensing module, the system further comprising a second sensing module that senses a plurality of non-electrophysiological parameters of the patient indicative of cardiac function, wherein the processor detects the first potential arrhythmia based on the electrical cardiac signals sensed by the first sensing module according to the first sense mode and a plurality of non-electrophysiological parameters sensed by the second sensing module, and determines whether the second potential arrhythmia is detected based on the electrical cardiac signals sensed by the first sensing module according to the second sense mode and a fewer number of non-electrophysiological parameters sensed by the second sensing module than in the first sense mode.

40. The system of claim 33, wherein the processor determines whether the second potential arrhythmia is detected based on the electrical cardiac signals sensed by the sensing module according to the second sense mode, and controls the sensing module to sense electrical cardiac signals according to the first sense mode if the second potential arrhythmia is not detected based on the electrical cardiac signals sensed according to the second sense mode.

41. The system of claim 25, wherein the first and second sense modes define at least one of different sensing threshold levels or different amplifier gains for sensing the electrical cardiac signals.

42. The system of claim 25, wherein the first and second sense modes comprise different filters that are applied to the sensed electrical cardiac signals.

43. The system of claim 25, wherein the first and second sense modes comprise different potential arrhythmia event detection algorithms.

44. The system of claim 43, wherein the first sense mode defines an arrhythmia event detection algorithm that detects a potential arrhythmia based on a duration of an S-T segment of a sensed electrical cardiac signal.

45. The system of claim 25, wherein the therapy module and sensing module are enclosed in a common housing.

46. The system of claim 25, wherein the therapy module is enclosed in a first housing of a first implantable medical device and the sensing module is enclosed in a second housing of a second implantable medical device that is physically separate from the first implantable medical device.

47. A system comprising:
   means for determining whether a therapy module is delivering electrical stimulation to a tissue site within a patient;
   means for sensing electrical cardiac signals according to a first sense mode when the therapy module is delivering electrical stimulation to the tissue site; and
   means for sensing electrical cardiac signals according to a second sense mode when the therapy module is not delivering electrical stimulation to the tissue site, wherein the first and second sense modes define different sense vectors for sensing the electrical cardiac signals.

48. The system of claim 47, further comprising:
   means for detecting a potential arrhythmia of the patient based on the electrical cardiac signals sensed according to the first sense mode; and
   means for sensing the electrical cardiac signals according to the second sense mode upon detecting the potential arrhythmia.

49. The system of claim 48, further comprising means for sensing a non-electrophysiological parameter of the patient indicative of cardiac function, wherein the means for detecting the potential arrhythmia of the patient based on the electrical cardiac signals sensed according to the first sense mode comprises means for detecting the arrhythmia based on the electrical cardiac signals and the non-electrophysiological parameter of the patient indicative of cardiac function.

50. A non-transitory computer-readable medium comprising instructions that cause a programmable processor to:
   determine whether a therapy module is delivering electrical stimulation to a tissue site within a patient;
   control a sensing module to sense electrical cardiac signals according to a first sense mode when the therapy module is delivering electrical stimulation to the tissue site; and
   control the sensing module to sense electrical cardiac signals according to a second sense mode when the therapy module is not delivering electrical stimulation to the tissue site, wherein the first and second sense modes define different sense vectors for sensing the electrical cardiac signals.

51. The non-transitory computer-readable medium of claim 50, wherein the instructions cause the programmable processor to:
  detect a potential arrhythmia of the patient based on the electrical cardiac signals sensed according to the first sense mode; and
  control the sensing module to sense the electrical cardiac signals according to the second sense mode upon detecting the potential arrhythmia.

52. A system comprising:
  a therapy module that delivers electrical stimulation to a tissue site within a patient;
  a sensing module that senses electrical cardiac signals of the patient; and
  a processor that determines whether the therapy module is delivering electrical stimulation to the tissue site, and, in response to determining the therapy module is delivering electrical stimulation to the tissue site, controls the sensing module to sense electrical cardiac signals according to a first sense mode, and, in response to determining the therapy module is not delivering electrical stimulation to the tissue site, controls the sensing module to sense electrical cardiac signals according to a second sense mode, wherein the first and second sense modes define different sense vectors for sensing the electrical cardiac signals.

\* \* \* \* \*